United States Patent
Dixon et al.

(10) Patent No.: US 7,582,645 B2
(45) Date of Patent: *Sep. 1, 2009

(54) PYRIMIDINE DERIVATIVES FOR TREATMENT OF HYPERPROLIFERATIVE DISORDERS

(75) Inventors: Julie A. Dixon, Bethany, CT (US); Dhanapalan Nagarathnam, Bethany, CT (US); Lei Zhang, Hamden, CT (US); Chunguang Wang, Hamden, CT (US); Lin Yi, Milford, CT (US); Yuanwei Chen, North Haven, CT (US); Jianqing Chen, New Haven, CT (US); Brian Bear, Oceanside, CA (US); Michael Brands, Wuppertal (DE); Alexander Hillisch, Velbert (DE); Donald Bierer, Bethany, CT (US); Ming Wang, Milford, CT (US); Wenlang Fu, Milford, CT (US); Martin F. Hentemann, Hamden, CT (US); Ann-Marie Bullion, Milford, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 437 days.

This patent is subject to a terminal disclaimer.

(21) Appl. No.: 10/573,227

(22) PCT Filed: Oct. 8, 2004

(86) PCT No.: PCT/US2004/033430

§ 371 (c)(1),
(2), (4) Date: Mar. 24, 2006

(87) PCT Pub. No.: WO2005/035507

PCT Pub. Date: Apr. 21, 2005

(65) Prior Publication Data

US 2007/0117817 A1     May 24, 2007

Related U.S. Application Data

(60) Provisional application No. 60/510,804, filed on Oct. 10, 2003.

(51) Int. Cl.
C07D 239/48 (2006.01)
C07D 401/12 (2006.01)
C07D 401/14 (2006.01)
C07D 403/12 (2006.01)
C07D 403/14 (2006.01)
C07D 409/14 (2006.01)
C07D 413/14 (2006.01)
A61K 31/506 (2006.01)
A61K 31/505 (2006.01)
A61P 35/00 (2006.01)

(52) U.S. Cl. ............... 514/269; 514/275; 544/323; 544/324; 544/326; 544/328; 544/329
(58) Field of Classification Search ............... 544/323, 544/324, 326, 328, 329; 514/275, 269
See application file for complete search history.

(56) References Cited

FOREIGN PATENT DOCUMENTS

WO    03062225    7/2003
WO    03062227    7/2003

OTHER PUBLICATIONS

Cecil Textbook of Medicine, edited by Bennet, J.C., and Plum F., 20th edition,vol. 1, 1004-1010, 1996.*
West, Anthony R., Solid State Chemistry and its Applications, Wiley, New York, 1988, pp. 358 & 365.*
Vippagunta et al., Advanced Drug Delivery Reviews 48: 3-26, 2001.*
Mass, R. D., Int. J. Radiation Oncology Bio. Phys.vol. 58(3): 932-940, 2004.*
Fabbro et al. Pharmacology & therapeutics 93, 79-98, 2002.*
Denny, Expert Opin.Emerg.Drugs, vol. 9(1), 105-133 (2004).*
Wood et al., Current Opinion in Pharmacology, 1, 370377, 2001.*
Malumbres et al., Trends in Biochemical Sciences, 30(11), 630-641, 2005.*
Lolli et al., Cell Cycle 4:4, 572-577, 2005.*
Sherr et al., Genes & Development 18, 2699-2711, 2004.*
Fischer Cell Cycle 3:6, 742-746, 2004.*

* cited by examiner

*Primary Examiner*—Venkataraman Balasubramanian
(74) *Attorney, Agent, or Firm*—Edwards Angell Palmer & Dodge LLP; Barry Kramer; Ralph A. Loren

(57) ABSTRACT

Pyrimidine derivatives of formula (I) in which J and Y represent aromatic or heteroaromatic rings; $R^2$, G, G', and G" represent substituent groups and $R^{2a}$ represents H or halogen; L represents a linking group; and M represents CH or N. Pharmaceutical compositions containing these compounds, and methods of using these compounds in treatment of hyperproliferative diseases such as cancer are also disclosed and claimed.

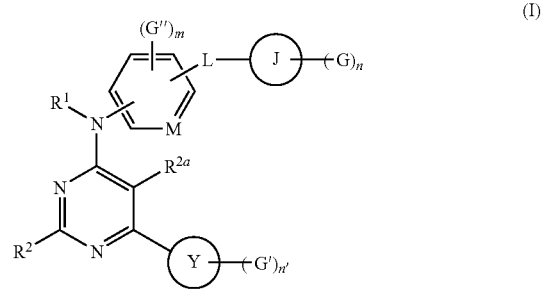

10 Claims, No Drawings

PYRIMIDINE DERIVATIVES FOR TREATMENT OF HYPERPROLIFERATIVE DISORDERS

FIELD

This application relates to small molecule heterocyclic pharmaceuticals, and more particularly, to amino-substituted pyrimidine derivatives having cytotoxic activity.

BACKGROUND

Nitrogen-containing heterocycles such as pyrimidine derivatives have been disclosed in patent and non-patent publications as having a variety of pharmaceutical properties and utilities. Several such publications are listed below.

WO 03/062225 (Bayer) relates to pyrimidine derivatives as rho-kinase inhibitors, and their use in treatment of rho-kinase mediated conditions including cancer.

WO 2001/87845 (Fujisawa) relates to N-containing heterocyclic compounds having 5-HT antagonistic activity. These compounds are stated as being useful for treating or preventing central nervous system disorders.

WO 95/10506 (Du Pont Merck) relates to 1N-alkyl-N-arylpyrimidinamines and derivatives thereof, which are stated to inhibit the corticopropin releasing factor (CRF) peptide and to be useful for treatment of psychiatric disorders and neurological diseases.

WO 2004/048365 (Chiron) relates to 2,4,6-trisubstituted pyrimidines as phosphotidylinositol (PI) 3-kinase inhibitors and their use in treatment of cancer.

WO 2004/000820 (Cellular Genomics) relates to N-containing heterocycles and other compounds as kinase modulators, and their use in treatment of numerous kinase-associated disorders including cancer.

WO 01/62233 (Hoffmann La Roche) relates to nitrogen-containing heterocycles and their use in treatment of diseases modulated by the adenosine receptor.

U.S. 2004/0097504 (Vertex) relates to nitrogen-containing heterocycles useful in treatment of various protein kinase-mediated disorders.

The pharmaceutical field is always interested in identifying new pharmaceutically active compounds. Such materials are the subject of the present application.

Compounds of the Invention

In a first embodiment, this invention relates to compounds of Formula (I)

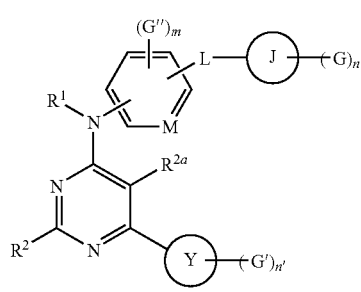

(I)

wherein
$R^1$ represents H, $(C_1-C_3)$alkyl, or cyclopropyl;
$R^2$ represents $(C_1-C_3)$alkyl, cyclopropyl, $O(C_1-C_3)$alkyl, or $NR^3R^4$
wherein $R^3$ and $R^4$ are H, $(C_1-C_3)$alkyl, or cyclopropyl;
$R^{2a}$ represents H or halogen;
M represents CH or N;
L represents a carbonyl group, O, $NR^5$, $CR^6R^7$, or $(C_2-C_3)$ alkylenyl which is optionally substituted up to twice by groups independently selected from halogen and OH;
wherein
$R^5$ is H or $(C_1-C_3)$alkyl; and
$R^6$ and $R^7$ are independently H, $CH_3$, halogen, or OH;
J represents an aromatic or heteroaromatic ring selected from the group consisting of

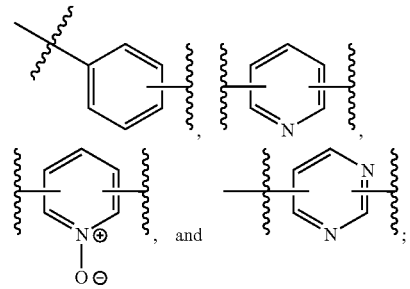

Y represents an aromatic or heteroaromatic ring selected from the group consisting of

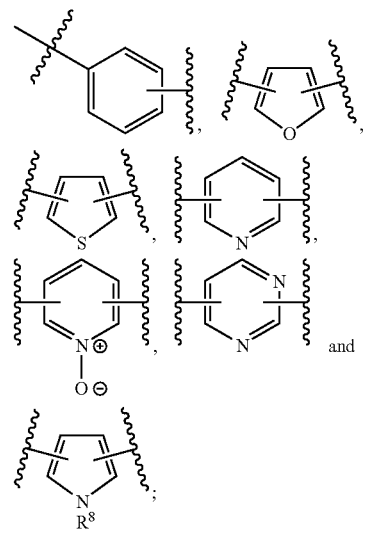

wherein $R^8$ represents H or $(C_1-C_3)$alkyl;
G" represents a substituent selected from the group consisting of $(C_1-C_3)$alkyl, cyclopropyl, $O(C_1-C_3)$alkyl, halogen, $CF_3$, CN and $CO_2R^9$;
wherein
$R^9$ represents H or $(C_1-C_3)$alkyl, and
m represents the number of substituents G", and is 0, 1, or 2;
G represents a substituent located on ring J;
G' represents a substituent located on ring Y;
n represents the number of substituents G; and
n' represents the number of substituents G';

n and n' are independently 0, 1, 2, or 3, subject to the provisos that
1) ring J and ring Y each may be substituted independently up to 3 times by substituents listed below as numbers G1-G2, to a maximum total of 4 substituents on rings J and Y,
2) ring J and ring Y each may be substituted independently up to 2 times by substituents listed below as numbers G3-G01, to a maximum total of 3 substituents on rings J and Y, and
3) ring J and ring Y each may be substituted independently once by a substituent selected from those listed below as numbers G12-G37;

and subject to the further provisos
4) when J is phenyl, G is other than OH or alkylthio; and when J is phenyl or pyridyl, n is 1, 2, or 3;
5) when J is phenyl, and G is G4 shown below, then $R^2$ is $NR^3R^4$;

G and G' moieties are independently selected from the group consisting of:
G1) halogen;
G2) $O(C_1-C_4)$alkyl which optionally is substituted up to two times by $O(C_1-C_2)$alkyl;
G3) OH;
G4) $(C_1-C_5)$alkyl, which is optionally substituted independently up to two times by groups selected from hydroxyl and cyano, or up to three times by halogen;
G5) $OCF_3$;
G6) $NHC(O)(C_1-C_3)$alkyl;
G7) $NHSO_2(C_1-C_3)$alkyl;
G8) $NR^{10}R^{11}$, wherein
  $R^{10}$ and $R^{11}$ are independently selected from
  H,
  $CH_3$,
  cyclopropyl,
  benzyl,
  $NR^{12}R^{13}$ wherein
    $R^{12}$ and $R^{13}$ are independently H or $(C_1-C_3)$alkyl, provided that both $R^{10}$ and $R^{11}$ are not $NR^{12}R^{13}$ simultaneously, and
  $(C_2-C_4)$alkyl which is optionally substituted up to three times by halogen, and up to two times by substituent groups independently selected from hydroxyl, $O(C_1-C_3)$alkyl, and $NR^{14}R^{15}$, wherein
    $R^{14}$ and $R^{15}$ are independently H or $(C_1-C_3)$alkyl, or
    $R^{14}$ and $R^{15}$ can join to form a heterocycle of formula

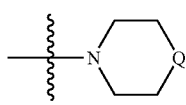

wherein
  Q represents $CH_2$, O, or $NR^{16}$, and
  $R^{16}$ represents H or $(C_1-C_3)$alkyl, or
  $R^{10}$ and $R^{11}$ may be joined to form a saturated 5-6-membered N-containing ring which is optionally substituted up to two times by OH,
  $NR^{17}R^{18}$, wherein
    $R^{17}$ and $R^{18}$ are H or $(C_1-C_3)$alkyl, or by
    $(C_1-C_3)$alkyl which is optionally substituted up to two times by halogen, OH, or $O(C_1-C_3)$alkyl;

G9) $(CH_2)_a$—$NR^{19}R^{20}$ wherein
  $R^{19}$ and $R^{20}$ are independently H, $(C_1-C_5)$alkyl, or $(C_3-C_6)$cycloalkyl, or may be joined to form a saturated 5-6-membered N-containing ring; and
  the subscript "a" is an integer of 1-4;

G10) 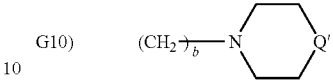

wherein
  Q' is O or $NR^{21}$;
  $R^{21}$ is H, $(C_1-C_3)$alkyl, or cyclopropyl; and
  the subscript "b" is an integer of 1-3;
G11) $CH_2NR^{22}(CH_2)_cOCH_3$ wherein
  $R^{22}$ is H, $(C_1-C_3)$alkyl, or cyclopropyl; and
  the subscript "c" is an integer of 2-4;
G12) $OSO_2NR^{23}R^{24}$ wherein
  $R^{23}$ and $R^{24}$ independently represent H, $CH_3$, or $(C_2-C_4)$alkyl which may optionally be substituted once by OH or $NR^{25}R^{26}$, wherein
    $R^{25}$ and $R^{26}$ independently represent H or $(C_1-C_3)$alkyl;
G13) CN;
G14) $NO_2$;
G15) cyclopropyl;
G16) $OR^{27}$, wherein
  $R^{27}$ represents phenyl or benzyl;
G17) $S(C_1-C_3)$alkyl;
G18) $CH=CH-(CH_2)_{1-3}-OR^5$; wherein
  $R^5$ represents H or $(C_1-C_3)$alkyl;

G19) 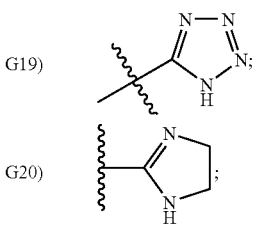

G20)

G21) $C(O)NR^{28}R^{29}$, wherein
  $R^{28}$ and $R^{29}$ are independently selected from H,
  cyclopropyl, provided that both $R^{28}$ and $R^{29}$ are not simultaneously cyclopropyl,

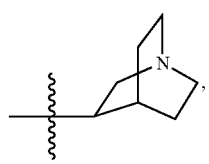

provided that this group does not constitute both $R^{28}$ and $R^{29}$ simultaneously, and
  $(C_1-C_3)$alkyl which is optionally substituted up to two times by OH; or
  $R^{28}$ and $R^{29}$ may be joined to form a saturated 5-6-membered N-containing ring which is optionally substituted up to two times by OH, or by $(C_1-C_3)$alkyl which in turn is optionally substituted up to two times by OH or $O(C_1-C_3)$alkyl;

G22) 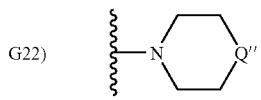

wherein
Q'' is O or NR$^{30}$, and
R$^{30}$ is H, cyclopropyl, or
  (C$_1$-C$_3$)alkyl which is optionally substituted once by halogen, OH, or O(C$_1$-C$_3$)alkyl;
G23) O—(CH$_2$)$_d$—NR$^{31}$R$^{32}$ wherein
  R$^{31}$ and R$^{32}$ are independently H, (C$_1$-C$_3$)alkyl, or cyclopropyl, or may be joined to form a saturated 5-6-membered N-containing ring; and
  the subscript "d" is an integer of 2-4;

G24) 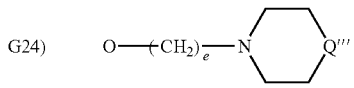

wherein
the subscript "e" is an integer of 2-3; and
Q''' is O or NR$^{33}$; and
R$^{33}$ is H, (C$_1$-C$_3$)alkyl, or cyclopropyl;

G25) 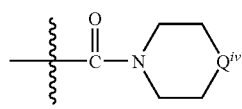

wherein
Q$^{iv}$ is O or NR$^{34}$; and
R$^{34}$ is H, (C$_1$-C$_3$)alkyl, or cyclopropyl;
G26) C(O)NR$^{35}$(CH$_2$)$_f$OR$^{36}$ wherein
  R$^{35}$ is H, (C$_1$-C$_3$)alkyl, or cyclopropyl;
  R$^{36}$ is (C$_1$-C$_6$)alkyl optionally substituted up to two times by halogen, OH, or O(C$_1$-C$_3$)alkyl, and
  the subscript "f" is an integer of 2-4;
G27) CO$_2$R$^{37}$ wherein
  R$^{37}$ is H or (C$_1$-C$_3$)alkyl;
G28) phenyl, which is optionally substituted by up to 2 groups selected from halogen, (C$_1$-C$_3$)alkyl, OR$^{38}$, CN, CF$_3$, and NR$^{39}$R$^{40}$ wherein
  R$^{38}$ represents H or (C$_1$-C$_3$)alkyl; and
  R$^{39}$ and R$^{40}$ represent H or (C$_1$-C$_3$)alkyl;
G29) NR$^{41}$SO$_2$NR$^{42}$R$^{43}$ wherein
  R$^{41}$ represents H, or (C$_1$-C$_4$)alkyl, and
  R$^{42}$ and R$^{43}$ independently represent H, CH$_3$, or (C$_2$-C$_3$) alkyl which may optionally be substituted once by —OH or NR$^{44}$R$^{45}$, wherein
    R$^{44}$ and R$^{45}$ independently represent H or (C$_1$-C$_3$) alkyl;
G30) OC(O)—CH$_2$—NR$^{46}$R$^{47}$ wherein
  R$^{46}$ and R$^{47}$ independently represent H, (C$_1$-C$_3$)alkyl, or CO$_2$(t-butyl), provided that R$^{46}$ and R$^{47}$ are not both simultaneously CO$_2$(t-butyl);
G31) N(R$^{48}$)C(O)R$^{49}$ wherein
  R$^{48}$ represents H or (C$_1$-C$_3$)alkyl; and
  R$^{49}$ represents
    (CH$_2$)$_{1-3}$—CO$_2$H,
    O(C$_2$-C$_4$)alkyl,
    (CH$_2$)$_{1-4}$—NR$^{50}$R$^{51}$ wherein
      R$^{50}$ and R$^{51}$ independently represent H or (C$_1$-C$_3$) alkyl, or
    CH(R$^{52}$)—NR$^{53}$R$^{54}$ wherein
      R$^{52}$ represents (CH$_2$)$_{1-4}$—NH$_2$, CH$_2$OH, CH(CH$_3$)OH, or (C$_1$-C$_3$)alkyl; and
      R$^{53}$ and R$^{54}$ independently represent H or (C$_1$-C$_3$) alkyl;
G32) C(O)—(C$_1$-C$_3$)alkyl;
G33) (CH$_2$)$_g$—N(R$^{55}$)—C(O)—R$^{56}$ wherein
  g represents 1, 2, or 3;
  R$^{55}$ represents H or (C$_1$-C$_3$)alkyl;
  R$^{56}$ represents
    (C$_1$-C$_3$)alkyl optionally substituted up to two times by OR$^{57}$ or NR$^{58}$R$^{59}$, wherein
      R$^{57}$ represents H or (C$_1$-C$_3$)alkyl, and
      R$^{58}$ and R$^{59}$ each represents H or (C$_1$-C$_3$)alkyl,
  or R$^{56}$ represents

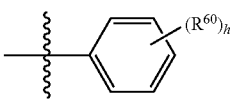

wherein
R$^{60}$ represents halogen, (C$_1$-C$_3$)alkyl, O(C$_1$-C$_3$)alkyl, CN, OH, CF$_3$, or NR$^{61}$R$^{62}$, wherein
  R$^{61}$ and R$^{62}$ represent H or (C$_1$-C$_3$)alkyl; and
h represents 0, 1, or 2;
G34) (CH$_2$)$_i$—N(R$^{63}$)—C(O)—NR$^{64}$R$^{65}$ wherein
  i represents 1, 2, or 3;
  R$^{63}$ represents H or (C$_1$-C$_3$)alkyl;
  R$^{64}$ and R$^{65}$ each represents H or (C$_1$-C$_3$)alkyl; or
  R$^{64}$ and R$^{65}$ may be joined to form

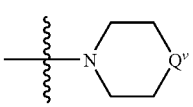

wherein
Q$^V$ represents CH$_2$, O or NR$^{66}$ wherein
  R$^{66}$ represents H or (C$_1$-C$_3$)alkyl;

G35)

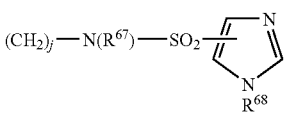

wherein
j represents 1, 2, or 3;
R$^{67}$ represents H or (C$_1$-C$_3$)alkyl; and
R$^{68}$ represents H or (C$_1$-C$_3$)alkyl;
G36) (CH$_2$)$_k$—N(R$^{69}$)—SO$_2$—R$^{70}$ wherein
  k represents 1, 2, or 3;
  R$^{69}$ represents H or (C$_1$-C$_3$)alkyl; and
  R$^{70}$ represents (C$_1$-C$_4$)alkyl, or phenyl which is optionally substituted up to perhalo by halogen or up to three times by OR$^{71}$, CN, CF$_3$, or NR$^{72}$R$^{73}$, wherein
    R$^{71}$ represents H or (C$_1$-C$_3$)alkyl; and
    R$^{72}$ and R$^{73}$ each represents H or (C$_1$-C$_3$)alkyl;

G37) CH=CH—(CH$_2$)$_{1-3}$—NR$^{74}$R$^{75}$ wherein
R$^{74}$ and R$^{75}$ represent H or (C$_1$-C$_3$)alkyl;

or a pharmaceutically acceptable salt, solvate, solvate of a salt, or stereoisomer thereof.

In a second embodiment, the invention relates to a compound of the above first embodiment, having the structure

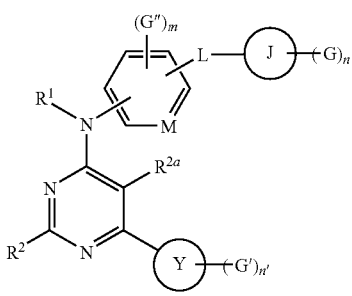

(I)

wherein the definitions of the variables are as given above in the first embodiment, except that in this second embodiment R$^1$ represents H;

M represents CH;

J represents a heteroaromatic ring selected from the group consisting of

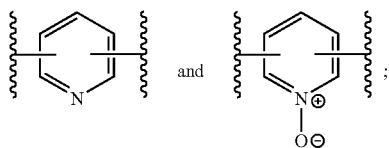

Y represents an aromatic or heteroaromatic ring selected from the group consisting of

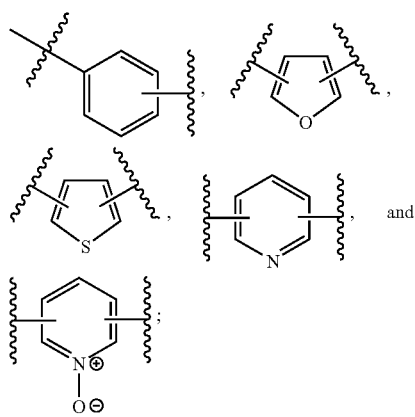

n and n' are independently 0, 1, 2, or 3, subject to the provisos that 1) ring J and ring Y each may be substituted independently up to 3 times by substituents listed below as numbers G1-G2, to a maximum total of 4 substituents on rings J and Y, 2) ring J and ring Y each may be substituted independently up to 2 times by substituents listed below as numbers G3-G5 and G8, to a maximum total of 3 substituents on rings J and Y, and 3) ring J and ring Y each may be substituted independently once by a substituent selected from those listed below as numbers G12, G13, G22, G29, and G31;

and subject to the further proviso 4) when J is pyridyl, n is 1, 2, or 3;

and proviso 5 does not apply;

G and G' moieties are independently selected from the group consisting of:
- G1) halogen;
- G2) O(C$_1$-C$_4$)alkyl which optionally is substituted up to two times by O(C$_1$-C$_2$)alkyl;
- G3) OH;
- G4) (C$_1$-C$_5$)alkyl, which is optionally substituted independently up to two times by groups selected from hydroxyl and cyano, or up to three times by halogen;
- G5) OCF$_3$;
- G8) NR$^{10}$R$^{11}$, wherein
    R$^{10}$ and R$^{11}$ are independently selected from H, CH$_3$, cyclopropyl, benzyl, NR$^{12}$R$^{13}$ wherein
        R$^{12}$ and R$^{13}$ are independently H or (C$_1$-C$_3$)alkyl, provided that both R$^{10}$ and R$^{11}$ are not NR$^{12}$R$^{13}$ simultaneously, and
    (C$_2$-C$_4$)alkyl which is optionally substituted up to three times by halogen, and up to two times by substituent groups independently selected from hydroxyl, O(C$_1$-C$_3$)alkyl, and NR$^{14}$R$^{15}$, wherein
        R$^{14}$ and R$^{15}$ are independently H or (C$_1$-C$_3$)alkyl, or
        R$^{14}$ and R$^{15}$ can join to form a heterocycle of formula

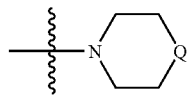

wherein
Q represents CH$_2$, O, or NR$^{16}$, and
R$^{16}$ represents H or (C$_1$-C$_3$)alkyl,
or
R$^{10}$ and R$^{11}$ may be joined to form a saturated 5-6-membered N-containing ring which is optionally substituted up to two times by OH,
NR$^{17}$R$^{18}$, wherein
R$^{17}$ and R$^{18}$ are H or (C$_1$-C$_3$)alkyl, or by
(C$_1$-C$_3$)alkyl which is optionally substituted up to two times by halogen, OH, or O(C$_1$-C$_3$)alkyl;

G12) OSO$_2$NR$^{23}$R$^{24}$ wherein
R$^{23}$ and R$^{24}$ independently represent H, CH$_3$, or (C$_2$-C$_4$) alkyl which may optionally be substituted once by OH or NR$^{25}$R$^{26}$, wherein
R$^{25}$ and R$^{26}$ independently represent H or (C$_1$-C$_3$) alkyl;

G13) CN;

G22)

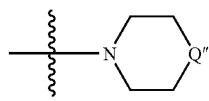

wherein
Q″ is O or $NR^{30}$, and
$R^{30}$ is
H,
cyclopropyl, or
$(C_1-C_3)$alkyl which is optionally substituted once by halogen, OH, or $O(C_1-C_3)$alkyl;
G29) $NR^{41}SO_2NR^{42}R^{43}$ wherein
$R^{41}$ represents H, or $(C_1-C_4)$alkyl, and
$R^{42}$ and $R^{43}$ independently represent H, $CH_3$, or $(C_2-C_3)$ alkyl which may optionally be substituted once by —OH or $NR^{44}R^{45}$, wherein
$R^{44}$ and $R^{45}$ independently represent H or $(C_1-C_3)$ alkyl; and
G31) $N(R^{48})C(O)R^{49}$ wherein
$R^{48}$ represents H or $(C_1-C_3)$alkyl; and
$R^{49}$ represents
$(CH_2)_{1-3}$—$CO_2H$,
$O(C_2-C_4)$alkyl,
$(CH_2)_{1-4}$—$NR^{50}R^{51}$ wherein
$R^{50}$ and $R^{51}$ independently represent H or $(C_1-C_3)$ alkyl, or
$CH(R^{12})$—$NR^{53}R^{54}$ wherein
$R^{52}$ represents $(CH_2)_{1-4}$—$NH_2$, $CH_2OH$, $CH(CH_3)$OH, or $(C_1-C_3)$alkyl; and
$R^{53}$ and $R^{54}$ independently represent H or $(C_1-C_3)$ alkyl.

In a third embodiment the invention relates to a compound of the above second embodiment, having the structure

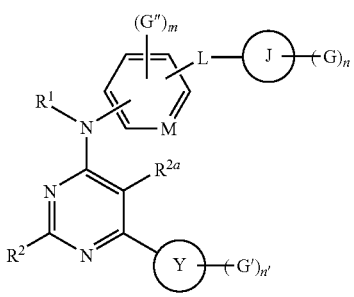

(I)

wherein the definitions of the variables are as given above in the second embodiment, except that in this third embodiment
$R^1$ represents H;
$R^2$ represents $O(C_1-C_3)$alkyl or $NR^3R^4$
wherein $R^3$ and $R^4$ are H or $(C_1-C_3)$alkyl;
$R^{2a}$ represents H;
L represents O or $CR^6R^7$ wherein
$R^6$ and $R^7$ are independently H, $CH_3$, or OH;
G″ represents a substituent selected from the group consisting of $O(C_1-C_3)$alkyl, halogen, and $CF_3$;
n and n′ are independently 0 or 1, and provisos 1-3 do not apply,
G and G′ moieties are independently selected from the group consisting of:
G1) Cl or F;
G2) $O(C_1-C_3)$alkyl;
G3) OH;
G4) $(C_1-C_3)$alkyl, which is optionally substituted up to three times by halogen;
G5) $OCF_3$;
G8) $NR^{10}R^{11}$, wherein
$R^{10}$ and $R^{11}$ are independently selected from
H,
$CH_3$,
cyclopropyl,
benzyl,
$NR^{12}R^{13}$ wherein
$R^{12}$ and $R^{13}$ are independently H or $(C_1-C_3)$alkyl, provided that both $R^{10}$ and $R^{11}$ are not $NR^{12}R^{13}$ simultaneously,
and
$(C_2-C_4)$alkyl which is optionally substituted up to three times by halogen, and up to two times by substituent groups independently selected from hydroxyl, $O(C_1-C_3)$alkyl, and $NR^{14}R^{15}$, wherein
$R^{14}$ and $R^{15}$ are independently H or $(C_1-C_3)$alkyl, or
$R^{14}$ and $R^{15}$ can join to form a heterocycle of formula

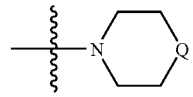

wherein
Q represents $CH_2$, O, or $NR^{16}$, and
$R^{16}$ represents H or $(C_1-C_3)$alkyl,
G12) $OSO_2NR^{23}R^{24}$ wherein
$R^{23}$ and $R^{24}$ independently represent H, $CH_3$, or $(C_2-C_4)$ alkyl which may optionally be substituted once by OH or $NR^{25}R^{26}$ wherein
$R^{25}$ and $R^{26}$ independently represent H or $(C_1-C_3)$ alkyl;
G13) CN;

G22)

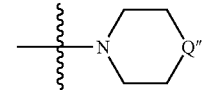

wherein
Q″ is O or $NR^{30}$, and
$R^{30}$ is H or $(C_1-C_3)$alkyl; and
G31) $N(R^{48})C(O)R^{49}$ wherein
$R^{48}$ represents H or $(C_1-C_3)$alkyl; and
$R^{49}$ represents
$(CH_2)_{1-3}$—$CO_2H$,
$O(C_2-C_4)$alkyl,
$(CH_2)_{1-4}$—$NR^{50}R^{51}$ wherein
$R^{50}$ and $R^{51}$ independently represent H or $(C_1-C_3)$ alkyl, or
$CH(R^{52})$—$NR^{53}R^{54}$ wherein
$R^{52}$ represents $(CH_2)_{1-4}$—$NH_2$, $CH_2OH$, $CH(CH_3)$OH, or $(C_1-C_3)$alkyl; and
$R^{53}$ and $R^{54}$ independently represent H or $(C_1-C_3)$ alkyl.

In a fourth embodiment, the invention relates to a compound of the above first embodiment, having the structure

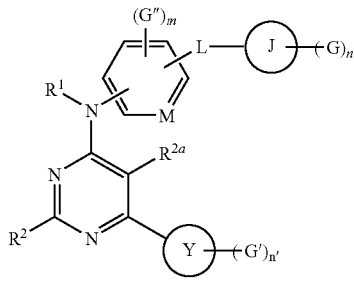
(I)

wherein the definitions of the variables are as given above in the first embodiment, except that in this fourth embodiment
$R^1$ represents H;
M represents CH;
J represents a heteroaromatic ring selected from the group consisting of

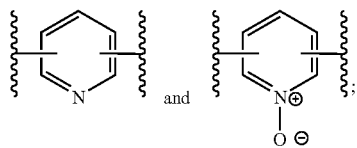

Y represents an aromatic or heteroaromatic ring selected from the group consisting of

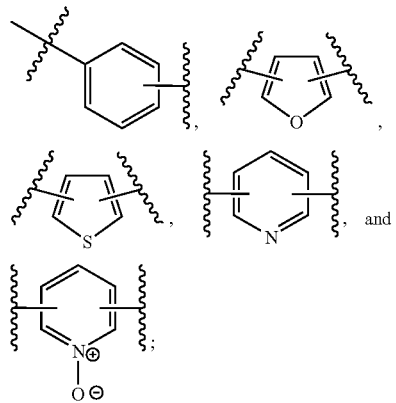

n and n' are independently 0, 1, 2, or 3, subject to the provisos that
1) ring J and ring Y each may be substituted independently up to 3 times by substituents listed below as numbers G1-G2, to a maximum total of 4 substituents on rings J and Y,
2) ring J and ring Y each may be substituted independently up to 2 times by substituents listed below as numbers G3-G5 and G8, to a maximum total of 3 substituents on rings J and Y, and 3) ring J and ring Y each may be substituted independently once by a substituent selected from those listed below as numbers G12, G21, G25, G26, and G31;

and subject to the further proviso
4) when J is pyridyl, n is 1, 2, or 3;

and proviso 5 does not apply;
G and G' moieties are independently selected from the group consisting of:
G1) halogen;
G2) O($C_1$-$C_4$)alkyl which optionally is substituted up to two times by O($C_1$-$C_2$)alkyl;
G3) OH;
G4) ($C_1$-$C_5$)alkyl, which is optionally substituted independently up to two times by groups selected from hydroxyl and cyano, or up to three times by halogen;
G5) $OCF_3$;
G8) $NR^{10}R^{11}$, wherein
$R^{10}$ and $R^{11}$ are independently selected from
H,
$CH_3$,
cyclopropyl,
benzyl,
$NR^{12}R^{13}$ wherein
$R^{12}$ and $R^{13}$ are independently H or ($C_1$-$C_3$)alkyl, provided that both $R^{10}$ and $R^{11}$ are not $NR^{12}R^{13}$ simultaneously,
and
($C_2$-$C_4$)alkyl which is optionally substituted up to three times by halogen, and up to two times by substituent groups independently selected from hydroxyl, O($C_1$-$C_3$)alkyl, and $NR^{14}R^{15}$, wherein
$R^{14}$ and $R^{15}$ are independently H or ($C_1$-$C_3$)alkyl, or
$R^{14}$ and $R^{15}$ can join to form a heterocycle of formula

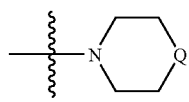

wherein
Q represents $CH_2$, O, or $NR^{16}$, and
$R^{16}$ represents H or ($C_1$-$C_3$)alkyl,
or
$R^{10}$ and $R^{11}$ may be joined to form a saturated 5-6-membered N-containing ring which is optionally substituted up to two times by
OH,
$NR^{17}R^{18}$, wherein
$R^{17}$ and $R^{18}$ are H or ($C_1$-$C_3$)alkyl,
or by
($C_1$-$C_3$)alkyl which is optionally substituted up to two times by halogen, OH, or O($C_1$-$C_3$)alkyl;
G12) $OSO_2NR^{23}R^{24}$ wherein
$R^{23}$ and $R^{24}$ independently represent H, $CH_3$, or ($C_2$-$C_4$) alkyl which may optionally be substituted once by OH or $NR^{25}R^{26}$ wherein
$R^{25}$ and $R^{26}$ independently represent H or ($C_1$-$C_3$) alkyl;

G21) C(O)NR$^{28}$R$^{29}$, wherein
R$^{28}$ and R$^{29}$ are independently selected from
H,
cyclopropyl, provided that both R$^{28}$ and R$^{29}$ are not simultaneously cyclopropyl,

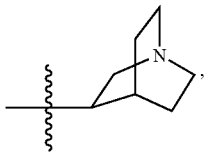

provided that this group does not constitute both R$^{28}$ and R$^{29}$ simultaneously,
and
(C$_1$-C$_3$)alkyl which is optionally substituted up to two times by OH;
or
R$^{28}$ and R$^{29}$ may be joined to form a saturated 5-6-membered N-containing ring which is optionally substituted up to two times by OH, or by (C$_1$-C$_3$)alkyl which in turn is optionally substituted up to two times by OH or O(C$_1$-C$_3$)alkyl;

G25) 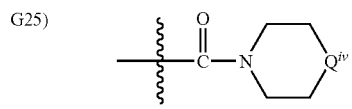

wherein
Q" is O or NR$^{34}$; and
R$^{34}$ is H, (C$_1$-C$_3$)alkyl, or cyclopropyl;
G26) C(O)NR$^{35}$(CH$_2$)$_f$OR$^{36}$ wherein
R$^{35}$ is H, (C$_1$-C$_3$)alkyl, or cyclopropyl;
R$^{36}$ is (C$_1$-C$_6$)alkyl optionally substituted up to two times by halogen, OH, or O(C$_1$-C$_3$)alkyl, and
the subscript "f" is an integer of 2-4; and
G31) N(R$^{48}$)C(O)R$^{49}$ wherein
R$^{48}$ represents H or (C$_1$-C$_3$)alkyl; and
R$^{49}$ represents
(CH$_2$)$_{1-3}$—CO$_2$H,
O(C$_2$-C$_4$)alkyl,
(CH$_2$)$_{1-4}$—NR$^{50}$R$^{51}$ wherein
R$^{50}$ and R$^{51}$ independently represent H or (C$_1$-C$_3$) alkyl, or
CH(R$^{52}$)—NR$^{53}$R$^{54}$ wherein
R$^{52}$ represents (CH$_2$)$_{1-4}$—NH$_2$, CH$_2$OH, CH(CH$_3$)OH, or (C$_1$-C$_3$)alkyl; and
R$^{53}$ and R$^{54}$ independently represent H or (C$_1$-C$_3$) alkyl.

In a fifth embodiment, the invention relates to a compound of the above fourth embodiment, having the structure

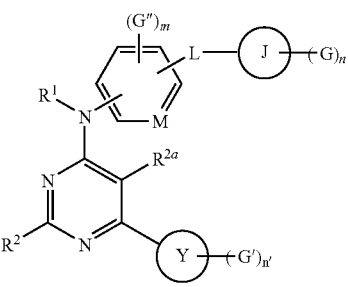

(I)

wherein the definitions of the variables are as given above in the fourth embodiment, except that in this fifth embodiment
R$^1$ represents H;
R$^2$ represents O(C$_1$-C$_3$)alkyl or NR$^3$R$^4$
wherein R$^3$ and R$^4$ are H or (C$_1$-C$_3$)alkyl;
R$^{2a}$ represents H;
L represents O or CR$^6$R$^7$, wherein
R$^6$ and R$^7$ are independently H, CH$_3$, or OH;
G" represents a substituent selected from the group consisting of O(C$_1$-C$_3$)alkyl, halogen, and CF$_3$;
n and n' are independently 0 or 1, and provisos 1-3 do not apply;
G and G' moieties are independently selected from the group consisting of:
G1) Cl or F;
G2) O(C$_1$-C$_3$)alkyl;
G3) OH;
G4) (C$_1$-C$_3$)alkyl, which is optionally substituted up to three times by halogen;
G5) OCF$_3$;
G8) NR$^{10}$R$^{11}$, wherein
R$^{10}$ and R$^{11}$ are independently selected from
H,
CH$_3$,
cyclopropyl,
benzyl,
NR$^{12}$R$^{13}$ wherein
R$^{12}$ and R$^{13}$ are independently H or (C$_1$-C$_3$)alkyl, provided that both R$^{10}$ and R$^{11}$ are not NR$^{12}$R$^{13}$ simultaneously,
and
(C$_2$-C$_4$)alkyl which is optionally substituted up to three times by halogen, and up to two times by substituent groups independently selected from hydroxyl, O(C$_1$-C$_3$)alkyl, and NR$^{14}$R$^{15}$, wherein
R$^{14}$ and R$^{15}$ are independently H or (C$_1$-C$_3$)alkyl,
or
R$^{14}$ and R$^{15}$ can join to form a heterocycle of formula

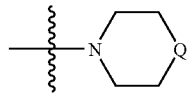

wherein
Q represents CH$_2$, O, or NR$^{16}$, and
R$^{16}$ represents H or (C$_1$-C$_3$)alkyl, G12) $OSO_2NR^{23}R^{24}$ wherein
$R^{23}$ and $R^{24}$ independently represent H, $CH_3$, or $(C_2\text{-}C_4)$ alkyl which may optionally be substituted once by OH or $NR^{25}R^{26}$, wherein
$R^{25}$ and $R^{26}$ independently represent H or $(C_1\text{-}C_3)$ alkyl;

G21) $C(O)NR^{28}R^{29}$, wherein
$R^{28}$ and $R^{29}$ are independently selected from
H
and
$(C_1\text{-}C_3)$alkyl which is optionally substituted up to two times by OH;

G25)

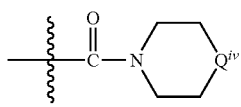

wherein
$Q^{iv}$ is O or $NR^{34}$; and
$R^{34}$ is H or $(C_1\text{-}C_3)$alkyl;

G26) $C(O)NR^{35}(CH_2)_T OR^{36}$ wherein
$R^{35}$ is H or $(C_1\text{-}C_3)$alkyl;
$R^{36}$ is $(C_1\text{-}C_6)$alkyl optionally substituted up to two times by halogen, OH, or $O(C_1\text{-}C_3)$alkyl, and
the subscript "T" is an integer of 2-4; and G31) $N(R^{48})C(O)R^{49}$ wherein
$R^{48}$ represents H or $(C_1\text{-}C_3)$alkyl; and
$R^{49}$ represents
$(CH_2)_{1-3}\text{—}CO_2H$,
$O(C_2\text{-}C_4)$alkyl,
$(CH_2)_{1-4}\text{—}NR^{51}R^{51}$ wherein
$R^{50}$ and $R^{51}$ independently represent H or $(C_1\text{-}C_3)$ alkyl, or
$CH(R^{52})\text{—}NR^{53}R^{54}$ wherein
$R^{52}$ represents $(CH_2)_{1-4}\text{—}NH_2$, $CH_2OH$, $CH(CH_3)$OH, or $(C_1\text{-}C_3)$alkyl; and
$R^{53}$ and $R^{54}$ independently represent H or $(C_1\text{-}C_3)$ alkyl.

In a sixth embodiment, the invention relates to a compound of the above first embodiment, having the structure

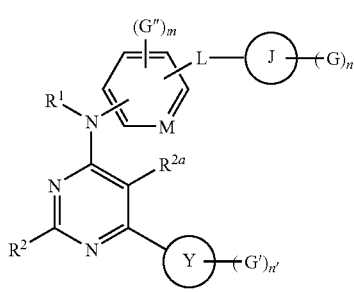

(I)

wherein the definitions of the variables are as given above in the first embodiment, except that in this sixth embodiment
$R^1$ represents H;
M represents CH;

J represents an aromatic or heteroaromatic ring selected from the group consisting of

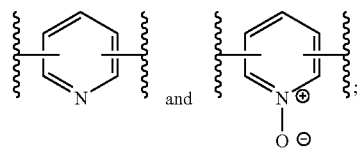

Y represents an aromatic or heteroaromatic ring selected from the group consisting of

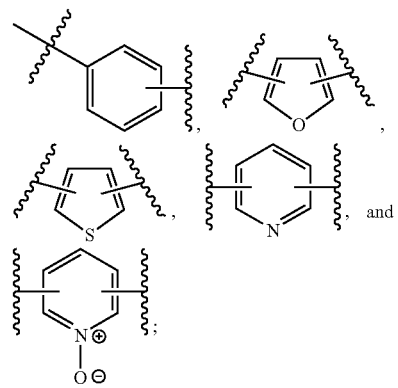

n and n' are independently 0, 1, 2, or 3, subject to the provisos that
1) ring J and ring Y each may be substituted independently up to 3 times by substituents listed below as numbers G1-G2, to a maximum total of 4 substituents on rings J and Y,
2) ring J and ring Y each may be substituted independently up to 2 times by substituents listed below as numbers G3-G5 and G8, to a maximum total of 3 substituents on rings J and Y, and
3) ring J and ring Y each may be substituted independently once by a substituent selected from those listed below as numbers G12, G22, and G31;
and subject to the further proviso
4) when J is pyridyl, n is 1, 2, or 3; and proviso 5 does not apply;

G and G' moieties are independently-selected from the group consisting of:
G1) halogen;
G2) $O(C_1\text{-}C_4)$alkyl which optionally is substituted up to two times by
$O(C_1\text{-}C_2)$alkyl;
G3) OH;
G4) $(C_1\text{-}C_5)$alkyl, which is optionally substituted independently up to two times by groups selected from hydroxyl and cyano, or up to three times by halogen;
G5) $OCF_3$;
G8) $NR^{10}R^{11}$, wherein
$R^{10}$ and $R^{11}$ are independently selected from
H,
$CH_3$,
cyclopropyl,
benzyl,
$NR^{12}R^{13}$ wherein
$R^{12}$ and $R^{13}$ are independently H or $(C_1\text{-}C_3)$alkyl, provided that both $R^{10}$ and $R^{11}$ are not $NR^{12}R^{13}$ simultaneously, and
(C$_2$-C$_4$)alkyl which is optionally substituted up to three times by halogen, and up to two times by substituent groups independently selected from hydroxyl, O(C$_1$-C$_3$)alkyl, and NR$^{14}$R$^{15}$, wherein R$^{14}$ and R$^{15}$ are independently H or (C$_1$-C$_3$)alkyl, or R$^{14}$ and R$^{15}$ can join to form a heterocycle of formula

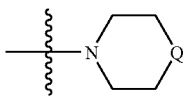

wherein
Q represents CH$_2$, O, or NR$^{16}$, and
R$^{16}$ represents H or (C$_1$-C$_3$)alkyl, or R$^{10}$ and R$^{11}$ may be joined to form a saturated 5-6-membered N-containing ring which is optionally substituted up to two times by
OH,
NR$^{17}$R$^{18}$, wherein
R$^{17}$ and R$^{18}$ are H or (C$_1$-C$_3$)alkyl,
or by
(C$_1$-C$_3$)alkyl which is optionally substituted up to two times by halogen, OH, or O(C$_1$-C$_3$)alkyl;

G12) OSO$_2$NR$^{23}$R$^{24}$ wherein
R$^{23}$ and R$^{24}$ independently represent H, CH$_3$, or (C$_2$-C$_4$) alkyl which may optionally be substituted once by OH or NR$^{25}$R$^{26}$, wherein
R$^{25}$ and R$^{26}$ independently represent H or (C$_1$-C$_3$) alkyl;

G22)

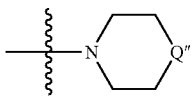

wherein
Q" is O or NR$^{30}$, and
R$^{30}$ is
H,
cyclopropyl, or
(C$_1$-C$_3$)alkyl which is optionally substituted once by halogen, OH, or O(C$_1$-C$_3$)alkyl; and G31) N(R$^{48}$)C(O)R$^{49}$ wherein
R$^{48}$ represents H or (C$_1$-C$_3$)alkyl; and
R$^{49}$ represents
(CH$_2$)$_{1-3}$—CO$_2$H,
O(C$_2$-C$_4$)alkyl,
(CH$_2$)$_{1-4}$—NR$^{50}$R$^{51}$ wherein
R$^{50}$ and R$^{51}$ independently represent H or (C$_1$-C$_3$) alkyl, or
CH(R$^{52}$)—NR$^{53}$R$^{54}$ wherein
R$^{52}$ represents (CH$_2$)$_{1-4}$—NH$_2$, CH$_2$OH, CH(CH$_3$)OH, or (C$_1$-C$_3$)alkyl; and
R$^{53}$ and R$^{54}$ independently represent H or (C$_1$-C$_3$) alkyl.

In a seventh embodiment, the invention relates to a compound of the above sixth embodiment, having the structure

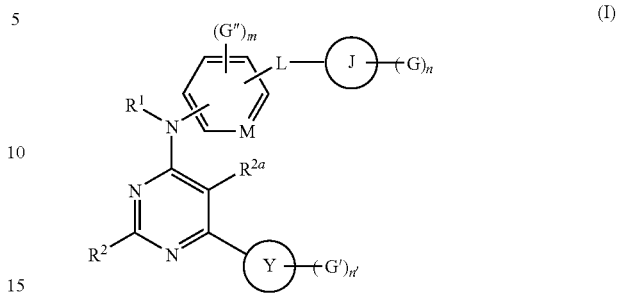

(I)

wherein the definitions of the variables are as given above in the sixth embodiment, except that in this seventh embodiment
R$^1$ represents H;
R$^2$ represents O(C$_1$-C$_3$)alkyl, or NR$^3$R$^4$
wherein R$^3$ and R$^4$ are H or (C$_1$-C$_3$)alkyl;
R$^{2a}$ represents H;
L represents O or CR$^6$R$^7$, wherein
R$^6$ and R$^7$ are independently H, CH$_3$, or OH;
G" represents a substituent selected from the group consisting of O(C$_1$-C$_3$)alkyl, halogen, and CF$_3$;
n and n' are independently 0 or 1, and provisos 1-3 do not apply;
G and G' moieties are independently selected from the group consisting of:
G1) Cl or F;
G2) O(C$_1$-C$_3$)alkyl;
G3) OH;
G4) (C$_1$-C$_3$)alkyl, which is optionally substituted up to three times by halogen;
G5) OCF$_3$;
G8) NR$^{10}$R$^{11}$, wherein
R$^{10}$ and R$^{11}$ are independently selected from
H,
CH$_3$,
cyclopropyl,
benzyl,
NR$^{12}$R$^{13}$ wherein
R$^{12}$ and R$^{13}$ are independently H or (C$_1$-C$_3$)alkyl, provided that both R$^{10}$ and R$^{11}$ are not NR$^{12}$R$^{13}$ simultaneously,
and
(C$_2$-C$_4$)alkyl which is optionally substituted up to three times by halogen, and up to two times by substituent groups independently selected from hydroxyl, O(C$_1$-C$_3$)alkyl, and NR$^{14}$R$^{15}$, wherein R$^{14}$ and R$^{15}$ are independently H or (C$_1$-C$_3$)alkyl,
or
R$^{14}$ and R$^{15}$ can join to form a heterocycle of formula

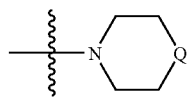

wherein
Q represents CH$_2$, O, or NR$^{16}$, and
R$^{16}$ represents H or (C$_1$-C$_3$)alkyl;

G12) $OSO_2NR^{23}R^{24}$ wherein
   $R^{23}$ and $R^{24}$ independently represent H, $CH_3$, or $(C_2-C_4)$ alkyl which may optionally be substituted once by OH or $NR^{25}R^{26}$ wherein
   $R^{25}$ and $R^{26}$ independently represent H or $(C_1-C_3)$ alkyl;

G22)

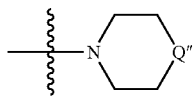

wherein
   Q" is O or $NR^{30}$, and
   $R^{30}$ is H or $(C_1-C_3)$alkyl; and
G331) $N(R^{48})C(O)R^{49}$ wherein
   $R^{48}$ represents H or $(C_1-C_3)$alkyl; and
   $R^{49}$ represents
      $(CH_2)_{1-3}$—$CO_2H$,
      $O(C_2-C_4)$alkyl,
      $(CH_2)_{1-4}$—$NR^{51}R^{51}$ wherein
         $R^{50}$ and $R^{51}$ independently represent H or $(C_1-C_3)$ alkyl, or
      $CH(R^{52})NR^{53}R^{54}$ wherein
         $R^{52}$ represents $(CH_2)_{1-4}$—$NH_2$, $CH_2OH$, $CH(CH_3)OH$, or $(C_1-C_3)$alkyl; and
         $R^{53}$ and $R^{54}$ independently represent H or $(C_1-C_3)$ alkyl.

Pharmaceutically acceptable salts of these compounds as well as commonly used prodrugs of these compounds such as, for example, O-acyl derivatives of invention compounds which contain hydroxy groups, ester derivatives of invention compounds which contain carboxyl groups, and amide derivatives of invention compounds which contain amino groups, are also within the scope of the invention.

It is to be understood that:

1) in compounds of the invention in which an alkyl moiety may bear substituents such as amino, hydroxyl, alkoxy, and halogen groups, a single carbon atom of this alkyl moiety may not simultaneously bear two groups independently selected from amino, hydroxyl, and alkoxy; and where this alkyl moiety bears a halogen, it may not simultaneously also bear an amino, hydroxyl, or alkoxy substituent.

2) in compounds of the invention in which any moiety is defined in terms of a numerical range of atoms and this moiety is further permitted to bear up to a certain number of substituents, if the total number of substituents possible exceeds the number of valences available for moieties at the lower end of the defined numerical range of atoms, then the number of substituents is limited to the number of available valences. For example, if a $(C_1-C_3)$alkyl moiety if defined as optionally bearing up to three halogens and up to two other defined substituents, this means that a $C_1$-alkyl group could bear up to three substituents (the number of available valences), all of which could be halogen, but no more than two of which could be other defined substituent groups.

The compounds of Formula (I) may contain one or more asymmetric centers, depending upon the location and nature of the various substituents desired. Asymmetric carbon atoms may be present in the (R) or (S) configuration. Preferred isomers are those with the absolute configuration which produces the compound of Formula (I) with the more desirable biological activity. In certain instances, asymmetry may also be present due to restricted rotation about a given bond, for example, the central bond adjoining two aromatic rings of the specified compounds.

It is intended that all isomers (including enantiomers and diastereomers), either by nature of asymmetric centers or by restricted rotation as described above, as separated, pure or partially purified isomers or racemic mixtures thereof, be included within the scope of the instant invention. The purification of said isomers and the separation of said isomeric mixtures may be accomplished by standard techniques known in the art.

The terms identified above have the following meaning throughout:

The term "optionally substituted" means that the moiety so modified may have from none to up to at least the highest number of substituents indicated. The substituent may replace any H atom on the moiety so modified as long as the replacement is chemically possible and chemically stable. When there are two or more substituents on any moiety, each substituent is chosen independently of any other substituent and can, accordingly, be the same or different.

The term "halogen" means an atom selected from Cl, Br, F, and I.

The terms "$(C_1-C_2)$alkyl," "$(C_1-C_3)$alkyl" "$(C_1-C_4)$alkyl" "$(C_1-C_5)$alkyl," and "$(C_1-C_6)$alkyl" mean linear or branched saturated carbon groups having from about 1 to about 2, about 3, about 4, about 5 or about 6 C atoms, respectively. Such groups include, but are not limited to, methyl, ethyl, n-propyl, isopropyl, sec-butyl, n-hexyl, and the like.

The term "alkylenyl" means a divalent linear or branched saturated carbon chain, usually having from about 1 to about 3 carbon atoms in this application. Such chains include, but are not limited to methylene (—$CH_2$—), ethylenyl (—$CH_2CH_2$—), and propylenyl (—$CH_2CH_2CH_2$—) and the like.

The term "$(C_3-C_6)$cycloalkyl" means a saturated monocyclic alkyl group of from about 3 to about 6 carbon atoms and includes such groups as cyclopropyl, cyclobutyl, cyclopentyl, cyclohexyl, and the like.

Pharmaceutical Compositions

The invention also relates to pharmaceutical compositions comprising at least one of the compounds of the invention, or a salt or prodrug thereof, in a pharmaceutically acceptable carrier.

Method of Treating Hyperproliferative Disorders

The present invention also relates to a method of using the compounds described above, including salts, prodrugs, and corresponding pharmaceutical compositions thereof, to treat mammalian hyperproliferative disorders. This method comprises administering to a patient an amount of a compound of this invention, or a pharmaceutically acceptable salt or prodrug thereof, which is effective to treat the patient's hyperproliferative disorder. A patient, for the purpose of this invention, is a mammal, including a human, in need of treatment for a particular hyperproliferative disorder. A pharmaceutically effective amount of a compound or composition is that amount which produces a desired result or exerts an influence on the particular hyperproliferative disorder being treated.

Hyperproliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. These disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (Giver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been well established in the art. For example, the therapeutic utility of taxol (Silvestrini; et al. *Stem Cells* 1993, 11(6), 528-35), taxotere (Bissery et al. *Ant Cancer Drugs* 1995, 6(3), 339), and topoisomerase inhibitors (Edelman et al. *Cancer Chemother. Pharmacol.* 1996, 37(5), 385-93) was demonstrated with the use of in vitro tumor proliferation assays.

In this application, where the plural form is used for compounds, salts, and the like, this is taken to mean also a single compound, salt, or the like.

Salts are especially the pharmaceutically acceptable salts of compounds of formula I such as, for example, acid addition salts, preferably with organic or inorganic acids, from compounds of formula I with a basic nitrogen atom. Suitable inorganic acids are, for example, halogen acids such as hydrochloric acid, sulfuric acid, or phosphoric acid. Suitable organic acids are, for example, carboxylic, phosphonic, sulfonic, or sulfamic acids, for example acetic acid, propionic acid, octanoic acid, decanoic acid, dodecanoic acid, glycolic acid, lactic acid, -hydroxybutyric acid, gluconic acid, glucosemonocarboxylic acid, fumaric acid, succinic acid, adipic acid, pimelic acid, suberic acid, azeiaic acid, malic acid, tartaric acid, citric acid, glucaric acid, galactaric acid, amino acids, such as glutamic acid, aspartic acid, N-methylglycine, acetytaminoacetic acid, N-acetylasparagine or N-acetylcysteine, pyruvic acid, acetoacetic acid, phosphoserine, 2- or 3-glycerophosphoric acid.

The compounds of the invention may be administered orally, dermally, parenterally, by injection, by inhalation or spray, or sublingually, rectally or vaginally in dosage unit formulations. The term 'administered by injection' includes intravenous, intraarticular, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired, other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations.

Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

Compounds of the invention may also be administered transdermally using methods known to those skilled in the art (see, for example: Chien; "Transdermal Controlled Systemic Medications"; Marcel Dekker, Inc.; 1987. Lipp et al. WO 94/04157 3 Mar. 94). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures one or more materials selected from lower alcohols, lower ketones, lower carboxylic acid esters, polar ethers, lower hydrocarbons, halogenated hydrocarbons.

Suitable penetration enhancing materials for transdermal delivery systems are known to those skilled in the art, and include, for example, monohydroxy or polyhydroxy alcohols such as ethanol, propylene glycol or benzyl alcohol, saturated or unsaturated $C_8$-$C_{18}$ fatty alcohols such as lauryl alcohol or cetyl alcohol, saturated or unsaturated $C_8$-$C_{18}$ fatty acids such as stearic acid, saturated or unsaturated fatty esters with up to 24 carbons such as methyl, ethyl, propyl, isopropyl, n-butyl, sec-butyl isobutyl tert-butyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures one or more materials selected from monohydroxy or polyhydroxy alcohols, saturated or unsaturated $C_8$-$C_{18}$ fatty alcohols, saturated or unsaturated $C_8$-$C_{18}$ fatty acids, saturated or unsaturated fatty esters with up to 24 carbons, diesters of saturated or unsaturated dicarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrene-butadiene copolymers, and natural and synthetic rubbers. Cellulose ethers, derivatized polyethylenes, and silicates may also be used as matrix components. Additional additives, such as viscous resins or oils may be added to increase the viscosity of the matrix.

For all regimens of use disclosed herein for compounds of Formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.1 to 200 mg administered between one to four times daily. The transdermal concentration will preferably be that required to maintain a daily dose of from 0.01 to 200 mg/Kg. The daily inhalation dosage regimen will preferably be from 0.01 to 10 mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, but not limited to the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional treatment tests.

General Preparative Methods

The compounds of the invention have the general chemical structure shown below and may be prepared by the use of known chemical reactions and procedures. The particular process to be utilized in the preparation of the compounds of this invention depends upon the specific compound desired. Such factors as the selection of the specific J and Y moieties, as well as the specific substituents possible at various locations on the molecule, all play a role in the path to be followed in the preparation of the specific compounds of this invention. Those factors are readily recognized by one skilled in the art.

Nevertheless, the following general preparative methods are presented to aid the reader in synthesizing the compounds of the invention, with more detailed particular examples being presented below in the experimental section describing the working examples.

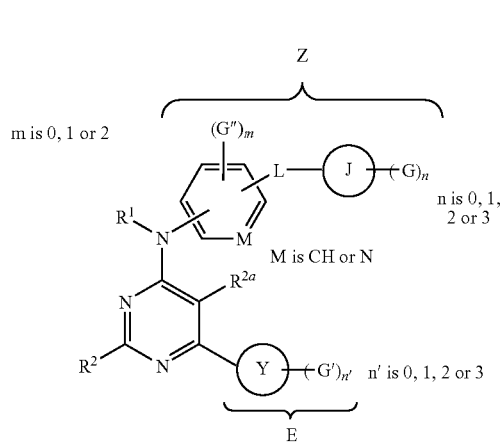

(I)

All variable groups of these methods are as described in the generic description if they are not specifically defined below. When a variable group or substituent with a given symbol (i.e. G, G', M) is used more than once in a given structure, it is to be understood that each of these groups or substituents may be independently varied within the range of definitions for that symbol.

Within these general methods the variable Z is equivalent to the moiety

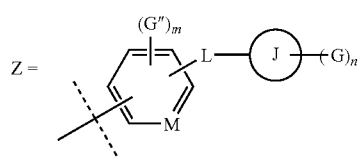

in which each variable group or substituent is allowed to vary independently within the limits defined for that symbol.

Within these general methods the variable E is equivalent to the moiety

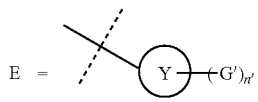

in which each variable group or substituent is allowed to vary independently within the limits defined for that symbol.

It is recognized that compounds of the invention with each claimed optional functional group cannot be prepared with each of the below-listed methods. Within the scope of each method optional substituents are used which are stable to the reaction conditions, or the functional groups which may participate in the reactions are present in protected form where necessary, and the removal of such protective groups is completed at appropriate stages by methods well known to those skilled in the art.

Additional compounds of formula (I) may be prepared from other formula (I) compounds by elaboration of functional groups present. Such elaboration includes, but is not limited to, hydrolysis, reduction, oxidation, alkylation, acylation, esterification, amidation and dehydration reactions. Such transformations may in some instances require the use of protecting groups by the methods disclosed in T. W. Greene and P. G. M. Wuts, *Protective Groups in Organic Synthesis*; Wiley: New York, (1999), and incorporated herein by reference. Such methods would be initiated after synthesis of the desired compound or at another place in the synthetic route that would be readily apparent to one skilled in the art.

General Method A—Invention compounds of formula 5 in which Z and E are as defined above, may be conveniently prepared according to a reaction sequence as shown in General Method "A". Thus, amidine or guanidine 1 and β-ketoester 2 are either obtained from commercial sources or made by one skilled in the art according to published procedures (amidine 1: Granik et al *Russ Chem. Rev.* 1983, 52, 377-393; β-ketoester 2: Tabuchi, H. et al. *Synlett* 1993, (9), 651-2). Amidine or guanidine 1 is treated with β-ketoester 2 in a refluxing mixed solvent such as alcohol and toluene or benzene to furnish pyrimidinone intermediate 3. The alcohol is typically a lower molecular weight alcohol such as ethanol, isopropanol, n-propanol, n-butanol, iso-butanol, or t-butanol. Compound 3 is treated with a chlorinating agent such as phosphorous oxychloride, thionyl chloride or phosphorous pentachloride to yield chloropyrimidine intermediate 4. Intermediate 4 is reacted with a nucleophile of formula NHR$^1$Z in a refluxing solvent such as alcohol, water, DMF, DMA, acetonitrile, acetone, dioxane or DMSO to furnish the invention compound of formula 5 [formula (I), where R$^{2a}$ is H]. Such reactions can also be done in a melt free of solvent or in a solvent catalyzed by acids such as HCl, H$_2$SO$_4$ or bases such as but not limited to triethylamine, Cs$_2$CO$_3$, K$_2$CO$_3$, Na$_2$CO$_3$, K$_3$PO$_4$, Na$_3$PO$_4$, NaOH, KOH, NaH, NaNH$_2$, KNH$_2$, or a sodium or potassium alkoxide or 1,8-diazobicyclo[5.4.0]undec-7-ene (DBU). Invention compounds of formula 5a [(I) where R$^{2a}$ is Cl, Br or I] can be prepared from compounds of formula 5 by halogenation with Cl$_2$, Br$_2$, or I$_2$. Invention compounds of formula 5a [(I) where R$^{2a}$ is F] can be prepared from the formula (I) compounds where R$^{2a}$ is Cl, Br or I by a nucleophilic substitution reaction using a fluoride source, e.g., KF.

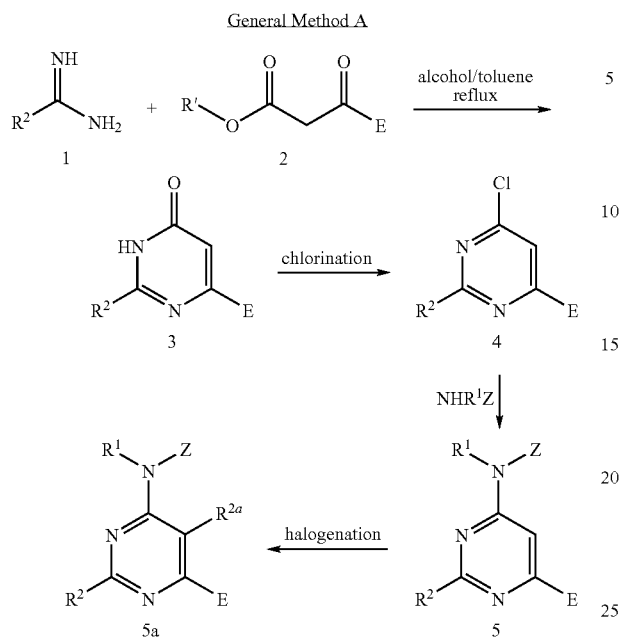

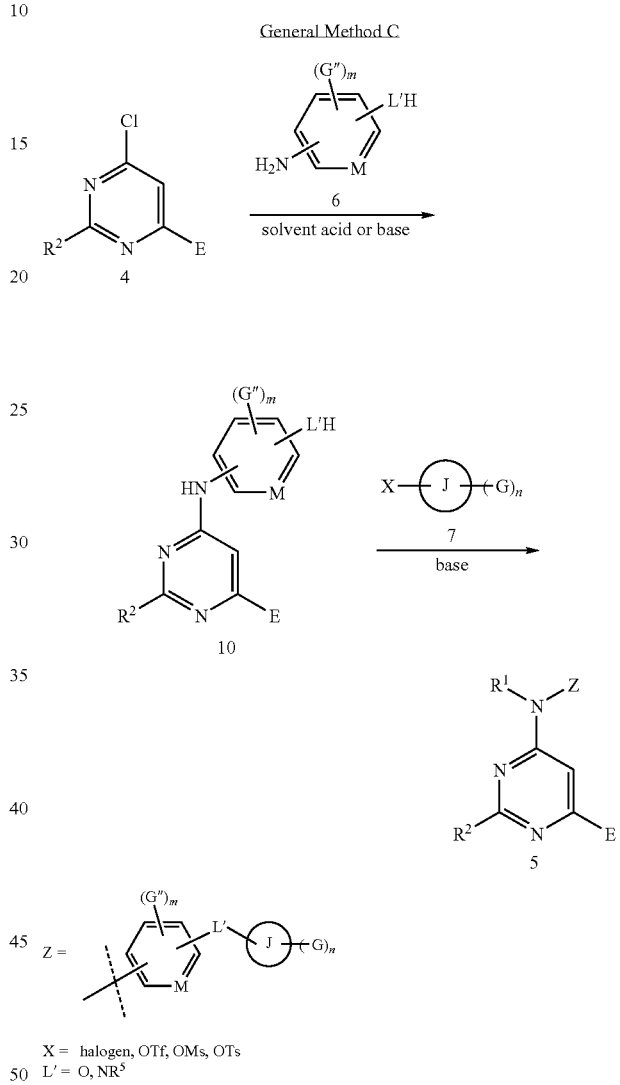

sequence outlined in General Method "C" below. Thus, intermediate 4 is reacted with a nucleophile of formula 6 using aforementioned conditions (General Method A) to furnish intermediate 10. Compound 10 is treated with an aromatic intermediate of formula 7 in an aprotic solvent and base (such as bases in General Method A) to furnish invention compounds of formula 5.

General Method B—Compounds of formula 5 in which $R^1$, $R^2$, Z and E are as previously defined can also be prepared via an alternative reaction sequence outlined in General Method "B" below. Thus, dichloropyrimidine 8, which is either commercially available or can be made by one skilled in the art according to published procedures (Bagli, J. et al, *J. Med. Chem.* 1988, 31(4), 814-23), is reacted with a nucleophile of formula NHR$^1$Z in a solvent such as alcohol, water, DMF or DMSO to furnish intermediate 9. Such condensations can also be done in a solvent catalyzed by acids such as HCl, $H_2SO_4$ or an aforementioned base. Compound 9 is reacted with a boronic acid or ester of formula E-B(OR')$_2$ where R' is H, alkyl or two R' may form a ring, under standard Suzuki coupling conditions (such as Pd(PPh$_3$)$_4$ or PdCl$_2$(dppf).CH$_2$Cl$_2$/base/solvent) to provide invention compound 5.

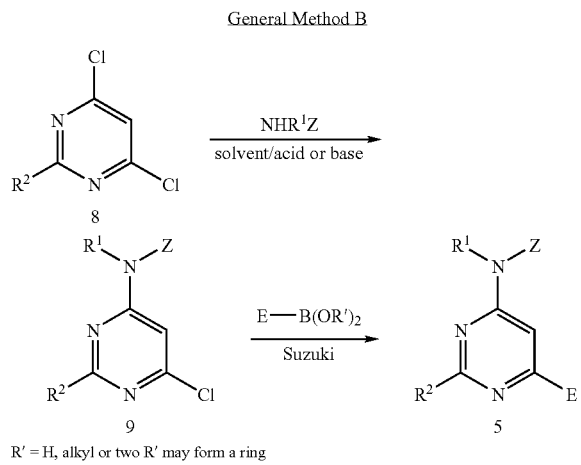

General Method C—Invention compounds of formula 5 in which $R^1$, $R^2$ and E are as defined above, and Z, L' are defined below can also be prepared via an alternative reaction X = halogen, OTf, OMs, OTs
L' = O, NR$^5$ General Method D—Invention compounds of formula 13 in which $R^1$, $R^2$ and Z are as defined above, and $R^D$ is G2, G12, G23, G24, G30, or benzyl can also be prepared via a reaction sequence as shown in General Method "D" below. Thus, demethylation of intermediate 11 (General method A or B or C) employing standard conditions (such as BBr$_3$, Me$_3$SiI, AlCl$_3$/EtSH etc.) provides intermediate 12. Subsequently, compound 12 can then undergo alkylation, acylation, or sulfamylation to introduce the $R^D$ substituent and provide the compound of formula 13. Standard reaction conditions for these transformations can be used, i.e., a reagent of formula $R^D$-halo in the presence a base. In addition, O-alkylation can be accomplished using a Mitsunobu reaction (i.e., DEAD/PPh$_3$) to provide invention compound 13 where $R^D$ is alkyl.

General Method D

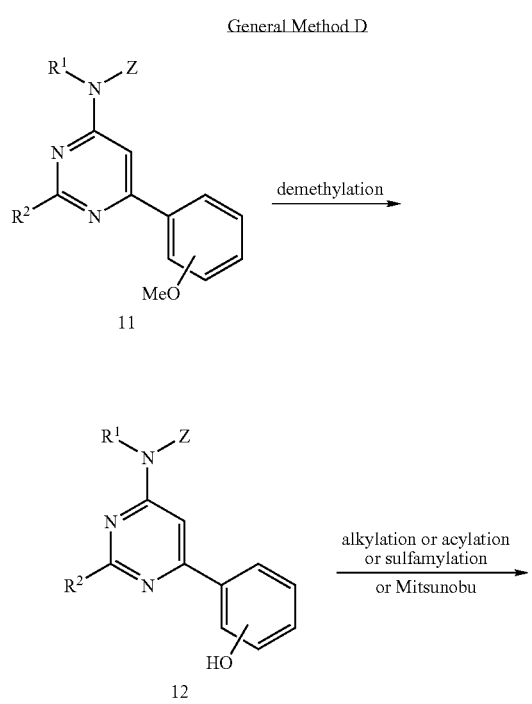

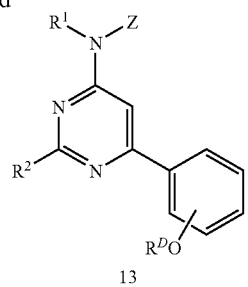

General Method E—Invention compounds of formula 16 and 17 in which $R^1$, $R^2$, G, G", m, n, and E are as defined above, and M' is CH or N, can be prepared via a reaction sequence as shown in General Method "E" below. Thus, the cyano group of intermediate 14 can be hydrolyzed and the resulting carboxylic acid can be coupled with an amine such as $NHR^{28}R^{29}$, a piperdine, or morpholine, under standard conditions to provide compound 16 where $G^{E-1}$ is G21, G25 or G26. Invention compound 17 can be prepared by reduction of the amide 16 with $LiAlH_4$ or $BH_3$, followed by optional sulfonylation or acylation. Alternatively, compound 17 can be prepared by alkylation or reductive amination of amine 15, which is prepared by reduction of 14 by a reducing agent such as $H_2$/Pd on C in acetic acid.

General Method E

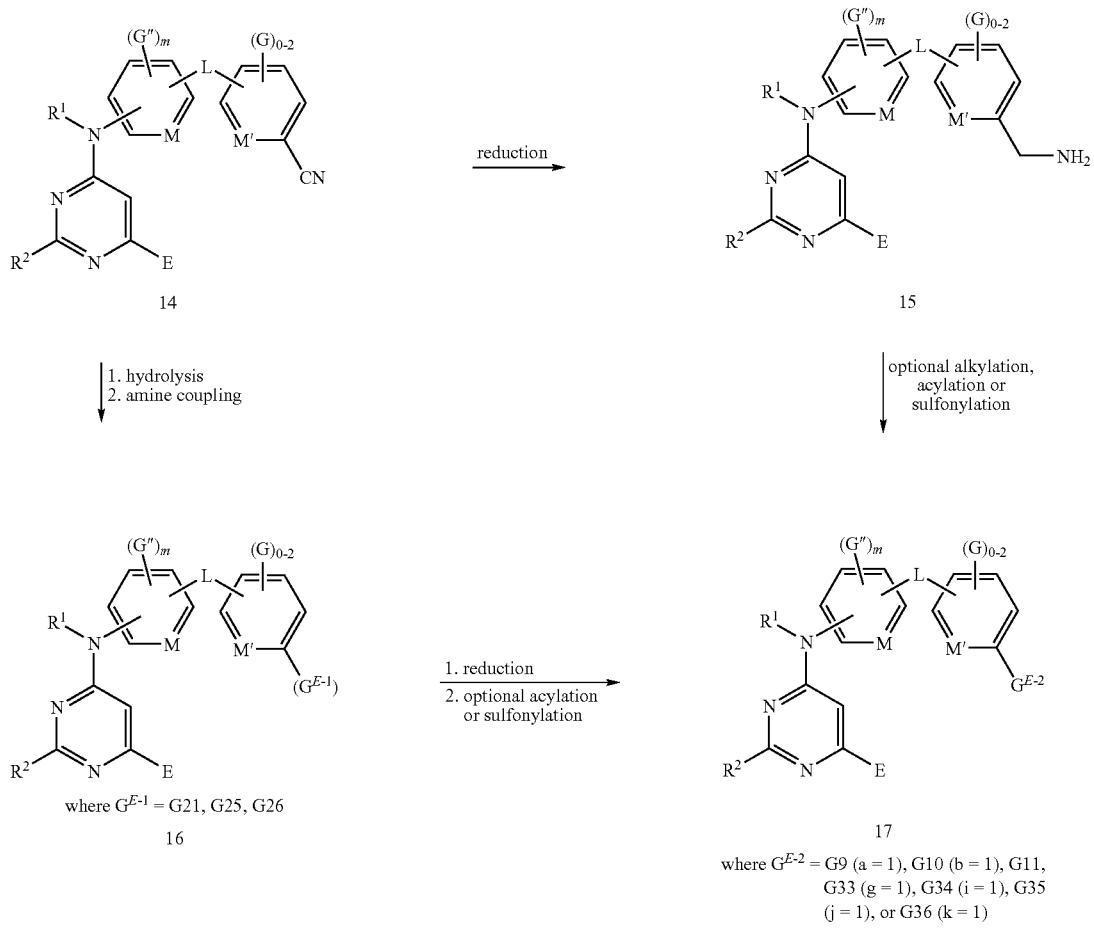

General Method F—Invention compounds of formula 17b can be prepared by displacement of the halo substituent on the compound of formula 17a with a sulfur, nitrogen or oxygen nucleophile, represented by $G^{F-1}$-H, e.g., a thiol, ammonia, a mono or dialkylamine, water or an optionally substituted alcohol, in the optional presence of a base such as triethylamine, $Cs_2CO_3$, $K_2CO_3$, $Na_2CO_3$, $K_3PO_4$, $Na_3PO_4$, NaOH, KOH, NaH, $NaNH_2$, $KNH_2$, or a sodium or potassium alkoxide or 1,8-diazobicyclo[5.4.0]undec-7-ene (DBU). Thus are prepared compounds of formula (I) in which $G^{F-1}$ is selected from G2, G3, G8, G16, G17, G22, G23, and G24. In addition, compounds of formula 17c may be prepared by acylation or sulfonylation of the compounds of formula 17b where at least one H may be replaced, using appropriate reagents such as acyl halides or alkylsulfonyl halides, generally in the presence of a base. Thus are prepared compounds of formula (I) in which $G^{F-2}$ is selected from G12, G29, G30 and G31.

General Method F

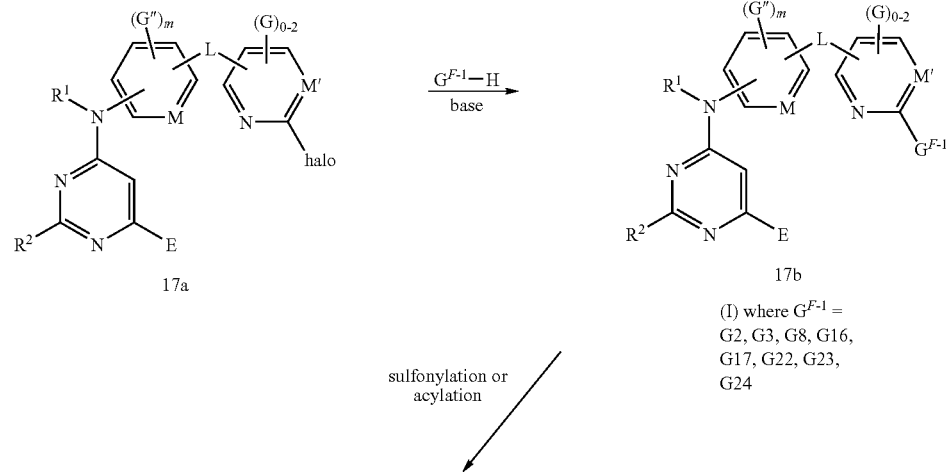

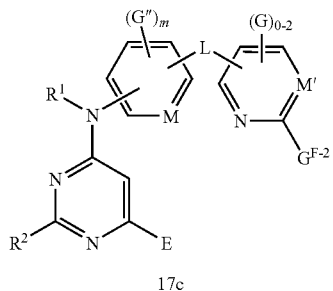

General Methods (a-e) for Preparation of Intermediate NHR¹Z

Method a—The compounds of formula 18 in which M, G, G", m and n are as defined above, M' is independently CH or N, and L' is O or NR⁵ can be conveniently prepared as shown in Method a below. Generally, the intermediate 18 may be prepared by an aromatic substitution reaction of intermediate 7 and intermediate 6. Thus, aniline or aminopyridine 6 is treated with an aromatic intermediate of formula 7 in an aprotic solvent such as DMF, DMA, acetonitrile, acetone, dioxane or DMSO and base to furnish the intermediate of formula 18 (when X=OTf, OMs, OTs see ref. Sammes, P. et al. *J. Chem. Soc. Perkin Trans* 1, 1988, (12), 3229-31). Compounds of formula 18a can be obtained through reductive amination of 18 with an aldehyde under reductive amination conditions such as NaBH₄, NaBH₃CN, or NaBH(OAc)₃.

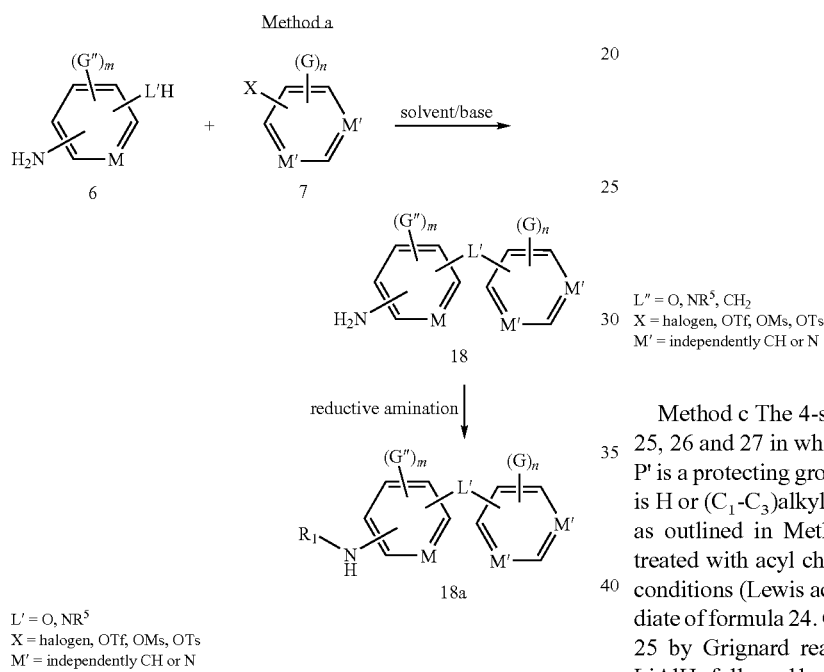

L' = O, NR⁵
X = halogen, OTf, OMs, OTs
M' = independently CH or N

Method b—Alternatively, compounds of formula 18b, in which M, G, G", m and n are as defined above, M' is independently CH or N, and L' is O, NR⁵ or CH₂, can be conveniently prepared as shown in Method b below. Thus, the aromatic intermediate of formula 20 is deprotonated with an aforementioned base or LDA, n-BuLi, t-BuLi in an aprotic solvent, followed by reaction with intermediate 19 to furnish the intermediate of formula 21. The nitro group of compound 21 can be reduced by one skilled in the art according to published procedures such as catalytic hydrogenation, Fe/HOAc and SnCl₂ to provide intermediate 18b.

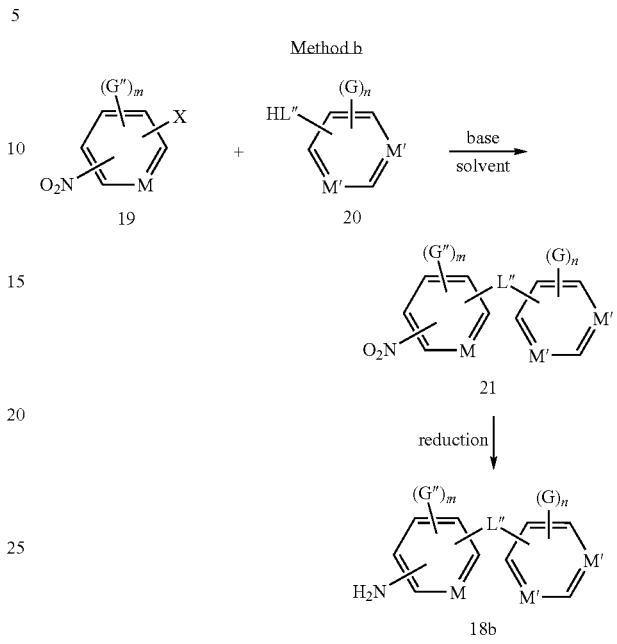

L" = O, NR⁵, CH₂
X = halogen, OTf, OMs, OTs
M' = independently CH or N

Method c The 4-substituted aniline compound of formula 25, 26 and 27 in which G, G", m and n are as defined above, P' is a protecting group, M' is independently CH or N, and R⁶ is H or (C₁-C₃)alkyl can be prepared via a reaction sequence as outlined in Method c below. Thus, intermediate 22 is treated with acyl chloride 23 under Friedel-Crafts acylation conditions (Lewis acid such as AlCl₃) to furnish the intermediate of formula 24. Compound 24 can be converted to aniline 25 by Grignard reaction with R⁶MgBr or reduction with LiAlH₄ followed by deprotection. Aniline 26 can be obtained by reduction of the carbonyl group of 24 by methods such as but not limited to N₂H₄/OH⁻, Pd/C/H₂, Et₃SiH/Lewis acid, or NaBH₄/Lewis acid (see ref Ono, A. et al, *Synthesis,* 1987, (8), 736-8) or alternatively by formation of a dithiane and subsequent desulfuration with Raney Nickel. In some instances, deprotection of aniline may be necessary to obtain 26. By deprotection of the amino group of compound 24, the aniline intermediate 27 can also be obtained.

Method c

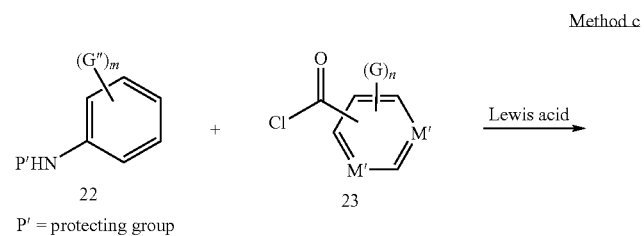

P' = protecting group

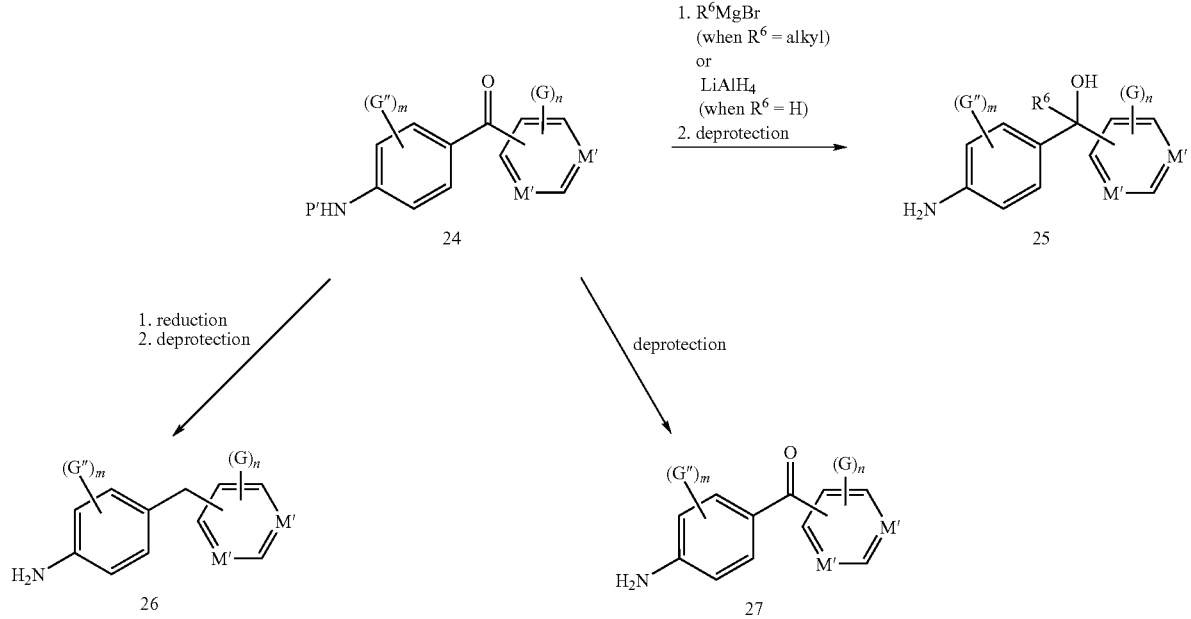

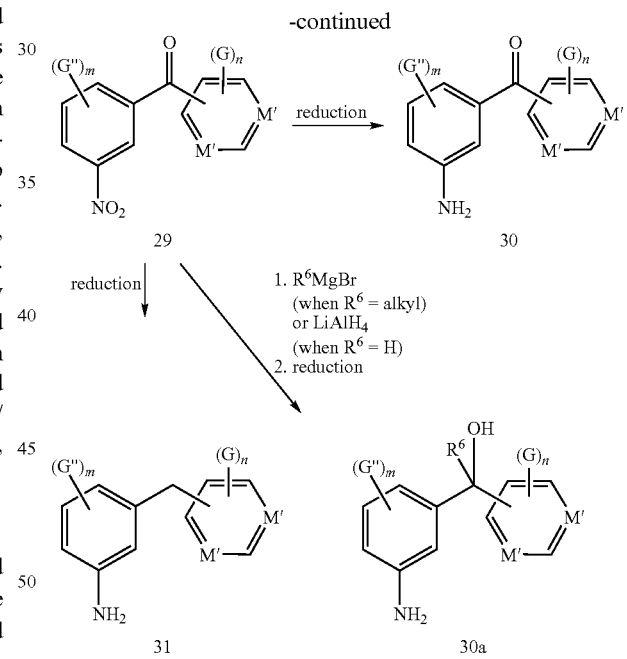

M' = independently CH or N

Method d The 3-substituted aniline compounds 30, 30a and 31 in which G, G", m and n are as defined above, M' is independently CH or N, and $R^6$ is H or $(C_1-C_3)$alkyl can be prepared conveniently via a reaction sequence as shown in Method d below. Thus, nitration of intermediate 28 employing standard nitration conditions such as but not limited to $HNO_3/H_2SO_4$, or $NaNO_3/HCl$ furnishes intermediate 29. Reduction of 29 with a reducing agent such as $SnCl_2$, Fe/HOAc, or catalytic hydrogenation provides aniline 30. Additionally, compound 29 can be converted to aniline 30a by treatment with $R^6MgBr$ or reduction with $LiAlH_4$ followed by the above-mentioned reduction conditions. Aniline 31 can be obtained by reduction of the carbonyl group by a method such as but not limited to $N_2H_4NaOH$, Pd—$C/H_2$, $Et_3SiH/$ Lewis acid, or NaBH/Lewis acid (see ref. Ono, A. et al, *Synthesis*, 1987, (8), 736-8) or alternatively by formation of dithiane and subsequent desulfuration with Raney Nickel. In some instances, reduction of the nitro group by an aforementioned method may be necessary to obtain aniline 31.

Method d

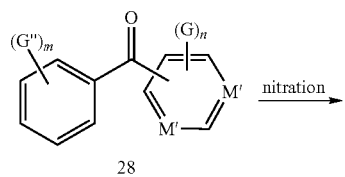

Method e The compounds of formula 36 and 37 in which M, G, G", m, n, $R^{10}$ and $R^{11}$ are as defined above and $R^e$ is G2, G16, G23, and G24, can be prepared conveniently via a reaction sequence as shown in Method e below. Thus, intermediate pyridine 32 is oxidized by a reagent such as m-CPBA, $H_2O_2$, $CH_3C(O)OOH$, or $CF_3C(O)OOH$ to the N-oxide, followed by chlorination with a chlorinating agent such as phosphorous oxychloride, thionyl chloride or phosphorous pentachloride to yield chloropyridine 33. Compound 33 can be converted to aniline 36 by treatment with alcohol in the presence of base such as NaH, followed by reduction of the nitro group with a reducing agent such as $SnCl_2$, $Fe/H^+$, or catalytic hydrogenation. Treatment of compound 33 with amine $HNR^{10}R^{11}$ followed by reduction of the nitro group of resulting compound 34 with the above mentioned reagents provides compound 37.

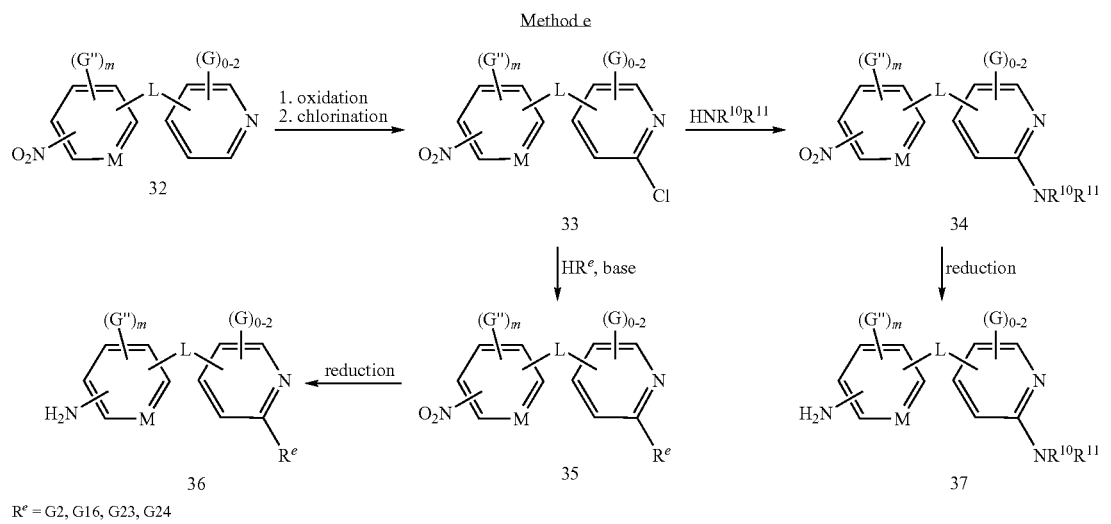

Method e $R^e$ = G2, G16, G23, G24

By using these above described methods, the compounds of the invention may be prepared. The following specific examples are presented to further illustrate the invention described herein, but they should not be construed as limiting the scope of the invention in any way.

Abbreviations and Acronyms

A comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meaning:

| | |
|---|---|
| 2× | two times |
| 3× | three times |
| $AlMe_3$ | trimethylaluminum |
| Boc | t-butoxycarbonyl |
| n-BuLi | butyllithium |
| t-BuOK | potassium t-butoxide |
| calcd | calculated |
| Celite ® | diatomaceous earth filtering agent, registered trademark of Celite Corp. |
| $CD_3OD$ | methanol-$d_4$ |
| $CHCl_3$-d | chloroform-d |
| d | doublet |
| DBU | 1,8-diazobicyclo[5.4.0]undec-7-ene |
| DCC | dicyclohexylcarbodiimide |
| DEAD | diethylazodicarboxylate |
| DIBAH | diisobutylaluminum hydride |
| DIEA | diisopropylethylamine |
| DMA | dimethylacetamide |
| DMAP | 4-dimethylaminopyridine |
| DME | dimethoxyethane |
| DMF | N,N-dimethylformamide |
| DMSO | dimethylsulfoxide |
| DMSO-$d_6$ | dimethylsulfoxide-$d_6$ |
| EDCI | 1-(3-dimethylaminopropyl)-3-ethylcarbodiimide hydrochloride |
| EtSH | ethanethiol |
| EtOAc | ethyl acetate |
| EtOH | ethanol |
| $Et_3SiH$ | triethylsilane |
| h | hour(s) |
| HATU | O-(7-azabenzotriazol-1-yl)-N,N,N',N'-tetramethyluronium hexafluorophosphate |
| Hex | hexanes |
| $^1H.NMR$ | proton nuclear magnetic resonance |
| HOAc | acetic acid |
| HPLC | high performance liquid chromatography |
| LC-MS | liquid chromatography/mass spectroscopy |
| LDA | lithium diisopropylamide |
| LiHMDS | lithium hexamethyldisilazide |
| m | multiplet |
| m-CPBA | 3-chloroperoxybenzoic acid |
| MeOH | methanol |
| min | minute(s) |
| $Me_3SiI$ | trimethylsilyl iodide |
| MS ES | mass spectroscopy with electrospray |
| $NaBH(OAc)_3$ | sodium triacetoxyborohydride |
| OMs | O-methanesulfonyl (mesylate) |
| OTs | O-p-toluenesulfononyl (tosyl) |
| OTf | O-trifluoroacetyl (triflyl) |

-continued

| | |
|---|---|
| Pd/C | palladium on carbon |
| Pd$_2$(dba)$_3$ | tris(dibenzylideneacetone)dipalladium(0) |
| Pd(PPh$_3$)$_4$ | tetrakis(triphenylphosphine)palladium(0) |
| PdCl$_2$(dppf)•CH$_2$Cl$_2$ | [1,1'-bis(diphenylphosphino)ferrocene]dichloropalladium(II) complex with dichloromethane |
| RT | retention time |
| rt | room temperature |
| R$_f$ | TLC Retention factor |
| s | singlet |
| t | triplet |
| TFA | trifluoroacetic acid |
| THF | tetrahydrofuran |
| TLC | thin layer chromatography |

General Analytical Procedures

The structure of representative compounds of this invention were confirmed using the following procedures.

Electron impact mass spectra (EI-MS) were obtained with a Hewlett Packard 5989A mass spectrometer equipped with a Hewlett Packard 5890 Gas Chromatograph with a J & W DB-5 column (0.25 uM coating; 30 m×0.25 mm). The ion source was maintained at 250° C. and spectra were scanned from 50-800 amu at 2 sec per scan.

High pressure liquid chromatography-electrospray mass spectra (LC-MS) were obtained using either a:

(A) Hewlett-packard 1100 HPLC equipped with a quaternary pump, a variable wavelength detector set at 254 nm, a YMC pro C-18 column (2×23 mm, 120A), and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA and B: 2% water in acetonitrile with 0.018% TFA. Gradient elution from 10% B to 95% over 3.5 min at a flowrate of 1.0 mL/min is used with an initial hold of 0.5 min and a final hold at 95% B of 0.5 min. Total run time is 6.5 min.

or (B) Gilson HPLC system equipped with two Gilson 306 pumps, a Gilson 215 Autosampler, a Gilson diode array detector, a YMC Pro C-18 column (2×23 mm, 120 A), and a Micromass LCZ single quadrupole mass spectrometer with z-spray electrospray ionization. Spectra were scanned from 120-800 amu over 1.5 seconds. ELSD (Evaporative Light Scattering Detector) data is also acquired as an analog channel. The eluents were either A: 2% acetonitrile in water with 0.02% TFA or B: 2% water in acetonitrile with 0.018% TFA. Gradient elution from 10% B to 90% over 3.5 min at a flowrate of 1.5 mL/min is used with an initial hold of 0.5 min and a final hold at 90% B of 0.5 min. Total run time is 4.8 min. An extra switching valve is used for column switching and regeneration.

Routine one-dimensional NMR spectroscopy is performed on 400 MHz Varian Mercury-plus spectrometers. The samples were dissolved in deuterated solvents obtained from Cambridge Isotope Labs, and transferred to 5 mm ID Wilmad NMR tubes. The spectra were acquired at 293 K. The chemical shifts were recorded on the ppm scale and were referenced to the appropriate solvent signals, such as 2.49 ppm for DMSO-d$_6$, 1.93 ppm for CD$_3$CN-d$_3$, 3.30 ppm for CD$_3$OD 5.32 ppm for CD$_2$Cl$_2$-d$_2$ and 7.26 ppm for CHCl$_3$-d for $^1$H spectra.

General HPLC Purification Method

Preparative reversed-phase HPLC chromatography was accomplished using a Gilson 215 system, typically using a YMC Pro-C18 AS-342 (150×20 mm I.D.) column. Typically, the mobile phase used was a mixture of (A) H$_2$O containing 0.1% TFA, and (B) acetonitrile. A typical gradient was:

| Time [min] | A: % | B: % | Flow [mL/min] |
|---|---|---|---|
| 0.50 | 90.0 | 10.0 | 1.0 |
| 11.00 | 0.0 | 100.0 | 1.0 |
| 14.00 | 0.0 | 100.0 | 1.0 |
| 15.02 | 100.0 | 0.0 | 1.0 |

EXPERIMENTAL EXAMPLES

Preparation of Chloropyrimidine Amine Intermediates

Intermediate 1A: Preparation of 4-chloro-6-phenylpyrimidin-2-amine

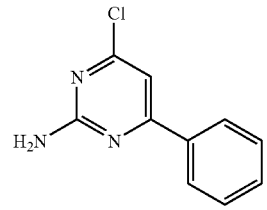

A suspension of guanidine carbonate (3.60 g, 20 mmol) in ethanol (120 mL) and toluene (20 mL) was refluxed under nitrogen for 1 h, during which time about 50 mL of solvent was removed by distillation. After the mixture was cooled to 45° C., ethyl 3-oxo-3-phenylpropanoate (7.68 g, 40 mmol) was added and the solution was heated at reflux overnight. The desired product precipitated as a white solid during the reaction. Water (50 mL) was added to the reaction and the mixture was refluxed for an additional 30 min. After cooling to rt, the mixture was neutralized with 1N HCl and placed in the refrigerator for 6 h. The solid was filtered, washed with water followed by ether and dried at 60° C. under vacuum to give the product as white solid (6.45 g, 86%). MS ES: 188 (M+H)$^+$, calcd 188; RT=0.91 min; TLC (CH$_2$Cl$_2$/2M NH$_3$ in MeOH 95/5) R$_f$=0.10.

A mixture of the above product (6.0 g, 32 mmol) and POCl$_3$ (100 mL) was heated at reflux for 1 h. The majority of the POCl$_3$ was removed in vacuo and the residue was diluted with EtOAc and poured over an ice/saturated NaHCO$_3$ solution. The aqueous layer was extracted with EtOAc and the combined organic layers were washed with brine, dried (Na$_2$SO$_4$), and concentrated. The crude organic concentrate was re-crystallized from EtOAc/ether to give the product 1A as an off-white powder (2.8 g, 43%). MS ES: 206 (M+H)$^+$, calcd 206; RT=2.49 min; TLC (CH$_2$Cl$_2$/2M NH$_3$ in MeOH 95/5) R$_f$=0.72. (Reference 1: H. L. Skulnick, S. D. Weed, E. E.

Edison, H. E. Renis, W. Wierenga, and D. A. Stringfellow, *J. Med. Chem.* 1985, 28, 1854-1869).

Intermediate 1B: Preparation of 4-chloro-6-(2-furyl)pyrimidin-2-amine

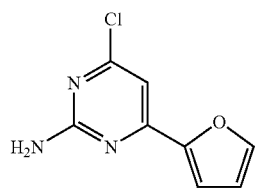

The (2-furyl) pyrimidin-2-amine intermediate 1B was prepared by an analogous method to that described for 1A, starting from guanidine carbonate and ethyl 3-(2-furyl)-3-oxopropanoate. MS ES: 196 (M+H)$^+$, calcd 196, RT=2.13 min.

Intermediate 1C: Preparation of 4-chloro-6-(3-furyl)pyrimidin-2-amine

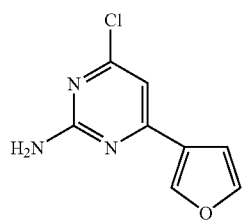

The (3-furyl) pyrimidin-2-amine intermediate 1C was prepared by an analogous method to that described for 1A, starting from guanidine carbonate and ethyl 3-(3-furyl)-3-oxopropanoate. MS ES: 196 (M+H)$^+$, calcd 196, RT=2.04 min.

Intermediate 1D: Preparation of 4-chloro-6-(2-thienyl)pyrimidin-2-amine

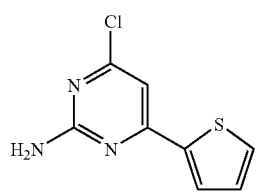

Step 1: Preparation of ethyl 3-oxo-3-(2-thienyl)propanoate

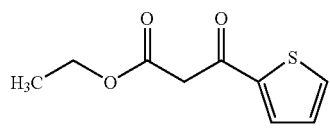

A solution of 2,2-ethyl-1,3-dioxane-4,6-dione (12 g, 83.26 mmol) and thiophene-2-carboxylic acid (8.97 g, 70.0 mmol) and DMAP (17.10 g, 140 mmol) in methylene chloride (100 mL was cooled in an ice bath and treated with a solution of DCC (15.88 g, 76.96 mmol) in methylen chloride (50 mL). The reaction was stirred at rt for 2 h. The resulting precipitate was filtered and the filtrate was concentrated and redissolved in EtOH (400 mL). To this solution was added p-toluenesulfonic (32 g) and the reaction mixture (32 g) and the reaction mixture was refluxed for 1 h. The solvent was removed in vacuo to afford the crude organic concentrate which was dissolved in ethyl acetate (1000 mL) and washed with water (300 mL). The organic layer was washed with saturated aqueous sodium bicarbonate (200 mL), 1N hydrochloric acid (200 mL), saturated aqueous sodium chloride, dried (Na$_2$SO$_4$), and concentrated. The residue was purified using silica gel column chromatography (0-7% ethyl acetate in hexane) to furnish the desired product as a colorless oil (3.67 g, 27%). MS ES 199 (M+H)$^+$, calcd 199; RT=2.12 min; TLC (25% ethyl acetate in hexane) R$_f$=0.50.

Step 2: Preparation of Title Compound (2-thienyl)pyrimidin-2-amine 1D (2-Thienyl) pyrimidin-2-amine 1D was prepared by an analogous method to that described for 1A, starting form guanidine carbonate and ethyl 3-oxo-3-(2-thienyl) propanoate. MS ES: 212 (M+H), calcd 212, RT=2.42 min; TLC (20% EtOAc-80% hexane): R$_f$=0.29.

Intermediate 1E: Preparation of 4-chloro-6-(3-methoxyphenyl)pyrimidin-2-amine

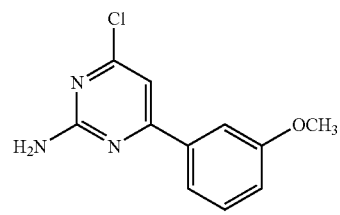

Step 1: Preparation of ethyl 3-oxo-3-(3-methoxyphenyl) propanoate

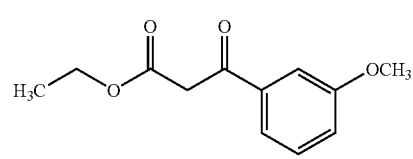

This material is prepared by a method analogous to that described for preparation of ethyl 3-oxo-3-(2-thienyl)propanoate in preparation of 1D, starting from 2,2-dimethyl-1,3-dioxane-4,6-dione and 3-methoxybenzoic acid.

Step 2: Preparation of the Title Compound 1E is prepared by a method analogous to that described for 1A, starting from guanidine carbonate and ethyl 3-oxo-3-(3-methoxyphenyl)propanoate.

Intermediate 1F: Preparation of 4-chloro-6-(4-methoxyphenyl)pyrimidin-2-amine

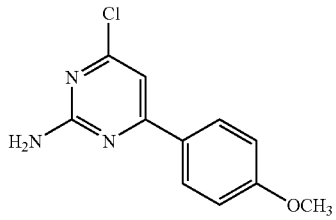

Step 1: Preparation of ethyl 3-oxo-3-(4-methoxyphenyl)propanoate

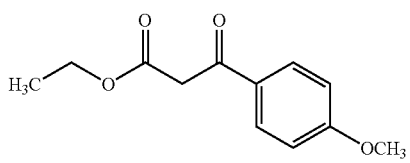

This material is prepared by a method analogous to that described for preparation of ethyl 3-oxo-3-(2-thienyl)propanoate in preparation of 1D, starting from 2,2-dimethyl-1,3-dioxane-4,6-dione and 4-methoxybenzoic acid.

Step 2: Preparation of Title Compound 1F is prepared by a method analogous to that described for 1A, starting from guanidine carbonate and ethyl 3-oxo-3-(4-methoxyphenyl)propanoate.

Intermediate 1G: Preparation of 4-chloro-6-[4-(trifluoromethyl)phenyl]pyrimidin-2-amine

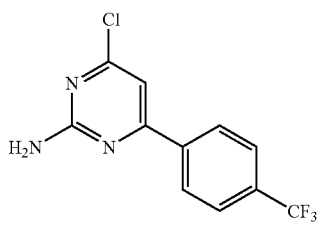

Step 1: Preparation of ethyl 3-oxo-3-[4-(trifluoromethyl)phenyl]propanoate

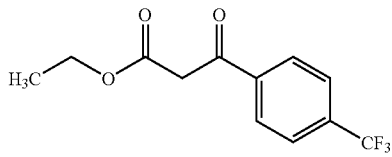

This material is prepared by a method analogous to that described for preparation of ethyl 3-oxo-3-(2-thienyl)propanoate in preparation of 1D, starting from 2,2-dimethyl-1,3-dioxane-4,6-dione and 4-(trifluoromethyl)benzoic acid.

Step 2: Preparation of Title Compound

This material is prepared by a method analogous to that described for 1A, starting from guanidine carbonate and 3-oxo-3-[4-(trifluoromethyl)phenyl]propanoate.

Intermediate 1H: Preparation of 4-chloro-6-(4-fluorophenyl)pyrimidin-2-amine

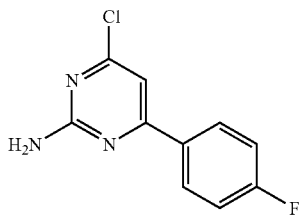

Step 1 Preparation of ethyl 3-(4-fluorophenyl)-3-oxopropanoate

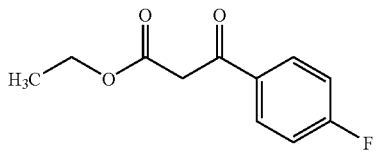

This material is prepared by a method analogous to that described for preparation of ethyl 3-oxo-3-(2-thienyl)propanoate in preparation of 1D, starting from 2,2-dimethyl-1,3-dioxane-4,6-dione and 4-fluorobenzoic acid.

Step 2: Preparation of Title Compound 1H is prepared by a method analogous to that described for 1A, starting from guanidine carbonate and the product from Step 1, ethyl 3-(4-fluorophenyl)-3-oxopropanoate.

Preparation of Substituted Aniline Intermediates

Intermediate 2A: Preparation of {4-[(2-ethylpyridin-4-yl)oxy]phenyl}amine

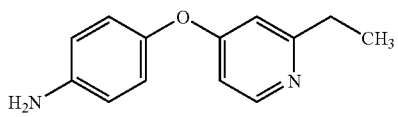

To a −78° C. solution of diisopropylamine (12.1 mL, 86.2 mmol) in THF (20 mL) was added a solution of n-BuLi in hexanes (1.60 M, 26.9 mL, 43.0 mmol) dropwise over 5 min. The mixture was stirred for 30 min, then a solution of 4-chloro-picoline (5.00 g, 39.2 mmol) in THF (20 mL) was added slowly over 30 min. The reaction mixture was warmed to −60° C. and stirred for 30 min. after which time a solution of methyl iodide (2.44 mL, 39.2 mmol) in 10 mL THF was added over a 20 min period. The reaction was stirred for 30 min at −60° C. and 1.5 h at −30° C. The reaction was quenched by pouring the mixture into cold brine. The mixture was extracted with dichloromethane. The organic layers were dried (sodium sulfate) and concentrated. Vacuum distillation of the residue (10 mm Hg, 70-80° C.) furnished 5 g of a 4.5:1 mixture of the desired 2-ethyl-4-chloropyridine and the isopropyl analog.

A well stirred, degassed solution of t-BuOK (5.43 g, 44.5 mmol), 4-aminophenol (4.16 g, 38.2 mmol) and 2-ethyl-4-chloropyridine (4.5 g, 32 mmol, contains 20% isopropyl analog) in dimethylacetamide (100 mL) was heated at 100° C. for 30 h. The reaction mixture was cooled to rt and concentrated in vacuo. The residue was partitioned between dichloromethane (200 mL) and 0.1 N NaOH (200 mL). The organic phase was washed with 0.1 N NaOH, dried (Na$_2$SO$_4$), and concentrated in vacuo. The crude oil was purified by silica gel chromatography (20% EtOAc to 60% EtOAc in hexanes) to provide 3.22 g of the desired ethyl compound 2A and 465 mg of the isopropyl analog. MS ES: 215 (M+H)$^+$, calcd 215, RT=0.19 min.

Intermediate 2B: Preparation of {4-[(2-methylpyridin-4-yl)oxy]phenyl}amine

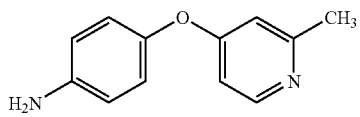

{4-[(2-Methylpyridin-4-yl)oxy)phenyl}amine (2B) was prepared by a method analogous to that described for 4-(3-aminophenoxy)pyridine-2-carboxamide (2C), starting from 4-aminophenol and 4-chloro-2-methylpyridine, MS ES: 201 (M+H)$^+$, calcd 201, RT=1.01 min.

Intermediate 2C: Preparation of 4-(3-aminophenoxy)pyridine-2-carboxamide

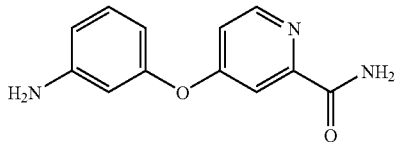

3-Aminophenol (18.12 g, 0.17 mmol) and potassium t-butoxide (12.07 g, 0.17 mmol) were suspended in NY-dimethylformide (350 mL) and stirred at rt for 30 min. 2-Amido-4-chloropyridine (20 g, 0.13 mmol) was added and the mixture was stirred at 90° C. overnight. The reaction mixture was concentrated in vacuo. The residue was partitioned between ethyl acetate and water. The aqueous layer was extracted with ethyl acetate. The organic layers were combined, dried (Na$_2$SO$_4$) and evaporated to dryness. The crude tan solid was recrystallized from ethyl acetate to afford 10.5 g (27%) of the desired product 2C. MS ES: 230 (M+H)$^+$, calcd 230, RT=1.29 min.

Intermediate 2D: Preparation of 4-(3-aminophenoxyamino]phenoxy)-N-methyl-pyridine-2-carboxamide

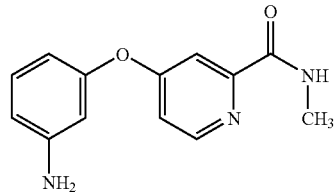

Aniline 2D was prepared by a procedure described in WO 00/42012 (Bayer Corporation, ω-Carboxyaryl Substituted Diphenyl Ureas as RAF kinase Inhibitors), starting from 3-aminophenol and 4-chloro-2-(N-methylamido)pyridine. MS ES: 244 (M+H)$^+$, calcd 244, RT=1.51 min.

Intermediate 2E: Preparation of {4-[(3,5-difluoropyridin-4-yl)oxy]phenyl}amine

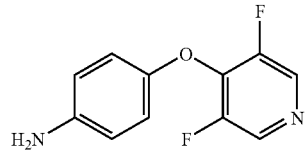

{4-[(3,5-Difluoropyridin-4-yl)oxy]phenyl}amine (2E) was prepared by a method analogous to that described for 4-(3-aminophenoxy) pyridine-2-carboxamide (2C), starting from 4-aminophenol and 3,4,5-trifluoropyridine, MS ES: 223 (M+H)$^+$, calcd 223, RT=0.50 min.

Intermediate 2F: Preparation of 4-(4-aminophenoxy)-N-methylpyridine-2-carboxamide

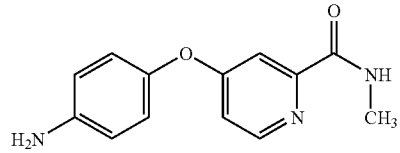

4-(4-Aminophenoxy)-N-methylpyridine-2-carboxamide (2F) was prepared by a procedure described in WO 00/42012 (Bayer Corporation, ω-Carboxyaryl Substituted Diphenyl Ureas as RAF kinase inhibitors), starting from 4-aminophenol and 4-chloro-2-(N-methylamido)pyridine MS ES: 244 (M+H)$^+$, calcd 244, RT=1.16 min.

Intermediate 2G: Preparation of 4-(4-amino-3-fluorophenoxy)pyridine-2-carbonitrile

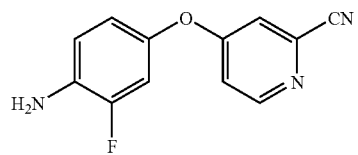

4-(4-Amino-3-fluorophenoxy) pyridine-2-carbonitrile (2G) was prepared by a method analogous to that described for 4-(3-aminophenoxy) pyridine-2-carboxamide (2C), starting from 4-amino-3-fluorophenol and 4-chloro-2-cyanopyridine, MS ES: 230 (M+H)+, calcd 230, RT=2.85 min.

Intermediate 2H: Preparation of 4-(4-amino-2-fluorophenoxy)pyridine-2-carbonitrile

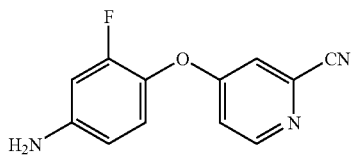

4-(4-Amino-2-fluorophenoxy)pyridine-2-carbonitrile (2H) was prepared by a method analogous to that described for 4-(3-aminophenoxy)pyridine-2-carboxamide (2C), starting from 4-amino-2-fluorophenol and 4-chloro-2-cyanopyridine, MS ES: 230 (M+H)+, calcd 230, RT=2.18 min.

Intermediate 2I: Preparation of 4-(4-aminophenoxy)pyridine-2-carbonitrile

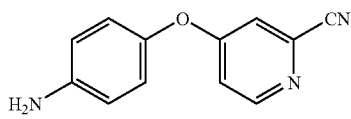

4-(4-Aminophenoxy) pyridine-2-carbonitrile (2I) was prepared by a method analogous to that described for 4-(3-aminophenoxy) pyridine-2-carboxamide (2C), starting from 4-aminophenol and 4-chloro-2-cyanopyridine, MS ES: 212 (M+H)+, calcd 212, RT=1.23 min.

Intermediate 2J: Preparation of {3-fluoro-4-[(2-methylpyridin-4-yl)oxy]phenyl}-amine

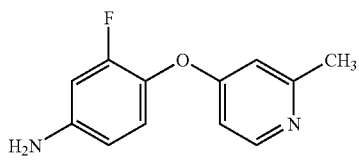

{3-Fluoro-4-[(2-methylpyridin-4-yl)oxy]phenyl}-amine (2J) was prepared by a method analogous to that described for 4-(3-aminophenoxy)pyridine-2-carboxamide (2C), starting from 4-amino-2-fluorophenol and 4-chloro-2-cyanopyridine, MS ES: 219 (M+H)+, calcd 219, RT=1.07 min.

Intermediate 2K: Preparation of [4-(4-methoxyphenoxy)phenyl]amine

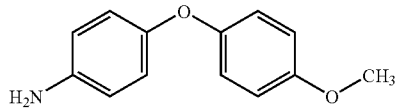

1-Fluoro-4-nitrobenzene (7.76 g, 55.0 mmol) and potassium carbonate (12.0 g, 86.8 mmol) were suspended in anhydrous DMF (100 mL) and stirred at 125° C. for 2 h. 4-Methoxyhenol (6.21 g, 50.0 mmol) was added and the mixture was stirred vigorously at 125° C. for 4 h. After cooling to rt, the reaction mixture was poured into ice-water (1000 mL) and stirred vigorously for 30 min. The resulting yellow solid was collected by vacuum filtration and washed with water to give 11.7 g of the nitro intermediate which was dried in vacuo-overnight. This nitro intermediate (8.00 g, 32.6 mmol) was suspended in ethanol (180 mL) and added to a flask charged with 10% Pd/C (0.35 g). The reaction mixture was flushed with hydrogen gas three times and then stirred at rt under hydrogen atmosphere overnight. The catalyst was removed by filtration and the filtrate was concentrated. The resulting precipitate was collected by vacuum filtration to give a white solid product (6.76 g, 96%). MS ES 216 (M+H)+, calcd 216, RT=1.24 min; TLC (25% ethyl acetate-hexane) $R_f$=0.18.

Intermediate 2L: Preparation of 4-[4-amino-3-(trifluoromethyl)phenoxyl pyridine-2-carbonitrile

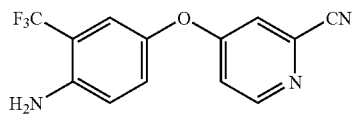

This material is prepared by a method analogous to that described for preparation of 2C, starting from 4-amino-3-(trifluoromethyl)phenol and 4-chloro-2-cyanopyridine.

Intermediate 2M: Preparation of {4-[(2-methylpyrimidin-4-yl)oxy]phenyl}amine

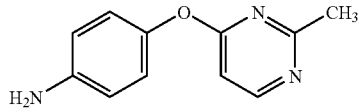

This material is prepared by a method analogous to that described for preparation of 2C, starting from 4-amino-phenol and 4-chloro-2-methylpyrimidine.

Intermediate 2N: Preparation of 4-(4-aminophenoxy)-N-(2-{[tert-butyl(dimethyl)silyl]oxy}ethyl)pyridine-2-carboxamide

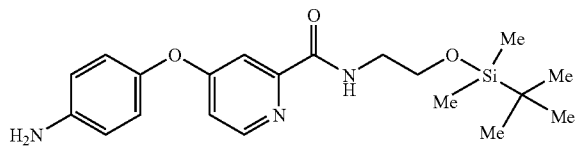

4-(4-Aminophenoxy)-N-(2-{[tert-butyl(dimethyl)silyl]oxy}ethyl)pyridine-2-carboxamide was prepared by a method analogous to that described for 4-(3-aminophenoxy)pyridine-2-carboxamide (Intermediate 2C), starting from 4-aminophenol and N-(2-{[tert-butyl(dimethyl)silyl]oxy}ethyl)chloropyridine-2-carboxamide MS ES: 388 (M+H)$^+$, calcd 388, RT=3.60 min.

Intermediate 2O: Preparation of 4-(4-fluoro-benzyl)-phenylamine

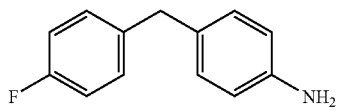

Step 1. Preparation of (4-fluoro-phenyl)-(4-nitrophenyl)-methanone

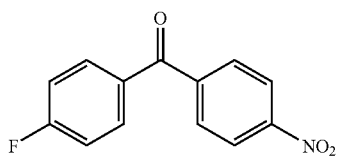

To a solution of 4-nitrobenzoyl chloride (2.3 g, 13 mmol) in nitroethane (20 mL) was added aluminum chloride (3.5 g, 26 mmol) followed by fluorobenzene (1.2 mL, 13 mmol). The mixture was stirred at rt for 4 h, then quenched carefully with 6M HCl. The reaction mixture was washed with dilute aqueous NaOH and brine, dried over sodium sulfate, filtered, and concentrated in vacuo to provide the crude product as a light yellow solid. The solid was purified by recrystallization from hexanes to give (4-fluoro-phenyl)-(4-nitrophenyl)-methanone (2.0 g, 65%). $^1$H NMR (CHCl$_3$-d) δ 8.41-8.32 (m, 5H), 7.90 (m, 1H), 7.84 (m, 1H), 7.20 (m, 1H).

Step 2. Preparation of 1-fluoro-4(4-nitrobenzyl)benzene

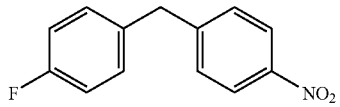

To a solution of (4-fluoro-phenyl)-(4-nitrophenyl)-methanone (2.0 g, 8.2 mmol) in dichloromethane (16 mL) at 0° C. was added trifluoromethanesulfonic acid (1.4 mL, 16 mmol) in dichloromethane (16 mL). A solution of triethylsilane (2 mL, 12 mmol) in dichloromethane (16 mL) was subsequently added dropwise, resulting in an exotherm. After 5 min. additional trifluoromethanesulfonic acid (1.4 mL, 16 mmol) was added, followed by triethylsilane (2.0 mL, 12 mmol). The reaction mixture was stirred at rt for 2 h, then poured into cold saturated sodium bicarbonate and extracted several times with dichloromethane. The combined organic extracts were dried over sodium sulfate and concentrated in vacuo. Purification by column chromatography eluting with 0-10% ethyl acetate in hexanes, gave the desired product as a white solid (260 mg, 14%). $^1$H NMR (CHCl$_3$-d) δ 8.14 (m, 2H), 7.31 (m, 2H), 7.12 (m, 2H), 7.01 (m, 2H), 4.06 (s, 2H).

Step 3. Preparation of the Title Compound.

To a solution of the product prepared in Step 2 (260 mg, 1.1 mmol) in ethanol (4 mL) and water (1.2 mL) was added iron powder (188 mg, 3.40 mmol) and ammonium chloride (36 mg, 0.70 mmol). The reaction was stirred at 85° C. for 2 h, cooled to rt, and filtered through Celite®. The filtrate was concentrated then diluted in dichloromethane, washed with water, and dried over sodium sulfate. The combined organic layers were concentrated in vacuo to afford 4-(4-fluoro-benzyl)-phenylamine as light brown oil which crystallized upon standing (150 mg, 67%). $^1$H NMR (CHCl$_3$-d) δ 7.11 (m, 2H), 6.95 (m, 4H), 6.62 (m, 2H), 3.85 (s, 2H), 3.59 (br s, 2H).

Intermediate 2P: Preparation of 4-(2-trifluoromethyl-pyridin-4-ylmethyl)-phenylamine

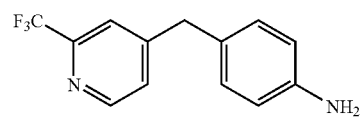

Step 1. Preparation of (4-nitro-phenyl)-(2-trifluoromethyl-pyridin-4-yl)-acetic acid ethyl ester

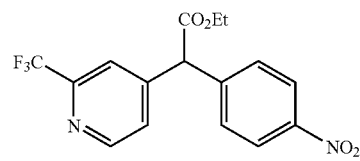

To a solution of ethyl (4-nitrophenyl)acetate (760 mg, 3.6 mmol) in DMF (10 mL) was added 60% sodium hydride (145 mg, 3.6 mmol). The deep purple reaction mixture was stirred at rt for 30 min, then 4-fluoro-2-trifluoromethyl-pyridine (500 mg, 3.0 mmol) was added. After heating at 70° C. for 2 h, the mixture was poured onto ice water and extracted with ethyl acetate. The organic layers were washed with water and brine, then dried over sodium sulfate and concentrated in vacuo. The residue was purified by column chromatography, eluting with 10-30% ethyl acetate in hexanes, to give (4-nitro-phenyl)-(2-trifluoromethyl-pyridin-4-yl)-acetic acid ethyl ester as a viscous yellow oil (440 mg, 41%). $^1$H NMR (CHCl$_3$-d) δ 8.70 (d, J=5.1 Hz, 1H), 8.23 (m, 2H), 7.63 (m, 1H), 7.50 (m, 2H), 7.44 (dd, J=5.0, 1.6 Hz, 1H), 5.15 (s, 1H), 4.27 (q, J=7.0 Hz, 2H), 1.30 (t, J=7.1 Hz, 3H).

Step 2. Preparation of 4-(4-nitrobenzyl)-2-(trifluoromethyl)pyridine

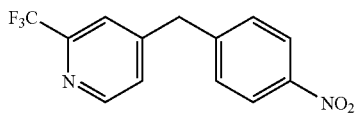

To a solution of the product prepared in Step 1 (440 mg, 1.24 mmol) in methanol (13 mL) containing a drop of water, was added powdered LiOH (36 mg, 1.5 mmol) and the mixture was stirred at rt overnight. The mixture was concentrated to remove the methanol, diluted in dichloromethane, and washed with water. The combined organic extracts were dried over sodium sulfate, concentrated in vacuo, and purified by column chromatography eluting with 10-25% ethyl acetate in hexanes to give 4-(4-nitrobenzyl)-2-(trifluoromethyl)pyridine as a light yellow solid (100 mg, 29%). $^1$H NMR (CHCl$_3$-d) δ 8.65 (d, J=4.7 Hz, 1H), 8.21 (m, 2H), 7.49 (s, 1H), 7.35 (m, 2H), 7.28 (m, 1H), 4.18 (s, 2H).

Step 3. Preparation of the Title Compound

10% Degussa Pd on carbon (15 mg, 0.14 mmol) was flushed with nitrogen then diluted in ethanol (2 mL). A solution of 4-(4-nitrobenzyl)-2-(trifluoromethyl)pyridine (100 mg, 0.35 mmol) in ethanol (2 mL) and pyridine (14 mg, 0.18 mmol) was subsequently added, and the mixture was flushed again with nitrogen prior to placing a hydrogen balloon on the flask. The mixture was stirred at rt overnight then filtered through Celite® and concentrated. The residue was dissolved in ethyl acetate and filtered through a silica gel plug, eluting with 50-100% ethyl acetate in hexanes, to give 4-(2-trifluoromethyl-pyridin-4-ylmethyl)-phenylamine as a clear colorless oil (76 mg, 85%). $^1$H NMR (CHCl$_3$-d) δ 8.57 (d, J=5.0 Hz, 1H), 7.47 (s, 1H), 7.26 (m, 1H), 6.93 (m, 2H), 6.65 (m, 2H), 3.92 (s, 2H), 3.57 (br s, 2H).

Intermediate 2Q: Preparation of 4-(4-amino-benzyl)-pyridine-2-carbonitrile

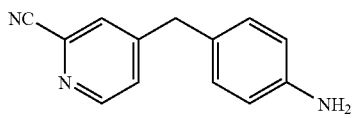

Step 1. Preparation of 4-(4-nitro-benzyl)-pyridine-2-carbonitrile

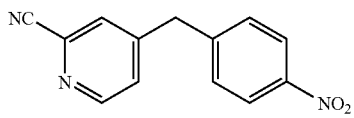

To a solution of 4-(4-nitro-benzyl)-pyridine 1-oxide (1.0 g, 4.3 mmol) in dichloromethane (9 mL) was added-trimethylsilyl cyanide (2.3 mL, 17 mmol). After 5 min, benzoyl chloride (1.0 mL, 8.7 mmol) was added dropwise and the mixture was stirred at rt for an additional 30 min. Water (10 mL) was carefully added, followed by solid potassium carbonate (2.1 g). After 30 min, the aqueous phase was extracted with dichloromethane and the combined organic layers were dried over sodium sulfate and concentrated in vacuo. Purification of the residue by column chromatography, eluting with 5-25% ethyl acetate in hexanes, gave an orange oil. This oil was subsequently triturated with toluene to afford 4-(4-nitro-benzyl)-pyridine-2-carbonitrile as a tan solid (353 mg, 34%). $^1$H NMR (CHCl$_3$-d) δ 8.63 (d, J=4.8 Hz, 1H), 8.21 (m, 2H), 7.49 (m, 1H), 7.32 (m, 3H), 4.15 (s, 2H).

Step 2. Preparation of the Title Compound

10% Degussa Pd on carbon (40 mg, 0.38 mmol) was flushed with nitrogen then diluted in ethanol (5 mL). 4-(4-Nitro-benzyl)-pyridine-2-carbonitrile (250 mg, 1.05 mmol) in ethanol (5 mL) and pyridine (42 mg, 0.52 mmol) was subsequently added, and the mixture was flushed again with nitrogen prior to placing a hydrogen balloon on the flask. The mixture was stirred at rt overnight then filtered through Celite® and concentrated. The residue was dissolved in ethyl acetate and filtered through a silica gel plug, eluting with 50-100% ethyl acetate in hexanes, to give 4-(4-amino-benzyl)-pyridine-2-carbonitrile (134 mg, 61%). $^1$H NMR (CHCl$_3$-d) δ 8.55 (d, J=5.2 Hz, 1H), 7.46 (s, 1H), 7.30 (d, J=4.8 Hz, 1H), 6.93 (d, J=8.3 Hz, 2H), 6.66 (d, J=8.2 Hz, 2H), 3.91 (s, 2H).

Intermediate 2R: Preparation of 4-(4-aminophenoxy)-2-chloropyridine

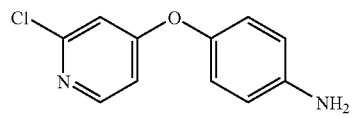

4-(4-Aminophenoxy)-2-chloropyridine was prepared by a method analogous to that described for 4-(3-aminophenoxy) pyridine-2-carboxamide (2C), starting from 4-aminophenol and 2,4-dichloropyridine MS ES: 221 (M+H)$^+$, calcd 221, RT=0.32 min.

Intermediate 2S: Preparation of 4-(2-chloro-pyridin-4-ylmethyl)-phenylamine

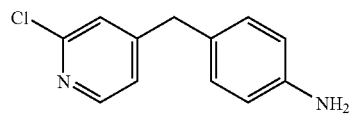

4-(2-Chloro-pyridin-4-ylmethyl)-phenylamine was prepared by a method analogous to that described for 4-(2-trifluoromethyl-pyridinylmethyl)-phenylamine (Intermediate 2P), starting from ethyl(4-nitrophenyl)acetate and 2-chloro-4-nitro-pyridine. $^1$H NMR (CHCl$_3$-d) δ 8.23 (dd, J=5.1, 0.5 Hz, 1H), 7.11 (m, 1H), 7.01 (m, 1H), 6.95 (m, 2H), 6.65 (m, 2H), 3.83 (s, 2H).

Intermediate 2T: Preparation of 4-[(4-bromopyridin-2-yl)oxy]aniline

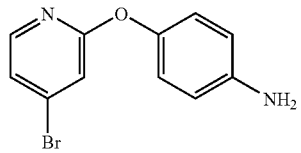

A solution of 4-aminophenol (1.86 g, 17.05 mmol) in anhydrous DMF was added to a suspension of potassium t-butoxide (2.10 g, 18.75 mmol) in DMF. The mixture was stirred at rt for 1 h. 4-Bromo-2-fluoropyridine (3.00 g, 17.05 mmol) was added into the reaction mixture and it was heated at 90° C. with stirring for 20 h. It was cooled down to rt and 100 ml of water was slowly added to quench the reaction. The reaction mixture was concentrated in vacuum to provide a residue which was extracted with EtOAc (3×) and washed with water (3×). The organic layer was dried (MgSO$_4$) and concentrated to give the crude product, which was purified by flash chromatography (Hexan:EtOAc=6:4) to provide 1.02 g (23%) of the intermediate 2T as a yellow solid. MS ES 265 (M+H)$^+$, calc. 265, RT=2.52 min. TLC (Hexane/EtOAc=6/4) R$_f$=0.26.

Intermediate 2U: Preparation of 4-{[2-(trifluoromethyl)pyridin-4-yl]oxy}aniline

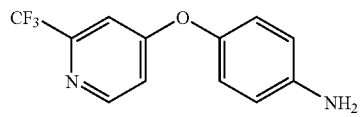

A cold (−5° C.), de-gassed solution of 4-aminophenol (41.6 g, 0.38 mol) in N,N-dimethylacetamide (250 mL) was treated with potassium tert-butoxide and stirred while warming to 20° C. A solution containing 4-fluoro-2-trifluoromethylpyridine (60 g, 0.36 mol) in dimethylacetamide (150 mL) was slowly added and the mixture was stirred at 25° C. for 18 h. The reaction mixture was then concentrated in vacuo and the residue was added to vigorously stirred water (1 L). The precipitated solids were collected by suction filtration and washed with isopropanol/ether (1:1) followed by ether and hexane. The yellow tan solids were dried to afford 72.8 g (79%) of product. $^1$H NMR (DMSO-d$_6$) δ 5.20 (s, 2H, —NH$_2$), 6.62 (m, 2H), 6.86 (m, 2H), 7.04 (dd, 1H, J=5.6, 2.4 Hz), 7.24 (d, 1H, J=2.4 Hz), 8.54 (d, 1H, 5.7 Hz). MS ES 255 (M+H)$^+$, calcd 255, RT=1.66 min.

Intermediate 2V: Preparation of methyl 4-(4-aminophenoxy)pyridine-2-carboxylate

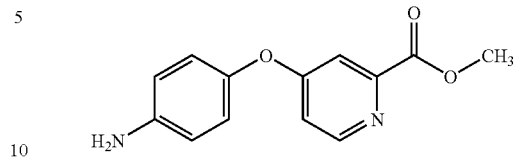

Step 1. Synthesis of methyl 4-chloropyridine-2-carboxylate HCl salt

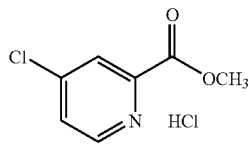

Anhydrous DMF (10.0 mL) was slowly added to SOCl$_2$ (300 mL) at 40-48° C. The solution was stirred at for 10 min., then picolinic acid (100 g, 812 mmol) was added over 30 min. The resulting solution was heated at 72° C. (vigorous SO$_2$ evolution) for 16 h to generate a yellow solid. The resulting mixture was cooled to rt, diluted with toluene (500 mL) and concentrated to 200 mL. The toluene addition/concentration process was repeated twice. The resulting nearly dry residue was filtered, and the solids were washed with toluene (50 mL) and dried under high vacuum for 4 h to afford 4-chloropyridine-2-carbonyl chloride HCl salt as an off-white solid (27.2 g, 16%). This material was set aside.

The red filtrate from above was added to MeOH (200 mL) at a rate which kept the internal temperature below 55° C. The contents were stirred at rt for 45 min, cooled to 5° C. and treated with Et$_2$O (200 mL) dropwise. The resulting solids were filtered, washed with Et$_2$O (200 mL) and dried under reduced pressure at 35° C. to provide methyl 4-chloropyridine-2-carboxylate HCl salt as a white solid (110 g, 65%): mp 108-112° C.; $^1$H-NMR (DMSO-d$_6$) δ 3.88 (s, 3H); 7.82 (dd, J=5.5, 2.2 Hz, 1H); 8.08 (d, J=2.2 Hz, 1H); 8.68 (d, J=5.5 Hz, 1H); 10.68 (br s, 1H); MS ES 172 (M+H)$^+$ calcd 172.

Step 2. Preparation of the Title Compound

Methyl 4-(4-aminophenoxy)pyridine-2-carboxylate was prepared by a method analogous to that described for 4-(3-aminophenoxy) pyridine-2-carboxamide (2C), starting from the product of step 1 and 4-aminophenol.

Preparation of Invention Compounds

Example 1

Preparation of N$^4$-{4-[(2-ethylpyridin-4-yl)oxy]phenyl}-6-phenyl-pyrimidine-2,4-diamine

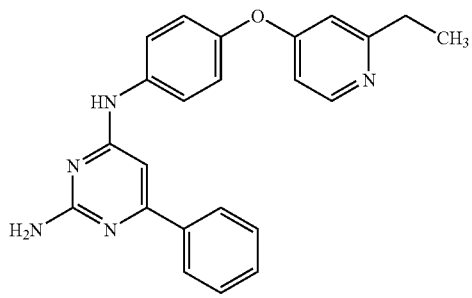

Chloropyrimidine 1A (75 mg, 0.35 mmol) and aniline 2A (72 mg, 0.35 mmol) were suspended in water (2 mL) containing concentrated hydrochloric acid (0.1 mL) and stirred at 100° C. for 17 h. After cooling to rt, the mixture was neutralized with 1 N aqueous sodium hydroxide and stirred for 20 min. The precipitate was collected by filtration and purified by silica gel column chromatography (0-5% methanol-methylene chloride) to afford 43 mg (32%) of the title compound as a yellow solid. $^1$H NMR (DMSO-$d_6$) δ 9.34 (s, 1H), 8.31 (d, 5.7 Hz, 1H), 7.91-7.93 (m, 2H), 7.86 (d, J=8.8 Hz, 2H), 7.45-7.47 (m, 3H), 7.07-7.09 (m, 2H), 6.76 (d, J=2.3 Hz, 1H), 6.68 (dd, J=5.6 Hz, 1.3 Hz, 1H), 6.49 (s, 1H), 6.37 (b, 2H), 2.69 (q, J=7.6 Hz, 2H), 1.19 (t, J=7.4 Hz, 3H), MS ES 384 (M+H)$^+$, calcd 384, RT=1.87 min; TLC (5/95 v/v methanol-methylene chloride) $R_f$=0.41. The reaction mixture can also be purified by preparative HPLC using an elution gradient from 15% to 85% acetonitrile in water containing 0.1% TFA over 15 min with Phenomenex Luna 5μ C18 150×30 mm column to provide the title compound as its TFA salt.

By dissolving the title compound in an appropriate solvent such as MeOH or dioxane, addition of either 1 N HCl or 1 N methanesulfonic acid, and filtration, the corresponding HCl or methanesulfonate salt is isolated.

By using the method described for Example 1, and by substituting appropriate starting materials, Examples 60-68 and 87 were similarly prepared.

Example 2

Preparation of N$^4$-{4-[(2-methylpyridin-4-yl)oxy]phenyl}-6phenylpyrimidine-2,4-diamine

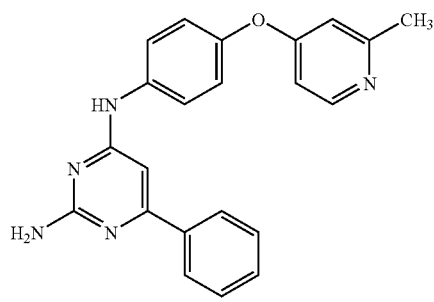

Stating from chloropyrimidine 1A and aniline 2B, this compound was prepared by a method analogous to that described for Example 1. $^1$H NMR (DMSO-$d_6$) δ 9.31 (s, 1H), 8.25 (d, J=5.7 Hz, 1H), 7.89-7.92 (m, 2H), 7.83-7.86 (m, 2H), 7.42-7.48 (m, 3H), 7.04 (d, J=8.9 Hz, 2H), 6.73 (d, J=2.4 Hz, 1H), 6.67-6.69 (m, 1H), 6.47 (s, 1H), 6.34 (s, 2H), 2.37 (s, 3H); MS ES: 370 (M+H)$^+$, calcd 370, RT=1.41 min; TLC (5/95 methanol-methylene chloride) $R_f$=0.33.

Example 3

Preparation of 4-{3-[(2-amino-6-phenylpyrimidin-4-yl)amino]phenoxy}pyridine-2-carboxamide

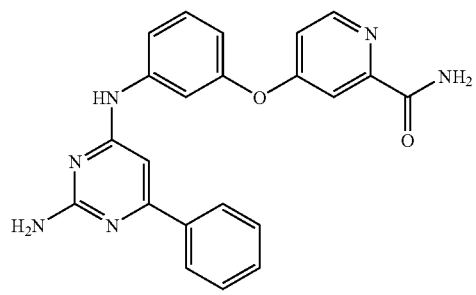

Starting from chloropyrimidine 1A and aniline 2C, this material was prepared using a method analogous to that described for Example 1. $^1$H NMR (DMSO-$d_6$) δ 9.43 (s, 1H), 8.50 (d, J=5.6 Hz, 1H), 8.12 (s, 1H), 7.88-7.90 (m, 2H), 7.75 (t, J=2.2 Hz, 1H), 7.70 (s, 1H), 7.60 (d, J=8.4 Hz, 1H), 7.43-7.46 (m, 4H), 7.38 (t, J=8 Hz, 1H), 7.19 (dd, J=5.5 Hz, 1.5 Hz, 1H), 6.75 (dd, J=7.5 Hz, 1.0 Hz, 1H), 6.48 (s, 1H), 6.38 (b, 2H); MS ES 399 (M+H)$^+$, calcd 399, RT=2.64 min; TLC (5/95 methanol-methylene chloride) $R_f$=0.27.

By using the method described for Example 3, and by substituting appropriate starting materials, Example 69-70 were similarly prepared.

Example 4

Preparation of 4-{3-[(2-amino-6-phenylpyrimidin-4-yl)amino]phenoxy}-N-methylpyridine-2-carboxamide

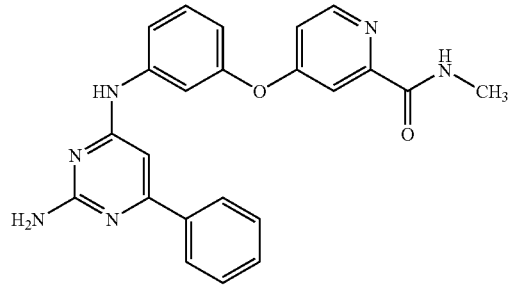

Starting from chloropyrimidine 1A and aniline 2D, this material was prepared using the method similar to Example 1. $^1$H NMR (DMSO-$d_6$) δ 9.43 (s, 1H), 8.76-8.79 (m, 1H), 8.50 (d, J=5.8 Hz, 1H), 7.88-7.90 (m, 2H), 7.75 (t, J=2.0 Hz, 1H), 7.59 (d, J=7.9 Hz, 1H), 7.42-7.47 (m, 4H), 7.38 (t, J=8.0 Hz, 1H), 7.17-7.19 (m, 1H), 6.75 (dd, J=8.0 Hz, 1.0 Hz, 1H), 6.48 (s, 1H), 6.38 (s, 2H), 2.78 (d, J=4.8 Hz, 3H); MS ES 413 (M+H)$^+$, calcd 413, RT=2.13 min; TLC (5/95 methanol-methylene chloride) $R_f$=0.31.

Example 5

Preparation of N$^4$-{4-[(3,5-difluoropyridin-4-yl)oxy]phenyl}-6-phenylpyrimidine-2,4-diamine

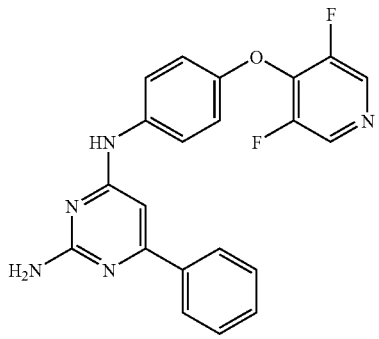

Staring from chloropyrimidine 1A and aniline 2E, this compound was prepared by a method analogous to that described for Example 1. $^1$H NMR (DMSO-d$_6$) δ 9.24 (s, 1H), 8.63 (s, 2H), 7.88-7.90 (m, 2H), 7.74 (d, J=9.0 Hz, 2H), 7.43-7.46 (m, 3H), 7.03 (d, J=9.0 Hz, 2H), 6.44 (s, 1H), 6.31 (b, 2H); MS ES 392 (M+H)$^+$, calcd 392, RT=2.27 min.

Example 6

Preparation of 4-(4-amino-3-fluorophenoxy)pyridine-2-carbonitrile hydrochloride

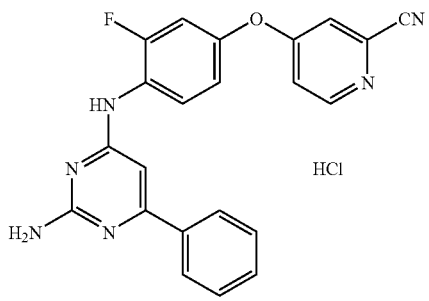

Starting from chloropyrimide 1A and aniline 2G, this material was prepared by a method analogous to that described for Example 1. After the reaction was complete, the solid was filtered and washed with MeOH to provide the title compound. $^1$H NMR (DMSO-d$_6$) δ 12.99 (s, broad, 1H, 10.51 (s, broad, 1H) 8.63 (d, J=6.0 Hz, 1H), 8.07 (s, broad, 1H), 7.88 (m, 2H), 7.79 (d, J=2.4 Hz, 1H), 7.66 (m, 3H), 7.45 (dd, J=11.2 Hz, 2.4 Hz, 1H), 7.30 (d, J=3.2 Hz, 1H), 7.16 (dd, J=8.8 Hz, 1.6 Hz, 1H), 6.82 (s, broad, 1H); MS ES: 399 (M+H)$^+$, calcd 399, RT=2.24 min.

By using the method described for Example 4, and by substituting appropriate starting materials, Examples 71-74 were similarly prepared.

Example 7

N$^4$-{3-fluoro-4-[(2-methylpyridin-4-yl)oxy]phenyl}-6-phenylpyrimidine-2,4-diamine

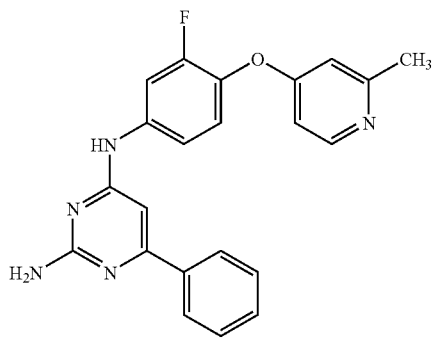

Starting from chloropyrimidine 1A and aniline 2E, this material was prepared by a method analogous to that described for Example 1. $^1$H NMR (DMSO-d$_6$) δ 9.54 (s, 1H), 8.24-8.30 (m, 2H), 7.19 (dd, J=7.6 Hz, 2.4 Hz, 2H), 7.44-7.48 (m, 3H), 7.23 (t, J=9.2 Hz, 1H), 6.70-6.76 (m, 2H), 6.49 (b, 2H), 2.41 (s, 3H); MS ES 388 (M+H)$^+$, calcd 388, RT=1.70 min.

Example 8

Preparation of 4-{4-[(2-amino-6-phenylpyrimidin-4-yl)amino]phenoxy}pyridine-2-carbonitrile

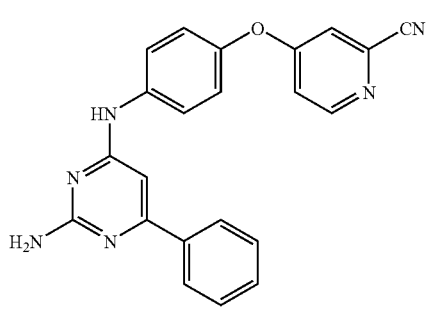

Starting from chloropyrimidine 1A and aniline 2I, this material was prepared by a method analogous to that described for Example 1. $^1$H NMR (DMSO-d$_6$) δ 12.73 (b, 1H), 10.85 (b, 2H), 8.56 (d, J=6.0 Hz, 1H), 7.94-7.96 (m, 2H), 7.83-7.85 (m, 2H), 7.71 (d, J=2.4 Hz, 1H), 7.63-7.67 (m, 3H), 7.29 (d, J=8.8 Hz, 2H), 7.18-7.21 (m, 1H), 6.65 (s, 1H); MS ES 381 (M+H)$^+$, calcd 381, RT=2.22 min.

By using the method described for Example 8, and by substituting appropriate starting materials, Example 75 was similarly prepared.

Example 9
Preparation of 4-(3-{[2-amino-6-(3-furyl)pyrimidin-4-yl]amino}phenoxy)-N-methylpyridine-2-carboxamide

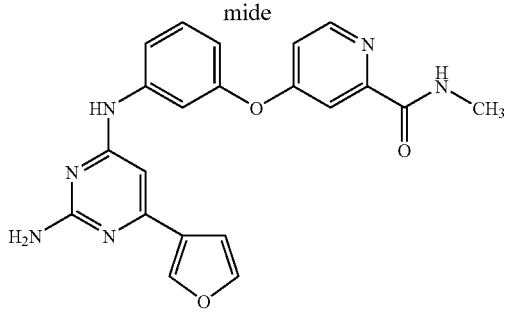

Starting from chloropyrimidine 1C and aniline 2D, this material was prepared by a method analogous to that described for Example 1. $^1$H NMR (DMSO-d$_6$) δ 9.37 (s, 1H), 8.77 (d, J=5.0 Hz, 1H), 8.50 (d, J=5.0 Hz, 1H), 8.11 (s, 1H), 7.71-7.74 (m, 2H), 7.56-7.59 (m, 1H), 7.43 (d, J=4.0 Hz, 1H), 7.36 (t, J=8.0 Hz, 1H), 7.16-7.18 (m, 1H), 6.79-6.80 (m, 1H), 6.72-6.73 (m, 1H), 6.29 (s, 2H), 6.22 (b, 1H), 2.78 (d, J=5.0 Hz, 3H); MS ES 403 (M+H)$^+$, calcd 403, RT=1.99 min; TLC (5/95 methanol-methylene chloride) R$_f$=0.27.

Example 10
Preparation of 4-(4-{[2-amino-6-(3-furyl)pyrimidin-4-yl]amino}-phenoxy)-N-methylpyridine-2-carboxamide

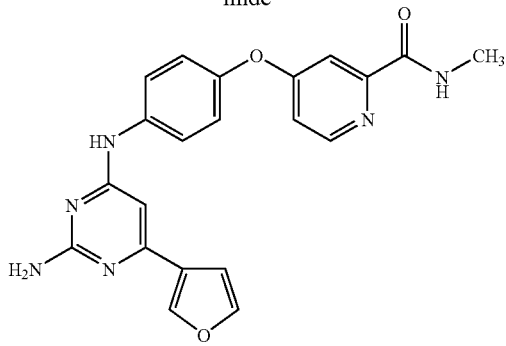

Starting from chloropyrimidine 1C and aniline 2F, this material was prepared by the method analogous to that described for Example 1. $^1$H NMR (DMSO-d$_6$) δ 9.31 (s, 1H), 8.76 (d, J=5.0 Hz, 1H), 8.47 (d, J=6.0 Hz, 1H), 8.12 (s, 1H), 7.85 (d, J=7.2 Hz, 2H), 7.74 (s, 1H), 7.36 (d, J=3.0 Hz, 1H), 7.10-7.14 (m, 3H), 6.81 (s, 1H), 6.18 (s, 2H), 6.23 (s, 1H), 2.78 (d, J=5.0 Hz, 3H); MS ES 403 (M+H)$^+$, calcd 403, RT=1.94 min; TLC (5/95 methanol-methylene chloride) R$_f$=0.26.

Example 11
Preparation of N$^4$-[4-(4-nitrophenoxy)phenyl]-6-phenylpyrimidine-2,4 diamine

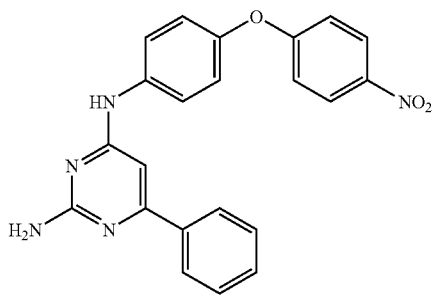

Starting from chloropyrimidine 1A and [4-(4-nitrophenoxy)phenyl]amine, this material was prepared by a method analogous to that described for Example 1. $^1$H NMR (DMSO-d$_6$) δ 9.36 (s, 1H), 8.23 (d, J=9.2 Hz, 2H), 7.87-7.93 (m, 4H), 7.43-7.48 (m, 3H), 7.08-7.12 (m, 4H), 6.49 (s, 1H), 6.37 (b, 2H); MS ES 400 (M+H)$^+$, calcd 400, RT=3.01 min; TLC (5/95 methanol-methylene chloride) R$_f$=0.67.

Example 12
Preparation of N$^4$-[4-(4-chlorophenoxy)phenyl]-6-phenylpyrimidine-2,4-diamine

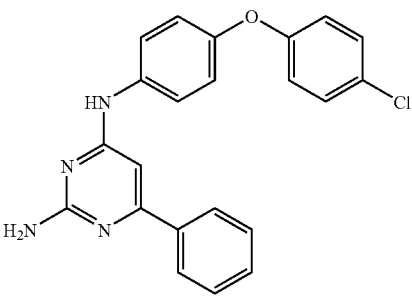

Starting from chloropyrimidine 1A and [4-(4-chlorophenoxy)phenyl]amine, this material was prepared by a method analogous to that described for Example 1. $^1$H NMR (DMSO-d$_6$) δ 9.24 (s, 1H), 7.90 (dd, J=7.8 Hz, 1.8 Hz, 2H), 7.79 (d, J=8.8 Hz, 2H), 7.45 (m, 3H), 7.39 (d, J=8.4 Hz, 2H), 6.99 (m, 4H), 6.46 (s, 1H), 6.31 (s, 2H); MS ES 389 (M+H)$^+$, calcd 389, RT=2.78 min; TLC (CH$_2$Cl$_2$/2M NH$_3$ in MeOH 95/5) R$_f$=0.33

Example 13
Preparation of N$^4$-[4-(4-methoxyphenoxy)phenyl]-6-phenylpyrimidine-2,4-diamine

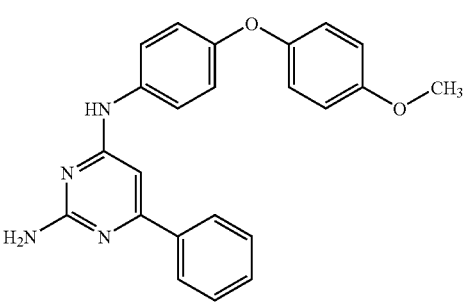

Starting from chloropyrimidine 1A and aniline 2K, this material was prepared by a method analogous to that described for Example 1. $^1$H NMR (DMSO-d$_6$) δ 9.15 (s, 1H), 7.90 (dd, J=9.6 Hz, 1.6 Hz, 2H), 7.70 (m, 2H), 7.44 (m, 3H), 6.93 (m, 4H), 6.88 (d, J=8.8 Hz, 2H), 6.43 (s, 1H), 6.27 (s, 2H), 3.72 (s, 3H); MS ES 385 (M+H)$^+$, calcd 385, RT=2.48 min.

Example 14

Preparation of 4-{4-[(2-amino-6-phenylpyrimidin-4-yl)amino]-2-fluorophenoxy}pyridine-2-carbonitrile

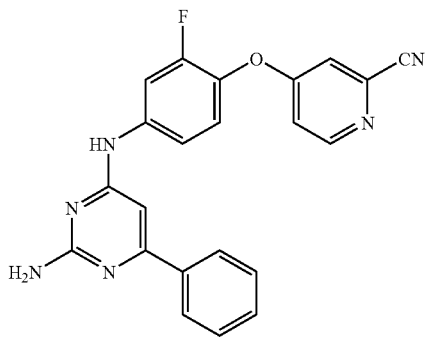

This material is prepared by a method analogous to that described in Example 1, starting from 2H and 1A.

Example 15

Preparation of 4-{4-[(2-amino-6-phenylpyrimidin-4-yl)amino]-3(trifluoromethyl)phenoxy}pyridine-2-carbonitrile

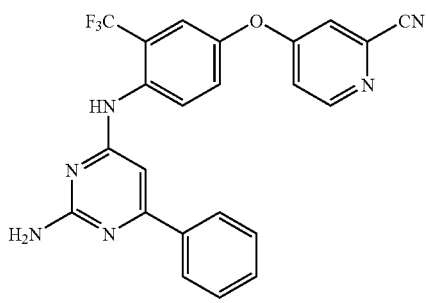

This material is prepared by a method analogous to that described in Example 1, starting from 2L and 1A.

Example 16

Preparation of $N^4$-{4-[(2-methylpyrimidin-4-yl)oxy]phenyl}-6-phenylpyrimidine-2,4-diamine

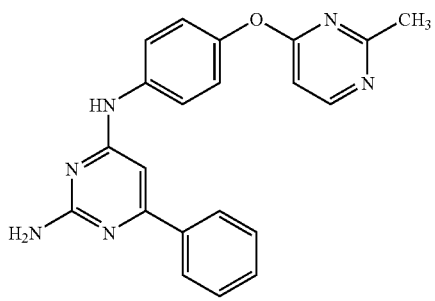

This material is prepared by a method analogous to that described in Example 1, starting from 2M and 1A.

Example 17

Preparation of $N^4$-{4-[(2-methylpyridin-4-yl)oxy]phenyl}-6-[4-(2-pyrrolidin-1-ylethoxy)phenyl]pyrimidine-2,4-diamine

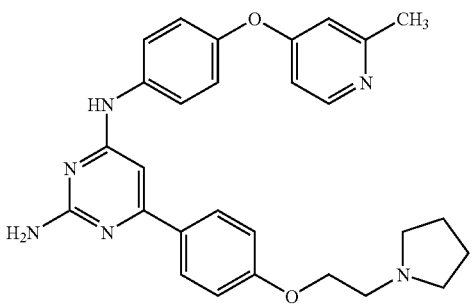

Step 1: Preparation of 6-(4-methoxyphenyl)-$N^4$-{4-[(2-methylpyridin-4-yl)oxy]phenyl}pyrimidine-2,4-diamine

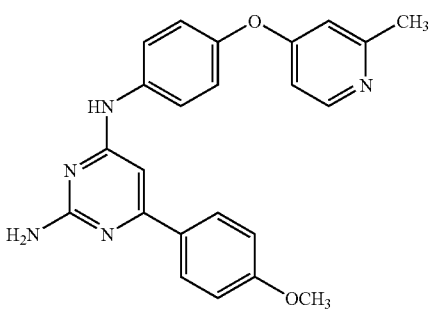

This material is prepared by a method analogous to that described for Example 1, starting from 1F and 2B.

Step 2: Preparation of 4-[2-amino-6-({4-[(2-methylpyridin-4-yl)oxy]phenyl}amino)pyrimidin-4-yl]phenol

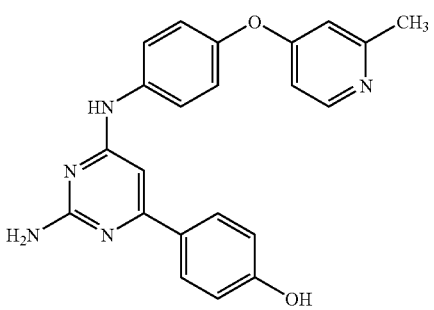

The intermediate from Step 1 above is treated with $BBr_3$ in methylene chloride at 0° C. for 12 h. After work-up and purification by a published procedure (J. F. W. McOmie and D. E. West, *Org. Synth., Collect*. Vol. V, 412 (1973)), the desired compound is obtained.

Step 3: Preparation of 6-[4-(2-bromoethoxy)phenyl]-N⁴-{4-[(2-methylpyridin-4-yl)oxy]phenyl}pyrimidine-2,4-diamine

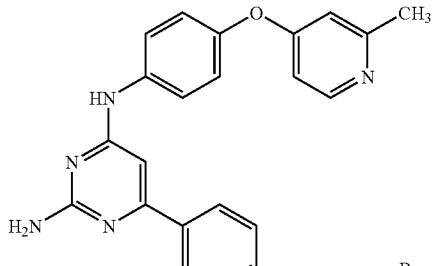

To a solution of Step 2 product (1 equiv) in DMF is added 1,2-dibromoethane (1 equiv) and K₂CO₃ (3 equiv). The mixture is refluxed overnight. After cooling to rt, the mixture is diluted with EtOAc and washed sequentially with 1N NaOH, water and brine. The organic layer is dried (Na₂SO₄) and concentrated to afford a crude product which is to be used in next step without further purification.

Step 4: Preparation of the Title Compound

A mixture of the product from Step 3 (1 equiv), pyrrolidine (2 equiv) and K₂CO₃ (8 equiv) in DMF is stirred at 65° C. overnight. The solvent is removed and the residue is dissolved in EtOAc. The organic solution is washed with water, dried, and evaporated to dryness. The residue is purified by chromatography on a silica column to afford the title compound.

By using the method described for Example 17, and by substituting appropriate starting materials, Examples 76-77 are similarly prepared.

Example 18

Preparation of 4-[4-({2-amino-6-[4-(2-piperidin-1-ylethoxy)phenyl]pyrimidin-4-yl}amino)phenoxy]pyridine-2-carbonitrile

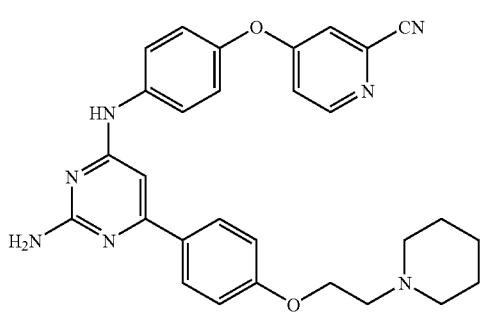

This is prepared by a method analogous to that described for Example 17, starting from 1F, 21 and using piperidine in step 4.

Example 19

Preparation of methyl 4-{4-[(2-amino-6-phenylpyrimidin-4-yl)amino]phenoxy}pyridine-2-carboxylate

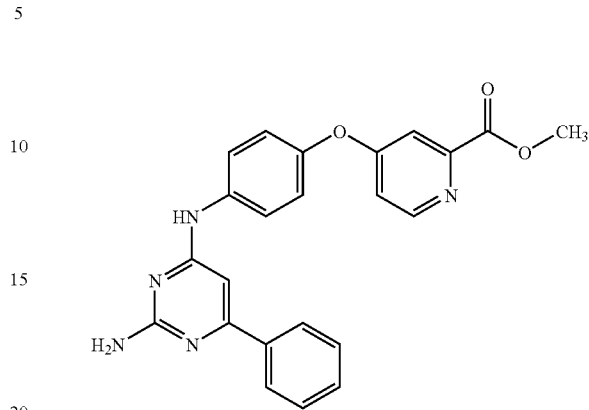

Starting from chloropyrimidine 1A and aniline 2V, this material was prepared using a method analogous to that described for Example 1. ¹H NMR (DMSO-d₆) δ 9.37 (s, 1H), 8.52 (d, 1H), 7.85 (m, 4H), 7.41 (m, 4H), 7.16 (m, 3H), 6.45 (s, 1H), 6.36 (s, 2H), 3.79 (s, 3H); MS ES 414 (M+H)⁺, calcd 414, RT=2.16 min.

Example 20

Preparation of 4-{4-[(2-amino-6-phenylpyrimidin-4-yl)amino]phenoxy}pyridine-2-carboxylic acid

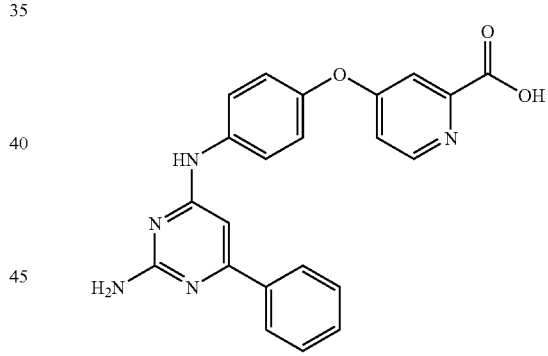

A solution containing the 4-{4-[(2-amino-6-phenylpyrimidin-4-yl)amino]phenoxy}pyridine-2-carbonitrile (20 g, 0.05 mol, Example 8) in concentrated sulfuric acid (150 mL) was heated at 70° C. for 12 h. The reaction mixture was then cooled to −40° C. and water (30 mL) was added, followed by heating at 70° C. for 12 h. The solution was cooled to rt and poured into vigorously stirred ice water (2 L) and stirring was continued for 2 h. The solids were then collected by suction filtration, washed with water (500 mL) and dried by air suction. The slightly damp material was then dissolved in a minimum volume of hot (90° C.) N,N-dimethylformamide and triethylamine was added until the mixture tested slightly acidic. The cooled solution was then poured into ice water (2 L), stirred for 0.5-1 h and the precipitated material was collected by suction filtration. The filter cake was washed with water, followed by isopropanol, diethyl ether, and finally hexane. Air-drying sequentially afforded the carboxylic acid as an off-white solid, 18.5 g (90%). ¹H NMR (DMSO-d₆) δ

9.40 (s, 1H). 8.53 (d, 1H, J=5.8 Hz), 7.90 (m, 4H), 7.46 (m, 3H), 7.40 (d, 1H, J=7.1 Hz), 7.16 (m, 1H,), 7.13 (d, 2H, J=9.1 Hz), 6.50 (s, 1H), 6.40 (s, 2H), 3.30 (br s, 1H), MS ES 400 (M+H)+, calcd 400, RT=1.71 min.

The HCl salt of the title compound, (Example 78) was prepared by addition of Example 20 to a 1N HCl.

Example 21

Preparation of N4-(4-{[2-(morpholin-4-ylcarbonyl)pyridin-4-yl]oxy}phenyl)-6-phenylpyrimidine-2,4-diamine

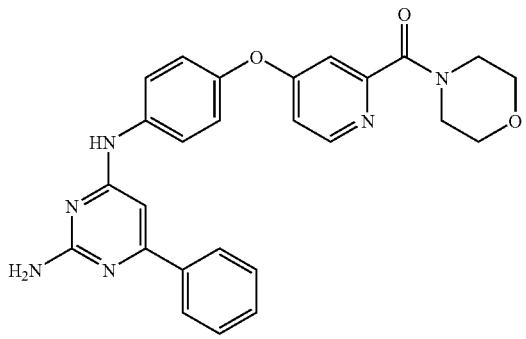

To a solution of 4-{4-[(2-amino-6-phenylpyrimidin-4-yl)amino]phenoxy}pyridine-2-carboxylic acid (Example 20, 0.15 g, 0.38 mmol) in dry DMA (3 mL) was added HATU (0.14 g, 0.38 mmol) and DIEA (0.15 g, 1.13 mmol). The solution was stirred at rt for 0.5 h, followed by addition of morpholine (0.16 g, 1.88 mmol). The resulting solution was stirred at rt overnight, followed by prep-HPLC separation to give 77 mg (35%) pure product. $^1$H NMR (DMSO-d$_6$) δ 10.79 (s, 1H), 8.40 (s, 1H), 7.85 (m, 2H), 7.74 (m, 2H), 7.60 (m, 3H), 7.21 (m, 2H), 7.00 (m, 2H), 6.59 (s, 1H), 3.49 (m, 8H); MS ES 469 (M+H)+, calcd 469.

Example 22

Preparation of 4-{4-[(2-amino-6-phenylpyrimidin-4-yl)amino]phenoxy}-N,N-dimethylpyridine-2-carboxamide

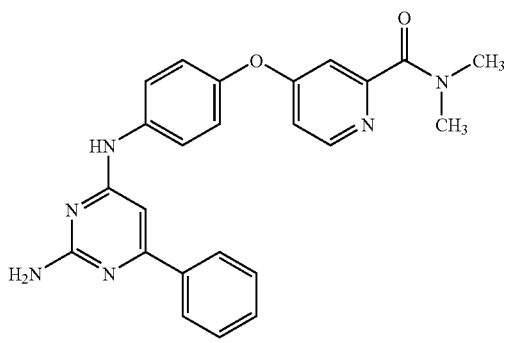

This material is prepared by a method analogous to that described for Example 21, starting from 4-{4-[(2-amino-6-phenylpyrimidin-4-yl)amino]phenoxy}pyridine-2-carboxylic acid and dimethylamine.

Example 23

Preparation of 4-{4-[(2-amino-6-phenylpyrimidin-4-yl)amino]phenoxy}-N-(2-methoxyethyl)pyridine-2-carboxamide

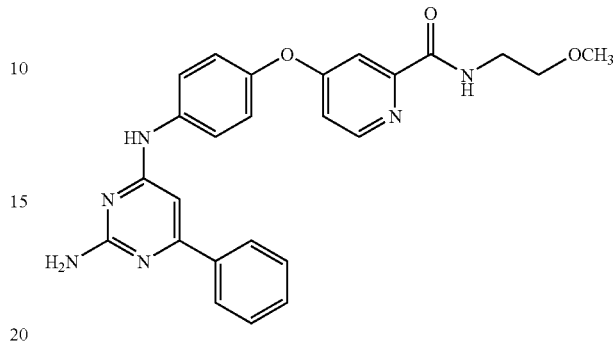

This material was prepared by a method analogous to that described for Example 21, starting from 4 {-[(2-amino-6-phenylpyrimidin-4-yl)amino]phenoxy}pyridine-2-carboxylic acid and 2-methoxyethylamine.

By using the method described for Example 23, and by substituting appropriate starting materials, Examples 79-82 were similarly prepared.

Example 24

Preparation of 4-[4-({2-amino-6-[4-(trifluoromethyl)phenyl]pyrimidin-4-yl}amino)phenoxy]-N-(2-methoxyethyl)pyridine-2-carboxamide

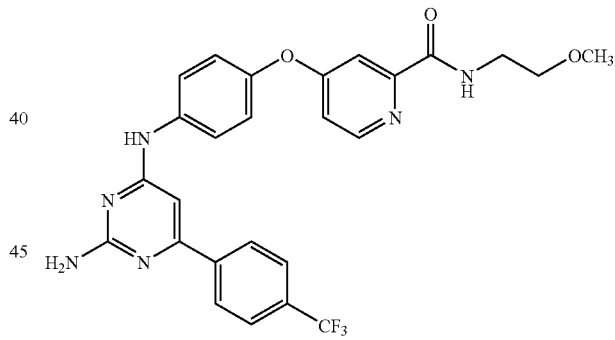

Step 1: Preparation of 4-[4-({2-amino-6-[4-(trifluoromethyl)phenyl]pyrimidin-4-yl}amino)phenoxy]pyridine-2-carboxylic acid

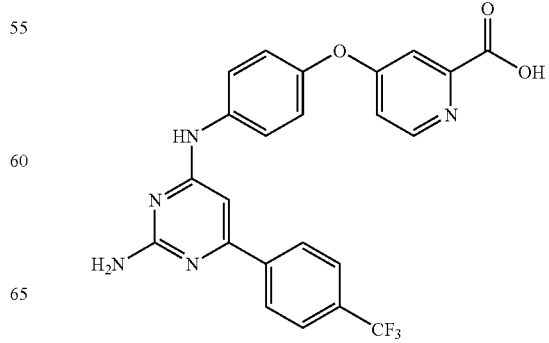

This material is prepared by methods analogous to that described for Example 1 and Example 20, starting from 2I and 1G.

Step 2: Preparation of the Title Compound

This material is prepared by a method analogous to that described for Example 21 starting from 2-methoxyethylamine and 4-[4-({2-amino-6 (trifluoromethyl)phenyl]pyrimidin-4-yl}amino)phenoxy]pyridine-2-carboxylic acid.

Example 25

Preparation of 4-{4-[(2-amino-6-phenylpyrimidin-4-yl)amino]phenoxy}-N-(2-methoxyethyl)-N-methylpyridine-2-carboxamide

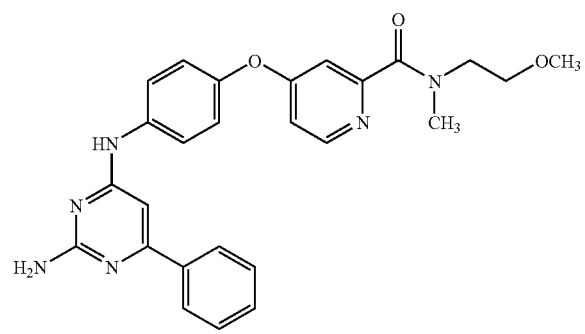

This material is prepared by a method analogous to that described for Example 21, starting from 4-{4-[(2-amino-6-phenylpyrimidin-4-yl)amino]phenoxy}pyridine-2-carboxylic acid and 2-methoxyethyl-N-methyl amine.

Example 26

Preparation of N'-[4-({2-[(4-methylpiperazin-1-yl)carbonyl]pyridin-4-yl}oxy)phenyl]-6-phenylpyrimidine-2,4-diamine

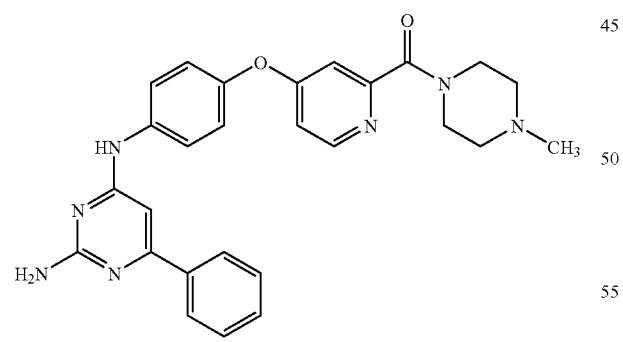

This material is prepared by a method analogous to that described for Example 21, starting from 4-{4-[(2-amino-6-phenylpyrimidin-4-yl)amino]phenoxy}pyridine-2-carboxylic acid (Example 20) and 1-methylpiperizine. $^1$H NMR (DMSO-$d_6$) δ 10.85 (s, 1H), 10.19 (s, 1H), 8.42 (d, 1H), 7.90 (m, 2H), 7.74 (m, 3H), 7.59 (m, 4H), 7.22 (m, 3H), 7.06 (m, 2H), 6.60 (s,1H), 4.51 (m, 1H), 4.08 (m, 1H), 3.45 (m, 3H), 3.17 (m, 3H), 2.78 (s, 3H); MS ES 482 (M+H)$^+$, calcd 482, RT=1.86 min.

Example 27

Preparation of N$^4$-{4-[(2-{[(2-methoxyethyl)amino]methyl}pyridin-4-yl)oxy]phenyl}-6-phenylpyrimidine-2,4-diamine

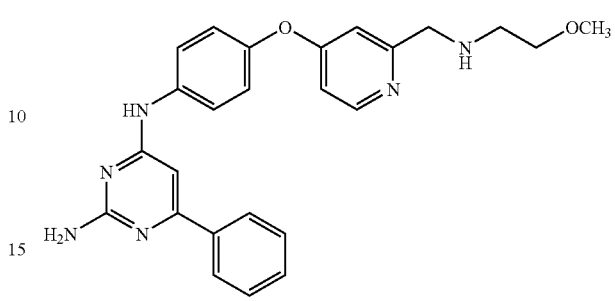

A solution of 4-{4-[(2-amino-6-phenylpyrimidin-4-yl)amino]phenoxy}-N-(2-methoxyethyl)pyridine-2-carboxamide from Example 23 (50 mmol) in anhydrous THF (50 mL) is added in portions to a pre-cooled in ice-bath solution of lithium aluminum hydride (100 mmol, 1.0 M in THF) in anhydrous THF (150 mL). The reaction is stirred at 0° C. for 30 min until evolution of hydrogen subsides. The reaction mixture is refluxed under nitrogen for 48 h. The mixture is brought to 5-10° C. and carefully quenched with water (3.8 mL), 15% NaOH (3.8 mL) and water (12 mL). The mixture is extracted with EtOAc and the organic layer-is-dined and concentrated to give a crude product which is purified by chromatography on a silica column to give the title compound.

(Reference: *Org. Synth. Collect,* 1988, Vol. VI, 382-385)

Example 28

Preparation of 6-(4-fluorophenyl)-N$^4$-(4-{[2-(piperidin-1-ylcarbonyl) pyridin-4-yl]oxy}phenyl)pyrimidine-2,4-diamine

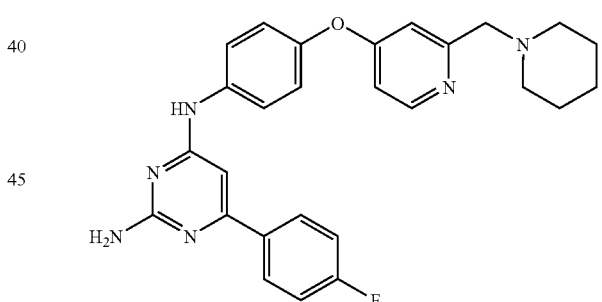

Step 1: Preparation of 4-(4-{[2-amino-6-(4-fluorophenyl)pyrimidin-4-yl]amino}phenoxy)pyridine-2-carboxylic acid

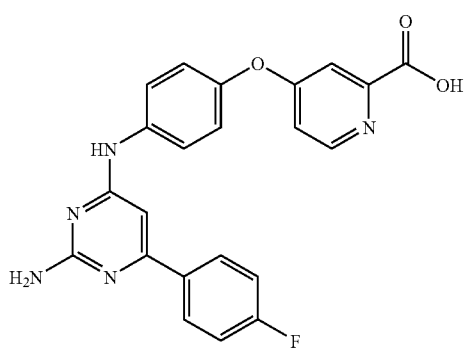

This material is prepared by a method analogous to that described for Examples 1 and 20 starting from 1H and 21.

Step 2: Preparation of 6-(4-methoxyphenyl)-N⁴-(4-{[2-(morpholin-4-ylcarbonyl)pyridin-4-yl]oxy}phenyl)pyrimidine-2,4-diamine

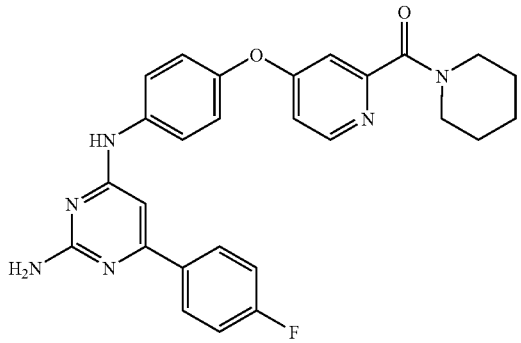

This material is prepared by a method analogous to that described for Example 21, starting from 6-(4-fluorophenyl)-N⁴-[4-(pyridin-4-yloxy)phenyl]pyrimidine-2,4-diamine and piperidine.

Step 3: Preparation of the Title Compound

This material is prepared by a method analogous to that described for Example 27, starting from 6-(4-methoxyphenyl)-N⁴-(4-{[2-(morpholin-4-ylcarbonyl)pyridin-4-yl]oxy}phenyl)pyrimidine-2,4-diamine.

Example 29

Preparation of 6-(4-methoxyphenyl)-N⁴-(4-{[2-(morpholin-4-ylmethyl)pyridin-4-yl]oxy}phenyl)pyrimidine-2,4-diamine

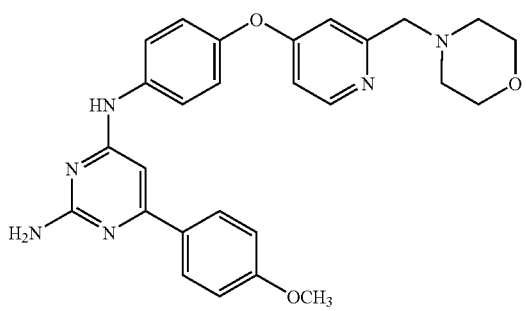

Step 1: Preparation of 4-(4-{[2-amino-6-(4-methoxyphenyl)pyrimidin-4-yl]amino}phenoxy)pyridine-2-carboxylic acid

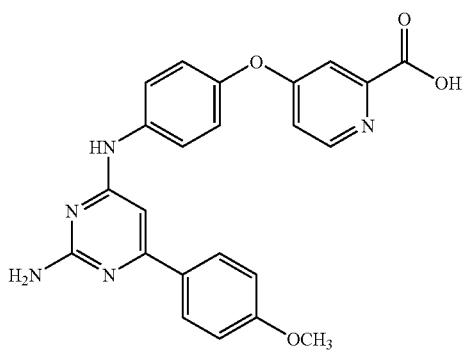

This material is prepared by a method analogous to that described for Examples 1 and 20, starting from 1F and 2I.

Step 2: Preparation of 6-(4-methoxyphenyl)-N⁴-(4-{[2-(morpholin-4-ylcarbonyl)pyridin-4-yl]oxy}phenyl)pyrimidine-2,4-diamine

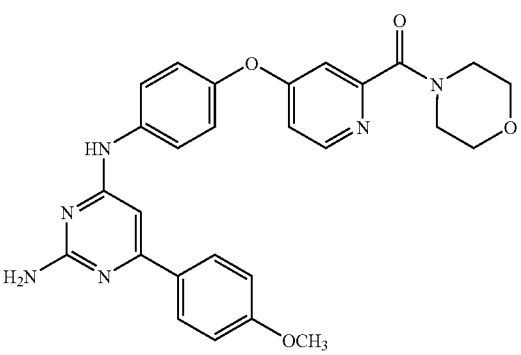

This material is prepared by a method analogous to that described for Example 21, starting from the product from step 1.

Step 3: Preparation of Title Compound

This material is prepared by a method analogous to that described for Example 27, starting from the product of step 2.

Example 30

Preparation of N²-ethyl-6-(3-methoxy-phenyl)-N⁴-[4-(2-trifluoromethyl-pyridin-4-yloxy)-phenyl]-pyrimidine-2,4-diamine

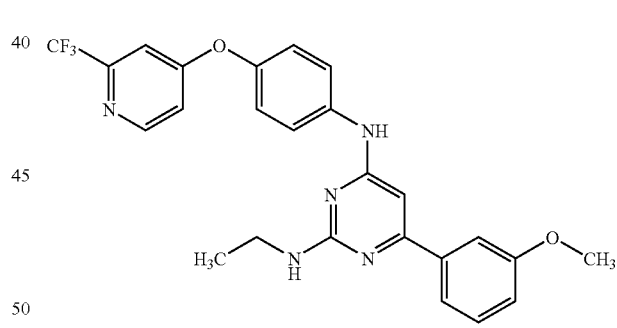

Step 1: Preparation of 2,4-dichloro-6-(3-methoxy-phenyl)-pyrimidine

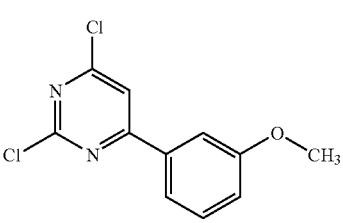

Trichloropyrimidine (11.83 g, 64.49 mmol) was added to a solution of 3-methoxyphenylboronic acid (9.8 g, 64.49 mmol) in a solvent mixture of ethanol (30 mL), toluene (30 mL) and 2M aqueous sodium bicarbonate (96.7 mL) at rt. The resulting mixture was degassed under vacuum for several min before the flask was purged with nitrogen. Dichloro[1,1'-bis(diphenylphosphino)ferrocene]palladium (II)dichloromethane adduct (2.4 g, 3.22 mmol) was added and the resulting mixture was heated for 3 h at 50° C. The cooled reaction mixture was filtered through a silica gel pad and the pad was washed with acetone. The filtrated was evaporated under reduced pressure. The crude material was purified by column chromatography eluting with a gradient of 0 to 45% ethyl acetate/hexanes to give 2,4-dichloro-6-(3-methoxyphenyl)-pyrimidine as a white solid (14.4 g, 65.4%). MS ES 255 (M+H)$^+$, calcd 255, RT=3.35 min.

Step 2: Preparation of [2-chloro-6-(3-methoxy-phenyl)-pyrimidin-4-yl]-[4-(2-trifluoromethyl-pyridinyloxy)-phenyl]-amine

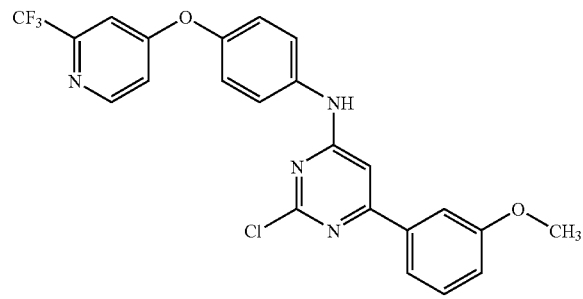

2,4-Dichloro-6-(3-methoxy-phenyl)-pyrimidine (1.0 g, 3.92 mmol) and 4-(2-trifluoromethyl-pyridinyloxy)-phenylamine Intermediate 2U (1.0 g, 3.92 mmol) were suspended in a mixture of isopropanol/water 2:8 (40 mL). The reaction mixture was heated at reflux for 24 h at which point the TLC showed a completed reaction. The reaction mixture was filtered with a fritted glass funnel. The crude residue was purified by HPLC eluting with a gradient of 0 to 71% acetonitrile/water containing 0.1% TFA in both solvents. The TFA salt of [2-chloro-6-(3-methoxy-phenyl)-pyrimidin-4-yl]-[4-(2-trifluoromethyl-pyridin-4-yloxy)-phenyl]-amine was obtained as a yellow oil which solidified on standing. (926 mg, 50.1%). MS ES 473 (M+H)$^+$, calcd 473, RT=3.98 min.

Step 3: Preparation of the title compound: N$^2$-ethyl-6-(3-methoxy-phenyl)-N$^4$-[4-(2-trifluoromethyl-pyridin-4-yloxy)-phenyl]-pyrimidine-2,4-diamine

[2-Chloro-6-(3-methoxy-phenyl)-pyrimidin-4-yl]-[4-(2-trifluoromethyl-pyridin-4-yloxy)-phenyl]-amine (100 mg, 0.21 mmol) and ethylamine (2M THF, 1 mL) were dissolved in n-butanol (3 mL) and the reaction mixture was heated at 120° C. overnight. The reaction mixture were evaporated under vacuum, and the crude residue was purified by HPLC eluting with a gradient of 10 to 85% acetonitrile/water containing 0.1% TFA in both solvents. The TFA salt of N$^2$-Ethyl-6-(3-methoxy-phenyl)-N$^4$-[4-(2-trifluoromethyl-pyridin-4-yloxy)-phenyl]-pyrimidine-2,4-diamine (13.9 mg, 11%) was obtained as a beige solid. $^1$H NMR (acetone-d$_6$) δ 10.36 (br, 1H), 10.06 (Br, 1H), 8.62 (d, J=6 Hz, 1H), 8.00 (br, 1H), 7.53-7.51 (m, 1H), 7.47-7.31 (m, 2H), 7.19-7.12 (m, 3H), 6.66 (s, 1H), 3.94 (s, 3H), 3.59-3.56 (m, 2H), 1.31 (t, J=7 Hz, 3H). MS ES 482 (M+H)$^+$, calcd 482, RT=2.83 min.

Example 31

Preparation of 4-[4-(2-amino-5-bromo-6-phenyl-pyrimidin-4-ylamino)-phenoxy]-pyridine-2-carbonitrile

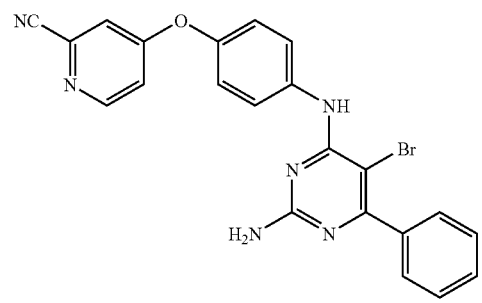

To a solution of 4-[4-(2-amino-6-phenyl-pyrimidin-4-ylamino)-phenoxy]-pyridine-2-carbonitrile (Example 8, 200 mg, 0.53 mmol) and sodium acetate (146.6 mg, 459.8 mmol) in acetic acid (4 mL) at rt was added bromine (84 mg, 0.53 mmol). The reaction was allowed to stand for 2 h after which time dichloromethane (20 mL) was added followed by water (20 mL). The phases were separated and the organic layer was washed with a saturated aqueous bicarbonate solution. The combined organic extracts were dried over MgSO$_4$ and then evaporated under vacuum. The crude material was purified by column chromatography eluting with a gradient of 0 to 60% AcOEt/Hexanes to give 4-[4-(2-Amino-5-bromo-6-phenyl-pyrimidin-4-ylamino)-phenoxy]-pyridine-2-carbonitrile as an orange solid (200 mg, 83%). $^1$H NMR (DMSO d$_6$) δ 8.58 (d, J=5 Hz, 1H, 8.50 (Br, 1H), 7.90-7.86 (m, 2H), 7.67 (d, J=2 Hz, 1H), 7.54-7.51 (m, 2H), 7.47-7.41 (m, 3H), 7.20-7.16 (m, 3H), 6.57 (Br, 2H).

MS ES 459 (M+H)$^+$, calcd 459, RT=2.85 min.

Example 32

Preparation of N$^4$-{4-[2-(2-morpholin-4-yl-ethoxy)-pyridin-4-yloxy]-phenyl}-6-phenyl-pyrimidine-2,4-diamine

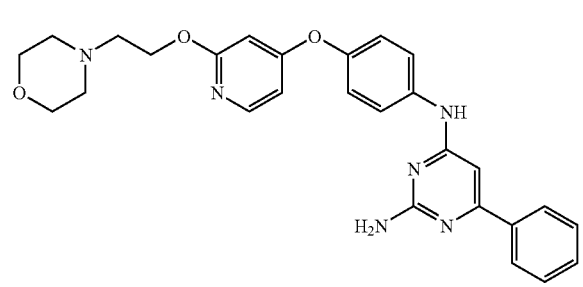

N$^4$-[4-(2-chloro-pyridin-4-yloxy)-phenyl]-6-phenyl-pyrimidine-2,4-diamine (Example 48, 75 mg, 0.19 mmol) was dissolved in toluene (1.5 mL). 2-Morpholin-4-yl-ethanol (61 mg, 0.46 mmol), powdered KOH (22 mg, 0.38 mmol), and 18-crown-6 (20 mg, 0.08 mmol) were subsequently added.

The mixture was stirred at 90° C. overnight, after which time it was diluted with water and extracted with both ethyl acetate and dichloromethane. The combined organic extracts were concentrated and the residue was purified by prep HPLC to give the title compound (14 mg, 15%). $^1$H NMR (DMSO-$d_6$) δ 10.79 (br s, 1H), 9.99 (br s, 1H), 8.08 (d, J=5.8 Hz, 1H), 7.90 (m, 2H), 7.77 (dd, J=7.6, 2.0 Hz, 2H), 7.64 (m, 3H), 7.21 (d, J=8.9 Hz, 2H), 6.69 (dd, J=5.8, 2.1 Hz, 1H), 6.60 (s, 1H), 6.22 (d, J=2.2 Hz, 1H), 4.57 (t, J=5.1 Hz, 2H), 3.96 (m, 2H), 3.68 (m, 2H), 3.50 (m, 4H), 3.15 (m, 2H); MS ES: 485 (M+H)$^+$, calcd 485, RT=1.96 min.

By using the method described for Example 32, and by substituting appropriate starting materials, Examples 83-86 were similarly prepared.

Example 33

Preparation of 6-phenyl-N$^4$-[4-(2-trifluoromethyl-pyridin-4-ylmethyl)-phenyl]-pyrimidin-2,4-diamine

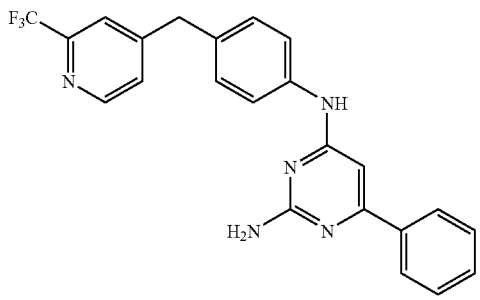

Starting from chloropyrimidine 1A and aniline 2P, this material was prepared using a method analogous to that described for Example 1. $^1$H NMR (DMSO-$d_6$) δ 12.90 (br s, 1H), 10.82 (br s, 1H), 8.64 (d, J=5.1 Hz, 1H), 7.83 (m, 3H), 7.74 (m, 2H), 7.64 (m, 4H), 7.31 (d, J=8.3 Hz, 2H), 6.67 (br s, 1H), 4.11 (s, 2H); MS ES: 422 (M+H)$^+$, calcd 422, RT=2.51 min.

Example 34

Preparation of N$^4$-[4-(2-chloro-pyridin-4-ylmethyl)-phenyl-6-phenyl-pyrimidine-2,4-diamine

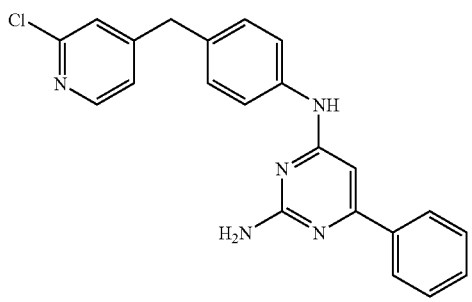

Starting from chloropyrimidine 1A and aniline 2S, this material was prepared using a method analogous to that described for Example 1. $^1$H NMR (DMSO-$d_6$) δ 12.80 (br s, 1H), 10.74 (br s, 1H), 8.29 (dd, J=5.4, 0.6 Hz, 1H), 7.83 (m, 2H), 7.67 (m, 2H), 7.63 (m, 3H), 7.41 (m, 1H), 7.30 (m, 3H), 6.61 (br s, 1H), 3.98 (s, 2H); MS ES: 388 (M+H)$^+$, calcd 388, RT=2.38 min.

Example 35

Preparation of 4-[4-(2-amino-6-phenyl-pyrimidin-4-ylamino)-benzyl]-pyridine-2-carbonitrile

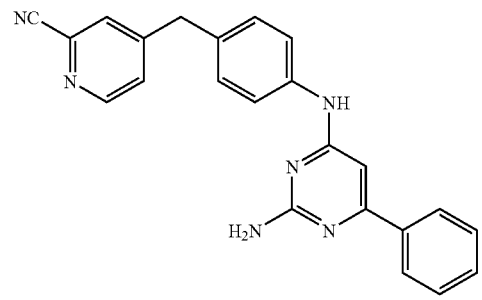

Starting from chloropyrimidine 1A and Intermediate 2Q, this material was prepared using a method analogous to that described for Example 1. $^1$H NMR (DMSO-$d_6$) δ 12.74 (br s, 1H), 10.73 (br s, 1H), 8.63 (d, J=4.9 Hz, 1H), 7.96 (s, 1H), 7.82 (m, 2H), 7.72 (m, 2H), 7.61 (m, 4H), 7.30 (d, J=7.9 Hz, 2H), 6.61 (s, 1H), 4.05 (s, 2H); MS ES: 379 (M+H)$^+$, calcd 379, RT=2.35 min.

By using the method described for Example 35, and by substituting appropriate starting materials, Examples 88-91 were similarly prepared.

Example 36

Preparation of N$^4$-[4-(2-aminomethyl-pyridin-4-ylmethyl)-phenyl]-6-phenyl-pyrimidine-2,4-diamine

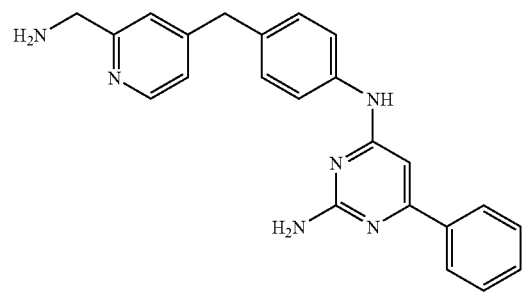

10% Degussa Pd on carbon (15 mg, 0.14 mmol) was flushed with nitrogen then diluted in methanol (1 mL). 4-[4-(2-amino-6-phenyl-pyrimidin-4-ylamino)-benzyl]-pyridine-2-carbonitrile (Example 35, 90 mg, 0.24 mmol) in methanol (2 mL) and concentrated HCl (0.03 mL) were subsequently added, and the mixture was flushed again with nitrogen prior to placing a hydrogen balloon on the flask. The mixture was stirred at rt for 3 h then filtered through Celite® and concentrated. The residue was purified by prep HPLC to give N$^4$-[4-(2-aminomethyl-pyridin-4-ylmethyl)-phenyl]-6-phenyl-pyrimidine-2,4-diamine (10 mg, 11%). $^1$H NMR (CD$_3$OD) δ 8.50 (d, J=5.3 Hz, 1H), 7.76 (m, 4H), 7.63 (m, 3H), 7.28 (m, 4H), 6.53 (s, 1H), 4.22 (s, 2H), 4.05 (s, 2H); MS ES: 383 (M+H)$^+$, calcd 383, RT=1.84 min.

Example 37

Preparation of 6-phenyl-N⁴-(4-{[2-(trifluoromethyl)pyridin-4-yl]oxy}phenyl)pyrimidine-2,4-diamine

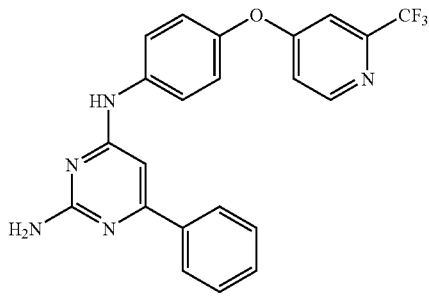

Starting from chloropyrimidine 1A and 4-(2-trifluoromethyl-pyridin-4-yloxy)-phenylamine 2U, the title compound was prepared using a method analogous to that described for Example 1. ¹H NMR (CD₃OD) δ ppm 6.59 (1H, s), 7.16 (1H, dd, J=5.6, 2.4 Hz), 7.29-7.33 (2H, m), 7.42 (1H, d, J=2.4 Hz), 7.61-7.67 (3H, m), 7.75-7.79 (2H, m), 7.94 (2H, s), 8.63 (1H, d, J=5.7 Hz), 10.79 (1H, s); MS ES 424 (M+H)⁺, calcd 424, RT=2.48 min.

Example 38

Preparation of N⁴-(4-{[1-oxido-2-(trifluoromethyl)pyridin-4-yl]oxy}phenyl)-6-phenylpyrimidine-2,4-diamine

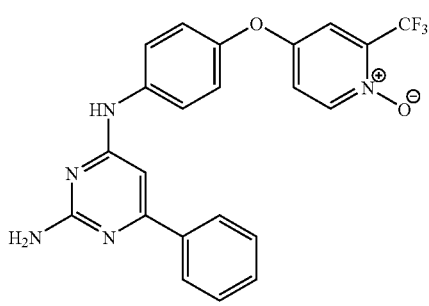

To a solution of 6-phenyl-N⁴-(4-{[2-(trifluoromethyl)pyridin-4-yl]oxy}phenyl)pyrimidine-2,4-diamine (0.10 g, 0.24 mmol, Example 37) in CHCl₃, m-CPBA (77%, 0.053 g, 0.24 mmol) was added and the mixture was stirred at rt overnight. Solvent was removed in vacuo, and the residue was taken up in DMF and purified by prep-HPLC to provide 11 mg of an off-white solid (11%). ¹H NMR (DMSO-d₆) δ 10.20 (s, 1H), 8.64 (d, J=5.7 Hz, 1H), 7.93 (s, 1H), 7.86-7.92 (m, 2H), 7.52-7.56 (m, 2H), 7.41-7.49 (m, 5H), 7.30-7.39 (m, 2H), 7.24 (dd, J=5.7 Hz, 1H), 6.71 (s, 1H). MS ES 440 (M+H)⁺, calcd 440, RT=2.97 min.

Example 39

N⁴-(4-{[2-(aminomethyl)pyridin-4-yl]oxy}phenyl)-6-phenylpyrimidine-2,4-diamine

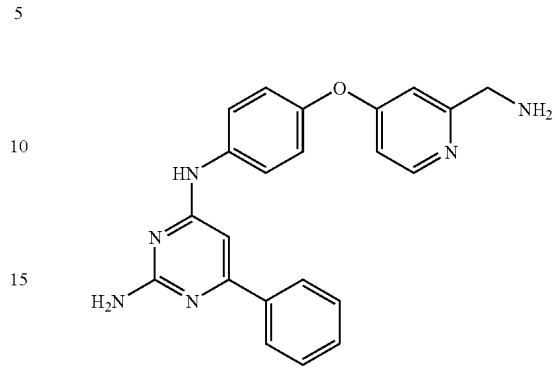

A mixture containing of 4-{4-[(2-amino-6-phenylpyrimidin-4-yl)amino]phenoxy}pyridine-2-carbonitrile (3.2 g, 8.4 mmol, Example 8) and 10% palladium on carbon catalyst (0.75 g, Degussa) in glacial acetic acid (100 mL) was shaken on a Parr hydrogenation apparatus (3 atm H₂) until hydrogen consumption ceased. The suspension was filtered through diatomaceous earth and the filtrate was concentrated in vacuo. The residue was dissolved in N,N-dimethylformamide and treated with triethylamine until basic, then was added to vigorously stirred ice water. The precipitated solids were collected by suction filtration and washed with water, isopropanol, diethyl ether and finally hexane. The product was dried by air suction to afford a tan powder, 2.36 g (73%). ¹H NM (DMSO-d₆) δ ppm 9.39 (s, 1H), 8.30 (m, 1H), 789 (m, 4H), 7.44 (m, 3H), 7.05 (m, 2H, 6.96 (dm, 1H), 6.69 (dm, 1H), 6.51 (s, 1H), 6.36 (s, 2H), 4.16 (d, 0.5H, J-5.8 Hz, CH₂NH₂), 3.73 (s, 1.5H, CH₂NH₂), 3.28 (br s, 2H, NH₂), MS ES 385 (M+H)⁺, calcd 385 RT=1.75 ml.

The TFA salt (Example 92) was obtained by preparative HPLC of the above reaction mixture.

Example 40

Preparation of N-[(4-{4-[(2-amino-6-phenylpyrimidin-4-yl)amino]-phenoxy}pyridin-2-yl)methyl]methanesulfonamide

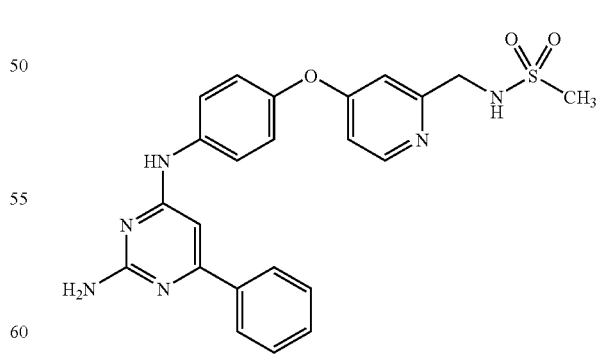

Methanesulfonyl chloride (0.040 mL, 0.52 mmol) was added to a solution of N⁴-(4-{[2-(aminomethyl)pyridin-4-yl]oxy}phenyl)-6-phenylpyrimidine-2,4-diamine (Example 39, 0.20 g, 0.52 mmol) and DMAP (0.064 g, 0.52 mmol) in pyridine (8.0 mL) at 0° C. The mixture was allowed to warm

Example 41

Preparation of N-[(4-{4-[(2-amino-6-phenylpyrimidin-4-yl)amino]phenoxy}pyridin-2-yl)methyl]4-fluorobenzamide

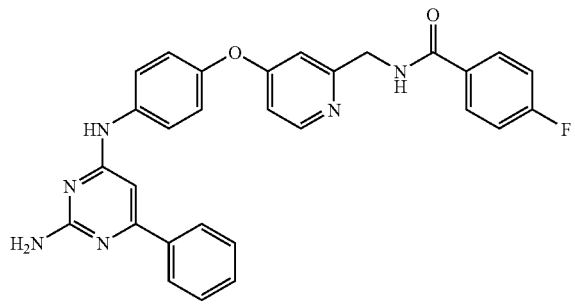

$N^4$-(4-{[2-(Aminomethyl)pyridin-4-yl]oxy}phenyl)-6-phenylpyrimidine-2,4-diamine (50 mg, 0.13 mmol, Example 39) and 4-fluorobenzoyl chloride (20.6 mg, 0.13 mmol) were suspended in THF (1 mL) and stirred at rt for 24 h. TLC and LC-MS indicated the reaction was completed. The mixture was extracted with EtOAc and washed with 1N aqueous sodium hydroxide solution (2×) and $H_2O$ (3×). The organic layer was dried and concentrated to give 68 mg of the crude product. The residue was purified by Prep-TLC ($CH_3OH$:EtOAc=2:8) to obtain 38 mg (58%) of the title product as a yellowish oil. $^1H$ NMR ($CD_3OD$) δ 8.34 (d, 1H), 7.82 (m, 4H), 7.78 (d, 2H), 7.44 (m, 3H), 7.15 (t, 2H), 7.02 (d, 2H), 6.85 (d, 1H), 6.82 (s, 1H), 6.42 (s, 1H), 4.59 (s, 2H); MS ES 507 $(M+H)^+$, calcd 507, RT=2.50 min; TLC (MeOH/EtOAc=20/80) $R_f$=0.57.

Example 42

Preparation of N'-[(4-{4-[(2-amino-6-phenylpyrimidin-4-yl)amino]phenoxy}pyridin-2-yl)methyl]-N,N-diethylurea

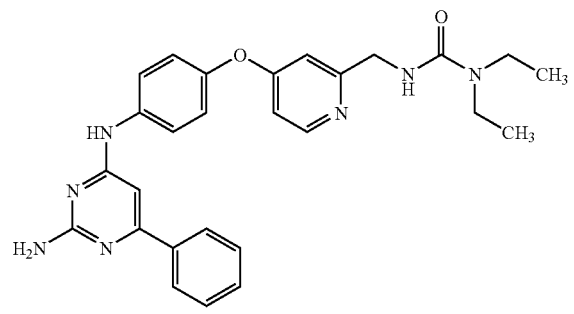

$N^4$-(4-{[2-(Aminoethyl)pyridin-4-yl]oxy}phenyl)-6-phenylpyrimidine-2,4-diamine (50 mg, 0.13 mmol, Example 39) and diethylcarbamyl chloride (20.6 mg, 0.13 mmol) were suspended in THF (1 mL) and stirred at rt for 24 h. TLC and LC-MS indicated that the reaction was complete. The mixture was extracted with EtOAc and washed with 1N aqueous sodium hydroxide solution (2×) and $H_2O$ (3×). The organic layer was dried and concentrated to give 72 mg of the crude product. The residue was purified by Prep-TLC ($CH_3OH$:EtOAc=2:8) to obtain 40 mg (63%) of the title product as a yellowish oil. $^1H$ NMR ($CD_3OD$) δ 8.28 (d, 1H), 7.84 (m, 3H), 7.81 (s, 1H), 7.48 (m, 3H), 7.05 (d, 2H), 6.84 (m, 1H), 6.75 (s, 1H), 6.44 (s, 1H), 4.39 (s, 2H), 3.23 (m, 4H), 1.20 (t, 6H); MS ES 484 $(M+H)^+$, calcd 484, RT=2.37 min; TLC (MeOH/EtOAc=20/80) $R_f$=0.4

By using the method described for Example 42, and by substituting appropriate starting materials, Examples 99-104 were similarly prepared.

Example 43

Preparation of $N^4$-[4-({4-[(2S)-(+)-2-methoxymethyl)pyrrolidin-1-yl]pyridin-2-yl}oxy)phenyl]-6-phenylpyrimidine-2,4-diamine

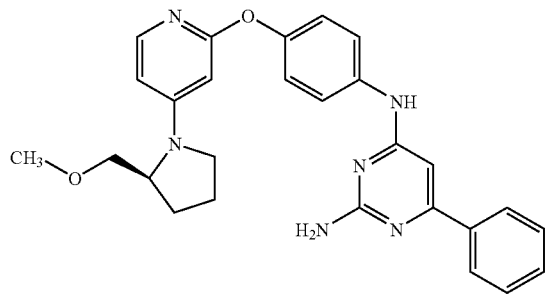

$N^4$-{4-[(4-Bromopyridin-2-yl)oxy]phenyl}-6-phenylpyrimidine-2,4-diamine (75 mg, 0.17 mmol, was prepared by the method of Example 1 using and Intermediates 2T and 1A as starting materials. $N^4$-[4-(4-bromo-pyridin-2-yloxy)-phenyl]-6-phenyl-pyrimidine-2,4-diamine, was then combined with (S)-(+)-2-(methoxymethyl)pyrrolidine (99.5 mg, 0.86 mmol) in a 5-mL reaction flask and heated at 108° C. with stirring for 24 h. TLC and LC-MS indicated that the reaction was complete. After cooling to rt, the reaction mixture was extracted with EtOAc and washed with 1N aqueous sodium hydroxide solution (2×) and $H_2O$ (3×). The organic layer was dried and concentrated to give 75 mg of the crude product. The residue was purified by Prep-TLC ($CH_3OH$:EtOAc=2:8) to obtain 32 mg (40%) of the title product as a yellowish oil. $^1H$ NMR ($CD_3OD$) δ 7.82 (m, 2H), 7.70 (m, 3H), 7.41 (m, 3H), 7.04 (d, 2H), 6.41 (m, 2H), 5.94 (s, 1H), 3.86 (s, 1H), 3.38 (m, 2H), 3.30 (m, 3H), 3.18 (m, 1H), 2.01 (m, 4H), 1.30 (m, 1H); MS ES 469 $(M+H)^+$, calcd 469, RT=1.9 min; TLC (EtOAc) $R_f$=0.2.

By using the method described for Example 43, and by substituting appropriate starting materials, Examples 105-109 were similarly prepared.

Example 44

Preparation of N[4]-[4-({2-[(isopropylamino)methyl]pyridin-4-yl}oxy)phenyl]-6-phenylpyrimidine-2,4-diamine

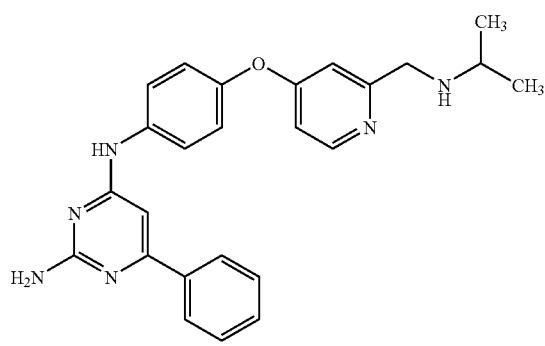

Acetone (11.51 mg, 0.20 mmol), N[4]-(4-{[2-(aminomethyl)pyridin-4-yl]oxy}phenyl)-6-phenylpyrimidine-2,4-diamine (80 mg, 0.21 mmol, Example 39) and titanium (IV) methoxide (68.2 mg, 0.40 mmol) were suspended in $CH_2Cl_2$ (5 mL) and stirred at rt for 24 h. Sodium triacetoxyborohydride (105 mg, 0.50 mmol) was added into the reaction mixture and the mixture was stirred at rt for another 24 h. The mixture was filtered through a Celite® pad and washed with $CH_2Cl_2$. A small amount of Celite® was added to the filtrate and 5 mL of water was added to quench the reaction. After it was stirred for 20 min, the $CH_2Cl_2$ was removed in vacuo. The residue was taken up in ethyl acetate and washed with 1N NaOH (2×) and water (3×). The organic layer was concentrated and purified by Prep-TLC (MeOH) to give 36 mg (42.2%) of the title product as a white solid. $^1$H NMR ($CD_3OD$) δ 8.35 (d, 1H), 7.82 (d, 2H), 7.00 (d, 2H), 7.44 (m, 3H), 7.08 (m, 2H), 7.01 (s, 1H), 6.82 (m, 1H), 6.46 (s, 1H), 3.81 (s, 2H), 2.80 (m, 1H), 1.10 (d, 6H); MS ES 427 (M+H)$^+$, calcd 427, RT=2.59 min; TLC (MeOH)$R_f$=0.38.

By using the method described for Example 44, and by substituting appropriate starting materials, Examples 110-111 were similarly prepared.

Example 45

Preparation of 4-[4-(2-Amino-6-phenylpyrimidin-4-ylamino)phenoxy]pyridine-2-carboxylic acid (2-hydroxyethyl)amide

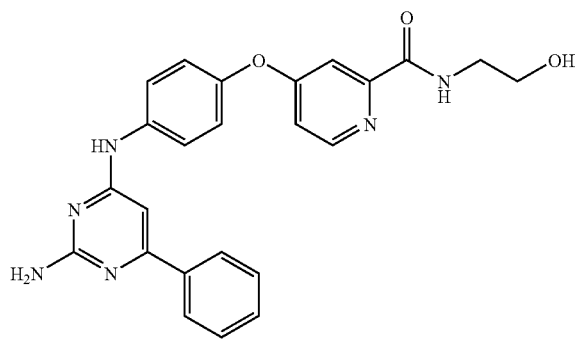

Chloropyrimidine 1A (0.2 g, 0.97 mmol) and Intermediate 2N (0.38 g, 0.97 mmol), were suspended in n-butanol (5 mL) and heated at 80° C. for 12 h. LC-MS indicated that the reaction was complete. KF was then added to the reaction mixture and heating was continued at 80° C. for 5 h. The solvent was removed by rotary evaporation, and the residue was treated with 10% sodium carbonate and extracted with EtOAc (20 mL×3). The organic extracts were combined, washed with water and brine, dried over magnesium sulfate, and evaporated to afford a solid that was washed with methanol to give pure product, 0.19 g (44%) $^1$H NMR (DMSO-$d_6$) δ 936 (s, 1H), 8.62 (t, 1H), 8.45 (d, 1H), 7.88 (m, 4H), 7.47 (1,3H), 7.38 (d, 1H), 7.11 (m, 3H), 6.45 (s, 1H), 6.34 (s, 2H), 3.49 (t, 2H), 3.36 (t, 2H); MS ES 443 (M+H)$^+$ calcd 443.

Example 46

Preparation of 6-phenyl-N[4]-{4-[2-(1H-tetrazol-5-yl)pyridin-4-yloxy]phenyl}pyrimidine-2,4-diamine

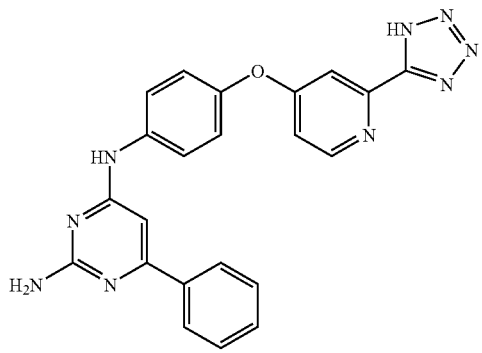

A mixture of 4-{4-[(2-amino-6-phenylpyrimidin-4-yl)amino]phenoxy}pyridine-2-carbonitrile (0.20 g, 0.53 mmol, prepared in Example 8), sodium azide (0.051 g, 0.79 mmol), and triethylamine (0.11 g, 0.79 mmol) in toluene (15 mL) was heated at 100° C. for 2 days. The mixture was then treated with cold water. The solid was collected by filtration, washed with water and methanol to give pure product, 0.14 g (63%). $^1$H NMR (DMSO-$d_6$) δ 9.51 (s, 1H), 8.62 (d, 1H), 7.94 (m, 4H), 7.55 (d, 1H), 7.48 (m, 3H), 7.19 (m, 3H), 6.48 (m, 3H); MS ES 424 (M+H)$^+$ calc 424.

Example 47

Preparation of N[4]-{4-[2-(4,5-Dihydro-1H-imidazol-2-yl)pyridin-4-yloxy]phenyl}-6-phenylpyrimidine-2,4-diamine

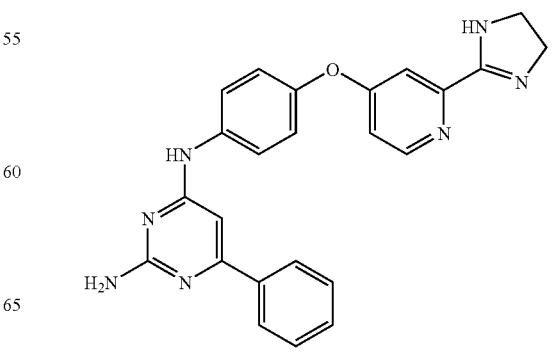

A mixture of 4-{4-[(2-amino-6-phenylpyrimidin-4-yl)amino]phenoxy}pyridine-2-carbonitrile (0.2 g, 0.53 mmol, prepared in Example 8), ethylene diamine (0.095 g, 1.58 mmol), and sulfur (0.05 g, 1.58 mmol) in DMF (3 mL) was heated at 80° C. for 3 days. The solvent was then removed by evaporation under reduced pressure. The residue was purified by preparative HPLC followed by preparative TLC (EtOAc: NH$_4$OH=99:2) to afford pure product, 0.01 g (5%). $^1$H NMR (DMSO-d$_6$) δ 9.39 (s, 1H), 8.41 (d, 1H), 7.84 (m, 4H), 7.42 (m, 3H), 7.37 (d, 1H), 7.09 (m, 3H), 6.95 (s, 1H), 6.46 (s, 1H), 6.37 (s, 2H); MS ES 424 (M+H)$^+$ calc 424.

Example 48

Preparation of N$^4$-[4-(2-Chloro-pyridin-4-yloxy)-phenyl]-6-phenyl-pyrimidine-2,4 diamine

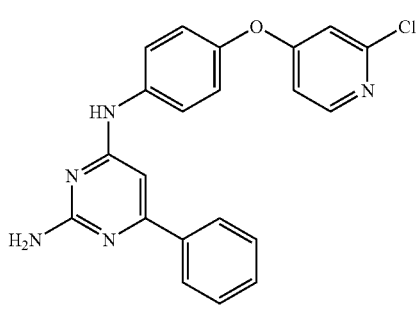

This compound was prepared by reaction of 1A with 2R by the method described in Example 1. $^1$H NMR (DMSO-d$_6$) δ 9.40 (s, 1H), 8.22 (d, 1H), 7.85 (m, 4H), 7.45 (m, 3H), 7.11 (m, 2H), 6.88 (m, 2H), 6.46 (s, 1H), 6.36 (s, 2H); MS ES 390 (M+H)$^+$, calcd 390, RT=2.27 min.

By using the method described for Example 48, and by substituting appropriate starting materials, Examples 113-118 were similarly prepared.

Example 49

Preparation of (S)—N$^4$-{4-[2-(2-Methoxymethylpyrrolidin-1-yl)pyridin-4-yloxy]phenyl}-6-phenylpyrimidine-2,4-diamine

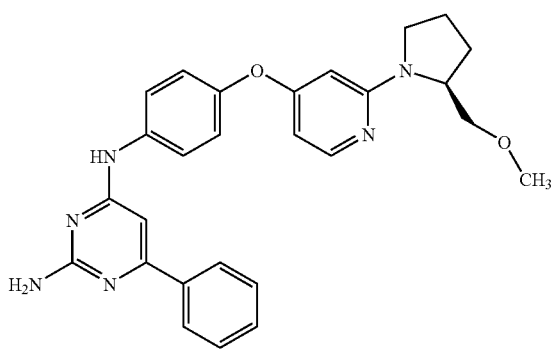

A mixture of N$^4$-{4-[(2-chloropyridin-4-yl)oxy]phenyl}-6-phenylpyrimidine-2,4-diamine (0.15 g, 0.38 mmol, prepared in Example 48) and (S)-(+)-2-(methoxymethyl)pyrrolidine (2 mL) was heated at 80° C. for 3 days. The mixture was cooled to rt and separated by preparative HPLC directly. The desired fractions were combined, neutralized by 10% sodium carbonate, and extracted with EtOAc (3×). The extracts were combined, dried over magnesium sulfate, and evaporated to furnish pure product, 0.04 g (22%). $^1$H NMR (DMSO-d$_6$) δ 9.24 (s, 1H), 7.89 (m, 3H), 7.78 (m, 2H), 7.42 (m, 3H), 7.00 (m, 2H), 6.44 (s, 1H), 6.34 (s, 2H), 6.10 (m, 1H), 5.85 (d, 1H), 4.06 (m, 2H), 3.40 (m, 1H), 3.21 (s, 3H), 3.08 (m, 4H), 1.82 (m, 4H); MS ES 469 (M+H)$^+$ calc 469.

By using the method described for Example 49, and by substituting appropriate starting materials, Examples 119-147 were similarly prepared.

Example 50

Preparation of 2-amino-N-(4-{2-amino-6-[4-(2-trifluoromethylpyridin-4-yloxy)phenylamino]pyrimidin-4-yl}phenyl)-3-hydroxypropionamide

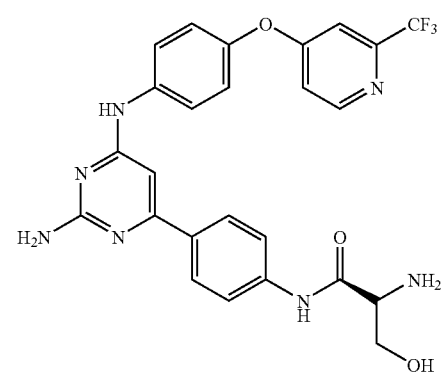

To a solution of (4S)-3-(tert-butoxycarbonyl)-2,2-dimethyl-1,3-oxazolidine-4-carboxylic acid (0.56 g, 2.3 mmol) in dry N,N-dimethylacetamide (10 mL) was added HATU (0.11 g, 2.87 mmol) and DIEA (0.742 g, 5.75 mmol). After the reaction solution was stirred at rt for 1 h, 6-(4-aminophenyl)-N$^4$-(4-{[2-(trifluoromethyl)pyridin-4-yl]oxy}phenyl)pyrimidine-2,4-diamine (Example 165, 0.84 g, 1.92 mmol) was added. The solution was stirred for an additional 24 h at rt and separated by preparative HPLC to afford a solid intermediate, which was treated with methanol (10 mL) and concentrated HCl (0.5 mL) for 12 h at rt. The resulting mixture was diluted with DMSO and purified by HPLC to give a solid. The solid was stirred with saturated sodium bicarbonate and EtOAc for 2 h. The organic layer was separated, washed with water and brine, dried over magnesium sulfate, and evaporated to afford 0.433 g (43%) of pure product. $^1$H NMR (DMSO-d$_6$) δ 9.34 (s, 1H), 8.59 (d, 1H), 7.88 (m, 4H), 7.76 (d, 2H), 7.37 (s, 1H), 7.16 (m, 3H), 6.45 (s, 1H), 6.36 (s, 2H), 4.88 (t, 1H), 3.56 (m, 2H), 3.39 (m, 1H); MS ES 526 (M+H)$^+$ calcd 526.

By using the method described for Example 50, and by substituting appropriate starting materials, Examples 148-152 were similarly prepared.

Example 51

Preparation of 4-{2-amino-6-[(4-{[2-(trifluoromethyl)pyridin-4-yl]oxy}phenyl)amino]pyrimidin-4-yl}phenol

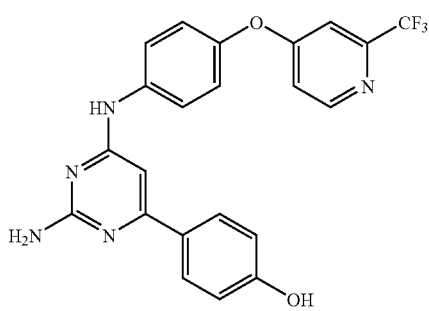

Step 1: Preparation of 6-chloro-$N^4$-(4-{[2-(trifluoromethyl)pyridin-4-yl]oxy}phenyl)pyrimidine-2,4-diamine

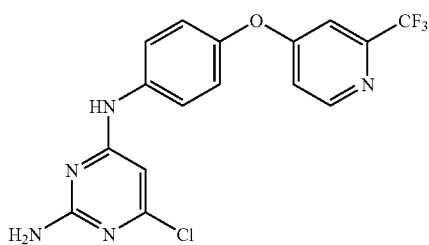

A stirred solution containing 2-amino-4,6-dichloropyrimidine (17.74 g, 0.11 mol) and 4-{[2-(trifluoromethyl)pyridin-4-yl]oxy}aniline (Intermediate 2U) in water (400 mL), isopropanol (100 mL) and concentrated hydrochloric acid (5 mL) was heated at 65° C. for 18 h. The reaction was cooled to 0° C. and the yellow-tan solid was collected by suction filtration and washed with water. The filtered product was dissolved in hot N,N-dimethylformamide (90° C.) and triethylamine was slowly added until the solution was slightly basic (pH~8). The solution was then cooled to rt, added to vigorously stirred ice water (1.2 L), and stirring was continued for 1 h. The tan solids were collected by suction filtration and washed sequentially with water, isopropanol, diethyl ether and finally hexane. The material was dried by air suction to afford a light tan solid, 28.8 g (77%). $^1$H NMR (DMSO-$d_6$) δ ppm 9.46 (s, 1H), 8.59 (d, 1H, J=5.6 Hz), 7.81 (d, 2H, J=9.0), 7.37 (d, 1H, J=2.4 Hz), 7.17 (d, 2H, J=9.0 Hz), 7.11 (dd, 1H, J=2.6, 5.6 Hz), 6.78 (s, 2H), 6.00 (s, 1H).

MS ES 382 (M+H)$^+$, calcd 382 RT=2.93 min.

Step 2: Preparation of the Title Compound

To a 8 mL microwave tube was added 6-chloro-$N^4$-(4-{[2-(trifluoromethyl)-pyridin-4-yl]oxy}phenyl)pyrimidine-2,4-diamine (0.2 g, 0.52 mmol), boronic ester (0.17 g, 0.79 mmol), PdCl$_2$dppf-CH$_2$Cl$_2$ complex (0.023 g, 0.03 mmol), potassium carbonate (0.18 g, 1.3 mmol), N,N-dimethylacetamide (3 mL), and water (1 mL). The mixture was degassed, flushed with nitrogen, and heated at 150° C. for 15 min in a microwave reactor. The mixture was filtered, and the filtrate was separated by prep HPLC. The desired fractions were combined, basified, and extracted with EtOAc (3×). The EtOAc extracts were then washed with water and brine, dried over magnesium sulfate, and evaporated to give 45 mg (20%) pure product. $^1$H NMR (DMSO-$d_6$) δ 9.75 (s, 1H), 9.22 (s, 1H), 8.58 (d, 1H), 7.86 (d, 2H), 7.76 (d, 2H), 7.35 (s, 1H), 7.12 (m, 3H), 6.78 (m, 2H), 6.39(s, 1H), 6.20 (s, 2H); MS ES 440 (M+H)$^+$, calcd 440.

By using the method described for Example 51, and by substituting appropriate starting materials, Examples 153-184 were similarly prepared.

Example 52

Preparation of sulfamic acid, 4-{2-amino-6-[4-(2-trifluoromethylpyridin-4-yloxy)phenylamino]pyrimidin-4-yl}phenyl ester

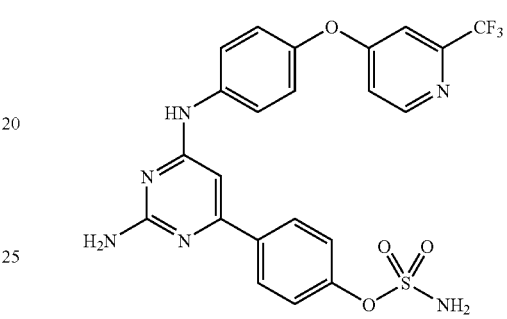

To neat chlorosulfonyl isocyanate (0.166 g, 1.37 mmol) was added dropwise formic acid (97%, 0.63 g, 1.37 mmol) while cooling in ice-water bath. The mixture was stirred at rt until gas evolution ceased. The resulting sulfamoyl chloride was added to a solution of 4-{2-amino-6-[(4-{[2-(trifluoromethyl)pyridin-4-yl]oxy}phenyl)amino]pyrimidin-4-yl}phenol (0.06 g, 0.14 mmol, Example 51) in dry N,N-dimethylacetamide at 0° C. The reaction mixture was then stirred at rt for 12 h. The solution was diluted with methanol and separated by preparative HPLC. The desired fractions were combined, basified with saturated sodium carbonate, and extracted with EtOAc (3×). The extracts were combined, washed with brine, dried over magnesium sulfate, and evaporated to give desired product, 0.025 g (35%). $^1$H NMR (DMSO-$d_6$) δ 9.42 (s, 1H), 8.59 (d, 1H), 8.09 (d, 2H), 7.98 (m, 2H), 7.85 (m, 2H), 7.35 (m, 3H), 7.10 (m, 3H), 6.42 (s, 1H), 6.36 (s, 2H); MS ES 519 (M+H)$^+$ calcd 519.

By using the method described for Example 52, and by substituting appropriate starting materials, Examples 185-186 and 332 were similarly prepared. In addition, by selection of the appropriate starting materials, this method can be used for the preparation of Examples 326-331, and 333-334

Example 53

Preparation of $N^4$-[4-(2-aminopyridin-4-yloxy)phenyl]-6-phenylpyrimidine-2,4-diamine

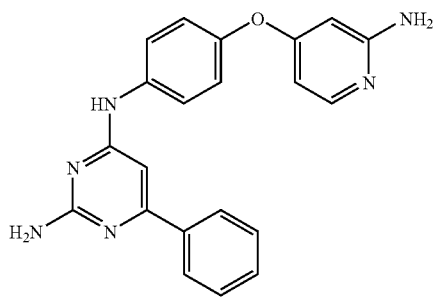

To a 8-mL vial was added Pd$_2$(dba)$_3$ (0.028 g, 0.03 mmol), 2-dicyclohexylphosphinobiphenyl (0.025 g, 0.070 mmol), and N$^4$-{4-[(2-chloropyridin-4-yl)oxy]phenyl}&phenylpyrimidine-2,4-diamine (0.20 g, 0.51 mmol, Example 48). The vial was sealed, evacuated, and back filled with nitrogen. THF was then added via syringe, followed by addition of LiHMDS (1M in THF, 0.72 mL, 0.72 mmol). The mixture was heated at 65° C. overnight. The mixture was then cooled to rt, treated with 1N HCl, and stirred for 12 h at rt. The mixture was then neutralized using 1N NaOH and extracted with methylene chloride (10 mL×3). The organic extracts were combined, washed with brine, dried over magnesium sulfate, and purified by preparative HPLC to furnish 0.035 g of the desired product (18%). $^1$H NMR (CD$_3$OD) δ 7.96 (d, 2H), 7.79 (m, 3H), 7.60 (m, 3H), 7.22 (m, 2H), 6.61 (d, 1H), 6.58 (s, 1H), 6.20 (s, 1H); MS ES 371 (M+H)$^+$ calcd 371.

Example 54

High-Speed Analoging (HSA) Synthesis Method A

To a mixture of 1 equivalent of the chloropyrimidine (100 mg, e.g. compound 9 General Method B), 2 equivalent of boronic acid (e.g. General Method B), and 0.06 equivalent of PdCl$_2$(dppf) CH$_2$Cl$_2$ complex in 2.3 mL anhydrous N,N-dimethylacetamide in a 5 mL microwave reaction vessel was added 3.1 equivalent of 2 M K$_2$CO$_3$ aqueous solution. After the resulting mixture was degassed for 10 min using N$_2$, the vial was sealed and heated at 150° C. for 20 min in a microwave reactor. The reaction mixture was filtered, and the filtrate was purified by pre-HPLC eluting with 15% to 85% acetonitrile using a Phenomenex Luna 5μ C18 150×30 mm column to provide the final product.

By using the appropriate starting materials, the method described for Example 54, was utilized for the preparation of Examples 112 and 187-219.

Example 55

High-Speed Analoging (HSA) Synthesis Method B

To a mixture of 1 equivalent of the chloropyrimidine (100 mg, e.g. compound 9 General Method B), 2 equivalents of boronic acid (General Method B), and 0.06 equivalent of PdCl$_2$(dppf) CH$_2$Cl$_2$ complex in 2.3 mL anhydrous N,N-dimethylacetamide in a 8 mL microwave reaction vessel was added 3.1 equivalent of 2M K$_2$CO$_3$ aqueous solution. After the resulting mixture was degassed for 10 min using N$_2$, the vial was sealed and heated at 140° C. for 20 min in a microwave reactor. The reaction mixture was filtered, and the filtrate was purified by pre-HPLC eluting with 15% to 85% acetonitrile using a Phenomenex Luna 5μ C18 150×30 mm column to provide the final product.

By using the appropriate starting materials, the method described for Example 55, was utilized for the preparation of Examples 220-279

Example 56

High-Speed Analoging (HSA) Synthesis Method C

A mixture of 1 equivalent chloropyrimidine (e.g. compound 9 General Method B), 2 equivalents of boronic acid (General Method B), and 0.1 equivalent of PdCl$_2$(dppf)-CH$_2$Cl$_2$ complex in 2.5 mL anhydrous N,N-dimethylacetamide and 0.5 mL of 2 M K$_2$CO$_3$ in water in a 5 mL microwave reaction vessel under nitrogen was heated at 140° C. for 20 min in the personal microwave reactor. The reaction mixture was filtered, and the filtrate was purified by pre-HPLC eluting with 15% to 85% acetonitrile containing 0.1% TFA using a Phenomenex Luna 5μ C18 150×30 mm column to provide the final product.

By using the appropriate starting materials, the method described for Example 56, was utilized for the preparation of Examples 280-325

Example 57

Preparation of 4-[2-amino-6-({4-[(2-chloropyridin-4-yl)oxy]phenyl}amino)pyrimidin-4-yl]phenol

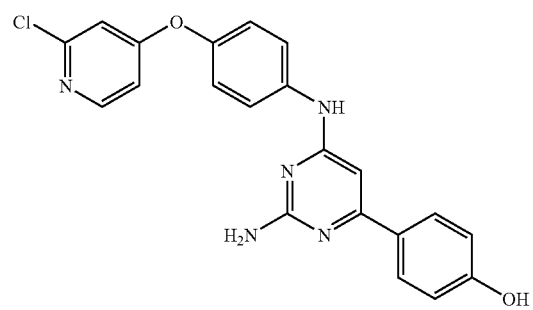

Step 1: Preparation of 4-(2-amino-6-chloropyrimidin-4-yl)phenyl tert-butyl carbonate

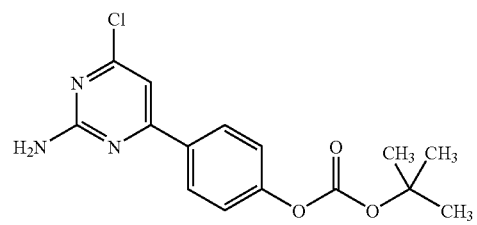

To a mixture of 2-amino-4,6-dichloropyrimidine (1.5 g, 9.15 mmol), t-butyl-4-(4,4,5,5-tetramethyl-1,3,2-dioxaborolan-2-yl)phenyl carbonate (2.9 g, 9.15 mmol), PdCl$_2$dppf CH$_2$Cl$_2$ complex (0.45 g, 0.55 mmol), and DME (14 mL) was added a solution of potassium carbonate (3.2 g, 22.9 mmol) in water (4 mL). The mixture was then degassed, flushed with nitrogen and heated at 80° C. overnight. The organic layer was separated, washed with water and brine, dried over magnesium sulfate, and evaporated. The residue was purified by column (2% MeOH:50% hexane:48% EtOAc) to afford 0.64 g (22%) desired product. MS ES 322 (M+H)$^+$, calcd 322, RT=3.37 min.

Step 2: Preparation of Title Compound

This material was prepared by a method analogous to that described for Example 1, starting from the product from 4-(2-amino-6-chloropyrimidin-4-yl)phenyl tert-butyl carbonate and Intermediate 2R. $^1$H NMR (DMSO-d$_6$) δ 9.79 (s, 1H), 9.25 (s, 1H), 8.22 (d, 1H), 7.86 (m, 2H), 7.74 (m, 2H), 7.09 (m, 2H), 6.95 (m, 2H), 6.80 (m, 2H), 6.39 (s, 1H), 6.23 (s, 2H); MS ES 406 (M+H)$^+$, calcd 406, RT=2.74 min.

Example 58

Preparation of (3E)-4-(4-{4-[(2-amino-6-phenylpyrimidin-4-yl)amino]phenoxy}pyridin-2-yl)but-3-en-1-ol

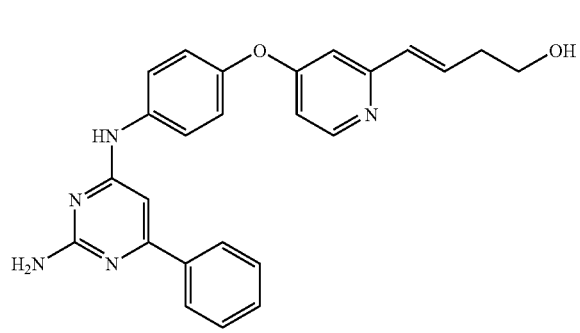

N⁴-{4-[(2-chloropyridin-4-yl)oxy]phenyl}-6-phenylpyrimidine-2,4-diamine (0.10 g, 0.26 mmol, Example 48), $K_2CO_3$ (0.089 g, 0.64 mmol), and DMA (2.5 mL) were placed into a small microwave vial. The mixture was degassed for 10 min before (3E)-4-(4,4,5,5-tetramethyl-1,3,2-dioxaborolan-2-yl)but-3-en-1-ol (0.10 g, 0.33 mmol) and Pd(dppf)Cl₂·CH₂Cl₂ complex (0.012 g, 0.020 mmol) were added. The mixture was heated at 150° C. for 20 min in a microwave reactor. The mixture was cooled, filtered, and purified by prep-HPLC. Concentration of the desired fractions gave 0.016 g of the title compound (10%).

MS ES: 426 (M+H)⁺, calcd 426, RT=1.90 min.

Example 59

Preparation of (4-{4-[(2-amino-6-phenylpyrimidin-4-yl)amino]phenoxy}pyridin-2-yl)methanol trifluoroacetate)

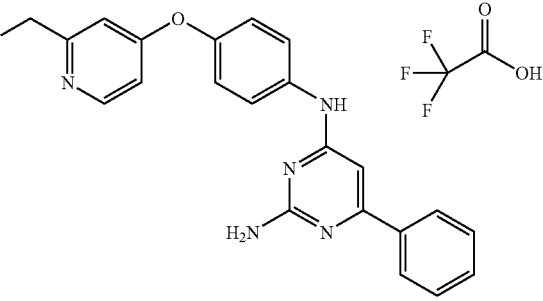

To a cloudy solution of 4-{4-[(2-amino-6-phenylpyrimidin-4-yl)amino]phenoxy}pyridine-2-carboxylic acid (748 mg, 1.87 mmol, Example 20) in anhydrous DMF (50 mL) at rt was added carbonyldiimidazole (456 mg, 2.81 mmol). The white suspension was stirred at 80° C. overnight, concentrated to a volume of 10 mL, and diluted with anhydrous THF (7 mL). The reaction mixture was cooled to 0° C. and water (10 mL) was added. The mixture was vigorously stirred as NaBH₄ (142 mg, 3.75 mmol) was added and was allowed to warm from 0° C. to rt over 2 h before it was quenched with conc. HCl (1 mL) in an ice bath. After stirring for 15 min, the mixture was slowly added to a stirred solution of sat. NaHCO₃ (20 mL) at 0° C. After stirring for 30 min, it was extracted with EtOAc (3×100 mL). The combined organic layers were dried over Na₂SO₄, filtered, and concentrated to give an off-white gum (420 mg, 85% pure). The crude material (100 mg) was purified by prep HPLC purification to give 37 mg (40% yield) of the title compound as a colorless gum. ¹H NMR (DMSO-d₆) δ 10.8 (s, 1H), 8.55 (d, 1H), 7.90 (m, 2H), 7.75 (m, 2H), 7.60 (m, 3H), 7.35 (d, 2H), 7.20 (m, 2H), 6.60 (s, 1H), 4.60 (s, 2H); MS ES 386 (+H)⁺ calcd 386, RT=1.73 min.

Examples of the compounds of the invention are summarized in Table 1 below. It is to be noted that in some of the IUPAC names, "N4*" is to be understood as a symbol for "N⁴".

TABLE 1

| Example No. | Structure | IUPAC Name* | LCMS: [M + H]⁺ (RT, min) |
|---|---|---|---|
| 1 | 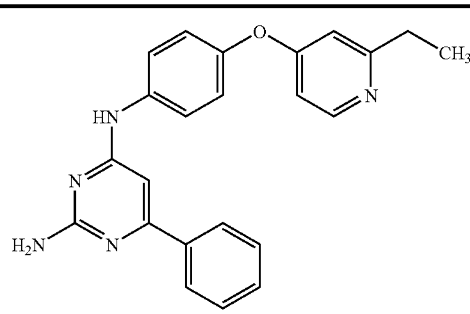 | N⁴-{4-[(2-ethylpyridin-4-yl)oxy]phenyl}-6-phenylpyrimidine-2,4-diamine | 384 (1.87) |

TABLE 1-continued

| Example No. | Structure | IUPAC Name* | LCMS: [M + H]+ (RT, min) |
|---|---|---|---|
| 2 | 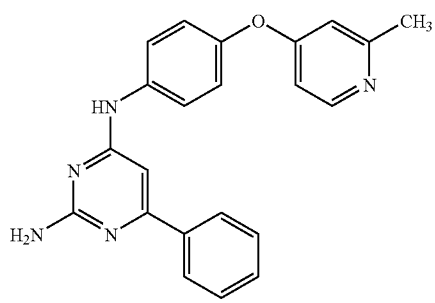 | N4-{4-[(2-methylpyridin-4-yl)oxy]phenyl}-6-phenylpyrimidine-2,4-diamine | 370 (1.41) |
| 3 | 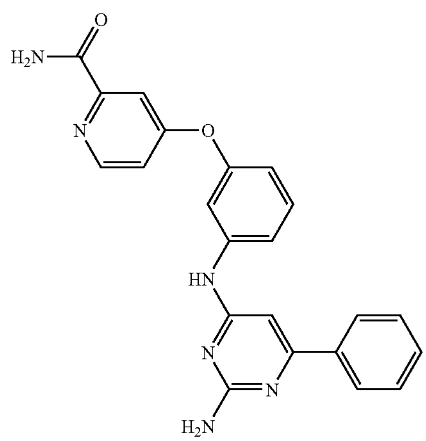 | 4-{3-[(2-amino-6-phenylpyrimidin-4-yl)amino]phenoxy}pyridine-2-carboxamide | 399.4 (2.74) |
| 4 | 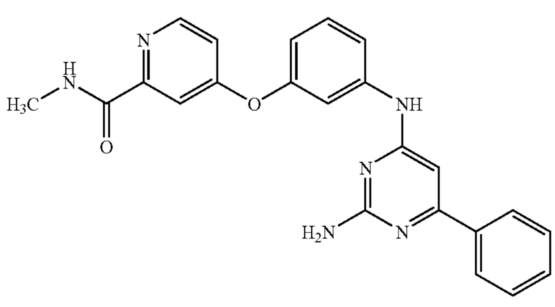 | 4-{3-[(2-amino-6-phenylpyrimidin-4-yl)amino]phenoxy}-N-methylpyridine-2-carboxamide | 413 (2.13) |
| 5 | 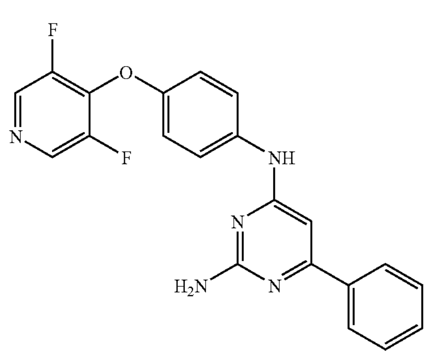 | N4-{4-[(3,5-difluoropyridin-4-yl)oxy]phenyl}-6-phenylpyrimidine-2,4-diamine | 392 (2.27) |

TABLE 1-continued

| Example No. | Structure | IUPAC Name* | LCMS: [M + H]+ (RT, min) |
|---|---|---|---|
| 6 | 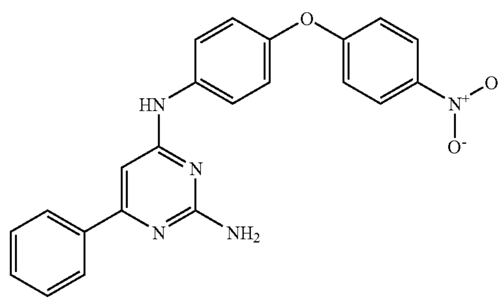 | 4-{4-[(2-amino-6-phenylpyrimidin-4-yl)amino]-3-fluorophenoxy}pyridine-2-carbonitrile hydrochloride | 399.3 (2.06) |
| 7 | 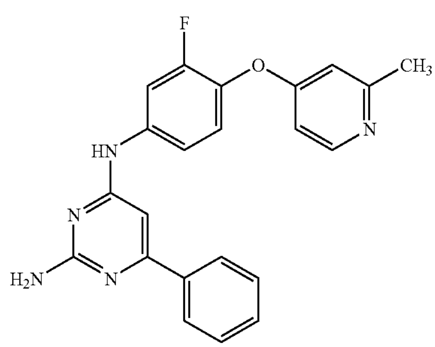 | N4*-{3-fluoro-4-[(2-methylpyridin-4-yl)oxy]phenyl}-6-phenylpyrimidine-2,4-diamine | 388 (1.70) |
| 8 | 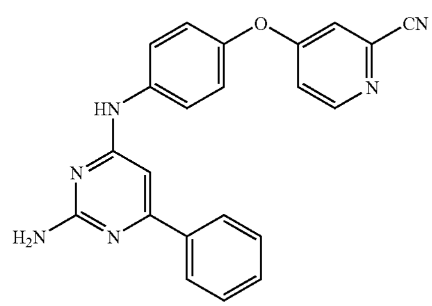 | 4-{4-[(2-amino-6-phenylpyrimidin-4-yl)amino]phenoxy}pyridine-2-carbonitrile | 381 (2.22) |
| 9 | 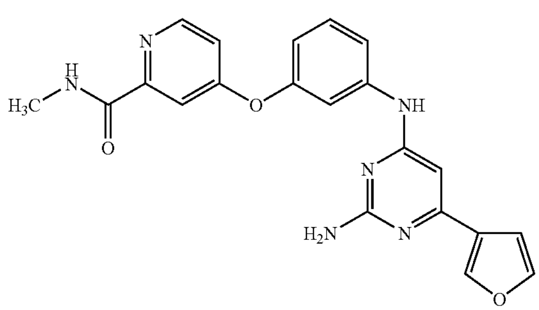 | 4-(3-{[2-amino-6-(3-furyl)pyrimidin-4-yl]amino}phenoxy)-N-methylpyridine-2-carboxamide | 403 (1.99) |

TABLE 1-continued

| Example No. | Structure | IUPAC Name* | LCMS: [M + H]+ (RT, min) |
|---|---|---|---|
| 10 | 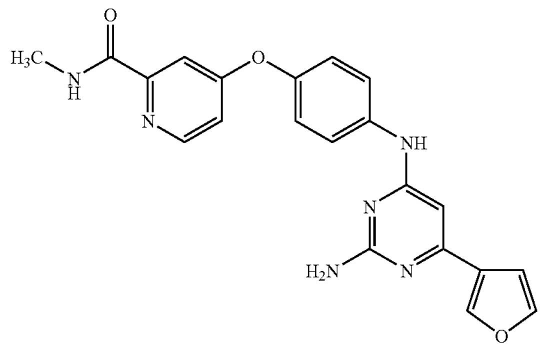 | 4-(4-{[2-amino-6-(3-furyl) pyrimidin-4-yl]amino} phenoxy)-N-methylpyridine-2-carboxamide | 403 (1.94) |
| 11 | 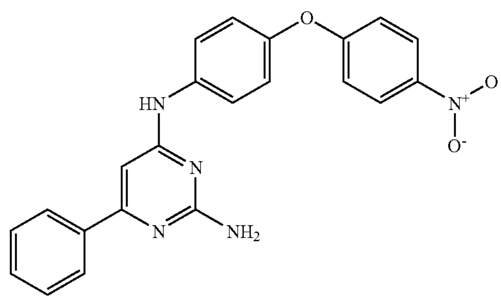 | N4*-[4-(4-nitrophenoxy) phenyl]-6-phenylpyrimidine-2,4-diamine | 400 (3.01) |
| 12 | 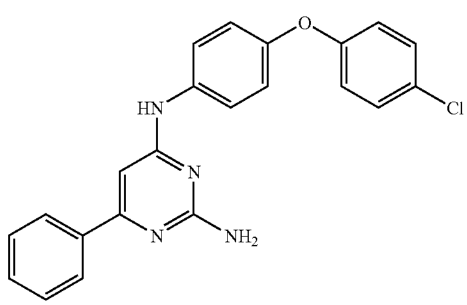 | N4*-[4-(4-chlorophenoxy) phenyl]-6-phenylpyrimidine-2,4-diamine | 389 (2.78) |
| 13 | 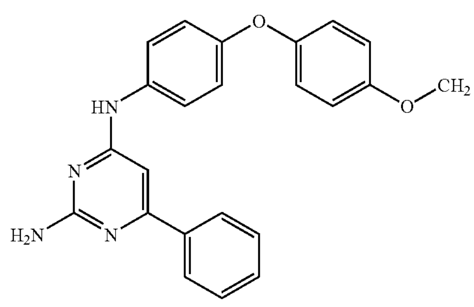 | N4*-[4-(4-methoxyphenoxy)phenyl]-6-phenylpyrimidine-2,4-diamine | 385 (2.48) |

TABLE 1-continued

| Example No. | Structure | IUPAC Name* | LCMS: [M + H]+ (RT, min) |
|---|---|---|---|
| 14 | 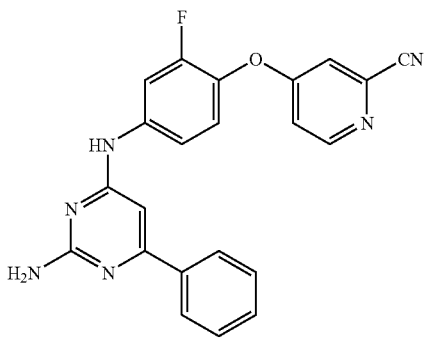 | 4-{4-[(2-amino-6-phenylpyrimidin-4-yl)amino]-2-fluorophenoxy}pyridine-2-carbonitrile | |
| 15 | 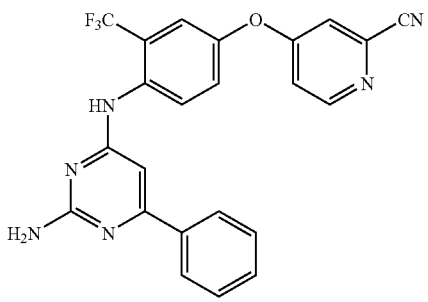 | 4-[4-[(2-amino-6-phenylpyrimidin-4-yl)amino]-3-(trifluoromethyl)phenoxy]pyridine-2-carbonitrile | |
| 16 | 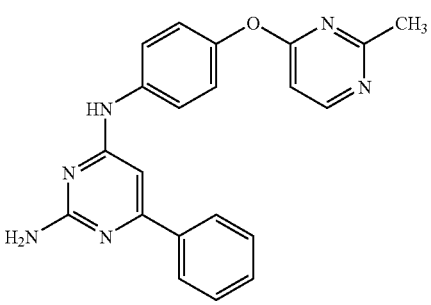 | $N^4$-{4-[(2-methylpyrimidin-4-yl)oxy]phenyl}-6-phenylpyrimidine-2,4-diamine | |
| 17 | 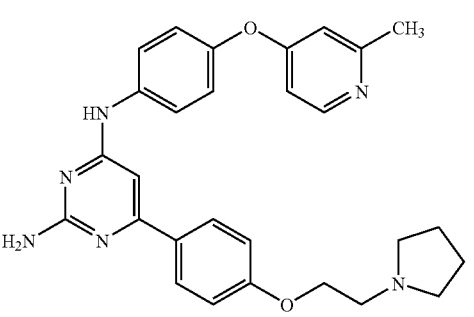 | $N^4$-{4-[(2-methylpyridin-4-yl)oxy]phenyl}-6-[4-(2-pyrrolidin-1-ylethoxy)phenyl]pyrimidine-2,4-diamine | |

TABLE 1-continued

| Example No. | Structure | IUPAC Name* | LCMS: [M + H]+ (RT, min) |
|---|---|---|---|
| 18 | 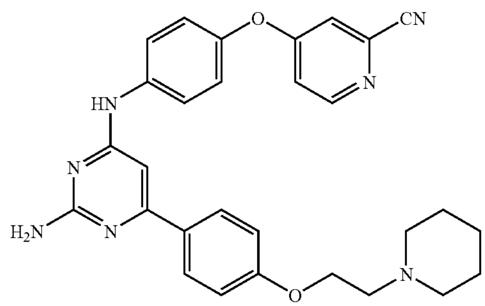 | 4-[4-({2-amino-6-[4-(2-piperidin-1-ylethoxy)phenyl]pyrimidin-4-yl}amino)phenoxy]pyridine-2-carbonitrile | |
| 19 | 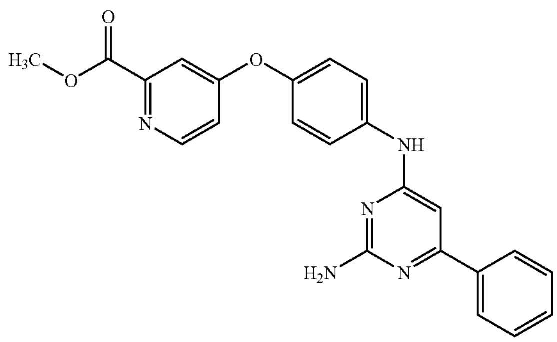 | methyl 4-{4-[(2-amino-6-phenylpyrimidin-4-yl)amino]phenoxy}pyridine-2-carboxylate | 414.2 (2.16) |
| 20 | 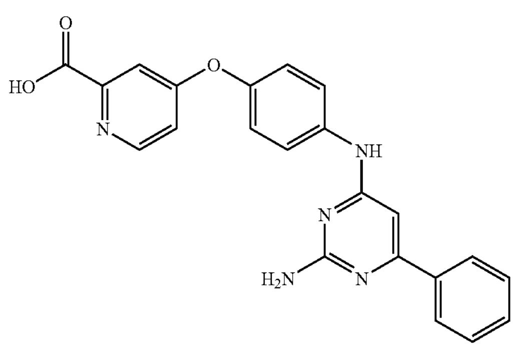 | 4-{4-[(2-amino-6-phenylpyrimidin-4-yl)amino]phenoxy}pyridine-2-carboxylic acid | 400 (1.71) |
| 21 | 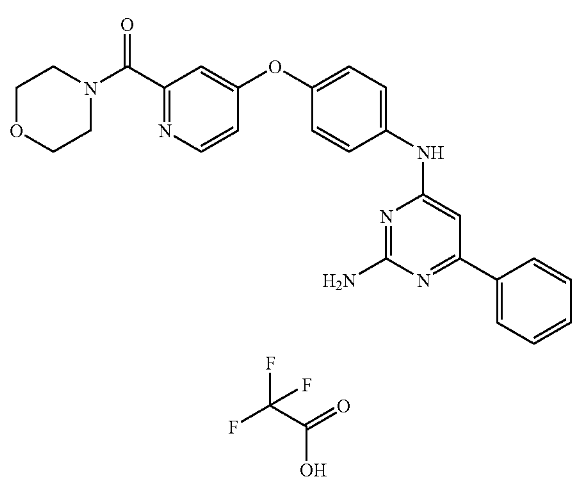 | N4*-(4-{[2-(morpholin-4-ylcarbonyl)pyridin-4-yl]oxy}phenyl)-6-phenylpyrimidine-2,4-diamine trifluoroacetate | 469.2 (2.13) |

TABLE 1-continued

| Example No. | Structure | IUPAC Name* | LCMS: [M + H]+ (RT, min) |
|---|---|---|---|
| 22 | 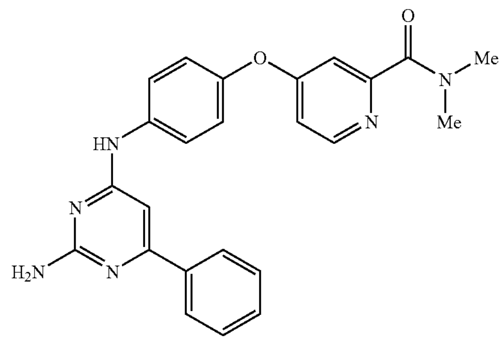 | 4-{4-[(2-amino-6-phenylpyrimidin-4-yl)amino]phenoxy}-N,N-dimethylpyridine-2-carboxamide | |
| 23 | 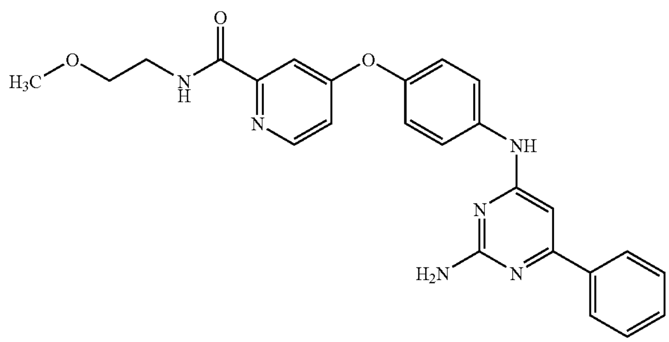 | 4-{4-[(2-amino-6-phenylpyrimidin-4-yl)amino]phenoxy}-N-(2-methoxyethyl)pyridine-2-carboxamide | 457.4 (2.17) |
| 24 | 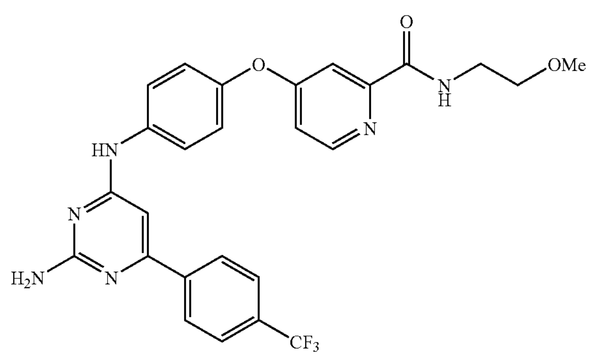 | 4-[4-({2-amino-6-[4-(trifluoromethyl)phenyl]pyrimidin-4-yl}amino)phenoxy]-N-(2-methoxyethyl)pyridine-2-carboxamide | |
| 25 | 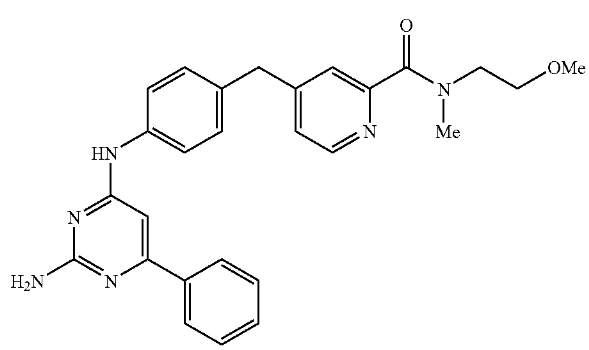 | 4-{4-[(2-amino-6-phenylpyrimidin-4-yl)amino]benzyl}-N-(2-methoxyethyl)-N-methylpyridine-2-carboxamide | |

TABLE 1-continued

| Example No. | Structure | IUPAC Name* | LCMS: [M + H]+ (RT, min) |
|---|---|---|---|
| 26 | 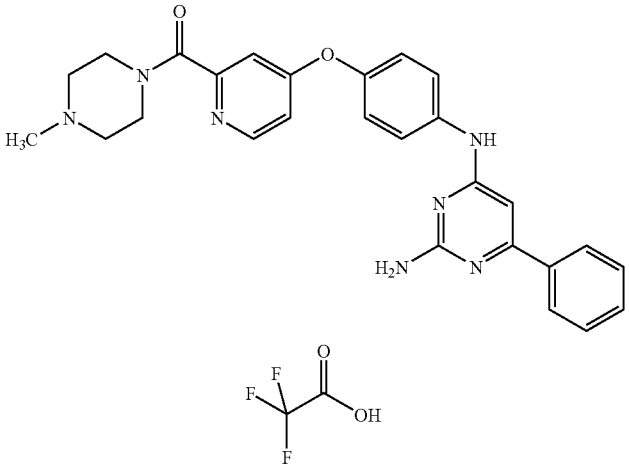 | N4*-[4-({2-[(4-methylpiperazin-1-yl)carbonyl]pyridin-4-yl}oxy)phenyl]-6-phenylpyrimidine-2,4-diamine trifluoroacetate | 482.2 (1.86) |
| 27 | 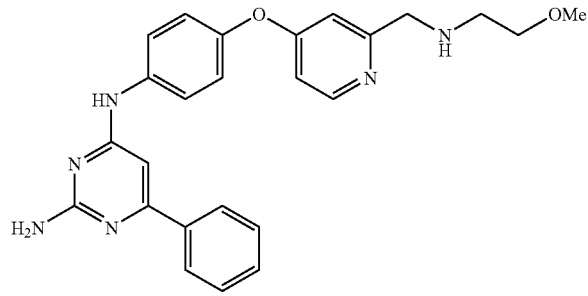 | $N^4$-{4-[(2-{[(2-methoxyethyl)amino]methyl}pyridin-4-yl)oxy]phenyl}-6-phenylpyrimidine-2,4-diamine | |
| 28 | 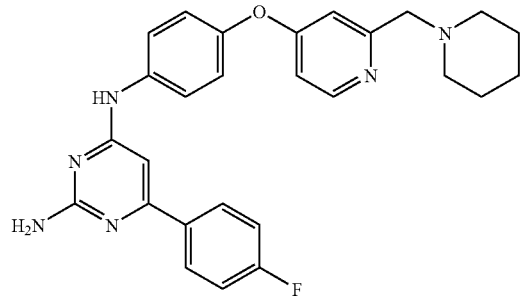 | 6-(4-fluorophenyl)-$N^4$-(4-{[2-(piperidin-1-ylmethyl)pyridin-4-yl]oxy}phenyl)pyrimidine-2,4-diamine | |
| 29 | 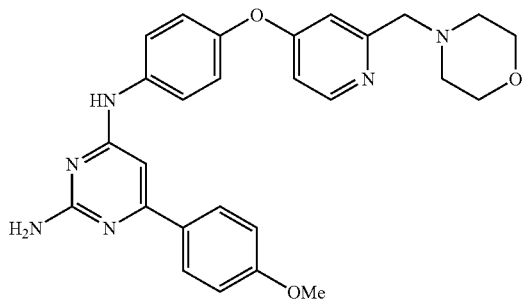 | 6-(4-methoxyphenyl)-$N^4$-(4-{[2-(morpholin-4-ylmethyl)pyridin-4-yl]oxy}phenyl)pyrimidine-2,4-diamine | |

TABLE 1-continued

| Example No. | Structure | IUPAC Name* | LCMS: [M + H]+ (RT, min) |
|---|---|---|---|
| 30 | 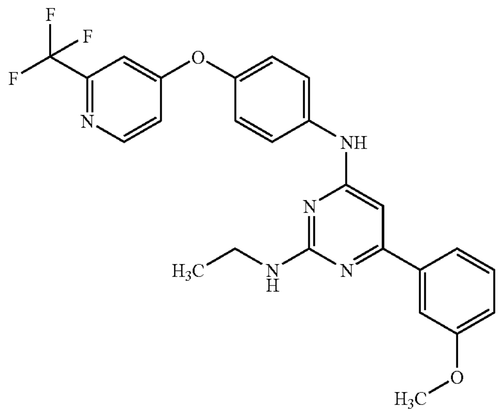 | $N^2$-ethyl-6-(3-methoxyphenyl)-N4*-(4-{[2-(trifluoromethyl) pyridin-4-yl]oxy}phenyl) pyrimidine-2,4-diamine trifluoroacetate | 482 (2.83) |
| 31 | 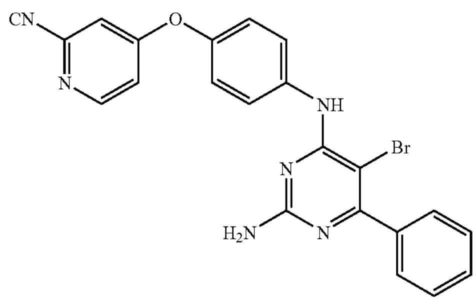 | 4-{4-[(2-amino-5-bromo-6-phenylpyrimidin-4-yl) amino]phenoxy}pyridine-2-carbonitrile | 459.3 (2.85) |
| 32 | 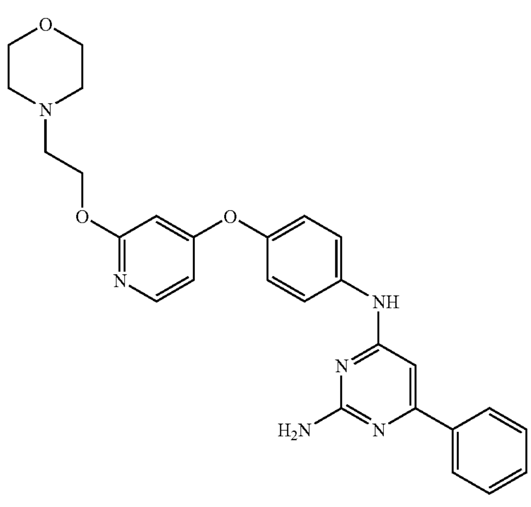 | N4*-(4-{[2-(2-morpholin-4-ylethoxy)pyridin-4-yl]oxy}phenyl)-6-phenylpyrimidine-2,4-diamine | 485.1 (1.96) |

TABLE 1-continued
| Example No. | Structure | IUPAC Name* | LCMS: [M + H]+ (RT, min) |
|---|---|---|---|
| 33 | 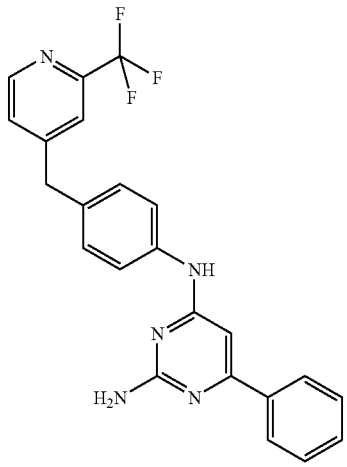 | 6-phenyl-N4-(4-{[2-(trifluoromethyl)pyridin-4-yl]methyl}phenyl)pyrimidine-2,4-diamine | 422.3 (2.51) |
| 34 | 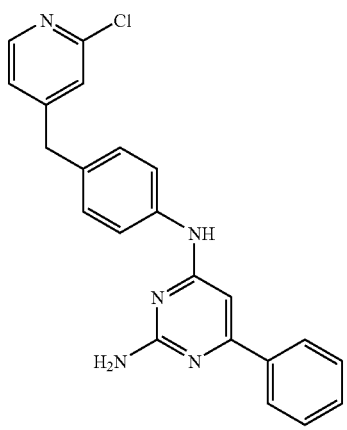 | N4*-{4-[(2-chloropyridin-4-yl)methyl]phenyl}-6-phenylpyrimidine-2,4-diamine | 388.3 (2.38) |
| 35 | 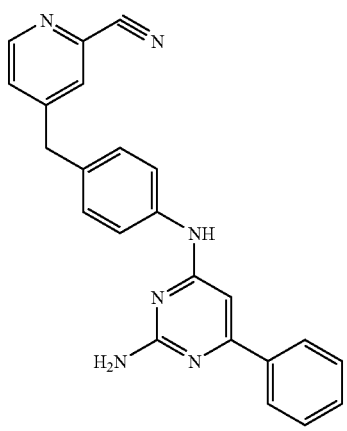 | 4-{4-[(2-amino-6-phenylpyrimidin-4-yl)amino]benzyl}pyridine-2-carbonitrile | 379.3 (2.35) |

TABLE 1-continued

| Example No. | Structure | IUPAC Name* | LCMS: [M + H]+ (RT, min) |
|---|---|---|---|
| 36 | 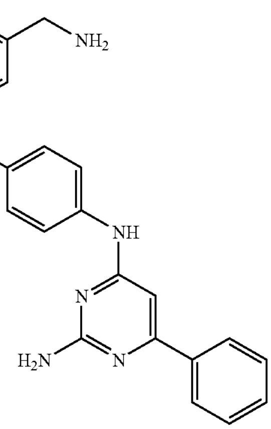 | N4*-(4-{[2-(aminomethyl) pyridin-4-yl]methyl} phenyl)-6-phenylpyrimidine-2,4-diamine | 383.3 (1.84) |
| 37 | 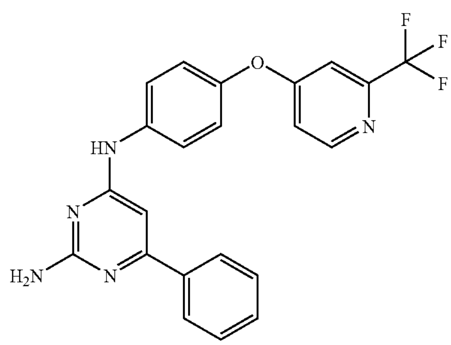 | 6-phenyl-N4*-(4-{[2-(trifluoromethyl)pyridin-4-yl]oxy}phenyl)pyrimidine-2,4-diamine | 424.3 (2.48) |
| 38 | 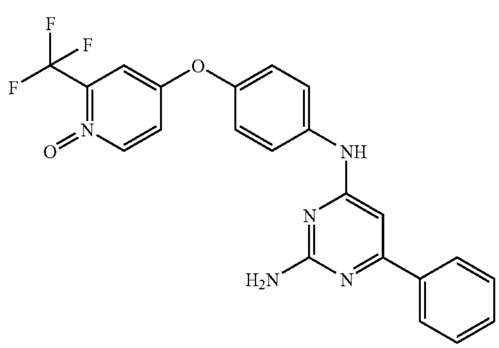 | N4*-(4-{[1-oxido-2-(trifluoromethyl)pyridin-4-yl]oxy}phenyl)-6-phenylpyrimidine-2,4-diamine | 440.3 (2.97) |
| 39 | 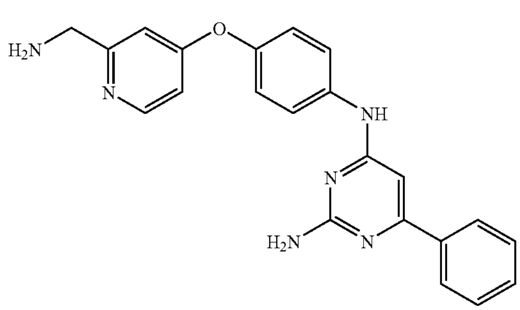 | N4*-(4-{[2-(aminomethyl) pyridin-4-yl]oxy}phenyl)-6-phenylpyrimidine-2,4-diamine | 385.2 (1.80) |

TABLE 1-continued

| Example No. | Structure | IUPAC Name* | LCMS: [M + H]+ (RT, min) |
|---|---|---|---|
| 40 | 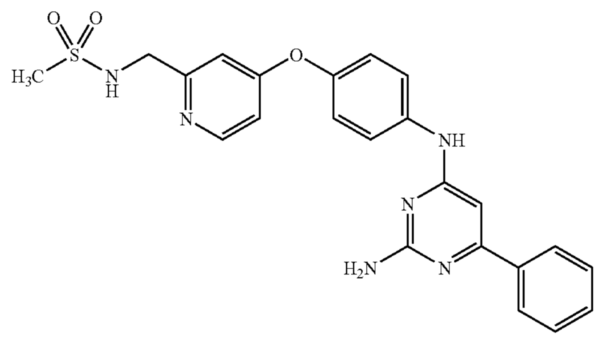 | N-[(4-{4-[(2-amino-6-phenylpyrimidin-4-yl)amino]phenoxy}pyridin-2-yl)methyl]methanesulfonamide trifluoroacetate | 463.3 (1.17) |
| 41 | 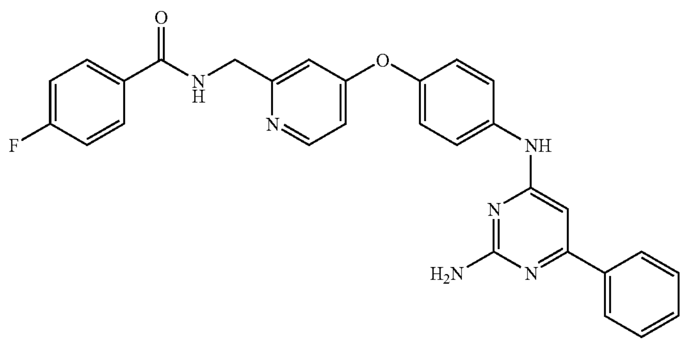 | N-[(4-{4-[(2-amino-6-phenylpyrimidin-4-yl)amino]phenoxy}pyridin-2-yl)methyl]-4-fluorobenzamide | 507.7 (2.5) |
| 42 | 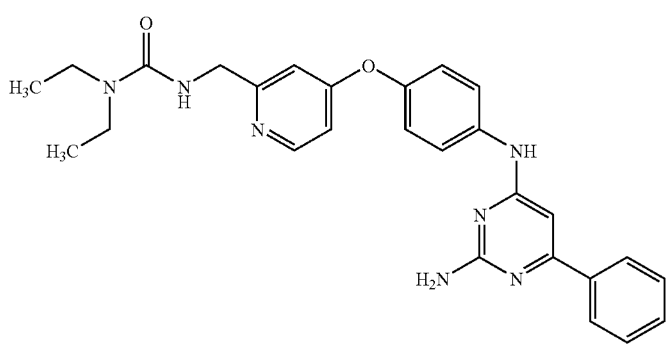 | N'-[(4-(4-[(2-amino-6-phenylpyrimidin-4-yl)amino]phenoxy}pyridin-2-yl)methyl]-N,N-diethylurea | 484.4 (2.37) |
| 43 | 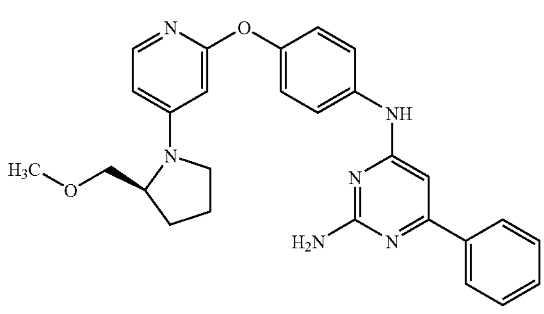 | N4*-[4-({4-[2-(methoxymethyl)pyrrolidin-1-yl]pyridin-2-yl}oxy)phenyl]-6-phenylpyrimidine-2,4-diamine | 469.4 (1.90) |

TABLE 1-continued

| Example No. | Structure | IUPAC Name* | LCMS: [M + H]+ (RT, min) |
|---|---|---|---|
| 44 | 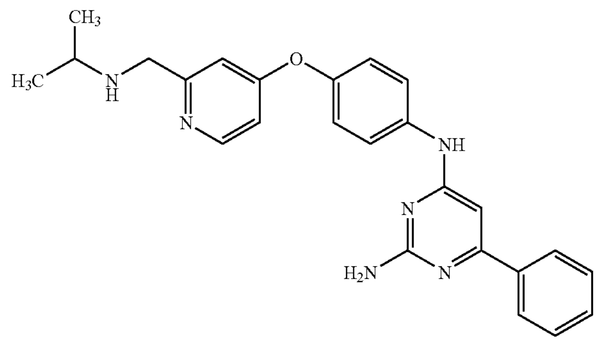 | N4*-[4-({2-[(isopropylamino)methyl]pyridin-4-yl}oxy)phenyl]-6-phenylpyrimidine-2,4-diamine | 427.1 (2.59) |
| 45 | 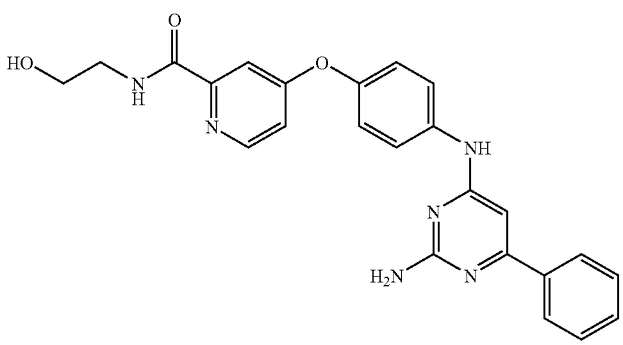 | 4-{4-[(2-amino-6-phenylpyrimidin-4-yl)amino]phenoxy}-N-(2-hydroxyethyl)pyridine-2-carboxamide | 443.3 (2.19) |
| 46 | 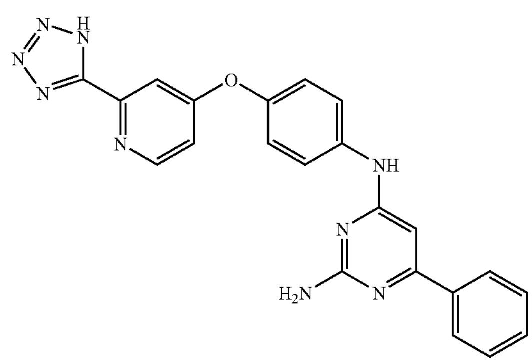 | 6-phenyl-N4*-(4-{[2-(1H-tetrazol-5-yl)pyridin-4-yl]oxy}phenyl)pyrimidine-2,4-diamine | 424.1 (1.84) |
| 47 | 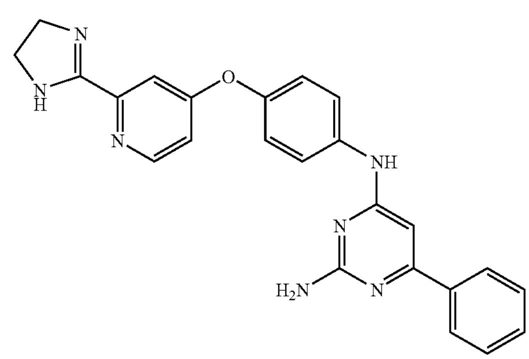 | N4*-(4-{[2-(4,5-dihydro-1H-imidazol-2-yl)pyridin-4-yl]oxy}phenyl)-6-phenylpyrimidine-2,4-diamine | 424.2 (0.81) |

TABLE 1-continued

| Example No. | Structure | IUPAC Name* | LCMS: [M + H]+ (RT, min) |
|---|---|---|---|
| 48 | 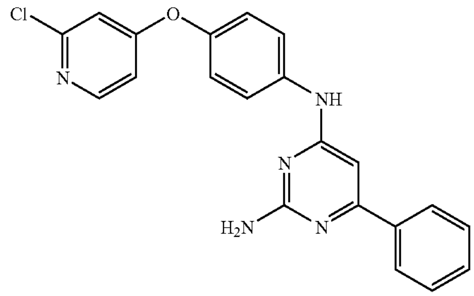 | N4*-{4-[(2-chloropyridin-4-yl)oxy]phenyl}-6-phenylpyrimidine-2,4-diamine | 390.3 (2.40) |
| 49 | Chiral | N4*-[4-({2-[(2S)-2-(methoxymethyl)pyrrolidin-1-yl]pyridin-4-yl}oxy)phenyl]-6-phenylpyrimidine-2,4-diamine | 469.3 (1.36) |
| 50 | 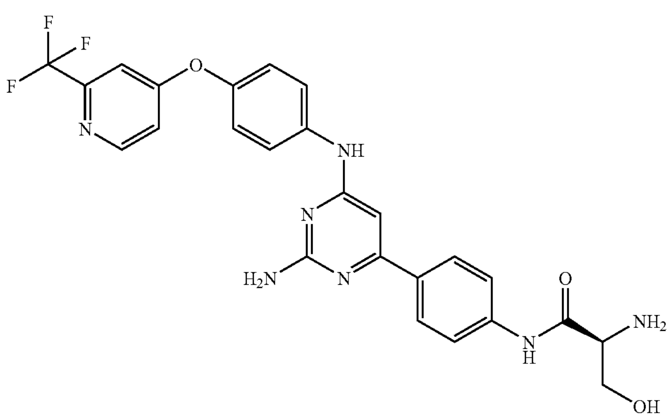 | N-(4-{2-amino-6-[(4-{(2-(trifluoromethyl)pyridin-4-yl]oxy}phenyl)amino]pyrimidin-4-yl}phenyl)serinamide | 536.1 (2.14) |
| 51 | 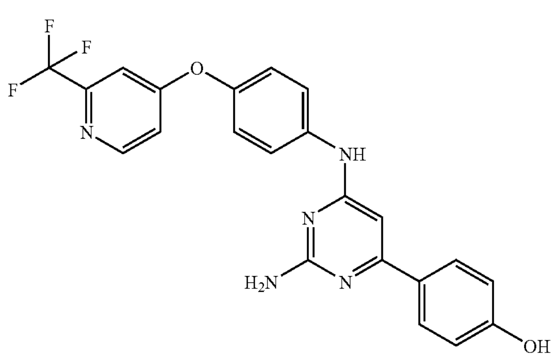 | 4-{2-amino-6-[(4-{[2-(trifluoromethyl)pyridin-4-yl]oxy}phenyl)amino]pyrimidin-4-yl}phenol | 440.3 (1.56) |

TABLE 1-continued

| Example No. | Structure | IUPAC Name* | LCMS: [M + H]+ (RT, min) |
|---|---|---|---|
| 52 | 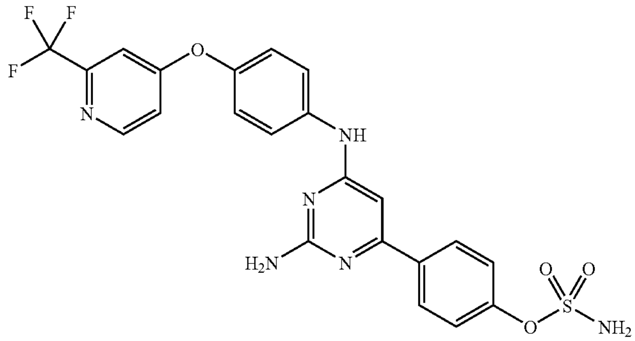 | 4-{2-amino-6-[(4-{[2-(trifluoromethyl)pyridin-4-yl]oxy}phenyl)amino]pyrimidin-4-yl}phenyl sulfamate | 519.1 (2.64) |
| 53 | 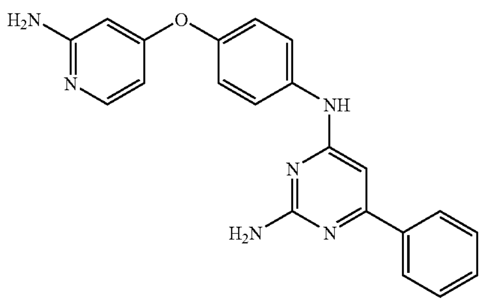 | N4*-{4-[(2-aminopyridin-4-yl)oxy]phenyl}-6-phenylpyrimidine-2,4-diamine | 371.4 (1.90) |
| 57 | 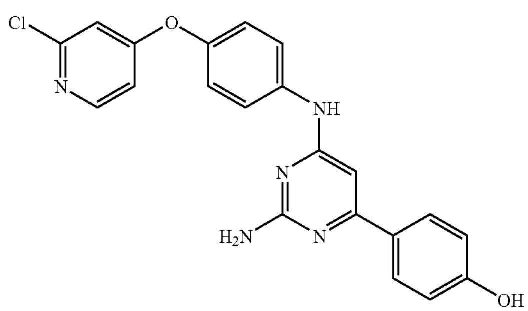 | 4-[2-amino-6-({4-[(2-chloropyridin-4-yl)oxy]phenyl}amino)pyrimidin-4-yl]phenol | 406.4 (2.74) |
| 58 | 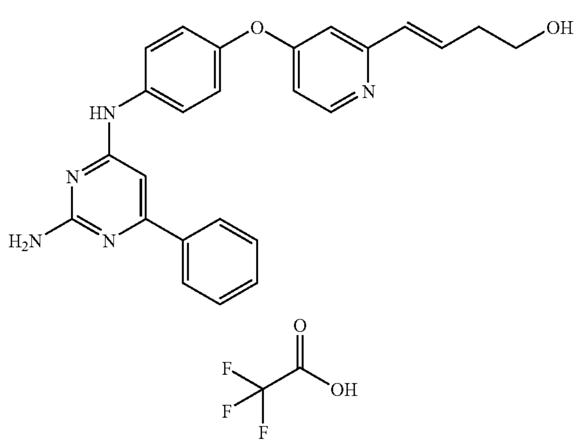 | (3E)-4-(4-{4-[(2-amino-6-phenylpyrimidin-4-yl)amino]phenoxy}pyridin-2-yl)but-3-en-1-ol trifluoroacetate (salt) | 426.3 (1.90) |

TABLE 1-continued
| Example No. | Structure | IUPAC Name* | LCMS: [M + H]+ (RT, min) |
|---|---|---|---|
| 59 | 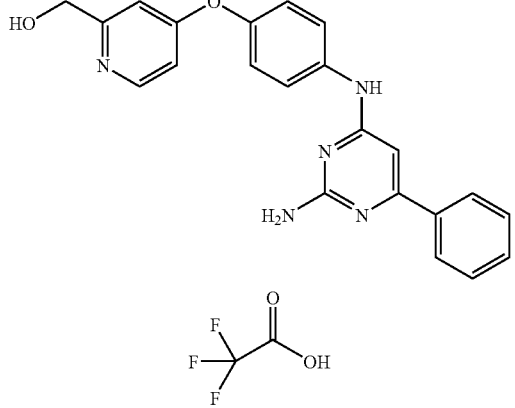 | (4-{4-[(2-amino-6-phenylpyrimidin-4-yl)amino]phenoxy}pyridin-2-yl)methanol trifluoroacetate | 386.2 (1.73) |
| 60 | 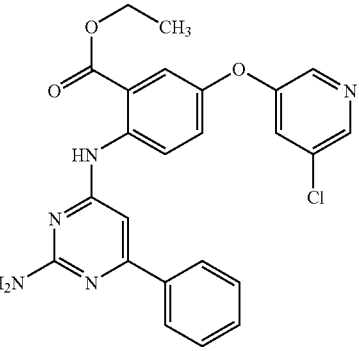 | ethyl 2-[(2-amino-6-phenylpyrimidin-4-yl)amino]-5-[(5-chloropyridin-3-yl)oxy]benzoate | 462.2 (2.53) |
| 61 | 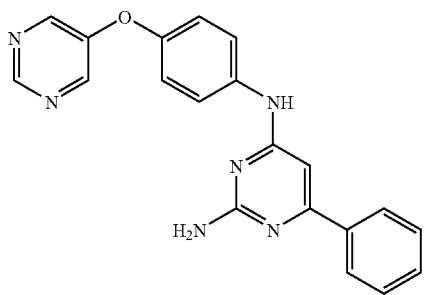 | 6-phenyl-N4*-[4-(pyrimidin-5-yloxy)phenyl]pyrimidine-2,4-diamine | 357.3 (2.07) |
| 62 | 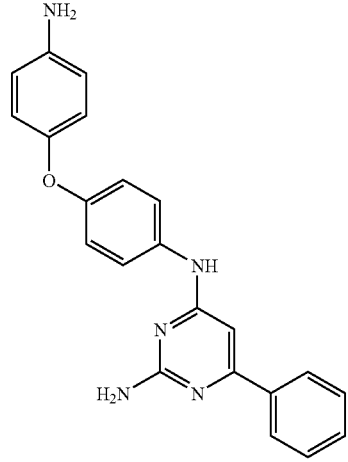 | $N^4$-[4-(4-aminophenoxy)phenyl]-6-phenylpyrimidine-2,4-diamine | 370.3 (2.08) |

TABLE 1-continued

| Example No. | Structure | IUPAC Name* | LCMS: [M + H]+ (RT, min) |
|---|---|---|---|
| 63 | 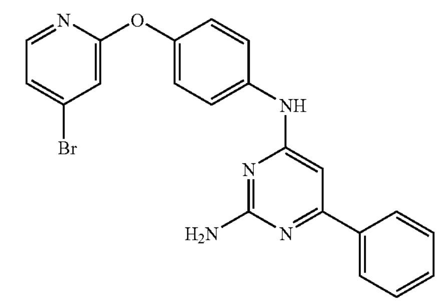 | N4*-{4-[(4-bromopyridin-2-yl)oxy]phenyl}-6-phenylpyrimidine-2,4-diamine | 436.1 (2.81) |
| 64 | 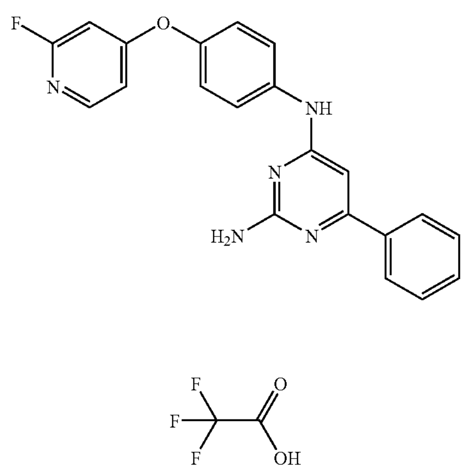 | N4*-{4-[(2-fluoropyridin-4-yl)oxy]phenyl}-6-phenylpyrimidine-2,4-diamine trifluoroacetate | 374.7 (2.52) |
| 65 | 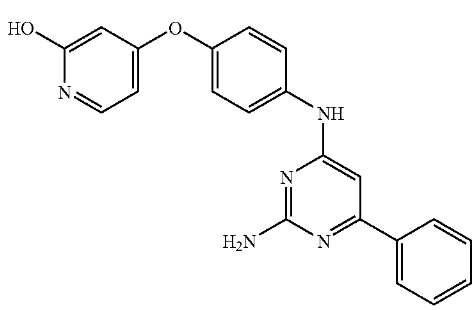 | 4-{4-[(2-amino-6-phenylpyrimidin-4-yl)amino]phenoxy}pyridin-2-ol | 372.9 (2.34) |
| 66 | 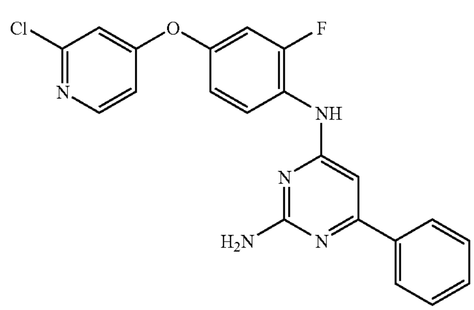 | N4*-{4-[(2-chloropyridin-4-yl)oxy]-2-fluorophenyl}-6-phenylpyrimidine-2,4-diamine | 408.3 (1.42) |

TABLE 1-continued

| Example No. | Structure | IUPAC Name* | LCMS: [M + H]+ (RT, min) |
|---|---|---|---|
| 67 | 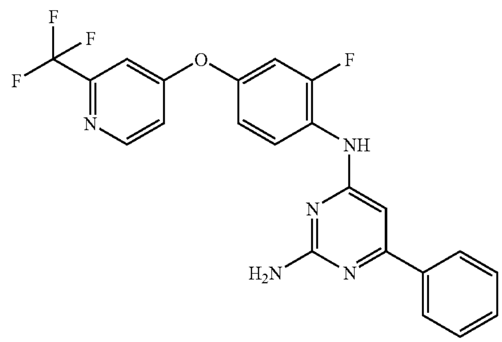 | N4*-(2-fluoro-4-{[2-(trifluoromethyl)pyridin-4-yl]oxy}phenyl)-6-phenylpyrimidine-2,4-diamine | 442.3 (2.54) |
| 68 | 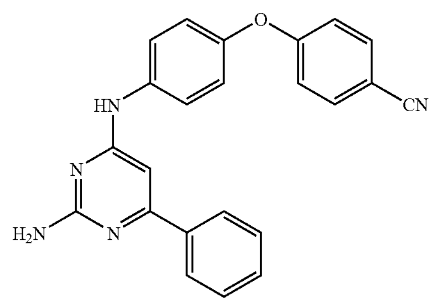 | 4-{4-[(2-amino-6-phenylpyrimidin-4-yl)amino]phenoxy}benzonitrile | 380.4 (2.39) |
| 69 | 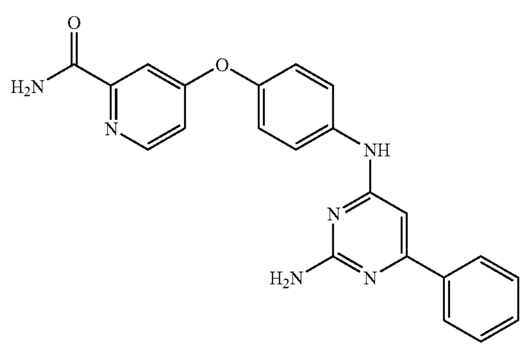 | 4-{4-[(2-amino-6-phenylpyrimidin-4-yl)amino]phenoxy}pyridine-2-carboxamide | 399.3 (2.54) |
| 70 | 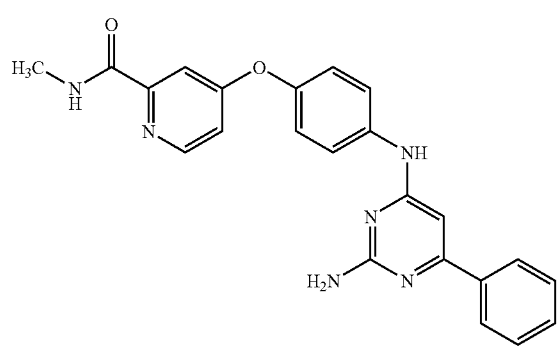 | 4-{4-[(2-amino-6-phenylpyrimidin-4-yl)amino]phenoxy}-N-methylpyridine-2-carboxamide | 413.3 (2.21) |

TABLE 1-continued

| Example No. | Structure | IUPAC Name* | LCMS: [M + H]+ (RT, min) |
|---|---|---|---|
| 71 | 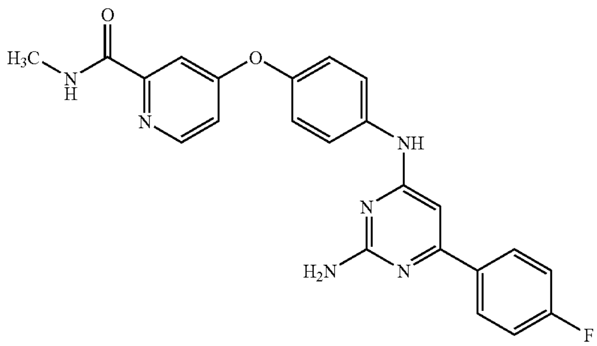 | 4-(4-{[2-amino-6-(4-fluorophenyl)pyrimidin-4-yl]amino}phenoxy)-N-methylpyridine-2-carboxamide | 431.3 (2.25) |
| 72 | 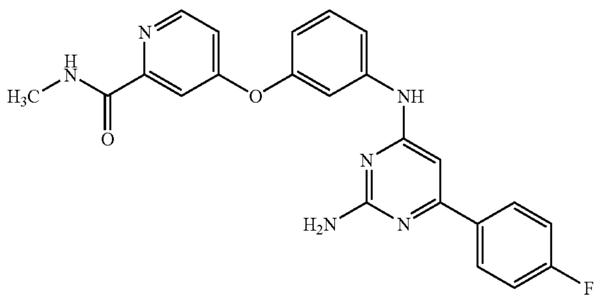 | 4-(3-{[2-amino-6-(4-fluorophenyl)pyrimidin-4-yl]amino}phenoxy)-N-methylpyridine-2-carboxamide | 431.5 (2.15) |
| 73 | 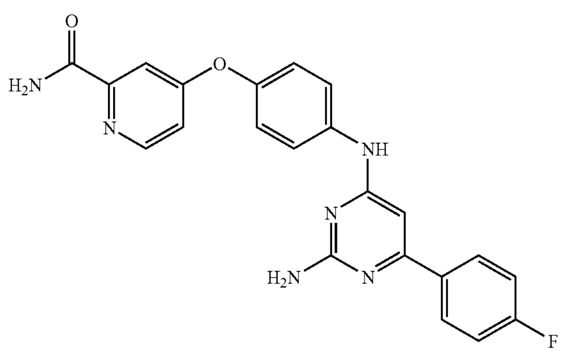 | 4-(4-{[2-amino-6-(4-fluorophenyl)pyrimidin-4-yl]amino}phenoxy)pyridine-2-carboxamide | 417.3 (2.07) |
| 74 | 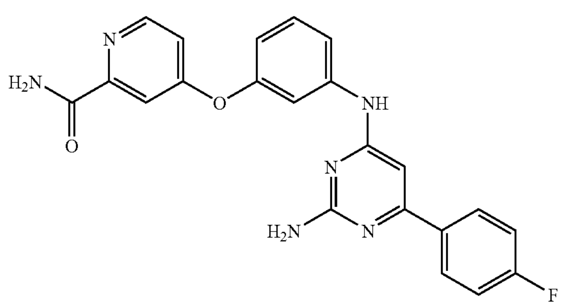 | 4-(3-{[2-amino-6-(4-fluorophenyl)pyrimidin-4-yl]amino}phenoxy)pyridine-2-carboxamide | 417.3 (2.09) |

TABLE 1-continued

| Example No. | Structure | IUPAC Name* | LCMS: [M + H]+ (RT, min) |
|---|---|---|---|
| 75 | 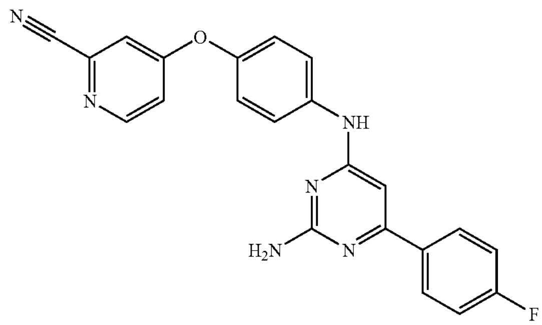 | 4-(4-{[2-amino-6-(4-fluorophenyl)pyrimidin-4-yl]amino}phenoxy)pyridine-2-carbonitrile | 399.4 (2.21) |
| 76 | 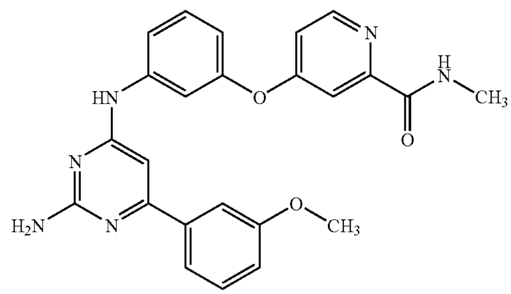 | 4-(3-{[2-amino-6-(3-methoxyphenyl)pyrimidin-4-yl]amino}phenoxy)-N-methylpyridine-2-carboxamide | 443.4 (2.18) |
| 77 | 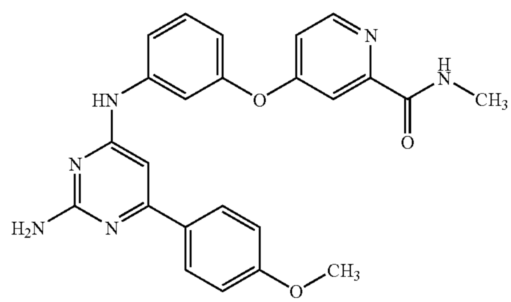 | 4-(3-{[2-amino-6-(4-methoxyphenyl)pyrimidin-4-yl]amino}phenoxy)-N-methylpyridine-2-carboxamide | 443.4 (2.19) |
| 78 | 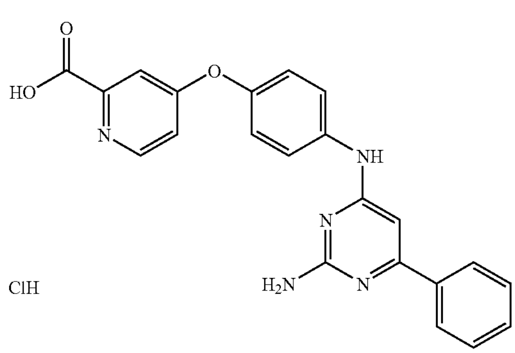 | 4-{4-[(2-amino-6-phenylpyrimidin-4-yl)amino]phenoxy}pyridine-2-carboxylic acid hydrochloride | 400.1 (1.67) |

TABLE 1-continued

| Example No. | Structure | IUPAC Name* | LCMS: [M + H]+ (RT, min) |
|---|---|---|---|
| 79 | 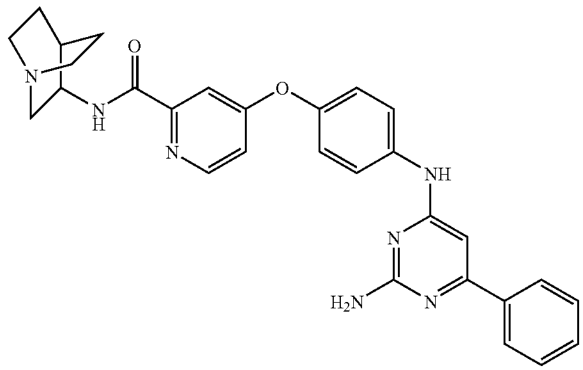 | 4-{4-[(2-amino-6-phenylpyrimidin-4-yl)amino]phenoxy}-N-1-azabicyclo[2.2.2]oct-3-ylpyridine-2-carboxamide trifluoroacetate | 508.3 (1.99) |
| 80 | 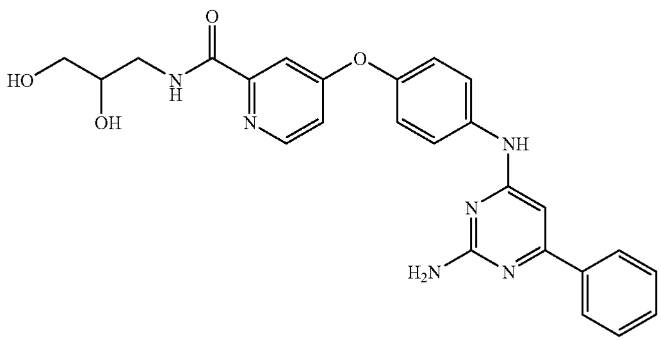 | 4-{4-[(2-amino-6-phenylpyrimidin-4-yl)amino]phenoxy}-N-(2,3-dihydroxypropyl)pyridine-2-carboxamide | 473.2 (2.11) |
| 81 | Chiral | N4*-{4-[(2-{[(2S)-2-(methoxymethyl)pyrrolidin-1-yl]carbonyl}pyridin-4-yl)oxy]phenyl}-6-phenylpyrimidine-2,4-diamine trifluoroacetate | 497.3 (2.23) |
| 82 | Chiral | (3R)-1-[(4-{4-[(2-amino-6-phenylpyrimidin-4-yl)amino]phenoxy}pyridin-2-yl)carbonyl]pyrrolidin-3-ol trifluoroacetate (salt) | 469.4 (1.98) |

TABLE 1-continued

| Example No. | Structure | IUPAC Name* | LCMS: [M + H]+ (RT, min) |
|---|---|---|---|
| 83 | 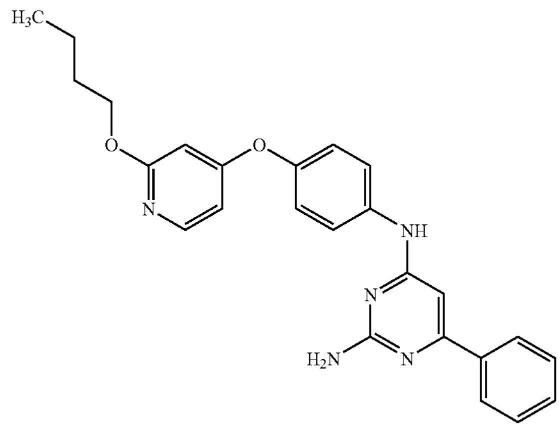 | N4*-{4-[(2-butoxypyridin-4-yl)oxy]phenyl}-6-phenylpyrimidine-2,4-diamine | 428.3 (2.56) |
| 84 | 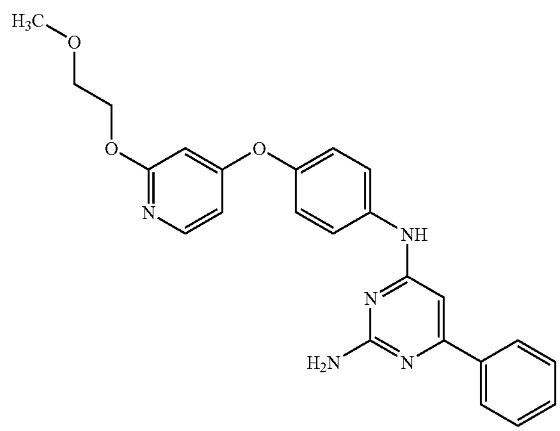 | $N^4$-(4-{[2-(2-methoxyethoxy)pyridin-4-yl]oxy}phenyl)-6-phenylpyrimidine-2,4-diamine | 430.3 (2.24) |
| 85 | 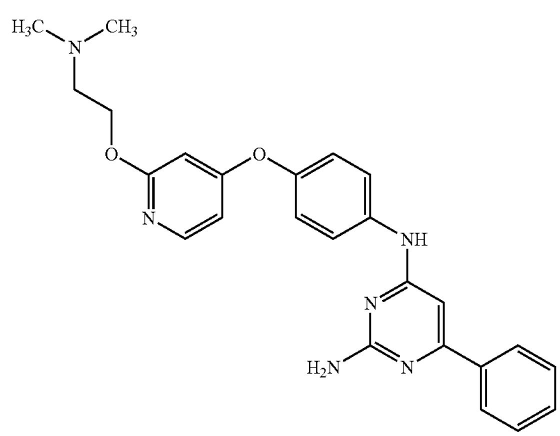 | $N^4$-[4-({2-[2-(dimethylamino)ethoxy]pyridin-4-yl}oxy)phenyl]-6-phenylpyrimidine-2,4-diamine | 443.1 (1.94) |

TABLE 1-continued
| Example No. | Structure | IUPAC Name* | LCMS: [M + H]+ (RT, min) |
|---|---|---|---|
| 86 | 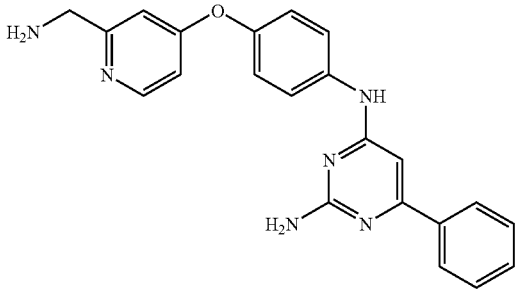 | N4*-{4-[(2-ethoxypyridin-4-yl)oxy]phenyl}-6-phenylpyrimidine-2,4-diamine | 400.3 (2.24) |
| 87 | 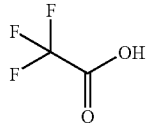 | 1-[4-({5-[(2-amino-6-phenylpyrimidin-4-yl)amino]pyridin-2-yl}oxy)phenyl]ethanone | 398.2 (2.29) |
| 88 | 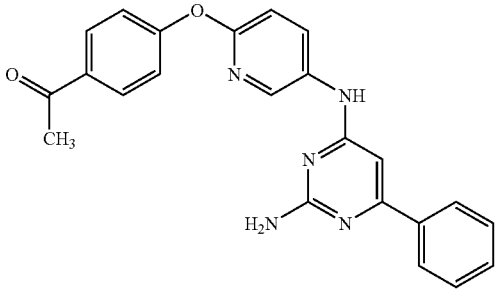 | $N^4$*-[4-(4-aminobenzyl)phenyl]-6-phenylpyrimidine-2,4-diamine | 368.3 (1.91) |
| 89 | 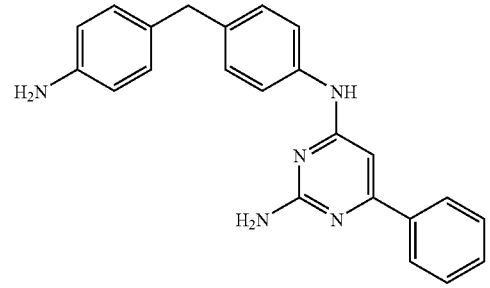 | $N^4$-[4-(4-methylbenzyl)phenyl]-6-phenylpyrimidine-2,4-diamine | 367.4 (2.78) |

TABLE 1-continued

| Example No. | Structure | IUPAC Name* | LCMS: [M + H]+ (RT, min) |
|---|---|---|---|
| 90 | 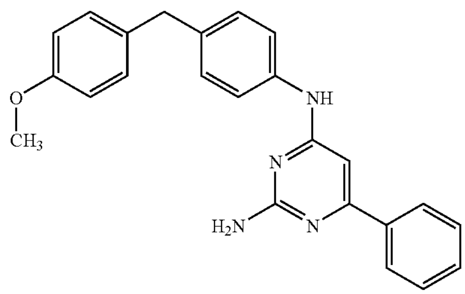 | N4-[4-(4-methoxybenzyl) phenyl]-6-phenylpyrimidine-2,4-diamine | 398.2 (2.29) |
| 91 | 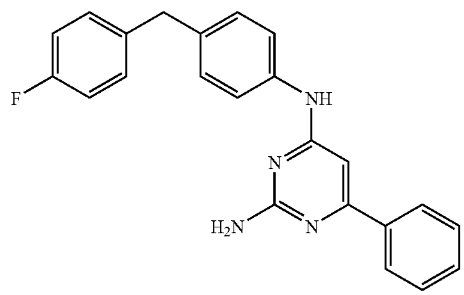 | N4-[4-(4-fluorobenzyl) phenyl]-6-phenylpyrimidine-2,4-diamine | 371.4 (2.68) |
| 92 | 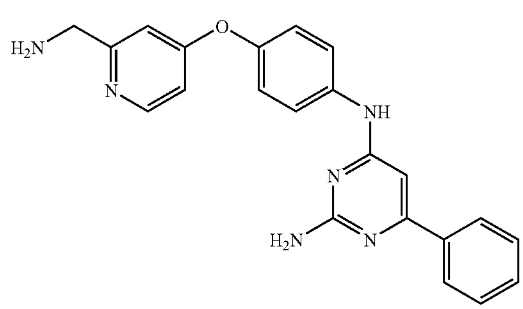 | N4*-(4-{[2-(aminomethyl) pyridin-4-yl]oxy}phenyl)-6-phenylpyrimidine-2,4-diamine trifluoroacetate | 385.2 (1.86) |
| 93 | 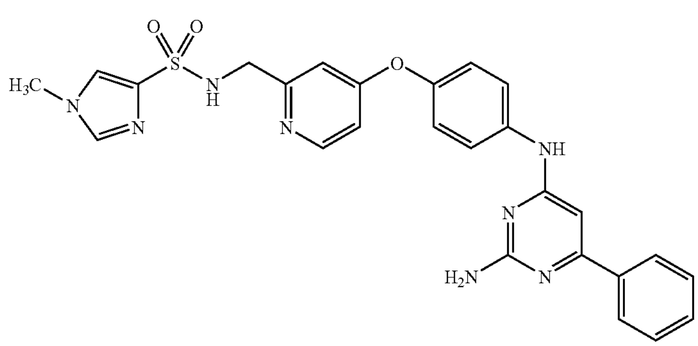 | N-[(4-{4-[(2-amino-6-phenylpyrimidin-4-yl) amino]phenoxy}pyridin-2-yl)methyl]-1-methyl-1H-imidazole-4-sulfonamide trifluoroacetate | 529.3 (1.15) |

TABLE 1-continued

| Example No. | Structure | IUPAC Name* | LCMS: [M + H]+ (RT, min) |
|---|---|---|---|
| 94 | 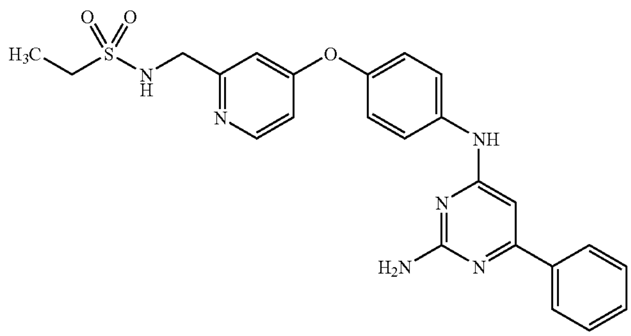 | N-[(4-{4-[(2-amino-6-phenylpyrimidin-4-yl)amino]phenoxy}pyridin-2-yl)methyl]ethanesulfonamide trifluoroacetate | 477.4 (1.89) |
| 95 | 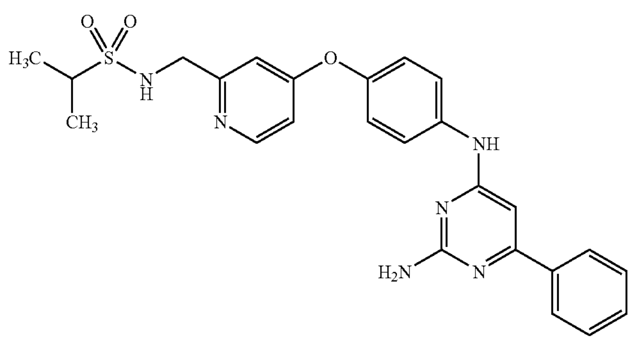 | N-[(4-{4-[(2-amino-6-phenylpyrimidin-4-yl)amino]phenoxy}pyridin-2-yl)methyl]propane-2-sulfonamide trifluoroacetate | 491.4 (2.06) |
| 96 | 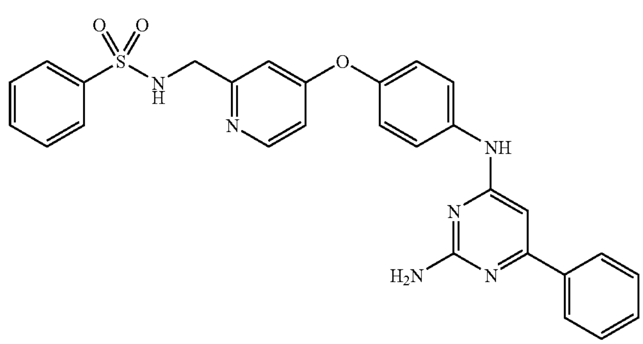 | N-[(4-{4-[(2-amino-6-phenylpyrimidin-4-yl)amino]phenoxy}pyridin-2-yl)methyl]benzenesulfonamide trifluoroacetate | 525.4 (2.20) |
| 97 | 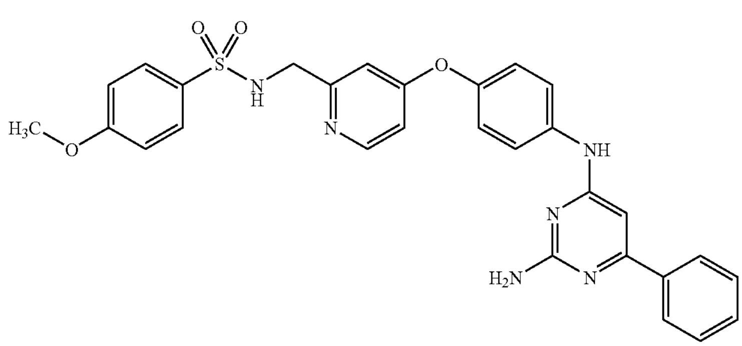 | N-[(4-{4-[(2-amino-6-phenylpyrimidin-4-yl)amino]phenoxy}pyridin-2-yl)methyl]-4-methoxybenzenesulfonamide trifluoroacetate | 555.4 (2.21) |

TABLE 1-continued

| Example No. | Structure | IUPAC Name* | LCMS: [M + H]+ (RT, min) |
|---|---|---|---|
| 98 | 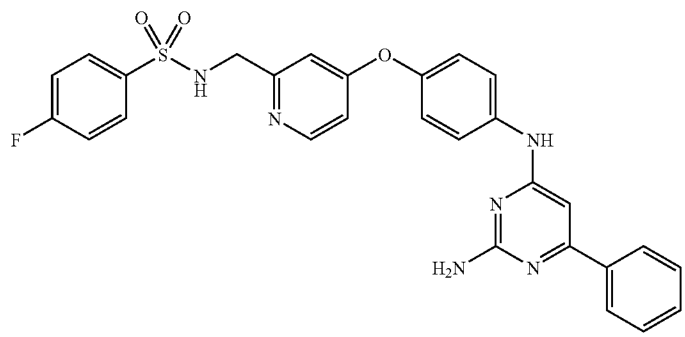 | N-[(4-{4-[(2-amino-6-phenylpyrimidin-4-yl)amino]phenoxy}pyridin-2-yl)methyl]-4-fluorobenzenesulfonamide trifluoroacetate | 543.4 (2.24) |
| 99 | 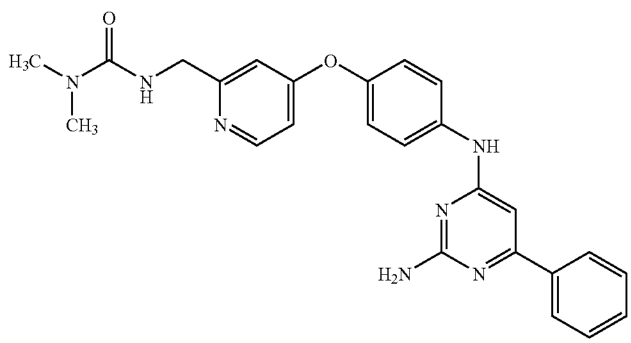 | N'-[(4-{4-[(2-amino-6-phenylpyrimidin-4-yl)amino]phenoxy}pyridin-2-yl)methyl]-N,N-dimethylurea | 457.1 (2.52) |
| 100 | 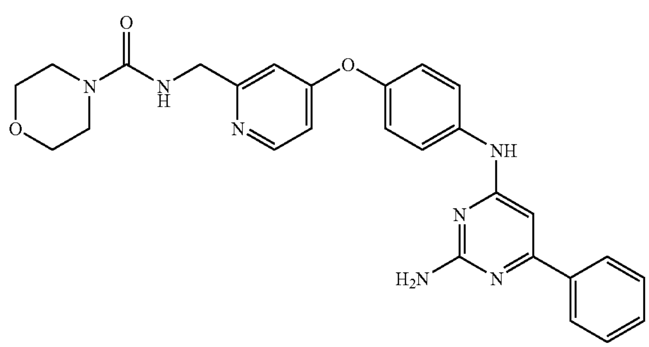 | N-[(4-{4-[(2-amino-6-phenylpyrimidin-4-yl)amino]phenoxy}pyridin-2-yl)methyl]morpholine-4-carboxamide | 498.4 (2.37) |
| 101 | 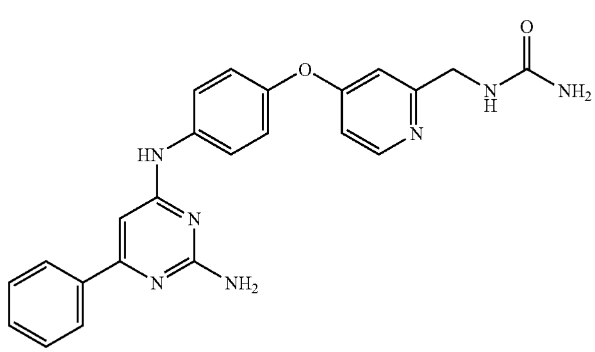 | N-[(4-{4-[(2-amino-6-phenylpyrimidin-4-yl)amino]phenoxy}pyridin-2-yl)methyl]urea trifluoroacetate | 428.3 (0.72) |

TABLE 1-continued

| Example No. | Structure | IUPAC Name* | LCMS: [M + H]+ (RT, min) |
| --- | --- | --- | --- |
| 102 | 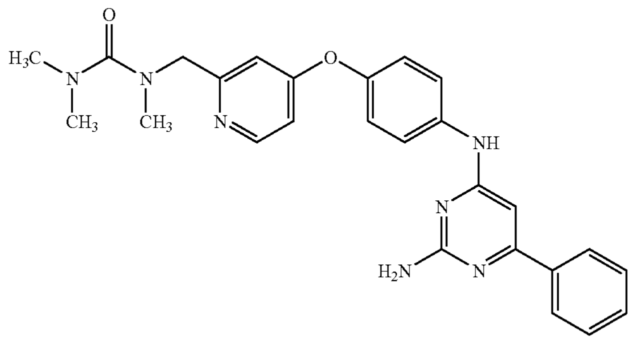 | N-[(4-{4-[(2-amino-6-phenylpyrimidin-4-yl)amino]phenoxy}pyridin-2-yl)methyl]-N,N',N'-trimethylurea | 470.1 (1.88) |
| 103 | 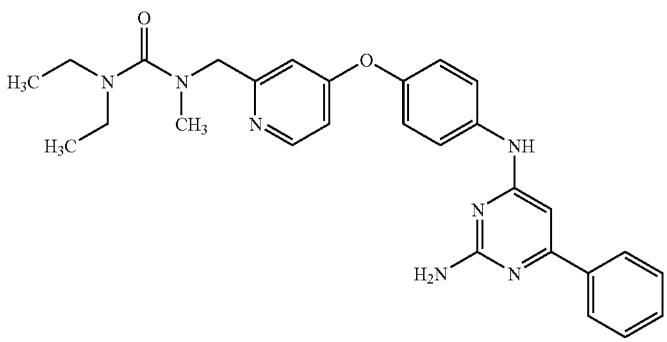 | N-[(4-{4-[(2-amino-6-phenylpyrimidin-4-yl)amino]phenoxy}pyridin-2-yl)methyl]-N',N'-diethyl-N-methylurea | 498.2 (2.04) |
| 104 | 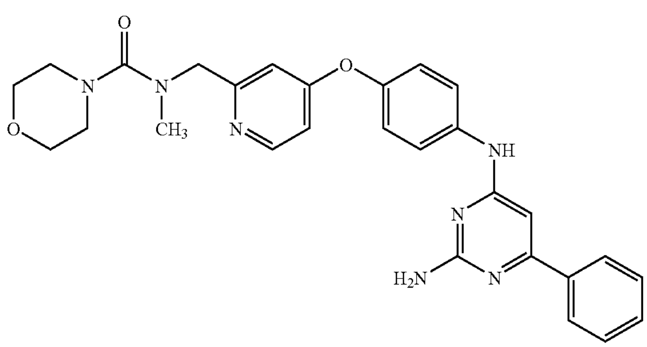 | N-[(4-{4-[(2-amino-6-phenylpyrimidin-4-yl)amino]phenoxy}pyridin-2-yl)methyl]-N-methylmorpholine-4-carboxamide | 512.2 (1.88) |
| 105 | 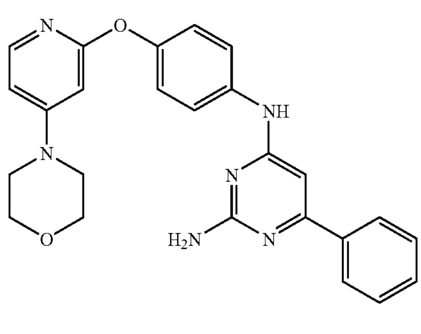 | N4*-{4-[(4-morpholin-4-ylpyridin-2-yl)oxy]phenyl}-6-phenylpyrimidine-2,4-diamine | 441.4 (1.27) |

TABLE 1-continued

| Example No. | Structure | IUPAC Name* | LCMS: [M + H]+ (RT, min) |
|---|---|---|---|
| 106 | 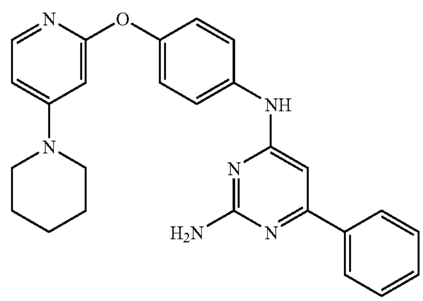 | 6-phenyl-N4*-{4-[(4-piperidin-1-ylpyridin-2-yl)oxy]phenyl}pyrimidine-2,4-diamine | 439.4 (1.93) |
| 107 | 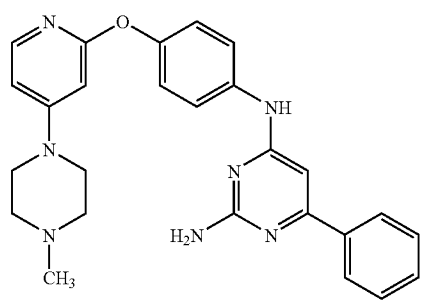 | N4*-(4-{[4-(4-methylpiperazin-1-yl)pyridin-2-yl]oxy}phenyl)-6-phenylpyrimidine-2,4-diamine | 454.2 (2.22) |
| 108 | 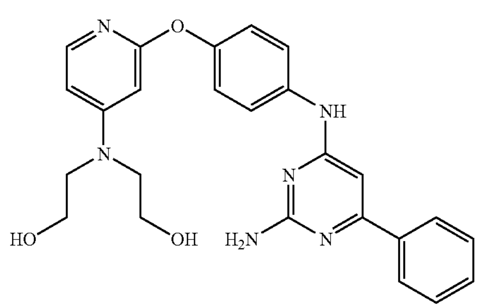 | 2,2'-[(2-{4-[(2-amino-6-phenylpyrimidin-4-yl)amino]phenoxy}pyridin-4-yl)imino]diethanol | 459.3 (2.38) |
| 109 | 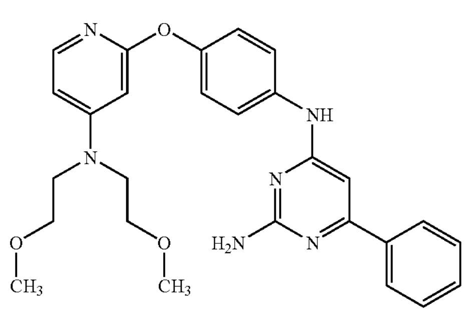 | N4*-[4-({4-[bis(2-methoxyethyl)amino]pyridin-2-yl}oxy)phenyl]-6-phenylpyrimidine-2,4-diamine | 488.0 (2.32) |

TABLE 1-continued

| Example No. | Structure | IUPAC Name* | LCMS: [M + H]+ (RT, min) |
|---|---|---|---|
| 110 | 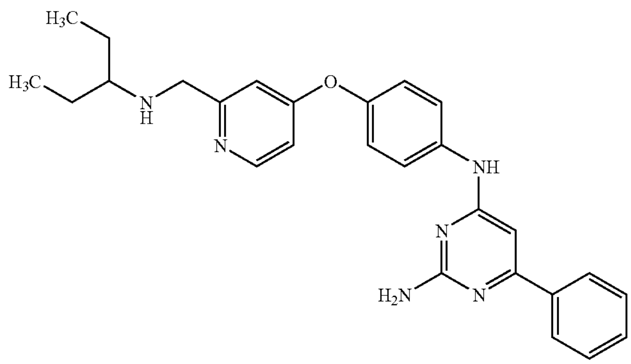 | N4*-{4-[(2-{[(1-ethylpropyl)amino]methyl}pyridin-4-yl)oxy]phenyl}-6-phenylpyrimidine-2,4-diamine | 455.2 (2.47) |
| 111 | 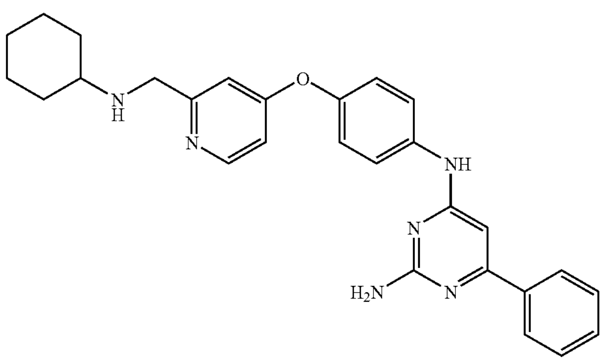 | N4*-[4-({2-[(cyclohexylamino)methyl]pyridin-4-yl}oxy)phenyl]-6-phenylpyrimidine-2,4-diamine | 467.1 (2.42) |
| 112 | 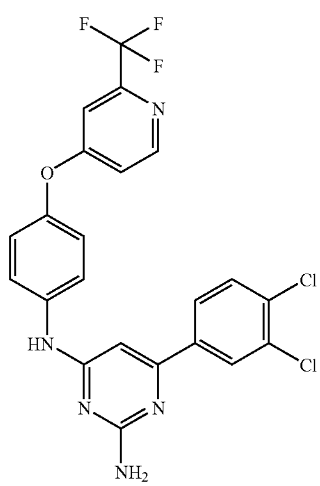 | 6-(3,4-dichlorophenyl)-N4*-(4-{[2-(trifluoromethyl)pyridin-4-yl]oxy}phenyl)pyrimidine-2,4-diamine | 492.3 (3.29) |
| 113 | 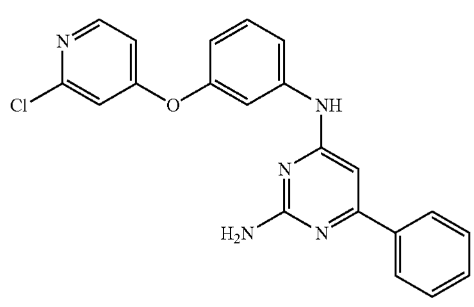 | N4*-{3-[(2-chloropyridin-4-yl)oxy]phenyl}-6-phenylpyrimidine-2,4-diamine | 390.3 (2.37) |

TABLE 1-continued

| Example No. | Structure | IUPAC Name* | LCMS: [M + H]+ (RT, min) |
|---|---|---|---|
| 114 | 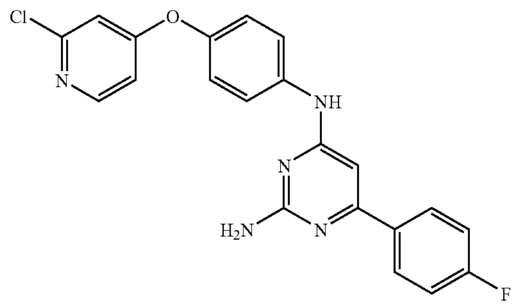 | N4*-{4-[(2-chloropyridin-4-yl)oxy]phenyl}-6-(4-fluorophenyl)pyrimidine-2,4-diamine | 408.3 (1.04) |
| 115 | 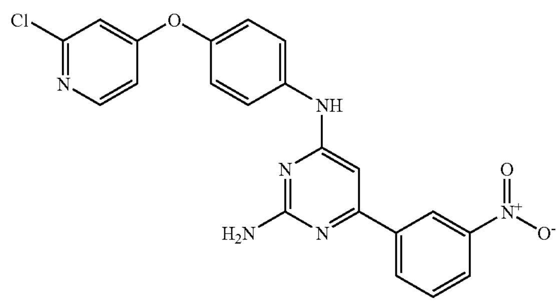 | N4*-{4-[(2-chloropyridin-4-yl)oxy]phenyl}-6-(3-nitrophenyl)pyrimidine-2,4-diamine | 435.2 (1.27) |
| 116 | 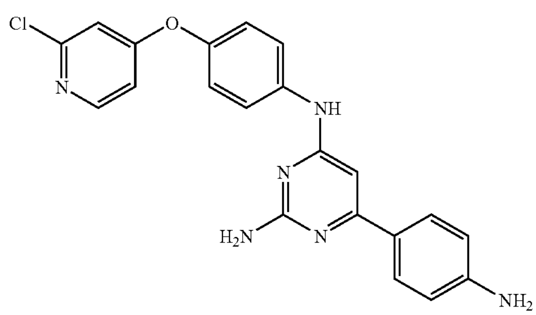 | 6-(4-aminophenyl)-N4*-{4-[(2-chloropyridin-4-yl)oxy]phenyl}pyrimidine-2,4-diamine | 405.3 (1.60) |
| 117 | 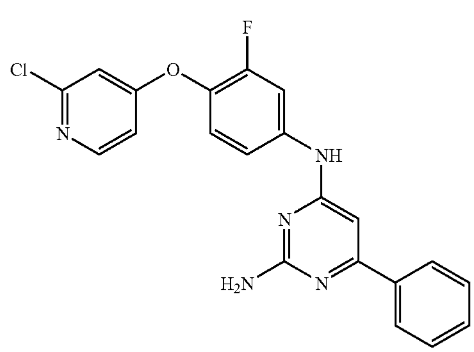 | N4*-{4-[(2-chloropyridin-4-yl)oxy]-3-fluorophenyl}-6-phenylpyrimidine-2,4-diamine | 408.2 (1.72) |

TABLE 1-continued

| Example No. | Structure | IUPAC Name* | LCMS: [M + H]+ (RT, min) |
|---|---|---|---|
| 118 | 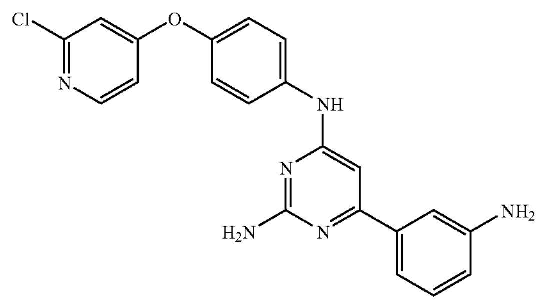 | 6-(3-aminophenyl)-N4*-{4-[(2-chloropyridin-4-yl)oxy]phenyl}pyrimidine-2,4-diamine | 405.3 (1.05) |
| 119 | 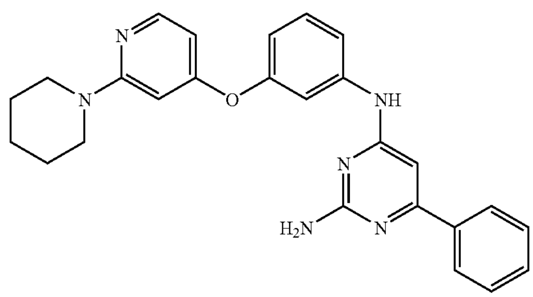 | 6-phenyl-N4*-{3-[(2-piperidin-1-ylpyridin-4-yl)oxy]phenyl}pyrimidine-2,4-diamine | 439.3 (0.25) |
| 120 | 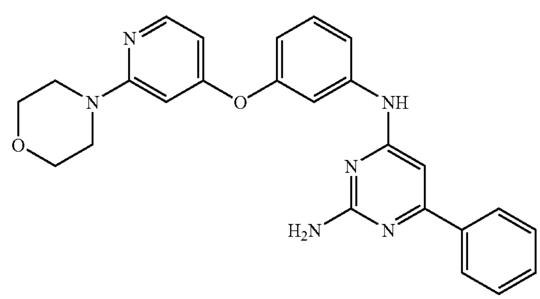 | N4*-{3-[(2-morpholin-4-ylpyridin-4-yl)oxy]phenyl}-6-phenylpyrimidine-2,4-diamine | 441.3 (0.25) |
| 121 | 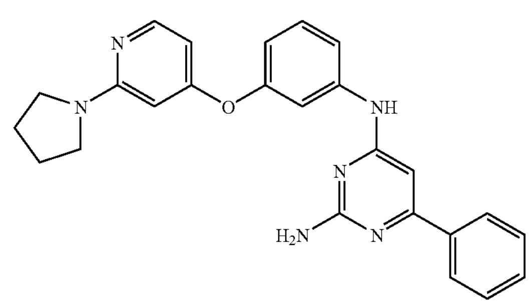 | 6-phenyl-N4*-{3-[(2-pyrrolidin-1-ylpyridin-4-yl)oxy]phenyl}pyrimidine-2,4-diamine | 425.3 (0.25) |
| 122 | 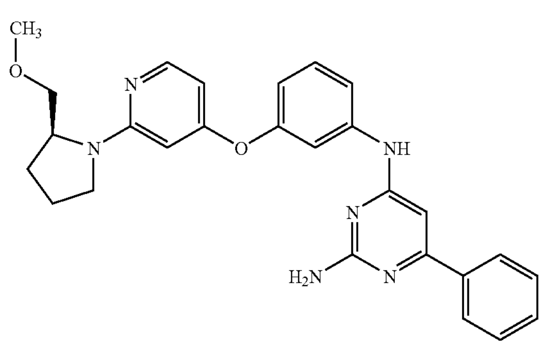 | N4*-[3-({2-[2-(methoxymethyl)pyrrolidin-1-yl]pyridin-4-yl}oxy)phenyl]-6-phenylpyrimidine-2,4-diamine | 469.3 (0.21) |

TABLE 1-continued

| Example No. | Structure | IUPAC Name* | LCMS: [M + H]+ (RT, min) |
|---|---|---|---|
| 123 | Chiral | [(2R)-1-(4-{3-[(2-amino-6-phenylpyrimidin-4-yl)amino]phenoxy}pyridin-2-yl)pyrrolidin-2-yl]methanol | 455.4 (2.34) |
| 124 | 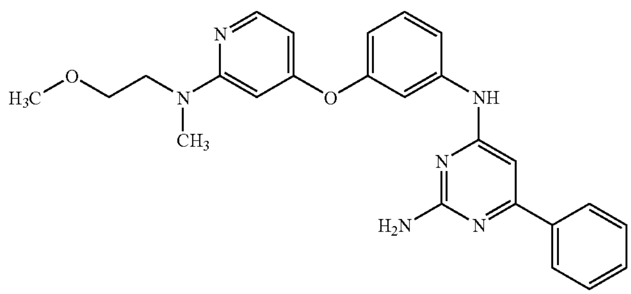 | N4*-[3-({2-[(2-methoxyethyl)(methyl)amino]pyridin-4-yl}oxy)phenyl]-6-phenylpyrimidine-2,4-diamine | 443.4 (1.71) |
| 125 | 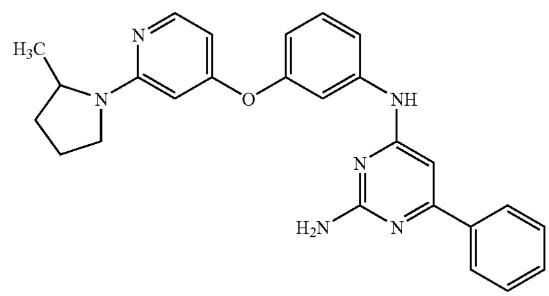 | N4*-(3-{[2-(2-methylpyrrolidin-1-yl)pyridin-4-yl]oxy}phenyl)-6-phenylpyrimidine-2,4-diamine | 439.3 (2.01) |
| 126 | 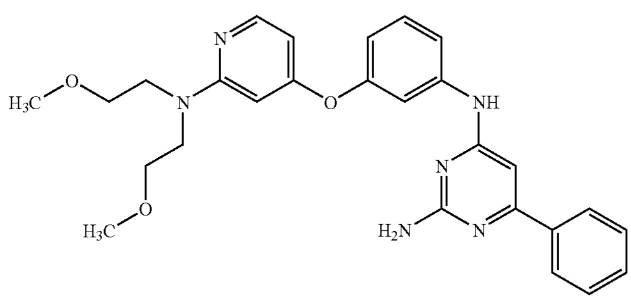 | N4*-[3-({2-[bis(2-methoxyethyl)amino]pyridin-4-yl}oxy)phenyl]-6-phenylpyrimidine-2,4-diamine | 487.2 (1.03) |
| 127 | 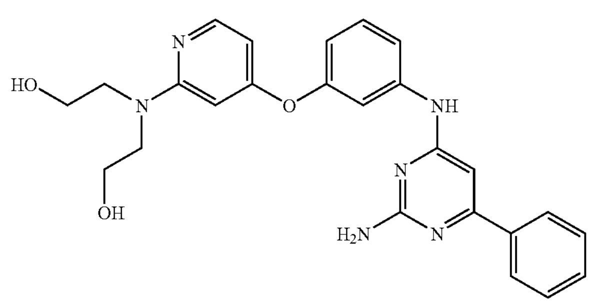 | 2,2'-[(4-{3-[(2-amino-6-phenylpyrimidin-4-yl)amino]phenoxy}pyridin-2-yl)imino]diethanol | 459.3 (0.93) |

TABLE 1-continued

| Example No. | Structure | IUPAC Name* | LCMS: [M + H]+ (RT, min) |
|---|---|---|---|
| 128 | Chiral | [(2S)-1-(4-{3-[(2-amino-6-phenylpyrimidin-4-yl)amino]phenoxy}pyridin-2-yl)pyrrolidin-2-yl]methanol | 455.4 (2.41) |
| 129 | 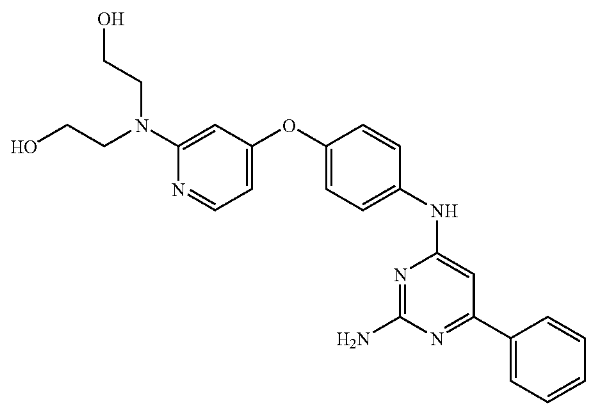 | 2,2'-[(4-{4-[(2-amino-6-phenylpyrimidin-4-yl)amino]phenoxy}pyridin-2-yl)imino]diethanol | 459.4 (2.34) |
| 130 | 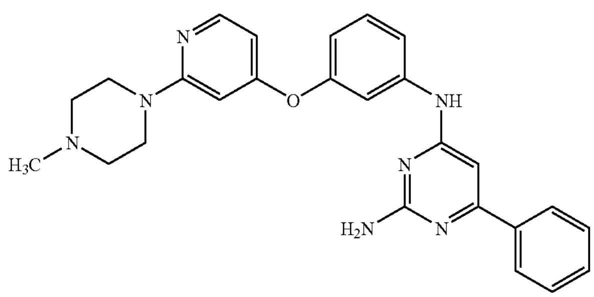 | N4*-(3-{[2-(4-methylpiperazin-1-yl)pyridin-4-yl]oxy}phenyl)-6-phenylpyrimidine-2,4-diamine | 454.3 (2.37) |
| 131 | 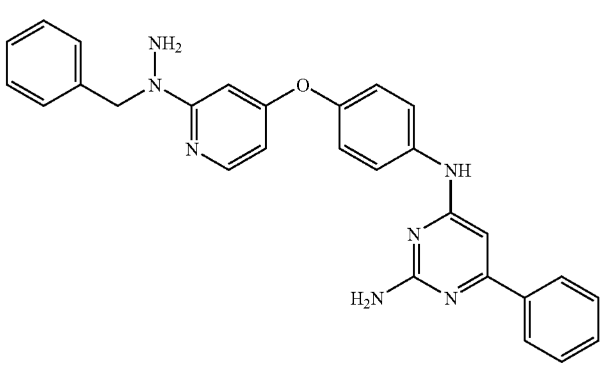 | N4*-(4-{[2-(1-benzylhydrazino)pyridin-4-yl]oxy}phenyl)-6-phenylpyrimidine-2,4-diamine | 476.2 (2.19) |

TABLE 1-continued

| Example No. | Structure | IUPAC Name* | LCMS: [M + H]+ (RT, min) |
|---|---|---|---|
| 132 | 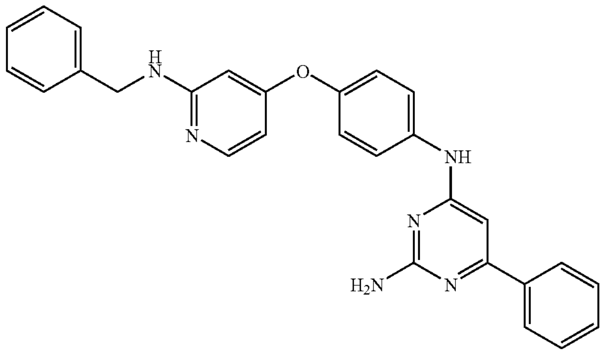 | N4*-(4-{[2-(benzylamino) pyridin-4-yl]oxy}phenyl)-6-phenylpyrimidine-2,4-diamine trifluoroacetate | 461.3 (2.10) |
| 133 | Chiral | N4*-[4-({2-[(2R)-2-(methoxymethyl)pyrrolidin-1-yl]pyridin-4-yl}oxy)phenyl]-6-phenylpyrimidine-2,4-diamine | 469.3 (0.96) |
| 134 | 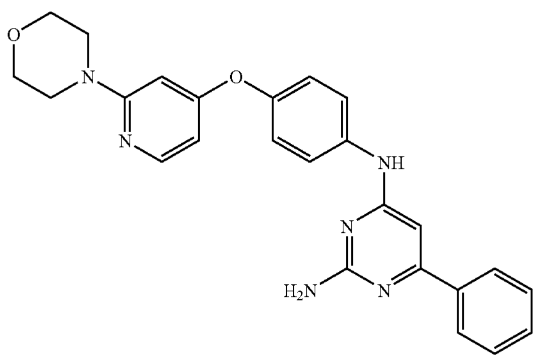 | N4*-{4-[(2-morpholin-4-ylpyridin-4-yl)oxy]phenyl}-6-phenylpyrimidine-2,4-diamine | 441.3 (1.74) |
| 135 | 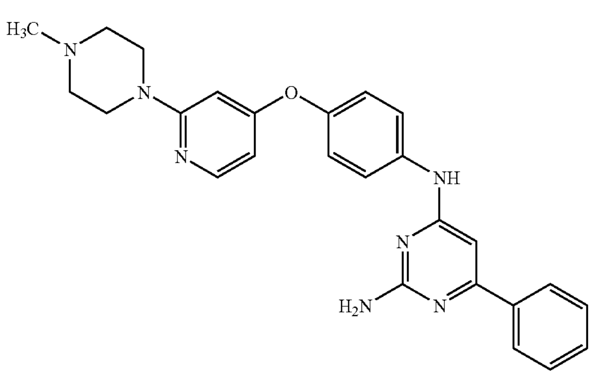 | N4*-(4-{[2-(4-methylpiperazin-1-yl)pyridin-4-yl]oxy}phenyl)-6-phenylpyrimidine-2,4-diamine | 454.2 (1.47) |

TABLE 1-continued

| Example No. | Structure | IUPAC Name* | LCMS: [M + H]+ (RT, min) |
|---|---|---|---|
| 136 | 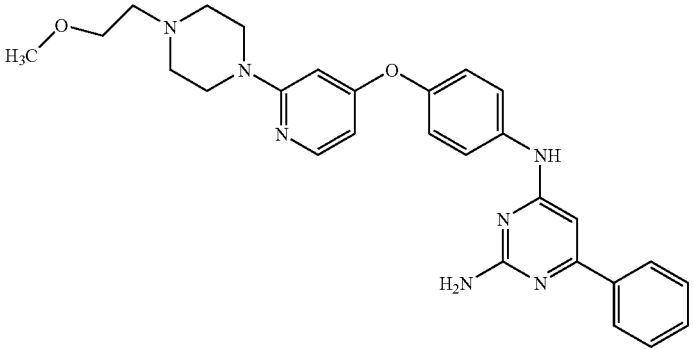 | N4*-[4-({2-[4-(2-methoxyethyl)piperazin-1-yl]pyridin-4-yl}oxy)phenyl]-6-phenylpyrimidine-2,4-diamine | 498.2 (1.59) |
| 137 | 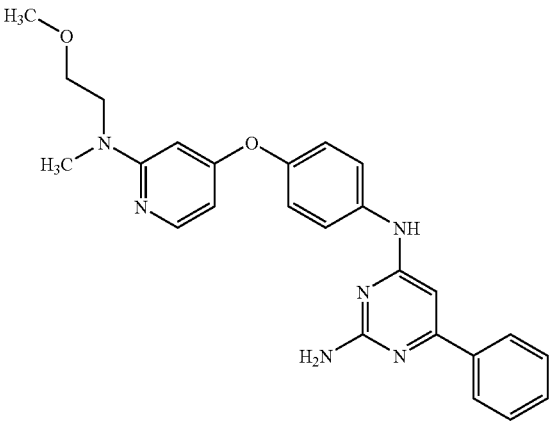 | N4*-[4-({2-[(2-methoxyethyl)(methyl)amino]pyridin-4-yl}oxy)phenyl]-6-phenylpyrimidine-2,4-diamine | 443.3 (0.82) |
| 138 | 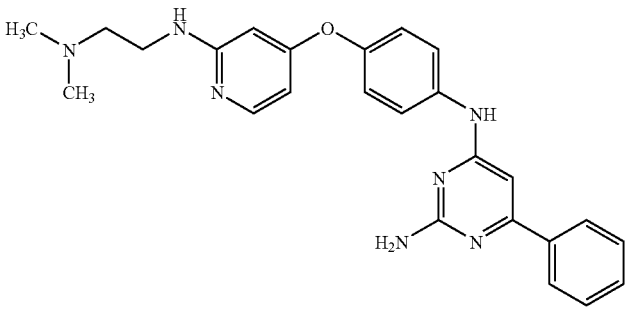 | N4*-{4-[(2-{[2-(dimethylamino)ethyl]amino}pyridin-4-yl)oxy]phenyl}-6-phenylpyrimidine-2,4-diamine | 442.2 (0.82) |
| 139 | 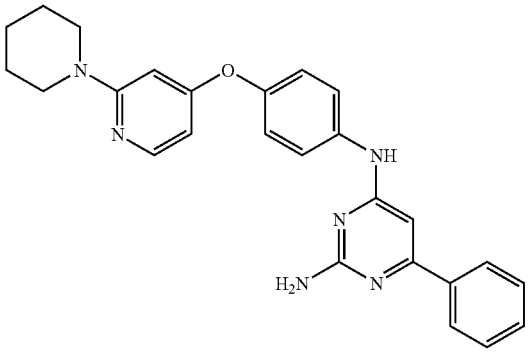 | 6-phenyl-N4*-{4-[(2-piperidin-1-ylpyridin-4-yl)oxy]phenyl}pyrimidine-2,4-diamine | 439.3 (1.82) |

TABLE 1-continued

| Example No. | Structure | IUPAC Name* | LCMS: [M + H]+ (RT, min) |
|---|---|---|---|
| 140 | 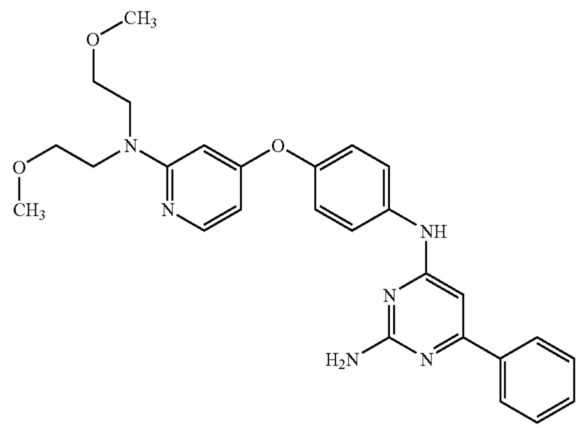 | N4*-[4-({2-[bis(2-methoxyethyl)amino]pyridin-4-yl}oxy)phenyl]-6-phenylpyrimidine-2,4-diamine | 487.2 (1.34) |
| 141 | 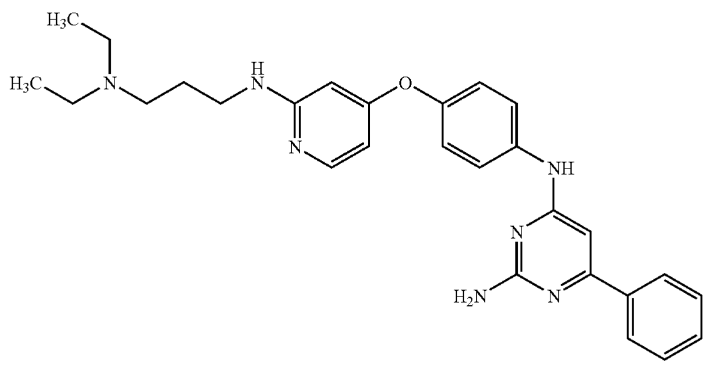 | N4*-{4-[(2-{[3-(diethylamino)propyl]amino}pyridin-4-yl)oxy]phenyl}-6-phenylpyrimidine-2,4-diamine | 484.2 (0.86) |
| 142 | 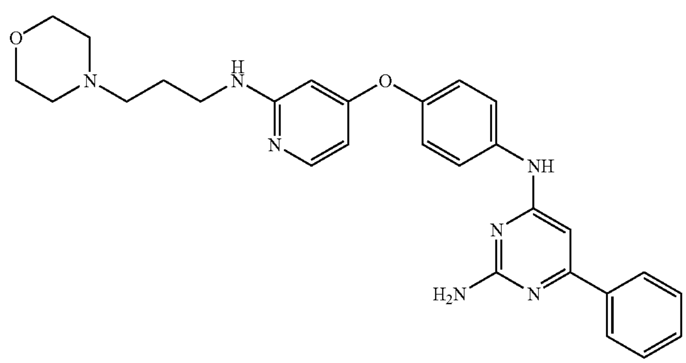 | N4*-[4-({2-[(3-morpholin-4-ylpropyl)amino]pyridin-4-yl}oxy)phenyl]-6-phenylpyrimidine-2,4-diamine | 498.2 (0.94) |
| 143 | 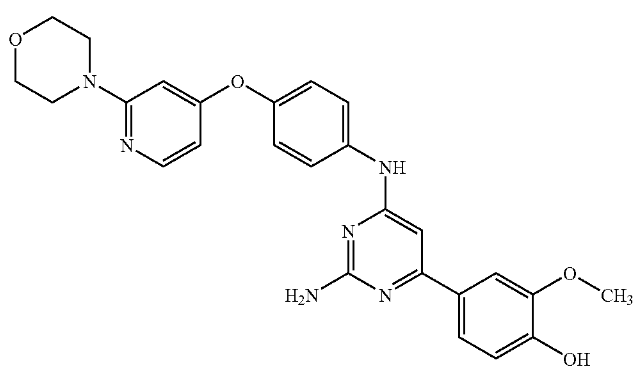 | 4-[2-amino-6-({4-[(2-morpholin-4-ylpyridin-4-yl)oxy]phenyl}amino)pyrimidin-4-yl]-2-methoxyphenol | 487.3 (0.97) |

TABLE 1-continued
| Example No. | Structure | | IUPAC Name* | LCMS: [M + H]+ (RT, min) |
|---|---|---|---|---|
| 144 | 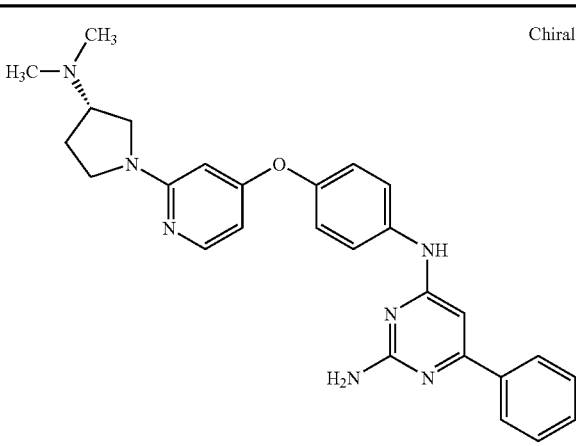 | Chiral | N4*-[4-({2-[(3S)-3-(dimethylamino)pyrrolidin-1-yl]pyridin-4-yl}oxy)phenyl]-6-phenylpyrimidine-2,4-diamine | 468.2 (1.01) |
| 145 | 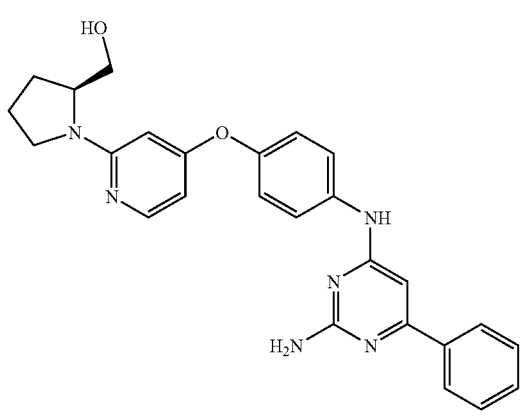 | Chiral | [(2S)-1-(4-{4-[(2-amino-6-phenylpyrimidin-4-yl)amino]phenoxy}pyridin-2-yl)pyrrolidin-2-yl]methanol | 455.3 (1.91) |
| 146 | 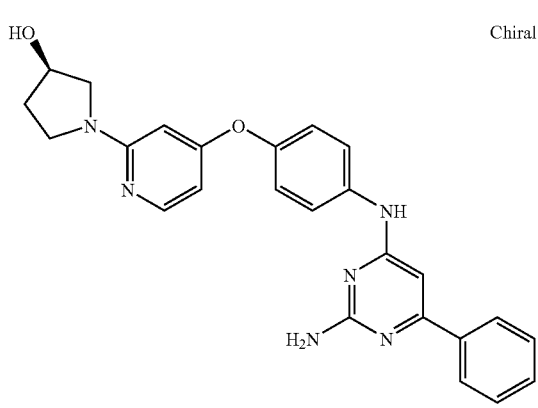 | Chiral | (3R)-1-(4-{4-[(2-amino-6-phenylpyrimidin-4-yl)amino]phenoxy}pyridin-2-yl)pyrrolidin-3-ol | 441.3 (1.31) |

TABLE 1-continued

| Example No. | Structure | IUPAC Name* | LCMS: [M + H]+ (RT, min) |
|---|---|---|---|
| 147 | 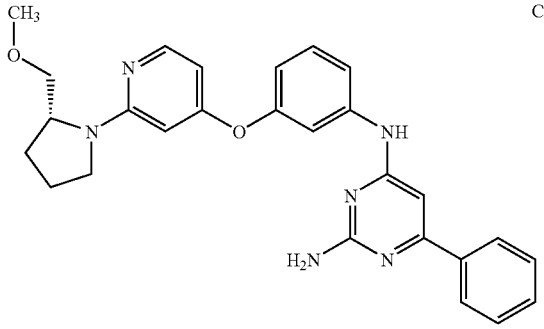 Chiral | N4*-[3-({2-[(2R)-2-(methoxymethyl)pyrroli-din-1-yl]pyridin-4-yl}oxy)phenyl]-6-phenylpyrimidine-2,4-diamine | 469.4 (1.71) |
| 148 | 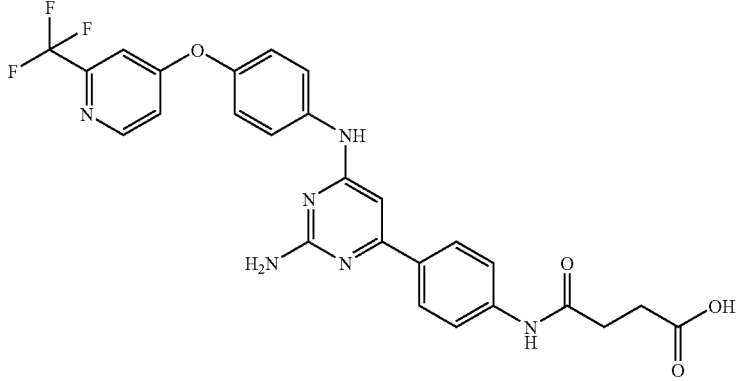 | 4-[(4-{2-amino-6-[(4-{[2-(trifluoromethyl)pyridin-4-yl]oxy}phenyl)amino]pyrimidin-4-yl}phenyl)amino]-4-oxobutanoic acid | 539.4 (2.25) |
| 149 | 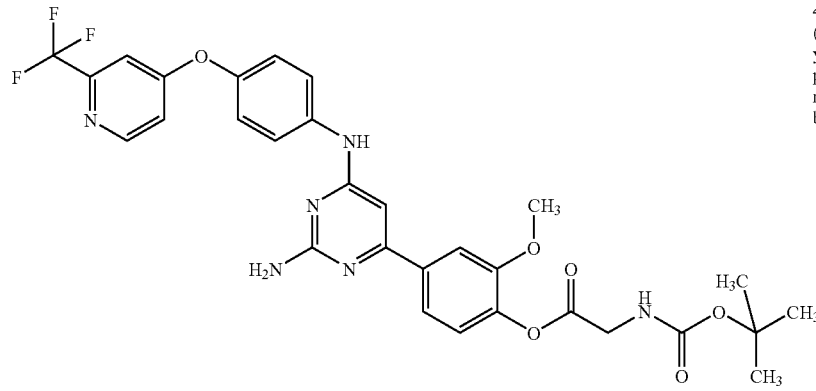 | 4-{2-amino-6-[(4-{[2-(trifluoromethyl)pyridin-4-yl]oxy}phenyl)amino]pyrimidin-4-yl}-2-methoxyphenyl N-(tert-butoxycarbonyl)glycinate | 627.0 (2.8) |
| 150 | 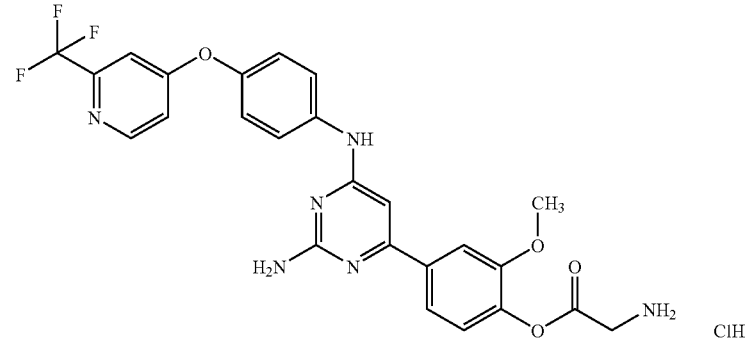 | 4-{2-amino-6-[(4-{[2-(trifluoromethyl)pyridin-4-yl]oxy}phenyl)amino]pyrimidin-4-yl}-2-methoxyphenyl glycinate hydrochloride | 527.2 (2.54) |

TABLE 1-continued

| Example No. | Structure | IUPAC Name* | LCMS: [M + H]+ (RT, min) |
|---|---|---|---|
| 151 | 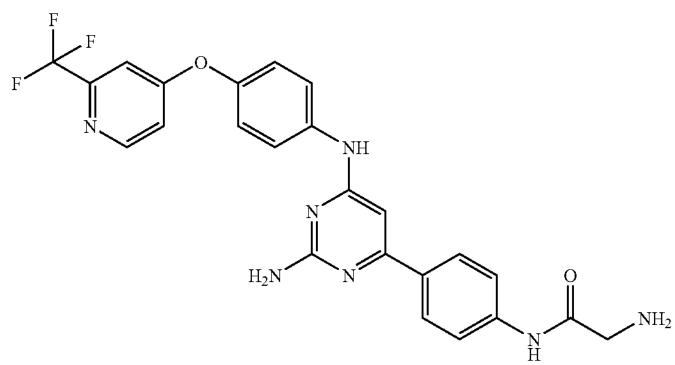 | N-(4-{2-amino-6-[(4-{[2-(trifluoromethyl)pyridin-4-yl]oxy}phenyl)amino]pyrimidin-4-yl}phenyl)glycinamide trifluoroacetate | 496.2 (2.11) |
| 152 | 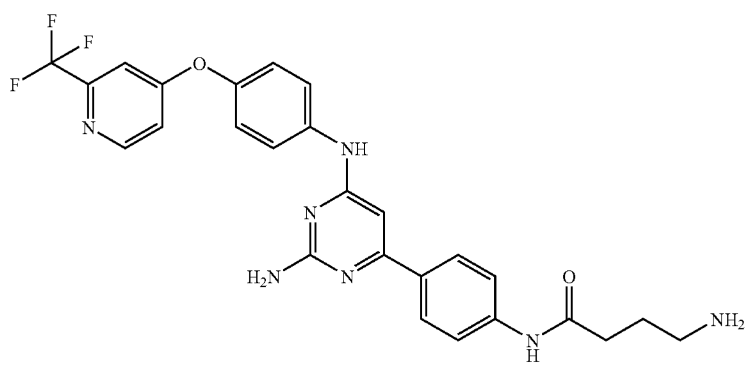 | 4-amino-N-(4-{2-amino-6-[(4-{[2-(trifluoromethyl)pyridin-4-yl]oxy}phenyl)amino]pyrimidin-4-yl}phenyl)butanamide trifluoroacetate | 524.1 (2.15) |
| 153 | 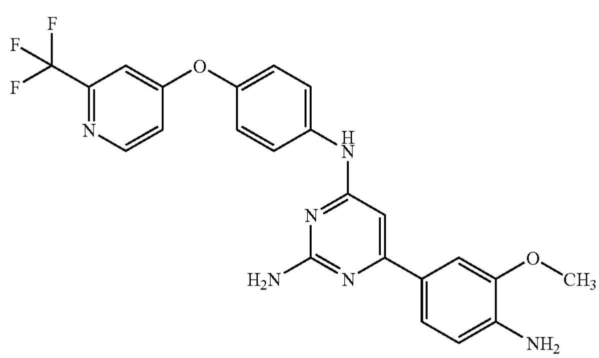 | 6-(4-amino-3-methoxyphenyl)-N4*-(4-{[2-(trifluoromethyl)pyridin-4-yl]oxy}phenyl)pyrimidine-2,4-diamine | 469.4 (2.67) |
| 154 | 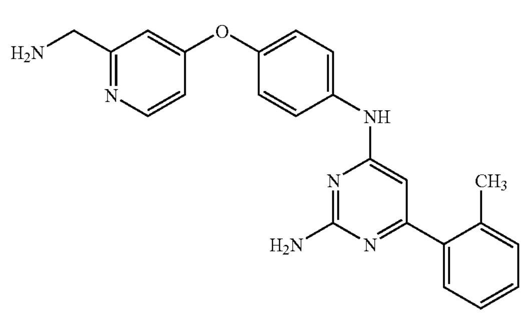 | N4*-(4-{[2-(aminomethyl)pyridin-4-yl]oxy}phenyl)-6-(2-methylphenyl)pyrimidine-2,4-diamine | 399.6 (2.15) |

TABLE 1-continued

| Example No. | Structure | IUPAC Name* | LCMS: [M + H]+ (RT, min) |
|---|---|---|---|
| 155 | 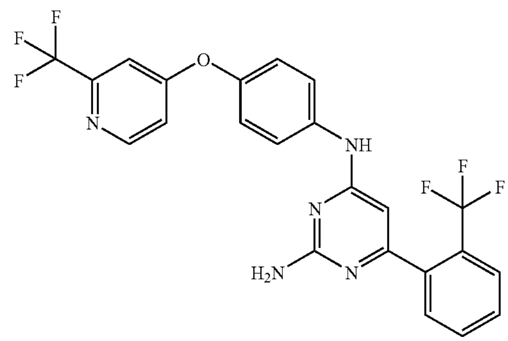 | 6-[2-(trifluoromethyl)phenyl]-N4*-(4-{[2-(trifluoromethyl)pyridin-4-yl]oxy}phenyl)pyrimidine-2,4-diamine | 493.0 (2.96) |
| 156 | 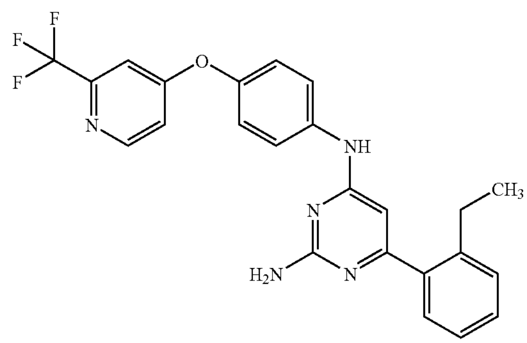 | 6-(2-ethylphenyl)-N4*-(4-{[2-(trifluoromethyl)pyridin-4-yl]oxy}phenyl)pyrimidine-2,4-diamine | 452.9 (2.89) |
| 157 | 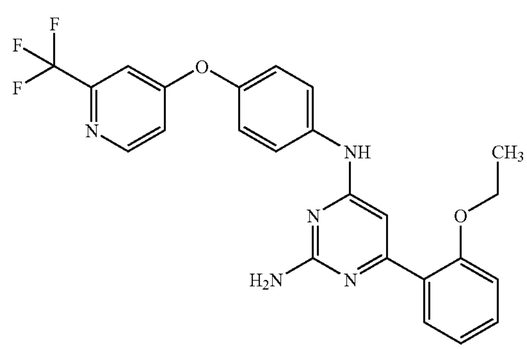 | 6-(2-ethoxyphenyl)-N4*-(4-{[2-(trifluoromethyl)pyridin-4-yl]oxy}phenyl)pyrimidine-2,4-diamine | 469.0 (2.81) |
| 158 | 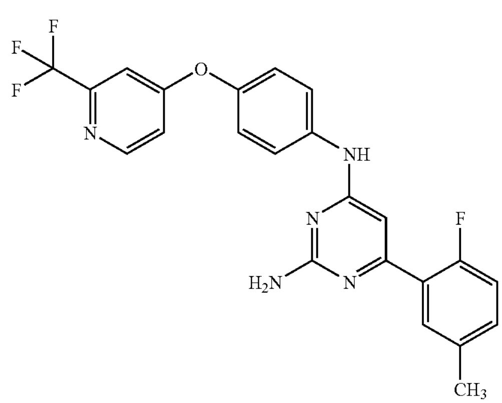 | 6-(2-fluoro-5-methylphenyl)-N4*-(4-{[2-(trifluoromethyl)pyridin-4-yl]oxy}phenyl)pyrimidine-2,4-diamine | 456.7 (2.87) |

TABLE 1-continued

| Example No. | Structure | IUPAC Name* | LCMS: [M + H]+ (RT, min) |
|---|---|---|---|
| 159 | 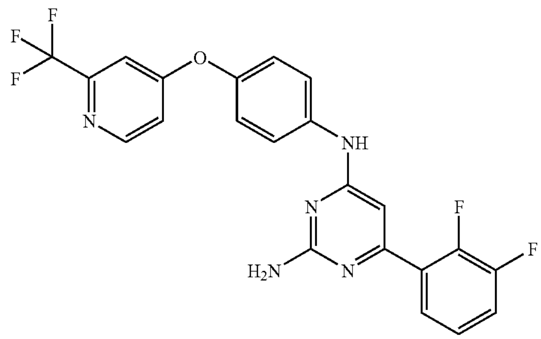 | 6-(2,3-difluorophenyl)-N4*-(4-{[2-(trifluoromethyl)pyridin-4-yl]oxy}phenyl)pyrimidine-2,4-diamine | 460.0 (2.89) |
| 160 | 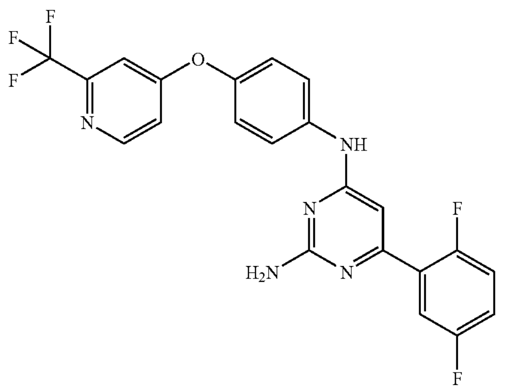 | 6-(2,5-difluorophenyl)-N4*-(4-{[2-(trifluoromethyl)pyridin-4-yl]oxy}phenyl)pyrimidine-2,4-diamine | 460.7 (2.78) |
| 161 | 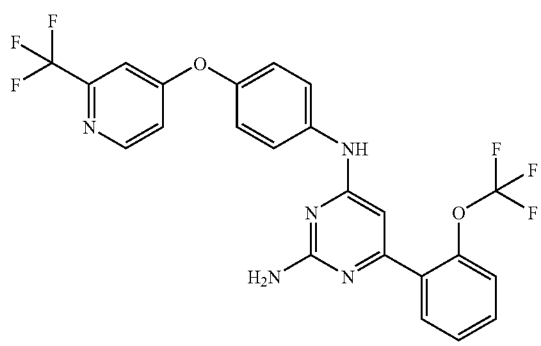 | 6-[2-(trifluoromethoxy)phenyl]-N4*-(4-{[2-(trifluoromethyl)pyridin-4-yl]oxy}phenyl)pyrimidine-2,4-diamine | 508.6 (2.78) |
| 162 | 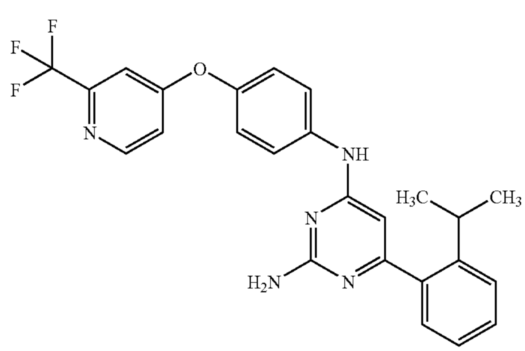 | 6-(2-isopropylphenyl)-N4*-(4-{[2-(trifluoromethyl)pyridin-4-yl]oxy}phenyl)pyrimidine-2,4-diamine | 466.7 (2.99) |

TABLE 1-continued

| Example No. | Structure | IUPAC Name* | LCMS: [M + H]+ (RT, min) |
|---|---|---|---|
| 163 | 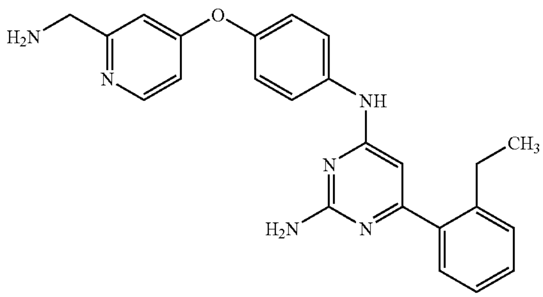 | N4*-(4-{[2-(aminomethyl)pyridin-4-yl]oxy}phenyl)-6-(2-ethylphenyl)pyrimidine-2,4-diamine | 413.3 (1.99) |
| 164 | 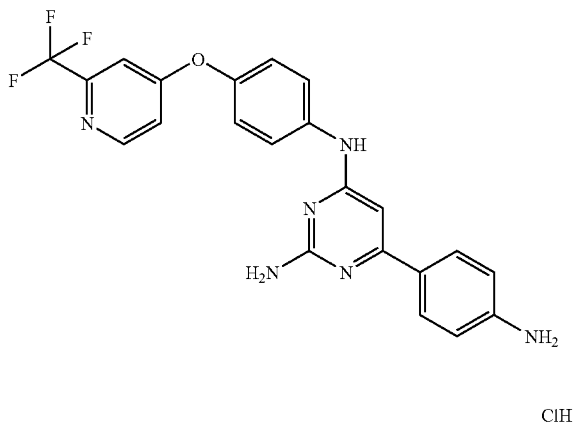 | 6-(4-aminophenyl)-N4*-(4-{[2-(trifluoromethyl)pyridin-4-yl]oxy}phenyl)pyrimidine-2,4-diamine hydrochloride | 439.3 (2.47) |
| 165 | 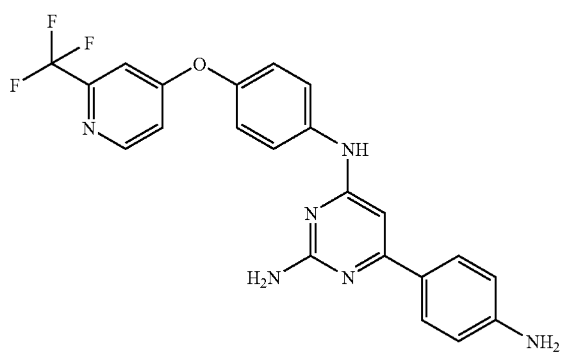 | 6-(4-aminophenyl)-N4*-(4-{[2-(trifluoromethyl)pyridin-4-yl]oxy}phenyl)pyrimidine-2,4-diamine | 439.3 (2.37) |
| 166 | 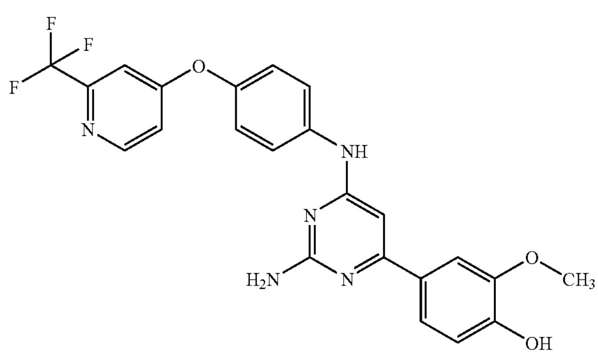 | 4-{2-amino-6-[(4-{[2-(trifluoromethyl)pyridin-4-yl]oxy}phenyl)amino]pyrimidin-4-yl}-2-methoxyphenol | 470.2 (1.46) |

TABLE 1-continued

| Example No. | Structure | IUPAC Name* | LCMS: [M + H]+ (RT, min) |
|---|---|---|---|
| 167 | 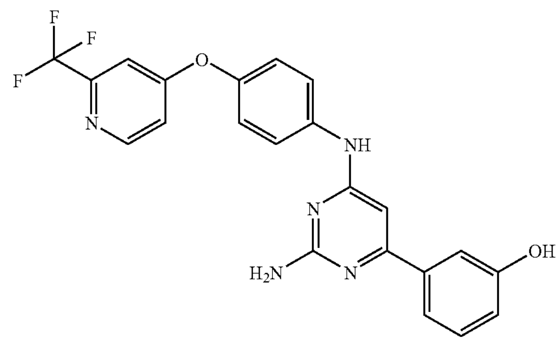 | 3-{2-amino-6-[(4-{[2-(trifluoromethyl)pyridin-4-yl]oxy}phenyl)amino]pyrimidin-4-yl}phenol | 440.3 (1.08) |
| 168 | 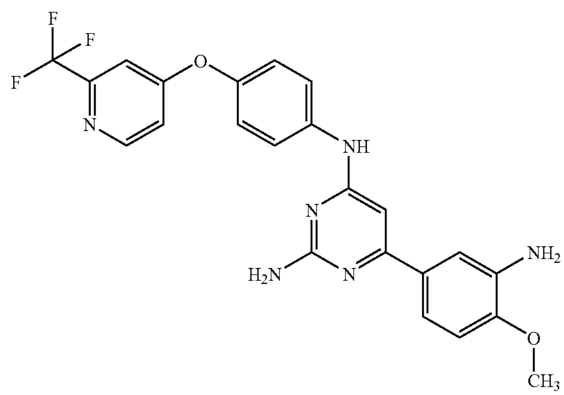 | 6-(3-amino-4-methoxyphenyl)-N4*-(4-{[2-(trifluoromethyl)pyridin-4-yl]oxy}phenyl)pyrimidine-2,4-diamine | 469.3 (2.45) |
| 169 | 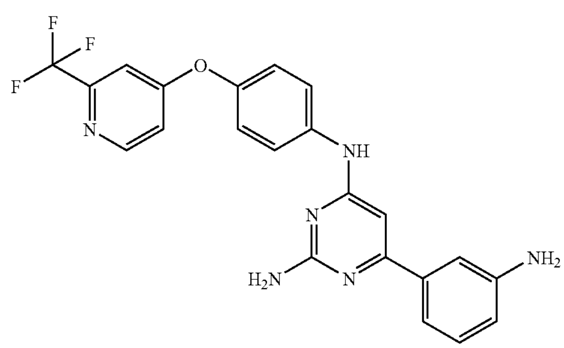 | 6-(3-aminophenyl)-N4*-(4-{[2-(trifluoromethyl)pyridin-4-yl]oxy}phenyl)pyrimidine-2,4-diamine | 439.3 (2.37) |
| 170 | 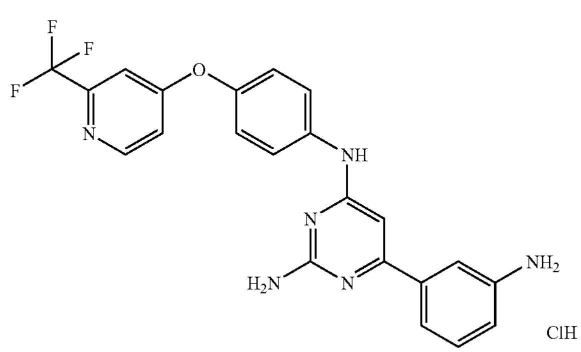 | 6-(3-aminophenyl)-N4*-(4-{[2-(trifluoromethyl)pyridin-4-yl]oxy}phenyl)pyrimidine-2,4-diamine hydrochloride | 439.4 (2.36) |

TABLE 1-continued

| Example No. | Structure | IUPAC Name* | LCMS: [M + H]+ (RT, min) |
|---|---|---|---|
| 171 | 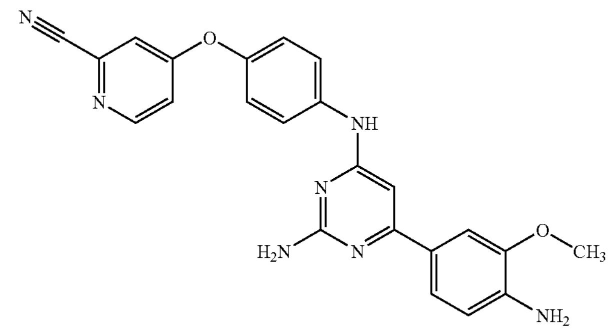 | 4-(4-{[2-amino-6-(4-hydroxy-3-methoxyphenyl)pyrimidin-4-yl]amino}phenoxy)pyridine-2-carbonitrile | 427.3 (2.16) |
| 172 | 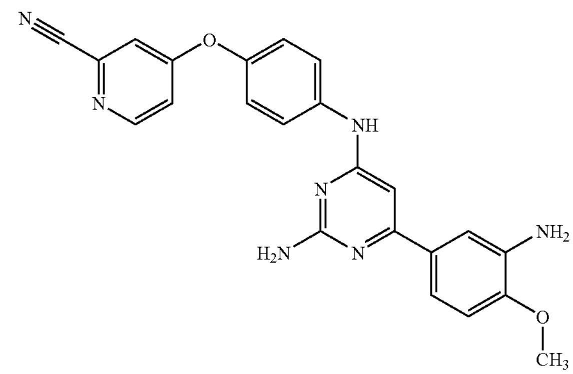 | 4-(4-{[2-amino-6-(3-amino-4-methoxyphenyl)pyrimidin-4-yl]amino}phenoxy)pyridine-2-carbonitrile | 426.3 (2.10) |
| 173 | 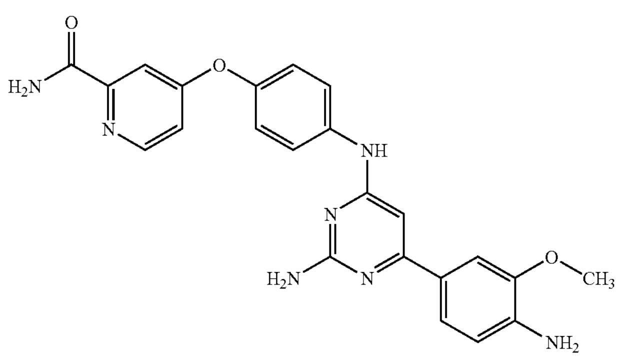 | 4-(4-{[2-amino-6-(4-amino-3-methoxyphenyl)pyrimidin-4-yl]amino}phenoxy)pyridine-2-carboxamide | 444.2 (2.22) |
| 174 | 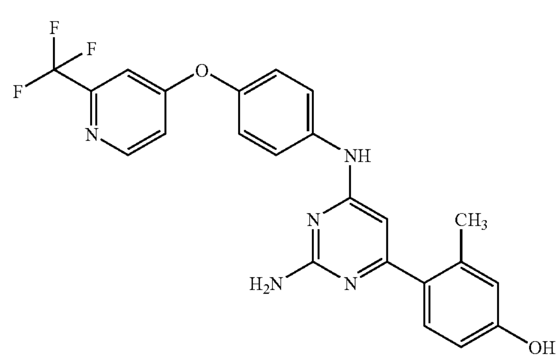 | 4-{2-amino-6-[(4-{[2-(trifluoromethyl)pyridin-4-yl]oxy}phenyl)amino]pyrimidin-4-yl}-3-methylphenol | 454.3 (2.48) |

TABLE 1-continued

| Example No. | Structure | IUPAC Name* | LCMS: [M + H]+ (RT, min) |
|---|---|---|---|
| 175 | 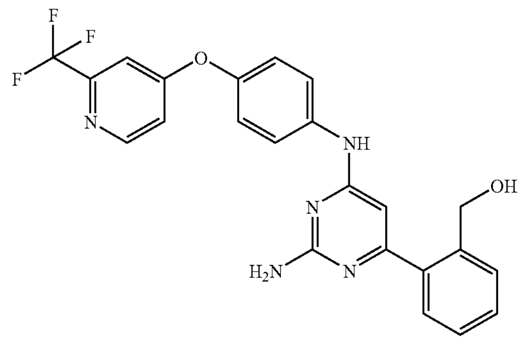 | (2-{2-amino-6-[(4-{[2-(trifluoromethyl)pyridin-4-yl]oxy}phenyl)amino]pyrimidin-4-yl}phenyl)methanol | 454.2 (2.38) |
| 176 | 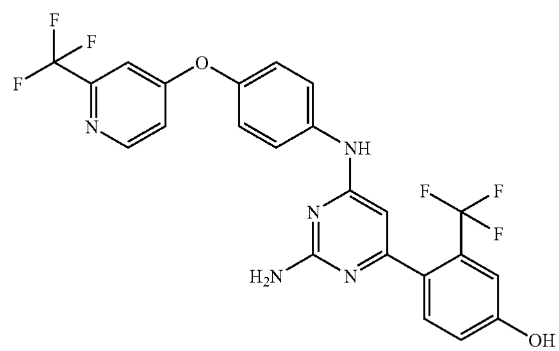 | 4-{2-amino-6-[(4-{[2-(trifluoromethyl)pyridin-4-yl]oxy}phenyl)amino]pyrimidin-4-yl}-3-(trifluoromethyl)phenol | 508.2 (2.62) |
| 177 | 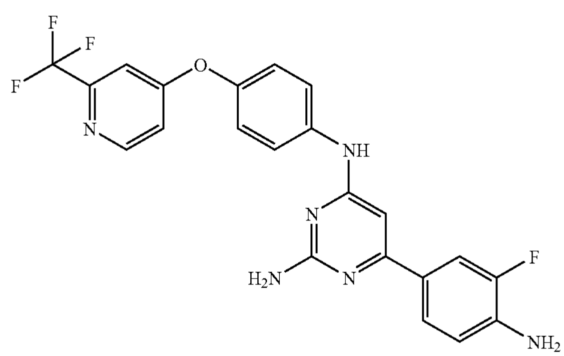 | 6-(4-amino-3-fluorophenyl)-N4*-(4-{[2-(trifluoromethyl)pyridin-4-yl]oxy}phenyl)pyrimidine-2,4-diamine | 457.3 (2.52) |
| 178 | 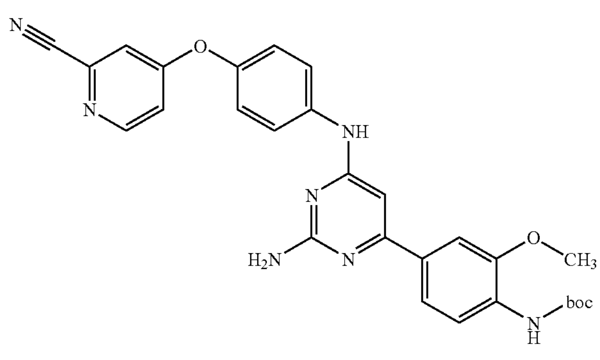 | tert-butyl {4-[2-amino-6-({4-[(2-cyanopyridin-4-yl)oxy]phenyl}amino)pyrimidin-4-yl]-2-methoxyphenyl}carbamate | 526.2 (2.79) |

TABLE 1-continued

| Example No. | Structure | IUPAC Name* | LCMS: [M + H]+ (RT, min) |
|---|---|---|---|
| 179 | 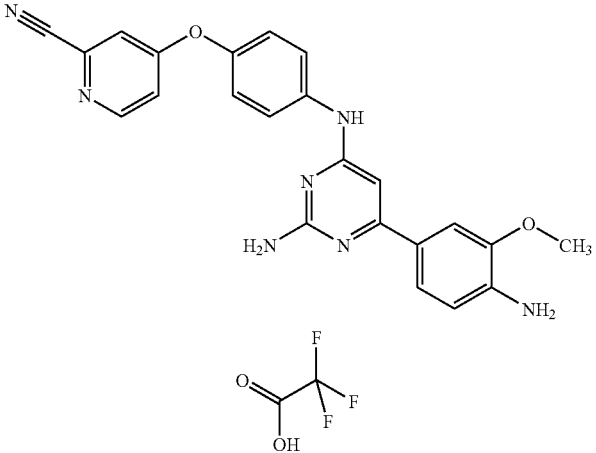 | 4-(4-{[2-amino-6-(4-amino-3-methoxyphenyl)pyrimidin-4-yl]amino}phenoxy)pyridine-2-carbonitrile trifluoroacetate | 426.2 (2.31) |
| 180 | 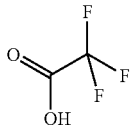 | 6-(4-amino-3-methylphenyl)-N4*-(4-{[2-(trifluoromethyl)pyridin-4-yl]oxy}phenyl)pyrimidine-2,4-diamine | 453.4 (2.26) |
| 181 | 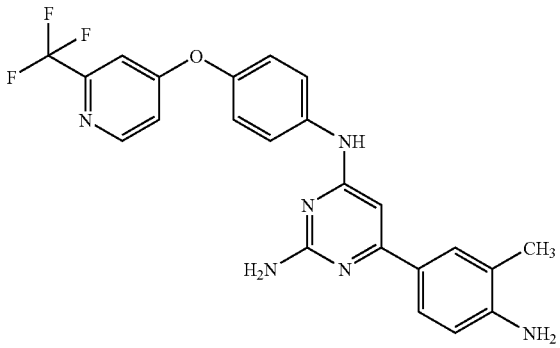 | 6-(6-aminopyridin-3-yl)-N4*-(4-{[2-(trifluoromethyl)pyridin-4-yl]oxy}phenyl)pyrimidine-2,4-diamine | 440.3 (2.01) |
| 182 | 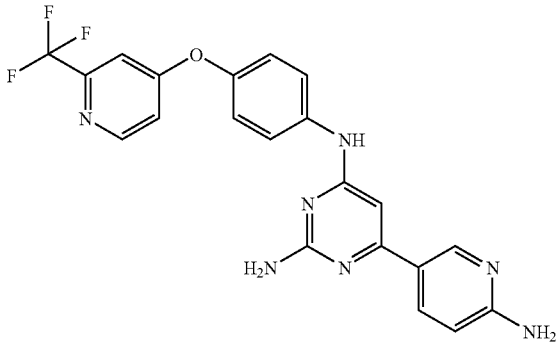 | 6-(3-amino-4-chlorophenyl)-N4*-(4-{[2-(trifluoromethyl)pyridin-4-yl]oxy}phenyl)pyrimidine-2,4-diamine | 473.3 (2.61) |

TABLE 1-continued

| Example No. | Structure | IUPAC Name* | LCMS: [M + H]+ (RT, min) |
|---|---|---|---|
| 183 | 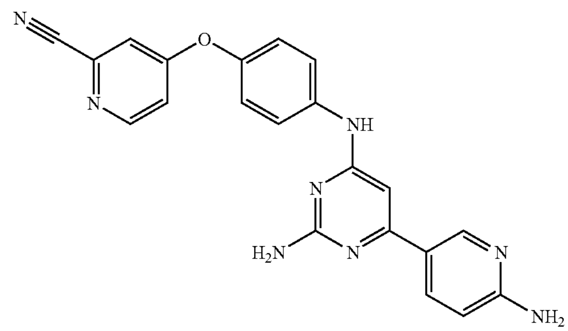 | 4-(4-{[2-amino-6-(6-aminopyridin-3-yl)pyrimidin-4-yl]amino}phenoxy)pyridine-2-carbonitrile | 397.3 (1.85) |
| 184 | 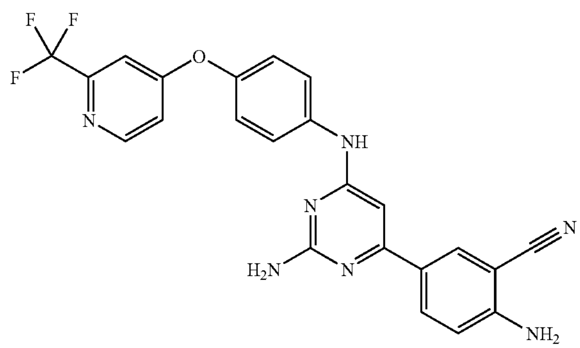 | 2-amino-5-{2-amino-6-[(4-{[2-(trifluoromethyl)pyridin-4-yl]oxy}phenyl)amino]pyrimidin-4-yl}benzonitrile | 464.4 (2.54) |
| 185 | 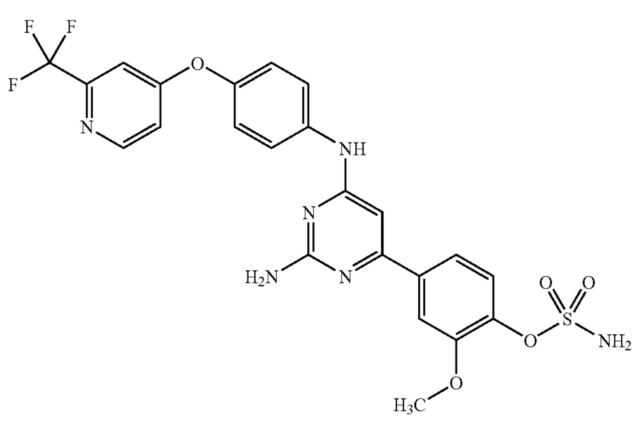 | 4-{2-amino-6-[(4-{[2-(trifluoromethyl)pyridin-4-yl]oxy}phenyl)amino]pyrimidin-4-yl}-2-methoxyphenyl sulfamate | 549.1 (2.66) |

TABLE 1-continued

| Example No. | Structure | IUPAC Name* | LCMS: [M + H]+ (RT, min) |
|---|---|---|---|
| 186 | 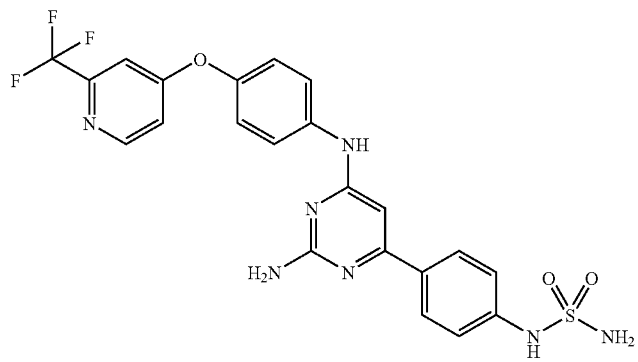 | N-(4-{2-amino-6-[(4-{[2-(trifluoromethyl)pyridin-4-yl]oxy}phenyl)amino]pyrimidin-4-yl}phenyl)sulfamide | 518.1 (2.42) |
| 187 | 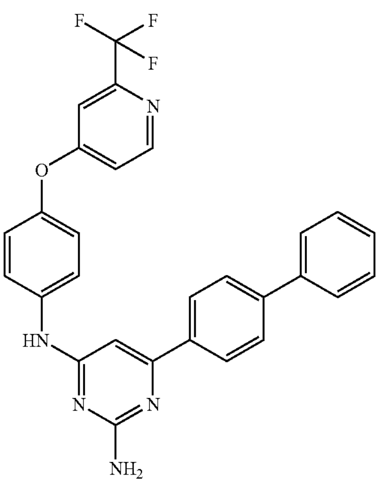 | 6-biphenyl-4-yl-N4*-(4-{[2-(trifluoromethyl)pyridin-4-yl]oxy}phenyl)pyrimidine-2,4-diamine | 499.5 (3.29) |

TABLE 1

| Example No. | Structure | IUPAC Name* | LCMS: [M + H]+ (RT, min) |
|---|---|---|---|
| 188 | 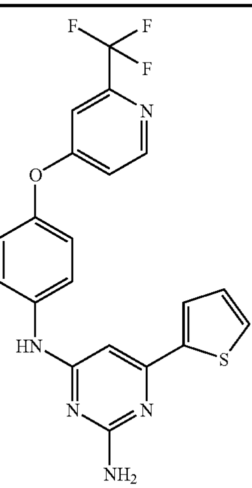 | 6-(2-thienyl)-N4*-(4-{[2-(trifluoromethyl)pyridin-4-yl]oxy}phenyl)pyrimidine-2,4-diamine | 429.4 (2.97) |

TABLE 1-continued

| Example No. | Structure | IUPAC Name* | LCMS: [M + H]+ (RT, min) |
|---|---|---|---|
| 189 | 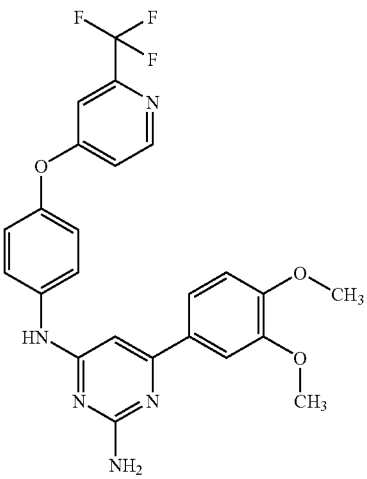 | 6-(3,4-dimethoxyphenyl)-N4*-(4-{[2-(trifluoromethyl)pyridin-4-yl]oxy}phenyl)pyrimidine-2,4-diamine | 483.4 (3.03) |
| 190 | 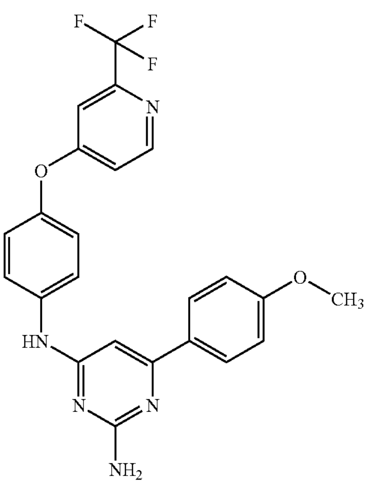 | 6-(4-methoxyphenyl)-N4*-(4-{[2-(trifluoromethyl)pyridin-4-yl]oxy}phenyl)pyrimidine-2,4-diamine | 453.4 (3.07) |
| 191 | 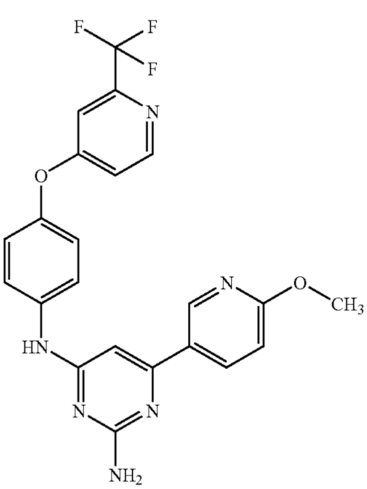 | 6-(6-methoxypyridin-3-yl)-N4*-(4-{[2-(trifluoromethyl)pyridin-4-yl]oxy}phenyl)pyrimidine-2,4-diamine | 454.4 (3.00) |

TABLE 1-continued

| Example No. | Structure | IUPAC Name* | LCMS: [M + H]+ (RT, min) |
|---|---|---|---|
| 192 | 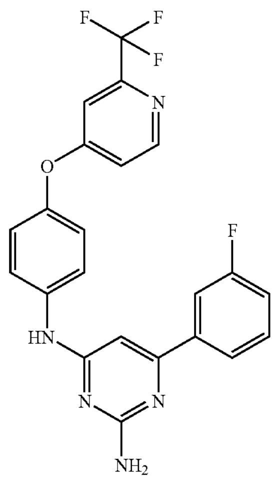 | 6-(3-fluorophenyl)-N4*-(4-{[2-(trifluoromethyl)pyridin-4-yl]oxy}phenyl)pyrimidine-2,4-diamine | 441.4 (3.03) |
| 193 | 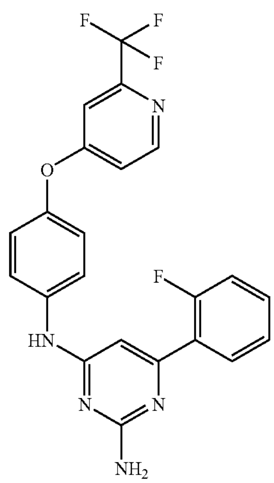 | 6-(2-fluorophenyl)-N4*-(4-{[2-(trifluoromethyl)pyridin-4-yl]oxy}phenyl)pyrimidine-2,4-diamine | 441.4 (3.03) |
| 194 | 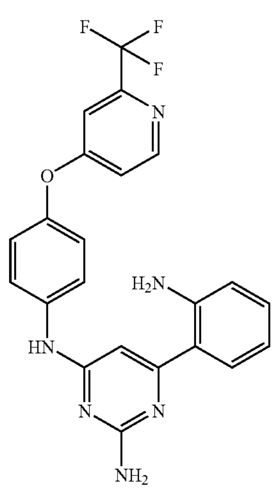 | 6-(2-aminophenyl)-N4*-(4-{[2-(trifluoromethyl)pyridin-4-yl]oxy}phenyl)pyrimidine-2,4-diamine | 438.4 (2.96) |

TABLE 1-continued

| Example No. | Structure | IUPAC Name* | LCMS: [M + H]+ (RT, min) |
|---|---|---|---|
| 195 | 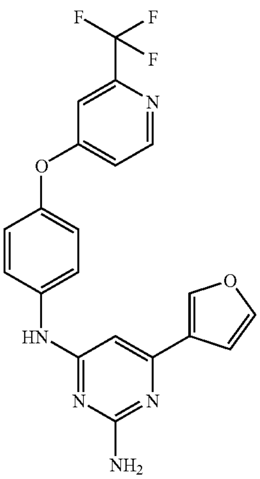 | 6-(3-furyl)-N4*-(4-{[2-(trifluoromethyl)pyridin-4-yl]oxy}phenyl)pyrimidine-2,4-diamine | 413.4 (2.94) |
| 196 | 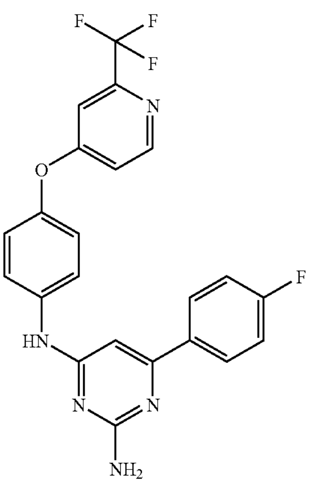 | 6-(4-fluorophenyl)-N4*-(4-{[2-(trifluoromethyl)pyridin-4-yl]oxy}phenyl)pyrimidine-2,4-diamine | 441.4 (3.03) |
| 197 | 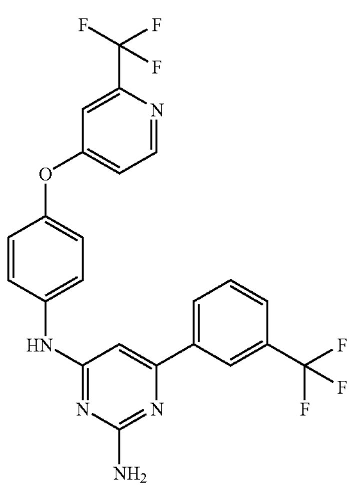 | 6-[3-(trifluoromethyl)phenyl]-N4*-(4-{[2-(trifluoromethyl)pyridin-4-yl]oxy}phenyl)pyrimidine-2,4-diamine | 491.4 (3.18) |

TABLE 1-continued

| Example No. | Structure | IUPAC Name* | LCMS: [M + H]+ (RT, min) |
|---|---|---|---|
| 198 | 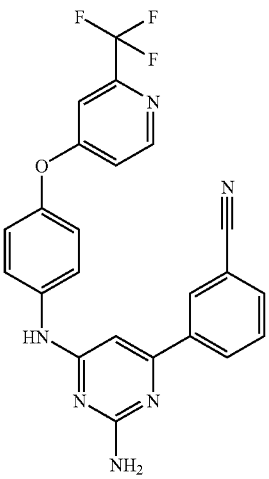 | 3-{2-amino-6-[(4-{[2-(trifluoromethyl)pyridin-4-yl]oxy}phenyl)amino]pyrimidin-4-yl}benzonitrile | 448.4 (3.00) |
| 199 | 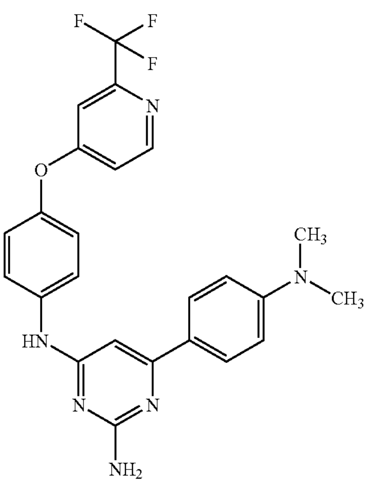 | 6-[4-(dimethylamino)phenyl]-N4*-(4-{[2-(trifluoromethyl)pyridin-4-yl]oxy}phenyl)pyrimidine-2,4-diamine | 466.4 (3.11) |
| 200 | 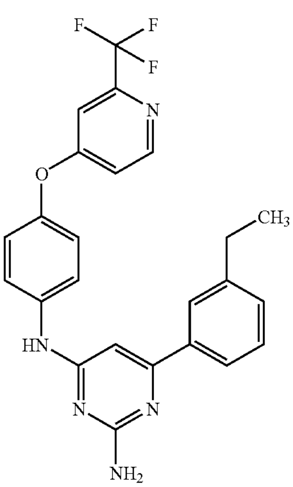 | 6-(3-ethylphenyl)-N4*-(4-{[2-(trifluoromethyl)pyridin-4-yl]oxy}phenyl)pyrimidine-2,4-diamine | 451.4 (3.18) |

TABLE 1-continued

| Example No. | Structure | IUPAC Name* | LCMS: [M + H]+ (RT, min) |
|---|---|---|---|
| 201 | 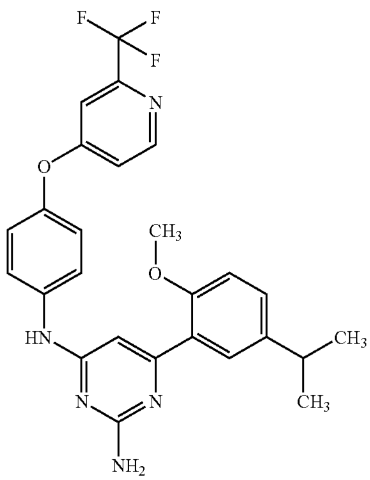 | 6-(5-isopropyl-2-methoxyphenyl)-N4*-(4-{[2-(trifluoromethyl)pyridin-4-yl]oxy}phenyl)pyrimidine-2,4-diamine | 495.5 (3.29) |
| 202 | 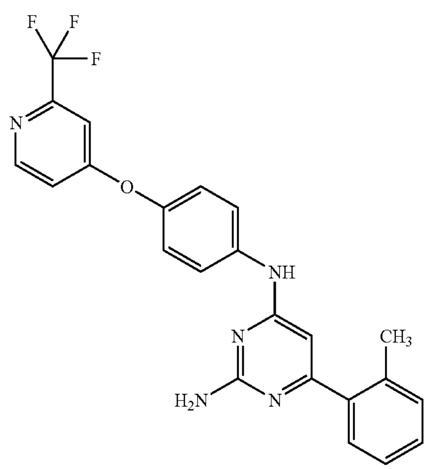 | 6-(2-methylphenyl)-N4*-(4-{[2-(trifluoromethyl)pyridin-4-yl]oxy}phenyl)pyrimidine-2,4-diamine | 437.4 (3.07) |
| 203 | 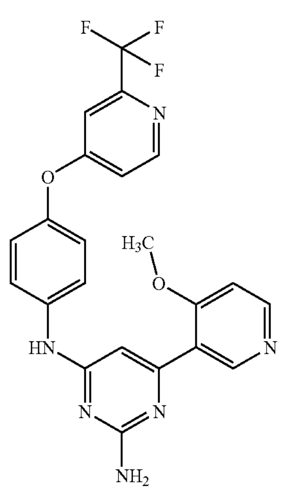 | 6-(4-methoxypyridin-3-yl)-N4*-(4-{[2-(trifluoromethyl)pyridin-4-yl]oxy}phenyl)pyrimidine-2,4-diamine | 454.4 (2.67) |

TABLE 1

| Example No. | Structure | IUPAC Name* | LCMS: [M + H]+ (RT, min) |
|---|---|---|---|
| 204 | 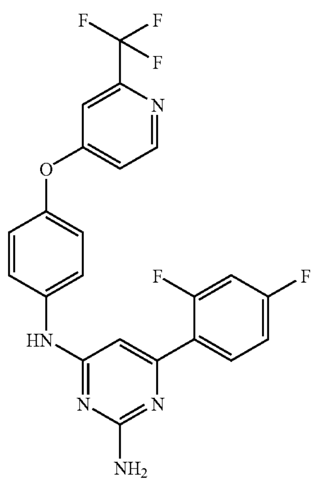 | 6-(2,4-difluorophenyl)-N4*-(4-{[2-(trifluoromethyl)pyridin-4-yl]oxy}phenyl)pyrimidine-2,4-diamine | 459.3 (3.03) |
| 205 | 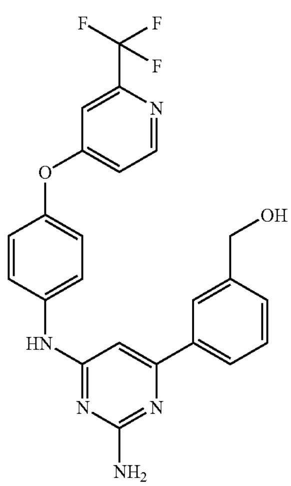 | (3-{2-amino-6-[(4-{[2-(trifluoromethyl)pyridin-4-yl]oxy}phenyl)amino]pyrimidin-4-yl}phenyl)methanol | 453.4 (2.92) |
| 206 | 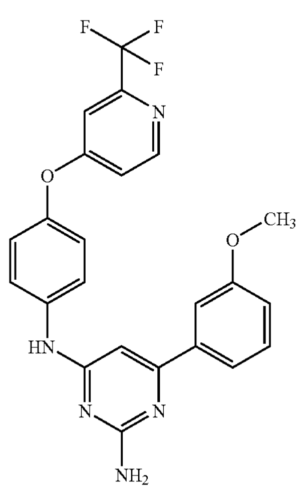 | 6-(3-methoxyphenyl)-N4*-(4-{[2-(trifluoromethyl)pyridin-4-yl]oxy}phenyl)pyrimidine-2,4-diamine | 453.4 (3.07) |

TABLE 1-continued

| Example No. | Structure | IUPAC Name* | LCMS: [M + H]+ (RT, min) |
|---|---|---|---|
| 207 | 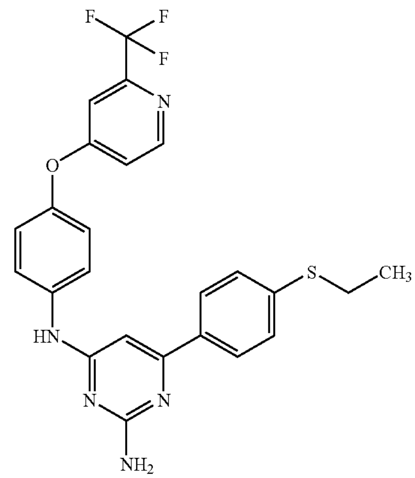 | 6-[4-(ethylthio)phenyl]-N4*-(4-{[2-(trifluoromethyl)pyridin-4-yl]oxy}phenyl)pyrimidine-2,4-diamine | 483.5 (3.18) |
| 208 | 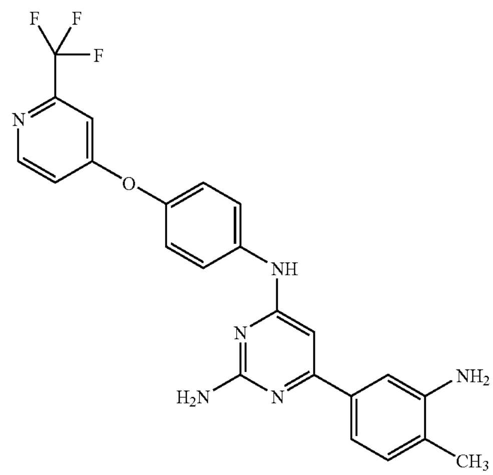 | 6-(3-amino-4-methylphenyl)-N4*-(4-{[2-(trifluoromethyl)pyridin-4-yl]oxy}phenyl)pyrimidine-2,4-diamine | 452.4 (3.03) |
| 209 | 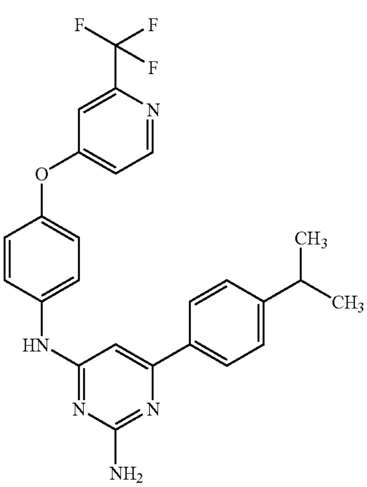 | 6-(4-isopropylphenyl)-N4*-(4-{[2-(trifluoromethyl)pyridin-4-yl]oxy}phenyl)pyrimidine-2,4-diamine | 465.5 (3.22) |

TABLE 1-continued

| Example No. | Structure | IUPAC Name* | LCMS: [M + H]+ (RT, min) |
|---|---|---|---|
| 210 | 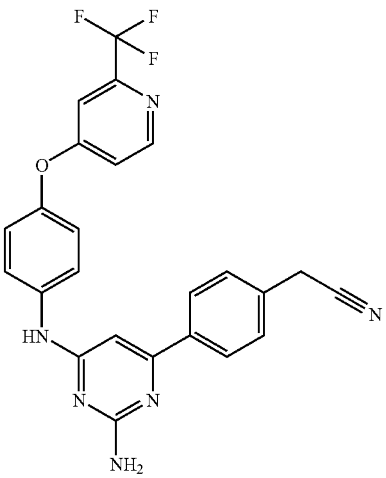 | (4-{2-amino-6-[(4-{[2-(trifluoromethyl)pyridin-4-yl]oxy}phenyl)amino]pyrimidin-4-yl}phenyl)acetonitrile | 462.4 (3.00) |
| 211 | 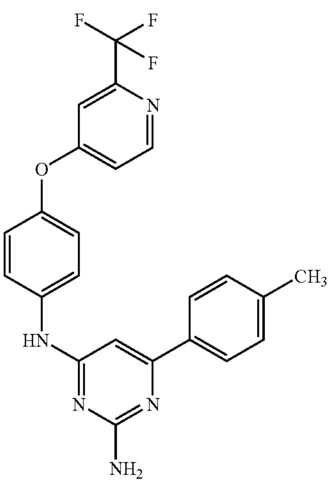 | 6-(4-methylphenyl)-N4*-(4-{[2-(trifluoromethyl)pyridin-4-yl]oxy}phenyl)pyrimidine-2,4-diamine | 437.4 (3.11) |
| 212 | 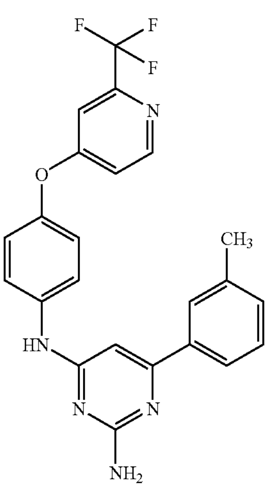 | 6-(3-methylphenyl)-N4*-(4-{[2-(trifluoromethyl)pyridin-4-yl]oxy}phenyl)pyrimidine-2,4-diamine | 437.4 (3.11) |

TABLE 1-continued

| Example No. | Structure | IUPAC Name* | LCMS: [M + H]+ (RT, min) |
|---|---|---|---|
| 213 | 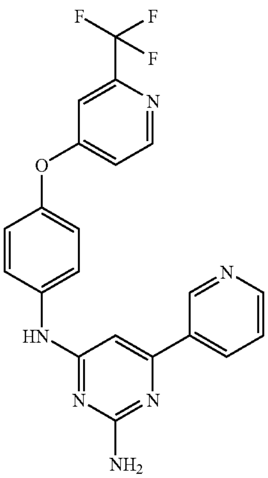 | 6-pyridin-3-yl-N4*-(4-{[2-(trifluoromethyl)pyridin-4-yl]oxy}phenyl)pyrimidine-2,4-diamine | 424.4 (2.81) |
| 214 | 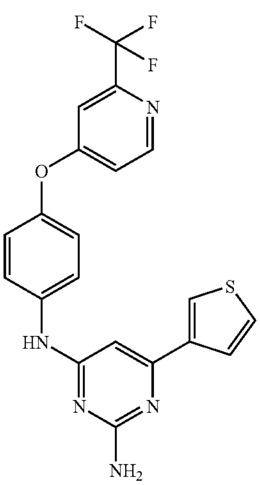 | 6-(3-thienyl)-N4*-(4-{[2-(trifluoromethyl)pyridin-4-yl]oxy}phenyl)pyrimidine-2,4-diamine | 429.4 (3.00) |
| 215 | 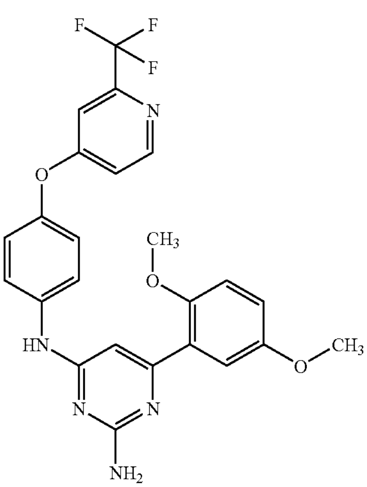 | 6-(2,5-dimethoxyphenyl)-N4*-(4-{[2-(trifluoromethyl)pyridin-4-yl]oxy}phenyl)pyrimidine-2,4-diamine | 483.4 (3.07) |

TABLE 1-continued

| Example No. | Structure | IUPAC Name* | LCMS: [M + H]+ (RT, min) |
|---|---|---|---|
| 216 | 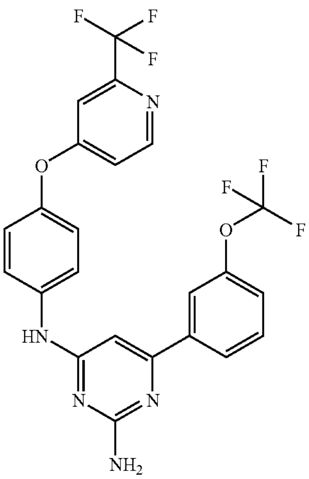 | 6-[3-(trifluoromethoxy)phenyl]-N4*-(4-{[2-(trifluoromethyl)pyridin-4-yl]oxy}phenyl)pyrimidine-2,4-diamine | 507.4 (3.22) |
| 217 | 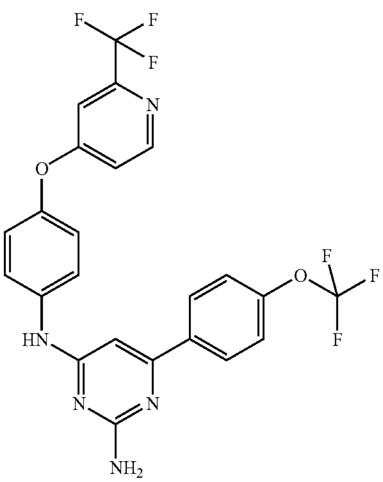 | 6-[4-(trifluoromethoxy)phenyl]-N4*-(4-{[2-(trifluoromethyl)pyridin-4-yl]oxy}phenyl)pyrimidine-2,4-diamine | 507.4 (3.22) |
| 218 | 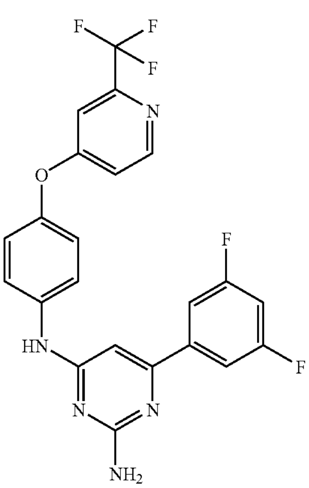 | 6-(3,5-difluorophenyl)-N4*-(4-{[2-(trifluoromethyl)pyridin-4-yl]oxy}phenyl)pyrimidine-2,4-diamine | 459.4 (3.07) |

TABLE 1-continued

| Example No. | Structure | IUPAC Name* | LCMS: [M + H]+ (RT, min) |
|---|---|---|---|
| 219 | ClH | 4-(4-{[2-amino-6-(1H-pyrrol-2-yl)pyrimidin-4-yl]amino}phenoxy)pyridine-2-carbonitrile hydrochloride | 370.3 (2.65) |
| 220 | 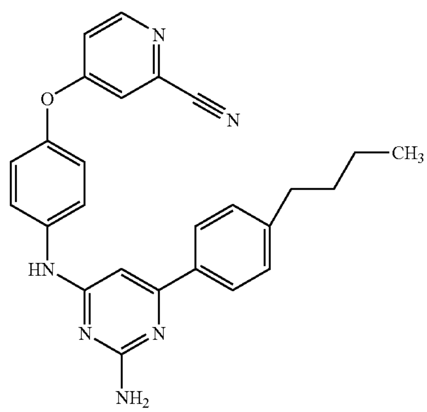 | 4-(4-{[2-amino-6-(4-butylphenyl)pyrimidin-4-yl]amino}phenoxy)pyridine-2-carbonitrile | 437.5 (3.47) |
| 221 | 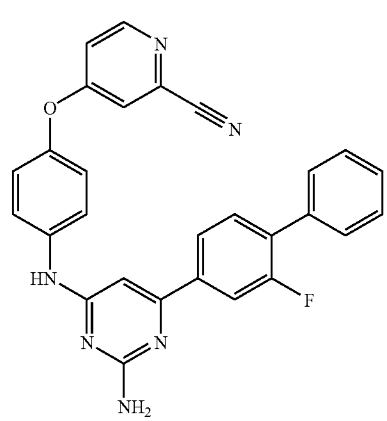 | 4-(4-{[2-amino-6-(2-fluorobiphenyl-4-yl)pyrimidin-4-yl]amino}phenoxy)pyridine-2-carbonitrile | 475.5 (3.36) |

TABLE 1-continued

| Example No. | Structure | IUPAC Name* | LCMS: [M + H]+ (RT, min) |
|---|---|---|---|
| 222 | 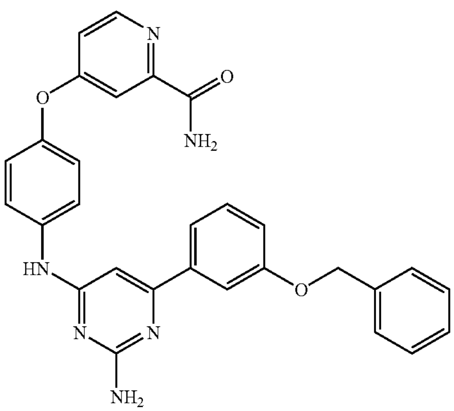 | 4-[4-({2-amino-6-[3-(benzyloxy) phenyl]pyrimidin-4-yl}amino) phenoxy]pyridine-2-carboxamide | 505.1 (3.29) |
| 223 | 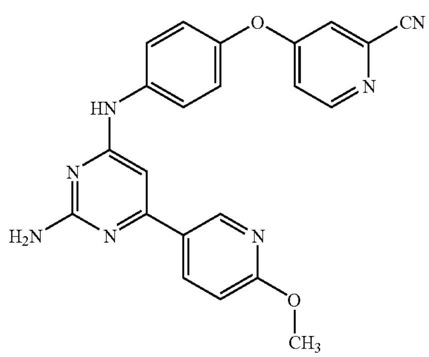 | 4-(4-{[2-amino-6-(6-methoxypyridin-3-yl)pyrimidin-4-yl]amino}phenoxy) pyridine-2-carbonitrile | 412.4 (2.92) |
| 224 | 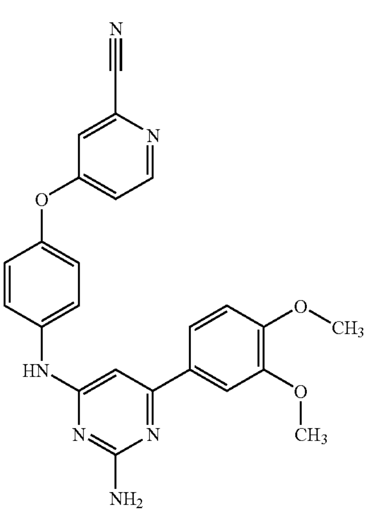 | 4-(4-{[2-amino-6-(3,4-dimethoxyphenyl)pyrimidin-4-yl] amino}phenoxy)pyridine-2-carbonitrile | 441.4 (2.92) |

TABLE 1-continued

| Example No. | Structure | IUPAC Name* | LCMS: [M + H]+ (RT, min) |
|---|---|---|---|
| 225 | 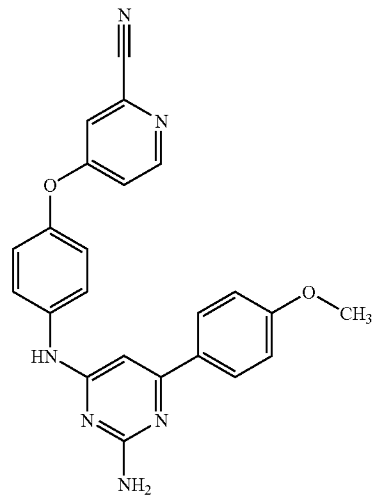 | 4-(4-{[2-amino-6-(4-methoxyphenyl) pyrimidin-4-yl]amino}phenoxy) pyridine-2-carbonitrile 4-(4-{[6-amino-2-(4-methoxyphenyl) pyrimidin-4-yl]amino}phenoxy) pyridine-2-carbonitrile | 411.4 (2.96) |
| 226 | 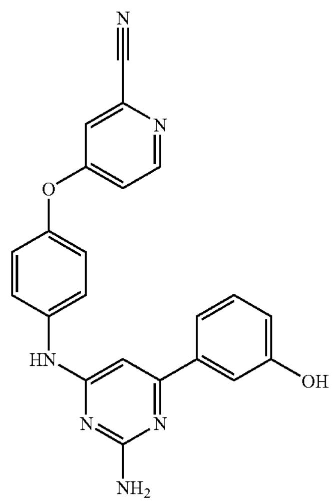 | 4-(4-{[2-amino-6-(3-hydroxyphenyl) pyrimidin-4-yl]amino}phenoxy) pyridine-2-carbonitrile 4-(4-{[6-amino-2-(3-hydroxyphenyl) pyrimidin-4-yl]amino}phenoxy) pyridine-2-carbonitrile | 397.4 (3.07) |
| 227 | 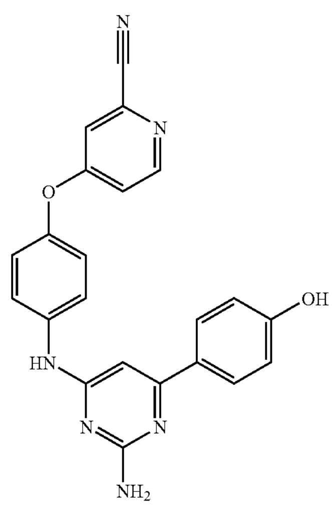 | 4-(4-{[2-amino-6-(4-hydroxyphenyl) pyrimidin-4-yl]amino}phenoxy) pyridine-2-carbonitrile 4-(4-{[6-amino-2-(4-hydroxyphenyl) pyrimidin-4-yl]amino}phenoxy) pyridine-2-carbonitrile | 397.4 (2.89) |

TABLE 1-continued

| Example No. | Structure | IUPAC Name* | LCMS: [M + H]+ (RT, min) |
|---|---|---|---|
| 228 | 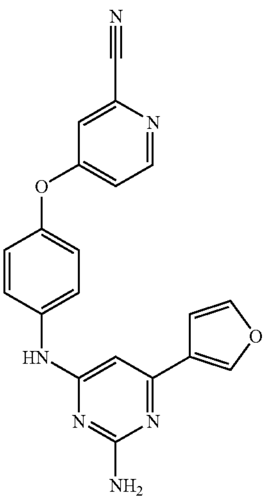 | 4-(4-{[2-amino-6-(3-furyl)pyrimidin-4-yl]amino}phenoxy)pyridine-2-carbonitrile 4-(4-{[6-amino-2-(3-furyl)pyrimidin-4-yl]amino}phenoxy)pyridine-2-carbonitrile | 371.4 (2.89) |
| 229 | 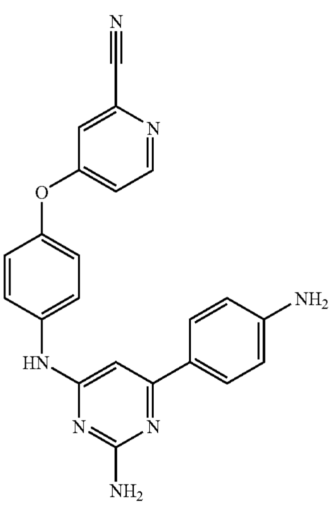 | 4-(4-{[2-amino-6-(4-aminophenyl)pyrimidin-4-yl]amino}phenoxy)pyridine-2-carbonitrile 4-(4-{[6-amino-2-(4-aminophenyl)pyrimidin-4-yl]amino}phenoxy)pyridine-2-carbonitrile | 396.4 (2.89) |
| 230 | 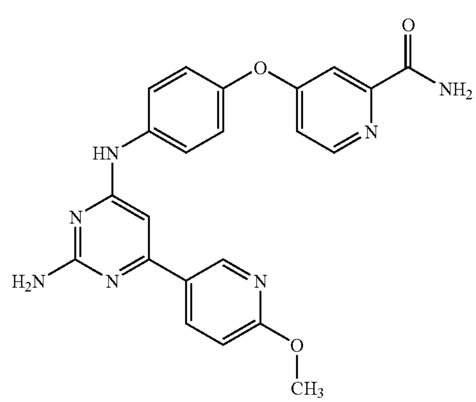 | 4-(4-{[2-amino-6-(6-methoxypyridin-3-yl)pyrimidin-4-yl]amino}phenoxy)pyridine-2-carboxamide | 430.4 (2.74) |

TABLE 1-continued
| Example No. | Structure | IUPAC Name* | LCMS: [M + H]+ (RT, min) |
|---|---|---|---|
| 231 | 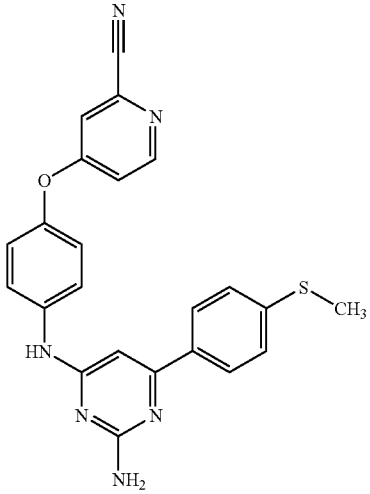 | 4-[4-({2-amino-6-[4-(methylthio) phenyl]pyrimidin-4-yl}amino) phenoxy]pyridine-2-carbonitrile | 427.5 (3.00) |
| 232 | 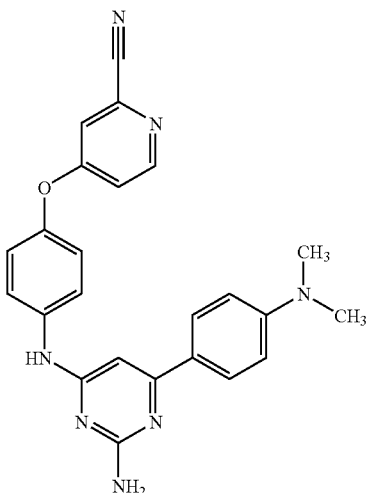 | 4-[4-({2-amino-6-[4-(dimethylamino) phenyl]pyrimidin-4-yl}amino) phenoxy]pyridine-2-carbonitrile | 424.4 (3.00) |
| 233 | 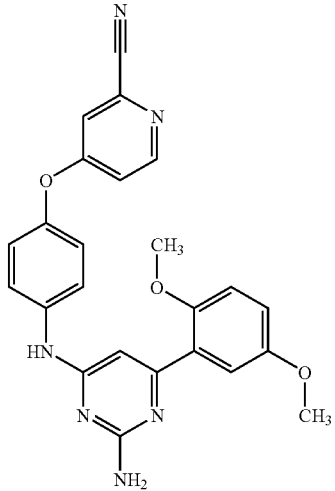 | 4-(4-{[2-amino-6-(2,5-dimethoxyphenyl)pyrimidin-4-yl] amino}phenoxy)pyridine-2-carbonitrile | 441.4 (3.00) |

TABLE 1-continued

| Example No. | Structure | IUPAC Name* | LCMS: [M + H]+ (RT, min) |
|---|---|---|---|
| 234 | 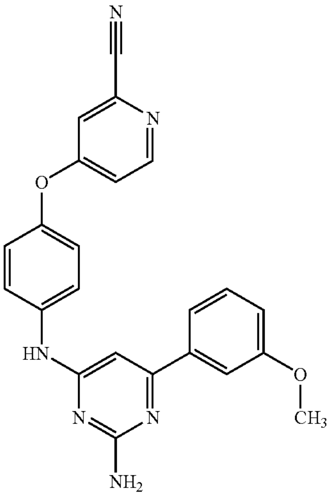 | 4-(4-{[2-amino-6-(3-methoxyphenyl) pyrimidin-4-yl]amino}phenoxy) pyridine-2-carbonitrile | 411.4 (2.92) |
| 235 | 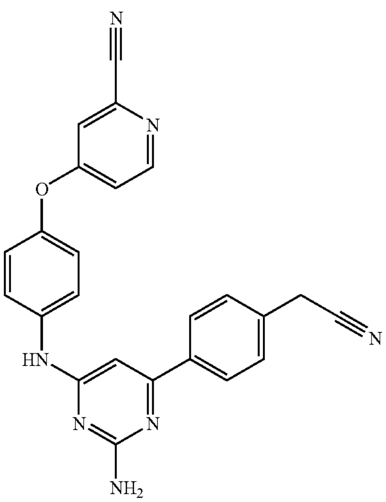 | 4-[4-({2-amino-6-(4-(cyanomethyl) phenyl]pyrimidin-4-yl}amino) phenoxy]pyridine-2-carbonitrile | 420.4 (2.89) |
| 236 | 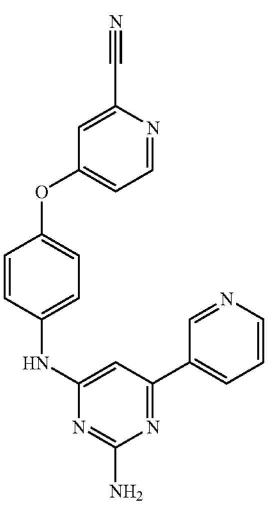 | 4-{4-[(2-amino-6-pyridin-3-ylpyrimidin-4-yl)amino]phenoxy} pyridine-2-carbonitrile | 382.4 (2.78) |

TABLE 1-continued

| Example No. | Structure | IUPAC Name* | LCMS: [M + H]+ (RT, min) |
|---|---|---|---|
| 237 | 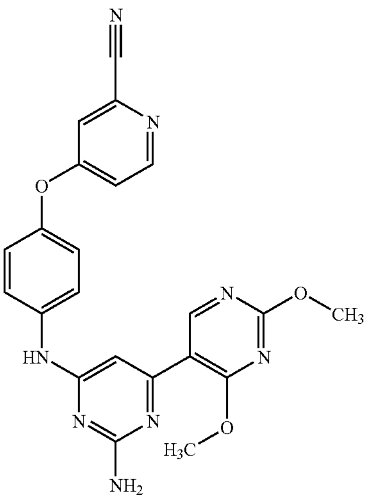 | 4-{4-[(2-amino-2',4'-dimethoxy-4,5'-bipyrimidin-6-yl)amino]phenoxy}pyridine-2-carbonitrile | 443.4 (2.85) |
| 238 | 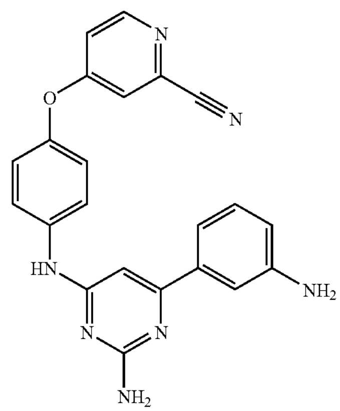 | 4-(4-{[2-amino-6-(3-aminophenyl)pyrimidin-4-yl]amino}phenoxy)pyridine-2-carbonitrile | 396.4 (3.00) |
| 239 | 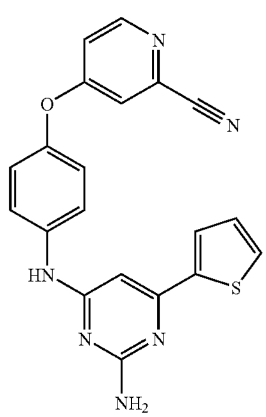 | 4-(4-{[2-amino-6-(2-thienyl)pyrimidin-4-yl]amino}phenoxy)pyridine-2-carbonitrile | 387.4 (3.07) |

TABLE 1-continued

| Example No. | Structure | IUPAC Name* | LCMS: [M + H]+ (RT, min) |
|---|---|---|---|
| 240 | 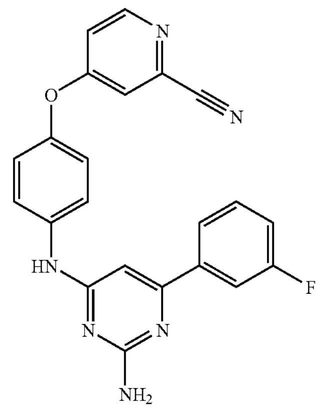 | 4-(4-{[2-amino-6-(3-fluorophenyl) pyrimidin-4-yl]amino}phenoxy) pyridine-2-carbonitrile | 399.4 (3.14) |
| 241 | 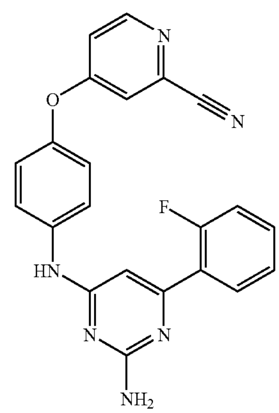 | 4-(4-{[2-amino-6-(2-fluorophenyl) pyrimidin-4-yl]amino}phenoxy) pyridine-2-carbonitrile | 399.4 (3.14) |
| 242 | 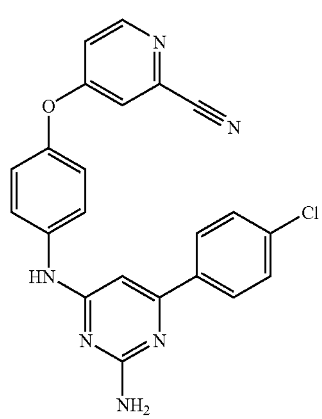 | 4-(4-{[2-amino-6-(4-chlorophenyl) pyrimidin-4-yl]amino}phenoxy) pyridine-2-carbonitrile | 415.8 (3.14) |

TABLE 1-continued

| Example No. | Structure | IUPAC Name* | LCMS: [M + H]+ (RT, min) |
|---|---|---|---|
| 243 | 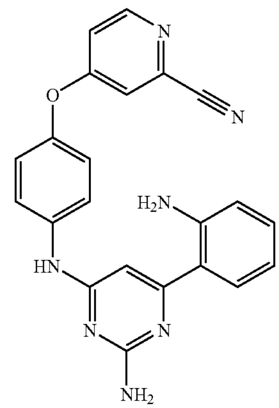 | 4-(4-{[2-amino-6-(2-aminophenyl)pyrimidin-4-yl]amino}phenoxy)pyridine-2-carbonitrile | 396.4 (3.11) |
| 244 | 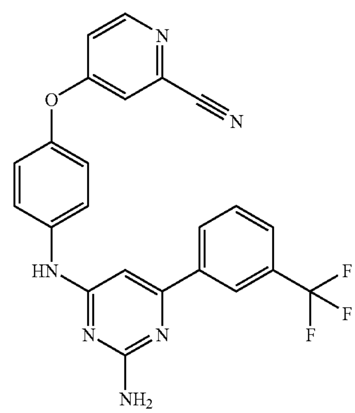 | 4-[4-({2-amino-6-[3-(trifluoromethyl)phenyl]pyrimidin-4-yl}amino)phenoxy]pyridine-2-carbonitrile | 449.4 (3.29) |
| 245 | 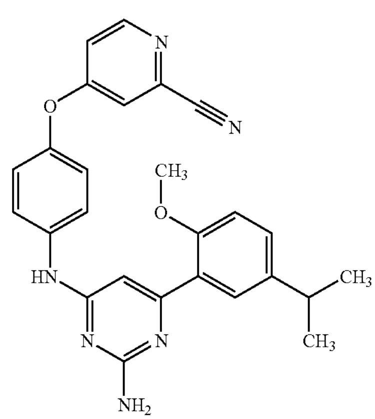 | 4-(4-{[2-amino-6-(5-isopropyl-2-methoxyphenyl)pyrimidin-4-yl]amino}phenoxy)pyridine-2-carbonitrile | 453.5 (3.36) |

TABLE 1-continued

| Example No. | Structure | IUPAC Name* | LCMS: [M + H]+ (RT, min) |
|---|---|---|---|
| 246 | 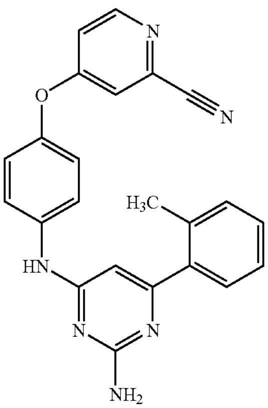 | 4-(4-{[2-amino-6-(2-methylphenyl) pyrimidin-4-yl]amino}phenoxy) pyridine-2-carbonitrile | 395.4 (3.14) |
| 247 | 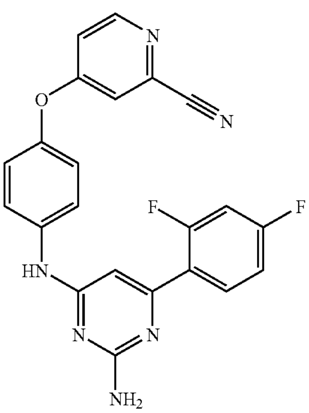 | 4-(4-{[2-amino-6-(2,4-difluorophenyl)pyrimidin-4-yl] amino}phenoxy)pyridine-2-carbonitrile | 417.4 (3.11) |
| 248 | 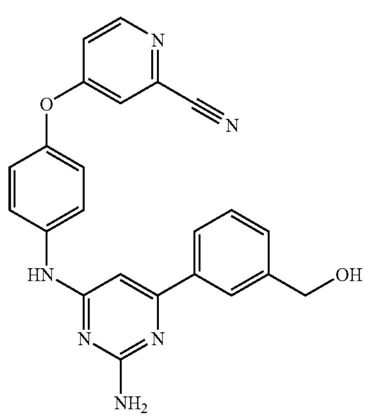 | 4-[4-({2-amino-6-[3-(hydroxymethyl) phenyl]pyrimidin-4-yl}amino) phenoxy]pyridine-2-carbonitrile | 411.4 (3.03) |

TABLE 1-continued

| Example No. | Structure | IUPAC Name* | LCMS: [M + H]+ (RT, min) |
|---|---|---|---|
| 249 | 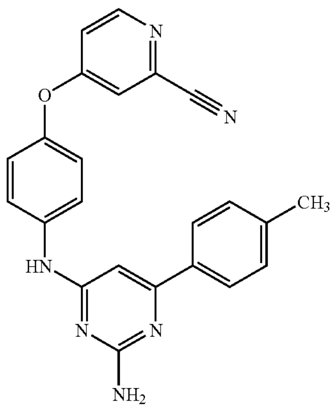 | 4-(4-{[2-amino-6-(4-methylphenyl)pyrimidin-4-yl]amino}phenoxy)pyridine-2-carbonitrile | 395.4 (3.18) |
| 250 | 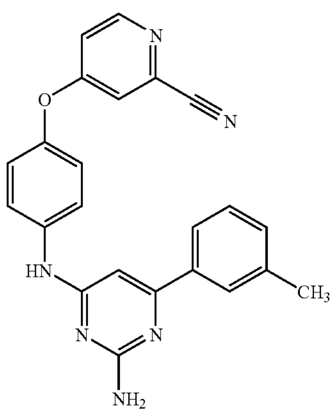 | 4-(4-{[2-amino-6-(3-methylphenyl)pyrimidin-4-yl]amino}phenoxy)pyridine-2-carbonitrile | 395.4 (3.22) |
| 251 | 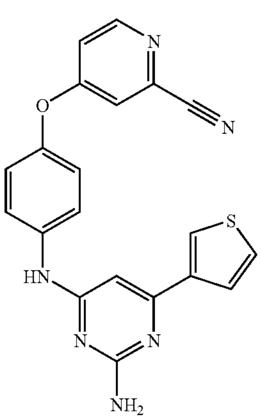 | 4-(4-{[2-amino-6-(3-thienyl)pyrimidin-4-yl]amino}phenoxy)pyridine-2-carbonitrile | 387.4 (3.07) |

TABLE 1-continued

| Example No. | Structure | IUPAC Name* | LCMS: [M + H]+ (RT, min) |
|---|---|---|---|
| 252 | 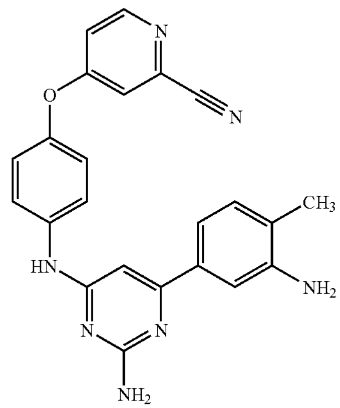 | 4-(4-{[2-amino-6-(3-amino-4-methylphenyl)pyrimidin-4-yl]amino}phenoxy)pyridine-2-carbonitrile | 410.5 (3.03) |
| 253 | 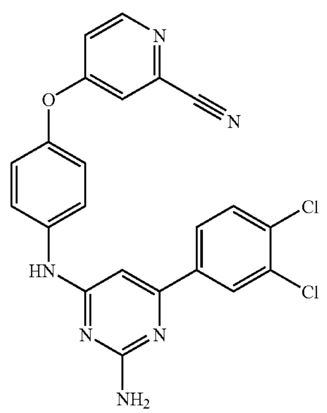 | 4-(4-{[2-amino-6-(3,4-dichlorophenyl)pyrimidin-4-yl]amino}phenoxy)pyridine-2-carbonitrile | 450 (3.33) |
| 254 | 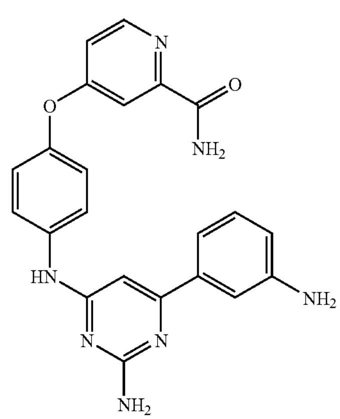 | 4-(4-{[2-amino-6-(3-aminophenyl)pyrimidin-4-yl]amino}phenoxy)pyridine-2-carboxamide | 414.2 (2.85) |

TABLE 1-continued

| Example No. | Structure | IUPAC Name* | LCMS: [M + H]+ (RT, min) |
|---|---|---|---|
| 255 | 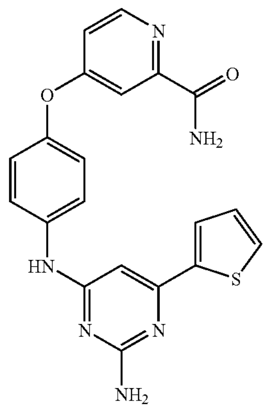 | 4-(4-{[2-amino-6-(2-thienyl) pyrimidin-4-yl]amino}phenoxy) pyridine-2-carboxamide | 405.1 (3.00) |
| 256 | 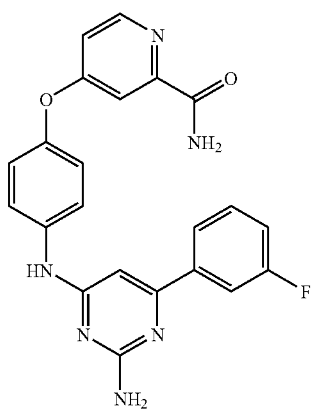 | 4-(4-{[2-amino-6-(3-fluorophenyl) pyrimidin-4-yl]amino}phenoxy) pyridine-2-carboxamide | 417.2 (2.96) |
| 257 | 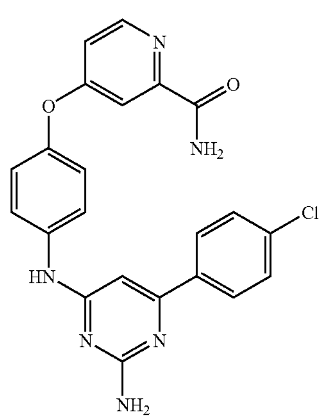 | 4-(4-{[2-amino-6-(4-chlorophenyl) pyrimidin-4-yl]amino}phenoxy) pyridine-2-carboxamide | 433.1 (3.07) |

TABLE 1-continued

| Example No. | Structure | IUPAC Name* | LCMS: [M + H]+ (RT, min) |
|---|---|---|---|
| 258 | 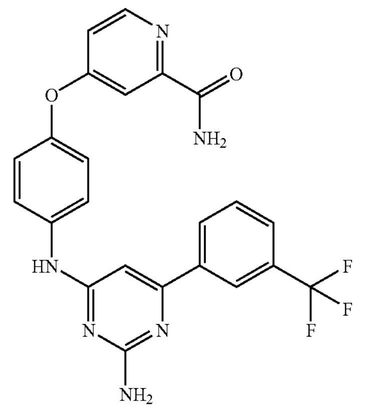 | 4-[4-({2-amino-6-[3-(trifluoromethyl) phenyl]pyrimidin-4-yl}amino) phenoxy]pyridine-2-carboxamide | 467.1 (3.11) |
| 259 | 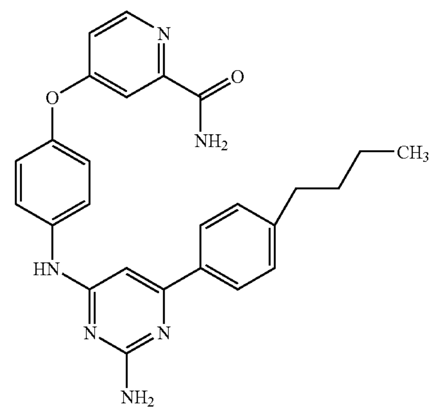 | 4-(4-{[2-amino-6-(4-butylphenyl) pyrimidin-4-yl]amino}phenoxy) pyridine-2-carboxamide | 455.2 (3.25) |
| 260 | 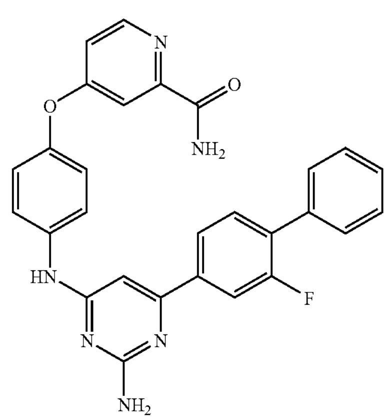 | 4-(4-{[2-amino-6-(2-fluorobiphenyl-4-yl)pyrimidin-4-yl]amino}phenoxy) pyridine-2-carboxamide | 493.1 (3.29) |

TABLE 1-continued

| Example No. | Structure | IUPAC Name* | LCMS: [M + H]+ (RT, min) |
|---|---|---|---|
| 261 | 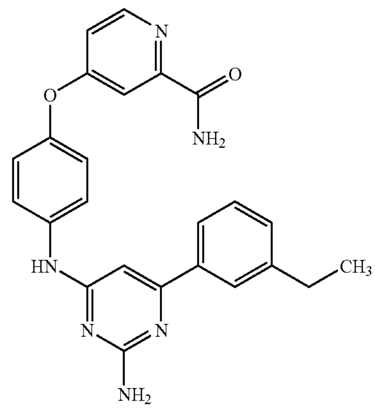 | 4-(4-{[2-amino-6-(3-ethylphenyl)pyrimidin-4-yl]amino}phenoxy)pyridine-2-carboxamide | 427.2 (3.11) |
| 262 | 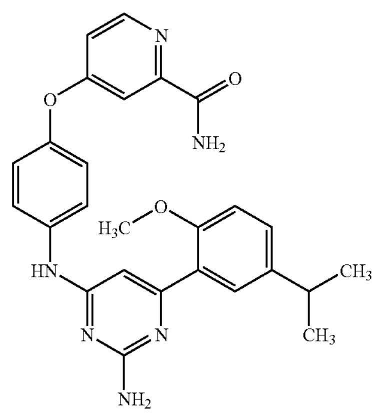 | 4-(4-{[2-amino-6-(5-isopropyl-2-methoxyphenyl)pyrimidin-4-yl]amino}phenoxy)pyridine-2-carboxamide | 471.2 (3.25) |
| 263 | 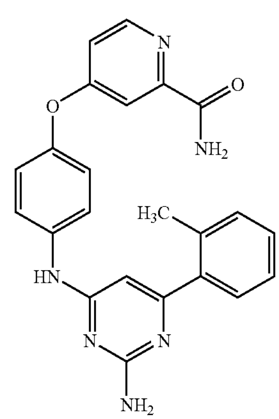 | 4-(4-{[2-amino-6-(2-methylphenyl)pyrimidin-4-yl]amino}phenoxy)pyridine-2-carboxamide | 413.2 (3.00) |

TABLE 1-continued

| Example No. | Structure | IUPAC Name* | LCMS: [M + H]+ (RT, min) |
|---|---|---|---|
| 264 | 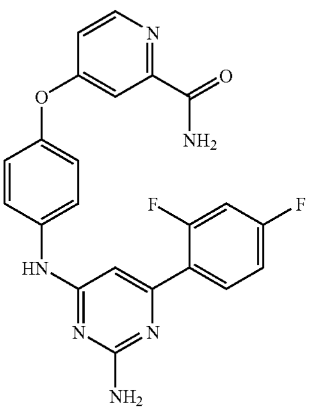 | 4-(4-{[2-amino-6-(2,4-difluorophenyl)pyrimidin-4-yl]amino}phenoxy)pyridine-2-carboxamide | 435.1 (3.00) |
| 265 | 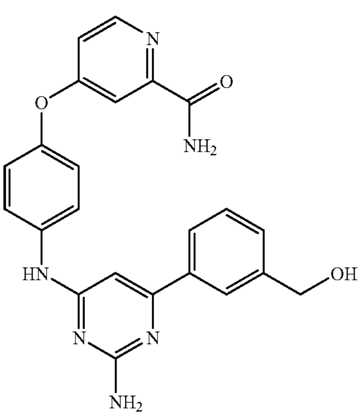 | 4-[4-({2-amino-6-[3-(hydroxymethyl)phenyl]pyrimidin-4-yl}amino)phenoxy]pyridine-2-carboxamide | 429.2 (2.89) |
| 266 | 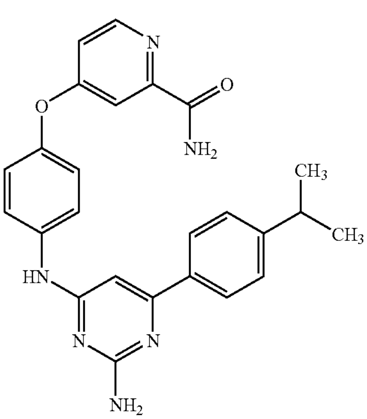 | 4-(4-{[2-amino-6-(4-isopropylphenyl)pyrimidin-4-yl]amino}phenoxy)pyridine-2-carboxamide | 441.2 (3.18) |

TABLE 1-continued

| Example No. | Structure | IUPAC Name* | LCMS: [M + H]+ (RT, min) |
|---|---|---|---|
| 267 | 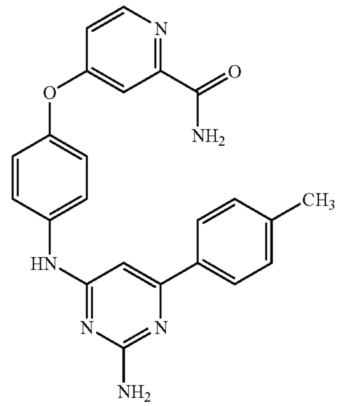 | 4-(4-{[2-amino-6-(4-methylphenyl) pyrimidin-4-yl]amino}phenoxy) pyridine-2-carboxamide | 413.2 (3.07) |
| 268 | 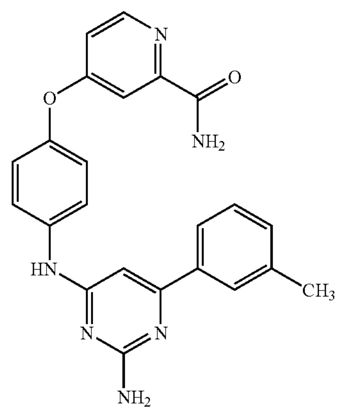 | 4-(4-{[2-amino-6-(3-methylphenyl) pyrimidin-4-yl]amino}phenoxy) pyridine-2-carboxamide | 413.2 (3.03) |
| 269 | 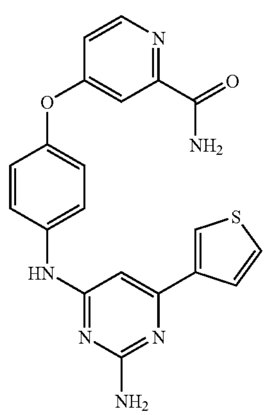 | 4-(4-{[2-amino-6-(3-thienyl) pyrimidin-4-yl]amino}phenoxy) pyridine-2-carboxamide | 405.1 (2.96) |

TABLE 1-continued

| Example No. | Structure | IUPAC Name* | LCMS: [M + H]+ (RT, min) |
|---|---|---|---|
| 270 | 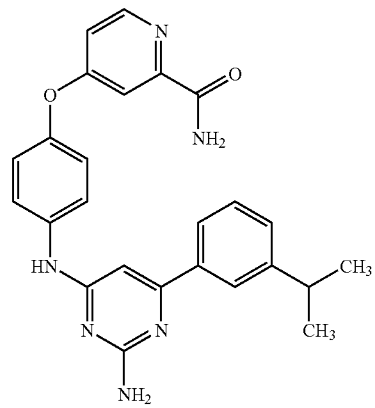 | 4-(4-{[2-amino-6-(3-isopropylphenyl)pyrimidin-4-yl]amino}phenoxy)pyridine-2-carboxamide | 441.2 (3.22) |
| 271 | 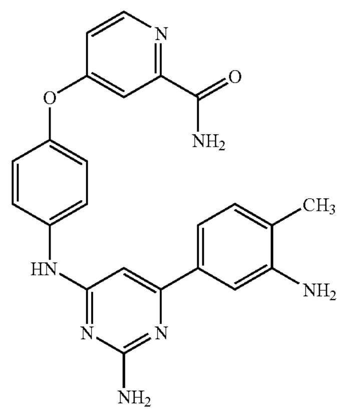 | 4-(4-{[2-amino-6-(3-amino-4-methylphenyl)pyrimidin-4-yl]amino}phenoxy)pyridine-2-carboxamide | 428.2 (2.89) |
| 272 | 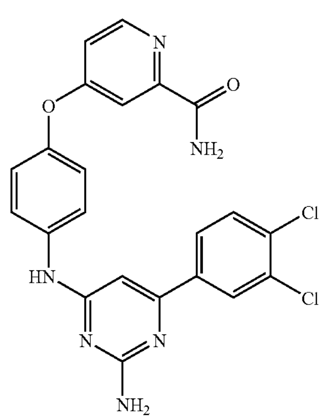 | 4-(4-{[2-amino-6-(3,4-dichlorophenyl)pyrimidin-4-yl]amino}phenoxy)pyridine-2-carboxamide | 467.1 (3.18) |

TABLE 1-continued

| Example No. | Structure | IUPAC Name* | LCMS: [M + H]+ (RT, min) |
|---|---|---|---|
| 273 | 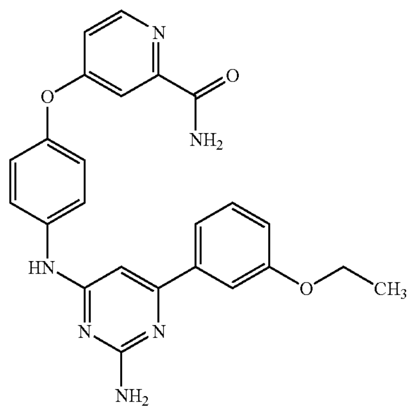 | 4-(4-{[2-amino-6-(3-ethoxyphenyl)pyrimidin-4-yl]amino}phenoxy)pyridine-2-carboxamide | 443.3 (2.81) |
| 274 | 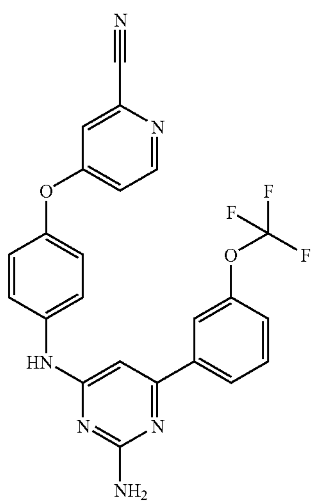 | 4-[4-({2-amino-6-[3-(trifluoromethoxy)phenyl]pyrimidin-4-yl}amino)phenoxy]pyridine-2-carbonitrile | 465.1 (3.00) |
| 275 | 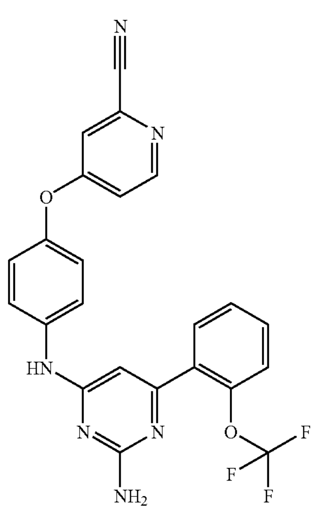 | 4-[4-({2-amino-6-[2-(trifluoromethoxy)phenyl]pyrimidin-4-yl}amino)phenoxy]pyridine-2-carbonitrile | 465.1 (2.92) |

TABLE 1-continued

| Example No. | Structure | IUPAC Name* | LCMS: [M + H]+ (RT, min) |
|---|---|---|---|
| 276 | 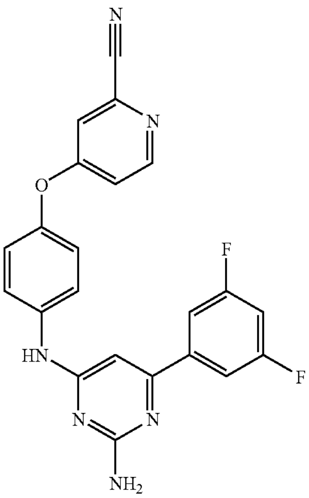 | 4-(4-{[2-amino-6-(3,5-difluorophenyl)pyrimidin-4-yl]amino}phenoxy)pyridine-2-carbonitrile | 417.2 (2.89) |
| 277 | 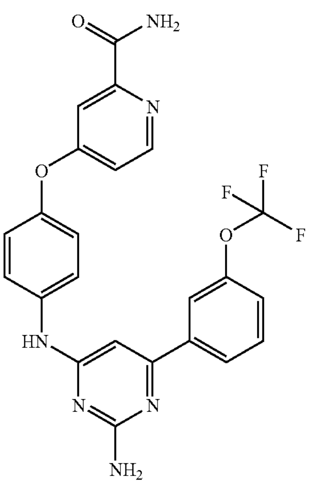 | 4-[4-({2-amino-6-[3-(trifluoromethoxy)phenyl]pyrimidin-4-yl}amino)phenoxy]pyridine-2-carboxamide | 483.4 (2.89) |
| 278 | 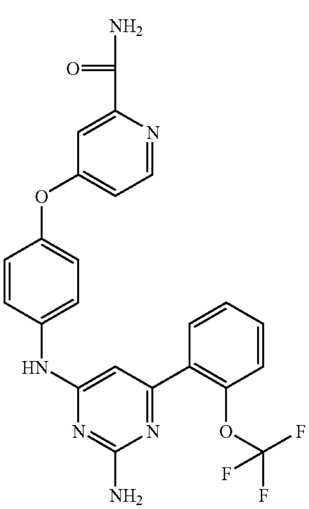 | 4-[4-({2-amino-6-[2-(trifluoromethoxy)phenyl]pyrimidin-4-yl}amino)phenoxy]pyridine-2-carboxamide | 483.4 (2.81) |

TABLE 1-continued

| Example No. | Structure | IUPAC Name* | LCMS: [M + H]+ (RT, min) |
|---|---|---|---|
| 279 | 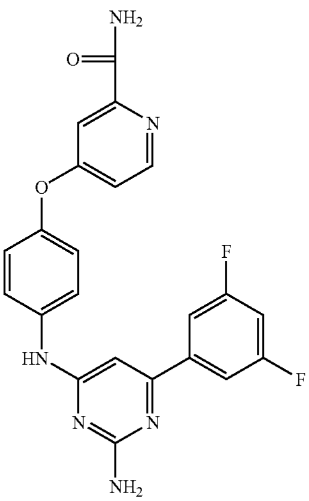 | 4-(4-{[2-amino-6-(3,5-difluorophenyl)pyrimidin-4-yl]amino}phenoxy)pyridine-2-carboxamide | 435.4 (2.74) |
| 280 | 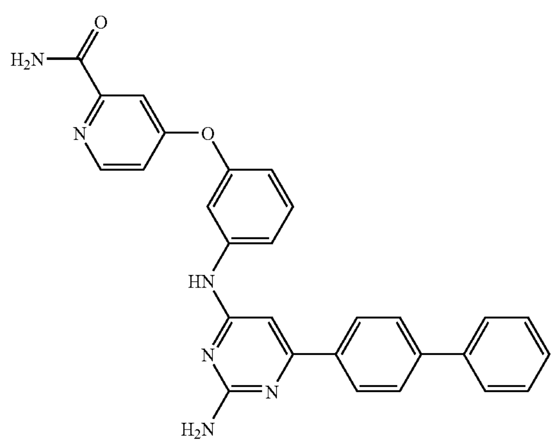 | 4-{3-[(2-amino-6-biphenyl-4-ylpyrimidin-4-yl)amino]phenoxy}pyridine-2-carboxamide | 475.5 (3.00) |
| 281 | 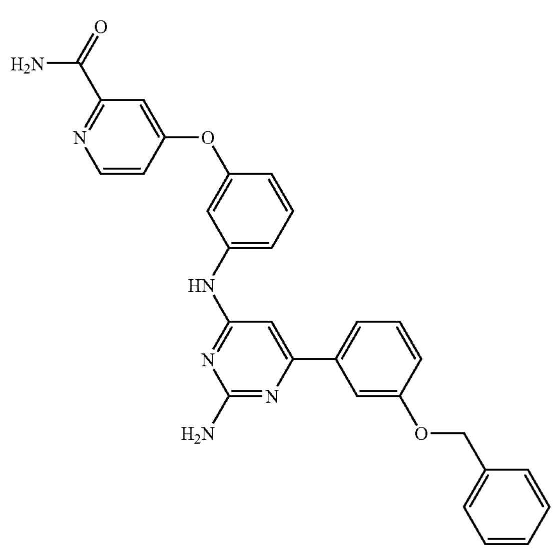 | 4-[3-({2-amino-6-[3-(benzyloxy)phenyl]pyrimidin-4-yl}amino)phenoxy]pyridine-2-carboxamide | 505.5 (3.07) |

TABLE 1-continued

| Example No. | Structure | IUPAC Name* | LCMS: [M + H]+ (RT, min) |
|---|---|---|---|
| 282 | 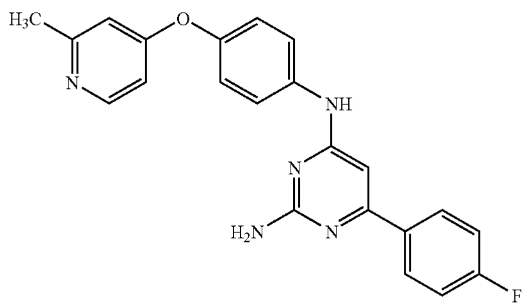 | 6-(4-fluorophenyl)-N4*-{4-[(2-methylpyridin-4-yl)oxy]phenyl}pyrimidine-2,4-diamine | 388.4 (2.54) |
| 283 | 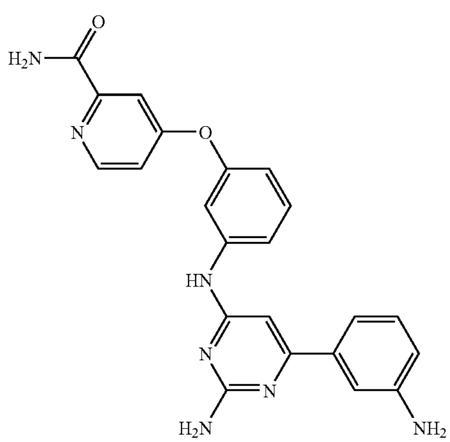 | 4-(3-{[2-amino-6-(3-aminophenyl)pyrimidin-4-yl]amino}phenoxy)pyridine-2-carboxamide | 414.4 (2.64) |
| 284 | 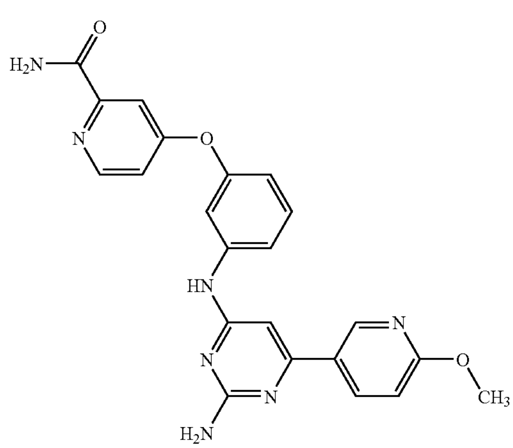 | 4-(3-{[2-amino-6-(6-methoxypyridin-3-yl)pyrimidin-4-yl]amino}phenoxy)pyridine-2-carboxamide | 430.4 (2.70) |

TABLE 1-continued

| Example No. | Structure | IUPAC Name* | LCMS: [M + H]+ (RT, min) |
|---|---|---|---|
| 285 | 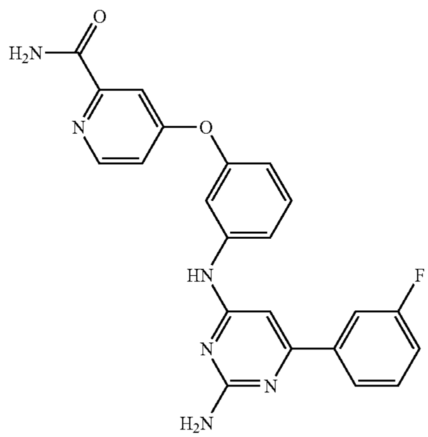 | 4-(3-{[2-amino-6-(3-fluorophenyl) pyrimidin-4-yl]amino}phenoxy) pyridine-2-carboxamide | 417.4 (2.77) |
| 286 | 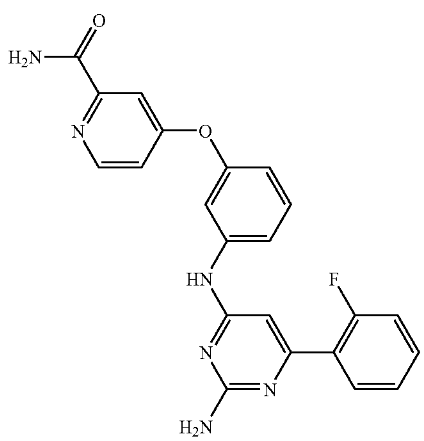 | 4-(3-{[2-amino-6-(2-fluorophenyl) pyrimidin-4-yl]amino}phenoxy) pyridine-2-carboxamide | 417.4 (2.74) |
| 287 | 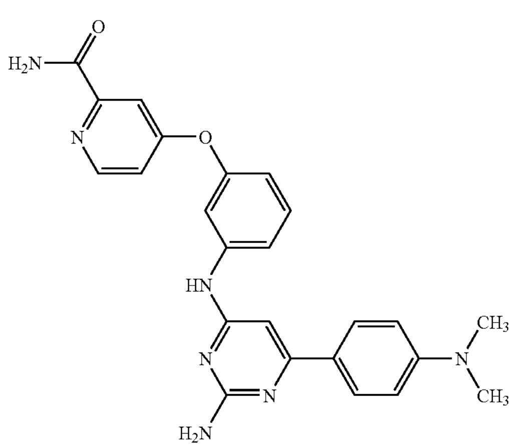 | 4-[3-({2-amino-6-[4-(dimethylamino) phenyl]pyrimidin-4-yl}amino) phenoxy]pyridine-2-carboxamide | 442.5 (2.85) |

TABLE 1-continued

| Example No. | Structure | IUPAC Name* | LCMS: [M + H]+ (RT, min) |
|---|---|---|---|
| 288 | 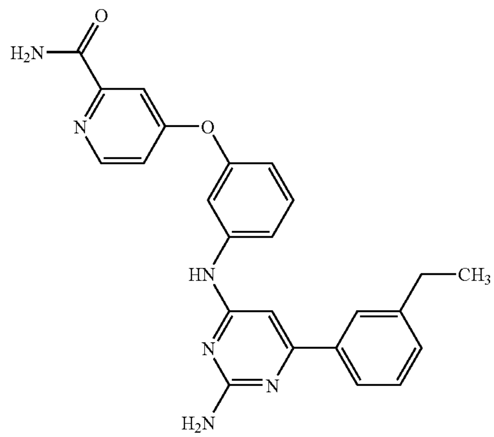 | 4-(3-{[2-amino-6-(3-ethylphenyl)pyrimidin-4-yl]amino}phenoxy)pyridine-2-carboxamide | 427.5 (2.88) |
| 289 | 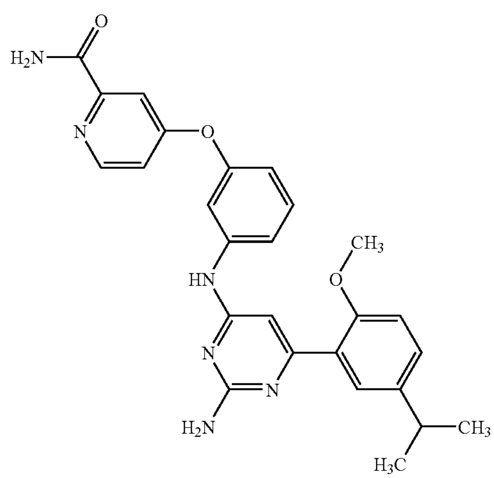 | 4-(3-{[2-amino-6-(5-isopropyl-2-methoxyphenyl)pyrimidin-4-yl]amino}phenoxy)pyridine-2-carboxamide | 471.5 (3.00) |
| 290 | 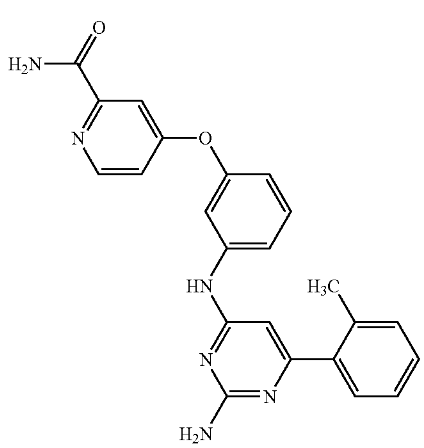 | 4-(3-{[2-amino-6-(2-methylphenyl)pyrimidin-4-yl]amino}phenoxy)pyridine-2-carboxamide | 413.5 (2.79) |

TABLE 1-continued

| Example No. | Structure | IUPAC Name* | LCMS: [M + H]+ (RT, min) |
|---|---|---|---|
| 291 | 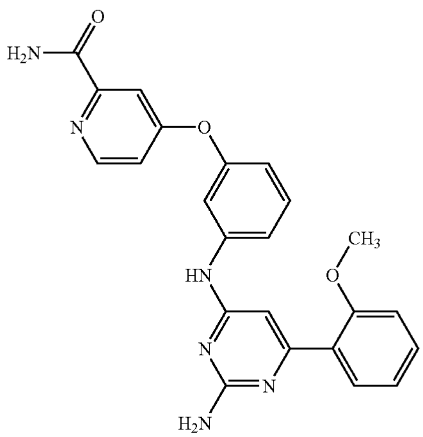 | 4-(3-{[2-amino-6-(2-methoxyphenyl) pyrimidin-4-yl]amino}phenoxy) pyridine-2-carboxamide | 429.5 (2.78) |
| 292 | 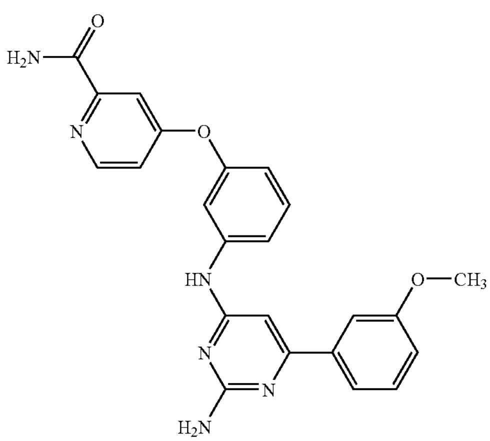 | 4-(3-{[2-amino-6-(3-methoxyphenyl) pyrimidin-4-yl]amino}phenoxy) pyridine-2-carboxamide | 429.5 (2.78) |
| 293 | 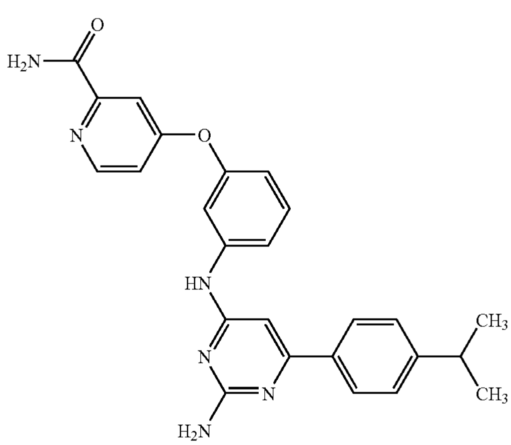 | 4-(3-{[2-amino-6-(4-isopropylphenyl) pyrimidin-4-yl]amino}phenoxy) pyridine-2-carboxamide | 441.5 (2.97) |

TABLE 1-continued

| Example No. | Structure | IUPAC Name* | LCMS: [M + H]+ (RT, min) |
|---|---|---|---|
| 294 | 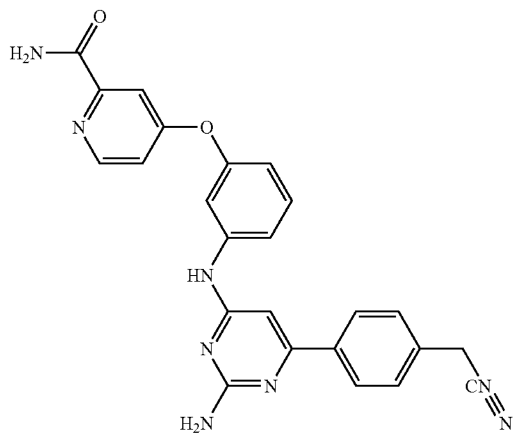 | 4-[3-({2-amino-6-[4-(cyanomethyl) phenyl]pyrimidin-4-yl}amino) phenoxy]pyridine-2-carboxamide | 438.5 (2.75) |
| 295 | 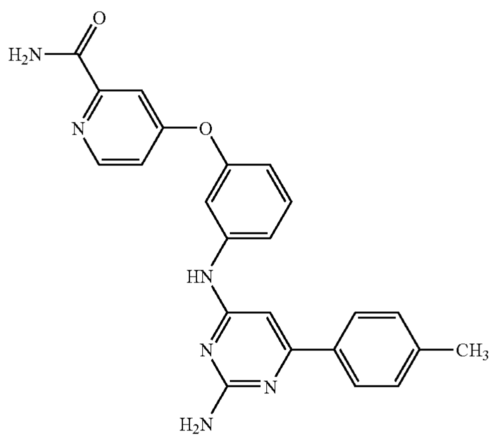 | 4-(3-{[2-amino-6-(4-methylphenyl) pyrimidin-4-yl]amino}phenoxy) pyridine-2-carboxamide | 413.5 (2.81) |
| 296 | 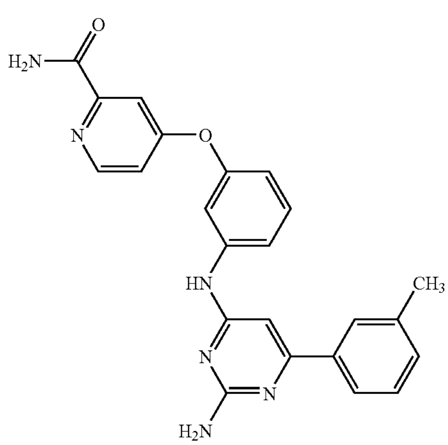 | 4-(3-{[2-amino-6-(3-methylphenyl) pyrimidin-4-yl]amino}phenoxy) pyridine-2-carboxamide | 413.5 (2.80) |

TABLE 1-continued

| Example No. | Structure | IUPAC Name* | LCMS: [M + H]+ (RT, min) |
|---|---|---|---|
| 297 | 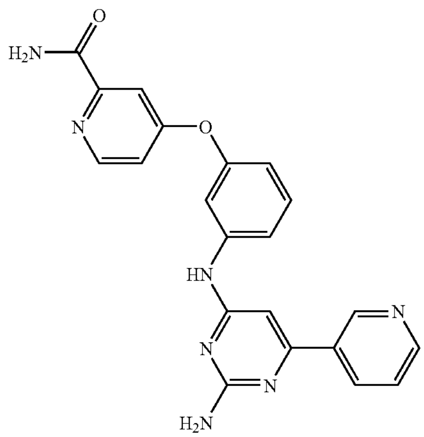 | 4-{3-[(2-amino-6-pyridin-3-ylpyrimidin-4-yl)amino]phenoxy}pyridine-2-carboxamide | 400.4 (2.58) |
| 298 | 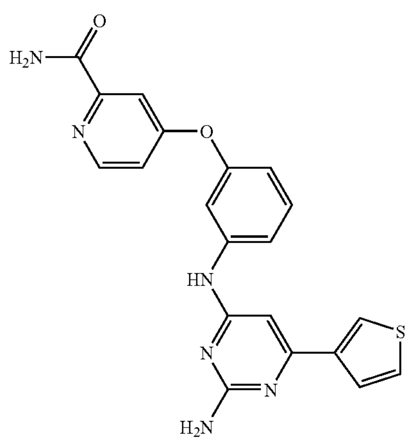 | 4-(3-{[2-amino-6-(3-thienyl)pyrimidin-4-yl]amino}phenoxy)pyridine-2-carboxamide | 405.5 (2.72) |
| 299 | 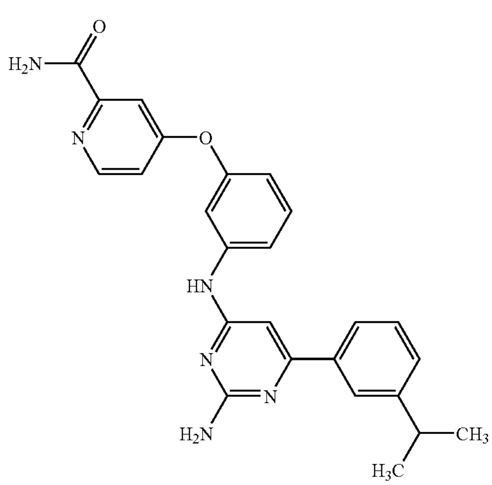 | 4-(3-{[2-amino-6-(3-isopropylphenyl)pyrimidin-4-yl]amino}phenoxy)pyridine-2-carboxamide | 441.5 (2.95) |

TABLE 1-continued

| Example No. | Structure | IUPAC Name* | LCMS: [M + H]+ (RT, min) |
|---|---|---|---|
| 300 | 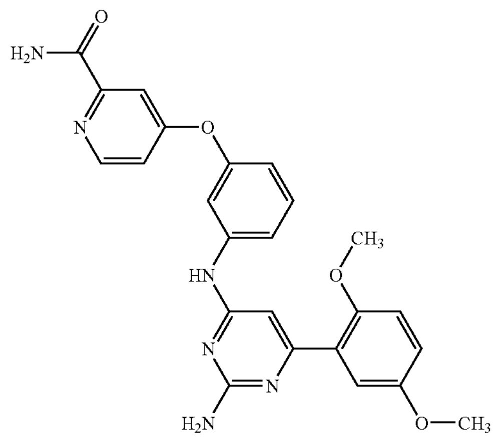 | 4-(3-{[2-amino-6-(2,5-dimethoxyphenyl)pyrimidin-4-yl]amino}phenoxy)pyridine-2-carboxamide | 459.5 (2.80) |
| 301 | 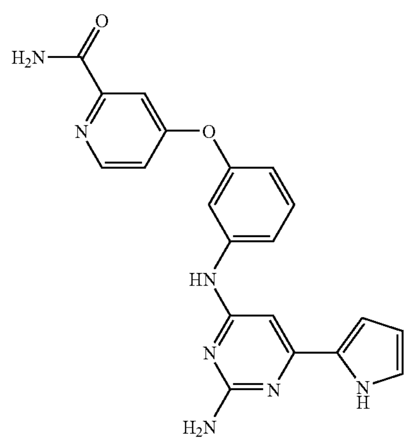 | 4-(3-{[2-amino-6-(1H-pyrrol-2-yl)pyrimidin-4-yl]amino}phenoxy)pyridine-2-carboxamide | 388.401 (2.69) |
| 302 | 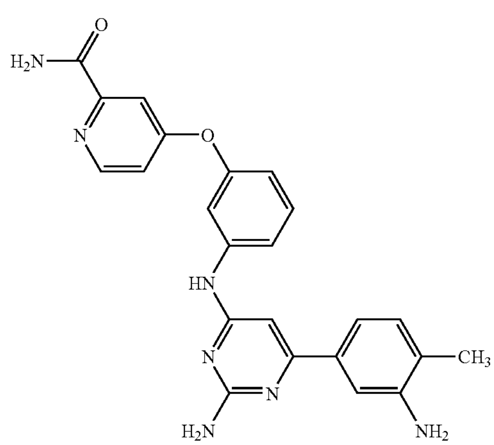 | 4-(3-{[2-amino-6-(3-amino-4-methylphenyl)pyrimidin-4-yl]amino}phenoxy)pyridine-2-carboxamide | 428.5 (2.71) |

TABLE 1-continued

| Example No. | Structure | IUPAC Name* | LCMS: [M + H]+ (RT, min) |
|---|---|---|---|
| 303 | 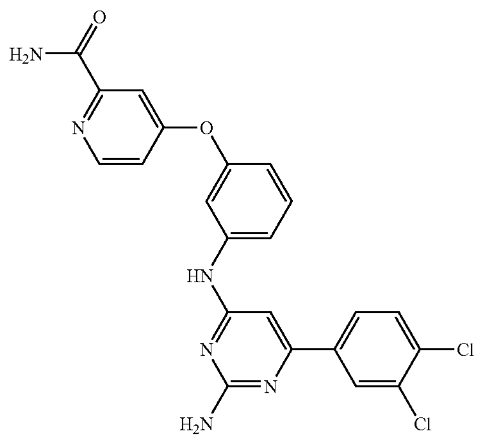 | 4-(3-{[2-amino-6-(3,4-dichlorophenyl)pyrimidin-4-yl]amino}phenoxy)pyridine-2-carboxamide | 468.3 (2.92) |
| 304 | 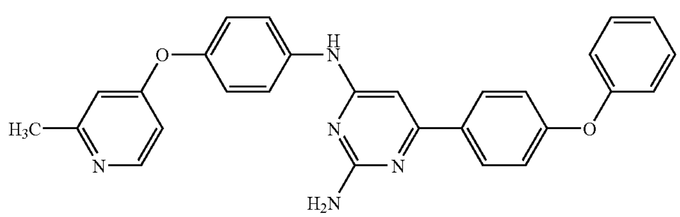 | N4*-{4-[(2-methylpyridin-4-yl)oxy]phenyl}-6-(4-phenoxyphenyl)pyrimidine-2,4-diamine | 462.5 (2.71) |
| 305 | 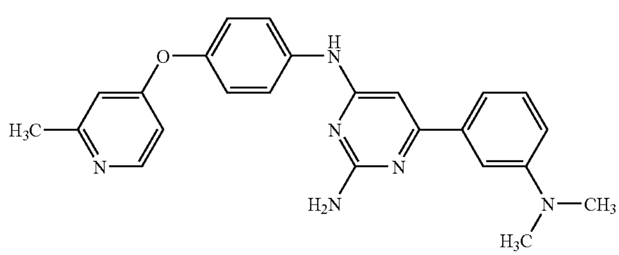 | 6-[3-(dimethylamino)phenyl]-N4*-{4-[(2-methylpyridin-4-yl)oxy]phenyl}pyrimidine-2,4-diamine | 413.5 (2.54) |
| 306 | 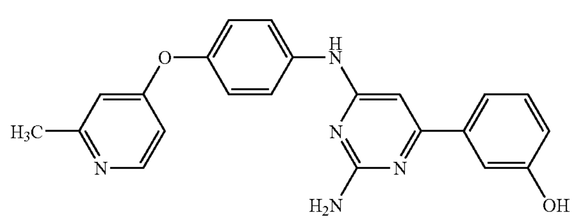 | 3-[2-amino-6-({4-[(2-methylpyridin-4-yl)oxy]phenyl}amino)pyrimidin-4-yl]phenol | 386.4 (2.48) |
| 307 | 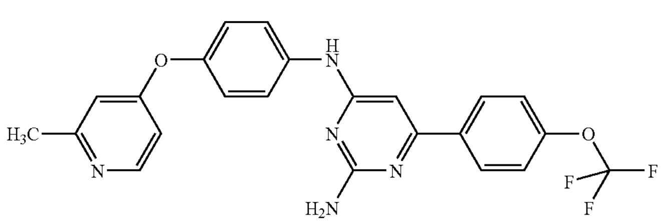 | N4*-{4-[(2-methylpyridin-4-yl)oxy]phenyl}-6-[4-(trifluoromethoxy)phenyl]pyrimidine-2,4-diamine | 454.4 (2.71) |

TABLE 1-continued

| Example No. | Structure | IUPAC Name* | LCMS: [M + H]+ (RT, min) |
|---|---|---|---|
| 308 | 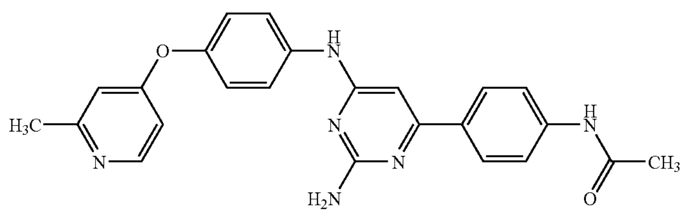 | N-{4-[2-amino-6-({4-[(2-methylpyridin-4-yl)oxy]phenyl}amino)pyrimidin-4-yl]phenyl}acetamide | 427.5 (2.47) |
| 309 | 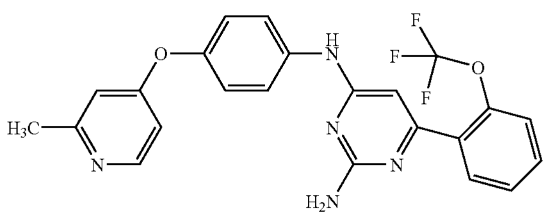 | N4-{4-[(2-methylpyridin-4-yl)oxy]phenyl}-6-[2-(trifluoromethoxy)phenyl]pyrimidine-2,4-diamine | 454.4 (2.61) |
| 310 | 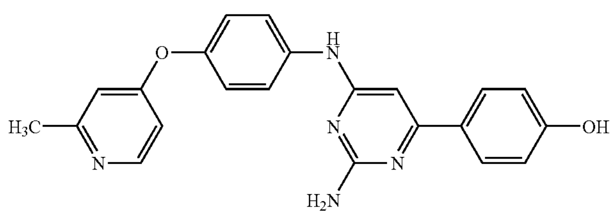 | 4-[2-amino-6-({4-[(2-methylpyridin-4-yl)oxy]phenyl}amino)pyrimidin-4-yl]phenol | 386.4 (2.49) |
| 311 | 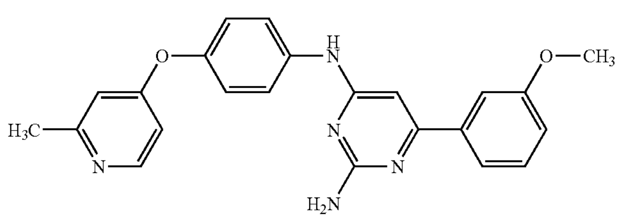 | 6-(2-methylphenyl)-N4*-{4-[(2-methylpyridin-4-yl)oxy]phenyl}pyrimidine-2,4-diamine | 384.5 (2.54) |
| 312 | 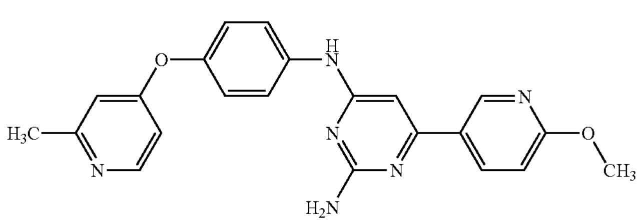 | 6-(6-methoxypyridin-3-yl)-N4*-{4-[(2-methylpyridin-4-yl)oxy]phenyl}pyrimidine-2,4-diamine | 401.4 (2.50) |
| 313 | 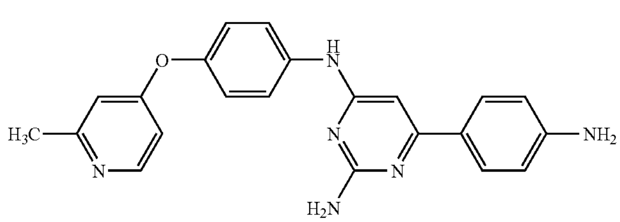 | 6-(4-aminophenyl)-N4*-{4-[(2-methylpyridin-4-yl)oxy]phenyl}pyrimidine-2,4-diamine | 385.4 (2.47) |

TABLE 1-continued

| Example No. | Structure | IUPAC Name* | LCMS: [M + H]+ (RT, min) |
|---|---|---|---|
| 314 | 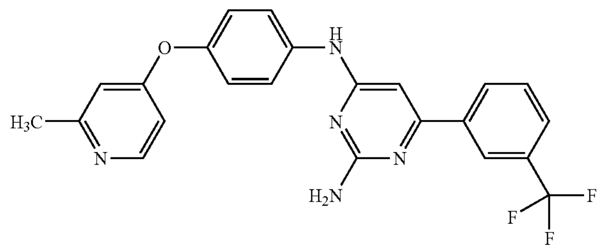 | N4*-{4-[(2-methylpyridin-4-yl)oxy]phenyl}-6-[3-(trifluoromethyl)phenyl]pyrimidine-2,4-diamine | 438.4 (2.66) |
| 315 | 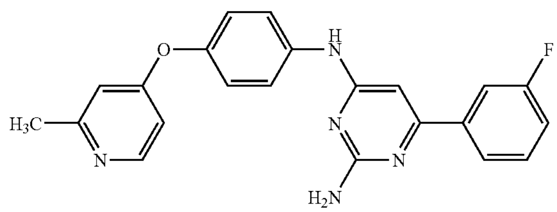 | 6-(3-fluorophenyl)-N4*-{4-[(2-methylpyridin-4-yl)oxy]phenyl}pyrimidine-2,4-diamine | 388.4 (2.55) |
| 316 | 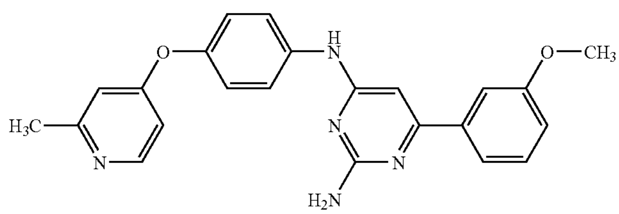 | 6-(3-methoxyphenyl)-N4*-{4-[(2-methylpyridin-4-yl)oxy]phenyl}pyrimidine-2,4-diamine | 400.5 (2.57) |
| 317 | 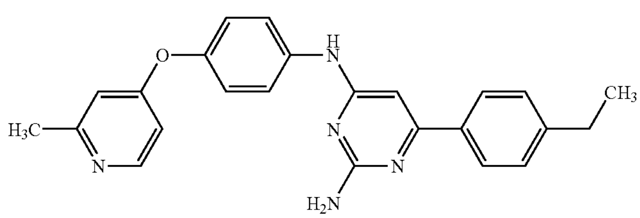 | 6-(4-ethylphenyl)-N4*-{4-[(2-methylpyridin-4-yl)oxy]phenyl}pyrimidine-2,4-diamine | 398.5 (2.66) |
| 318 | 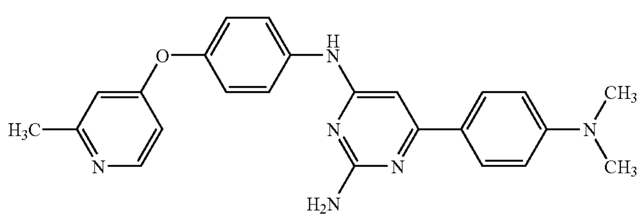 | 6-[4-(dimethylamino)phenyl]-N4*-{4-[(2-methylpyridin-4-yl)oxy]phenyl}pyrimidine-2,4-diamine | 413.5 (2.63) |
| 319 | 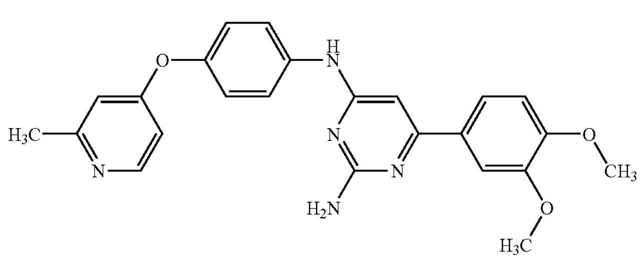 | 6-(3,4-dimethoxyphenyl)-N4*-{4-[(2-methylpyridin-4-yl)oxy]phenyl}pyrimidine-2,4-diamine | 430.5 (2.55) |

TABLE 1-continued

| Example No. | Structure | IUPAC Name* | LCMS: [M + H]+ (RT, min) |
|---|---|---|---|
| 320 | 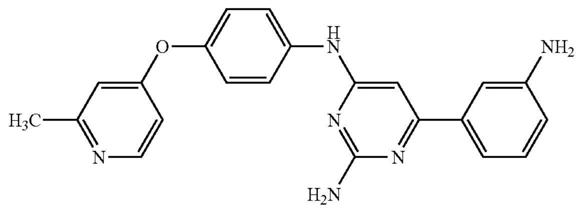 | 6-(3-aminophenyl)-N4*-{4-[(2-methylpyridin-4-yl)oxy]phenyl}pyrimidine-2,4-diamine | 385.4 (2.41) |
| 321 | 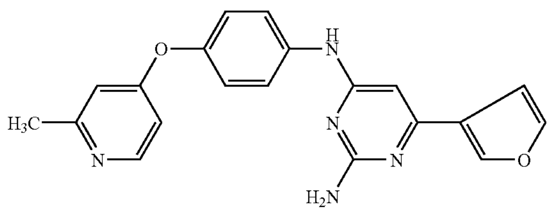 | 6-(3-furyl)-N4*-{4-[(2-methylpyridin-4-yl)oxy]phenyl}pyrimidine-2,4-diamine | 360.4 (2.49) |
| 322 | 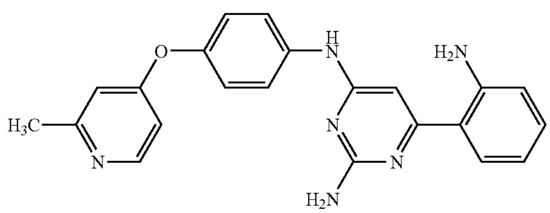 | 6-(2-aminophenyl)-N4*-{4-[(2-methylpyridin-4-yl)oxy]phenyl}pyrimidine-2,4-diamine | 385.4 (2.49) |
| 323 | 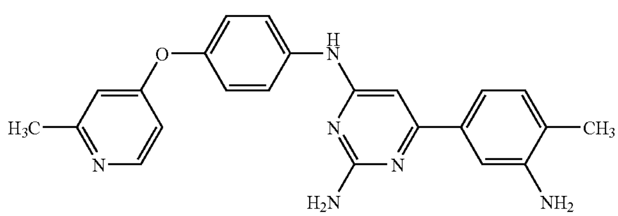 | 6-(3-amino-4-methylphenyl)-N4*-{4-[(2-methylpyridin-4-yl)oxy]phenyl}pyrimidine-2,4-diamine | 399.5 (2.48) |
| 324 | 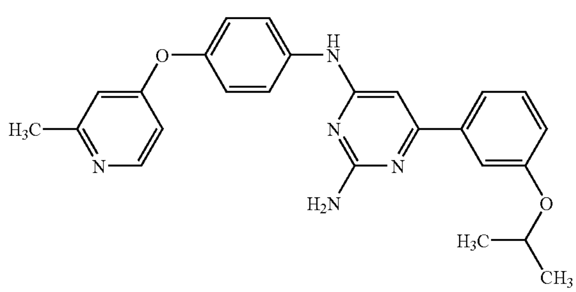 | 6-(3-isopropoxyphenyl)-N4*-{4-[(2-methylpyridin-4-yl)oxy]phenyl}pyrimidine-2,4-diamine | 428.5 (2.68) |
| 325 | 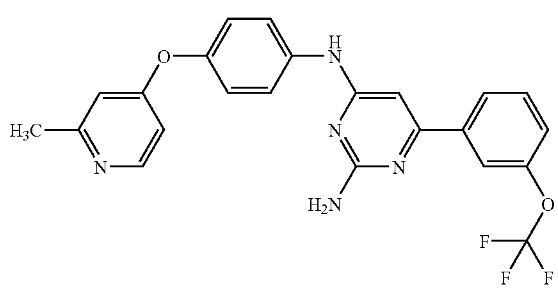 | N4*-{4-[(2-methylpyridin-4-yl)oxy]phenyl}-6-[3-(trifluoromethoxy)phenyl]pyrimidine-2,4-diamine | 454.4 (2.69) |

TABLE 1-continued

| Example No. | Structure | IUPAC Name* | LCMS: [M + H]+ (RT, min) |
|---|---|---|---|
| 326 | 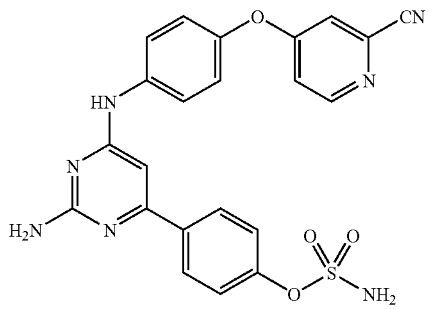 | 4-[2-amino-6-({4-[(2-cyanopyridin-4-yl)oxy]phenyl}amino)pyrimidin-4-yl] phenyl sulfamate | |
| 327 | 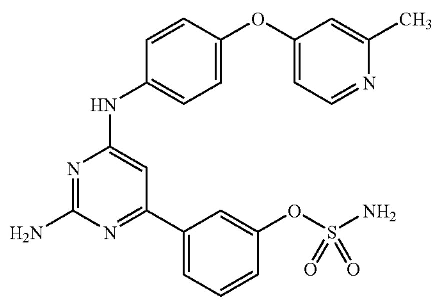 | 3-[2-amino-6-({4-[(2-methylpyridin-4-yl)oxy]phenyl}amino)pyrimidin-4-yl]phenyl sulfamate | |
| 328 | 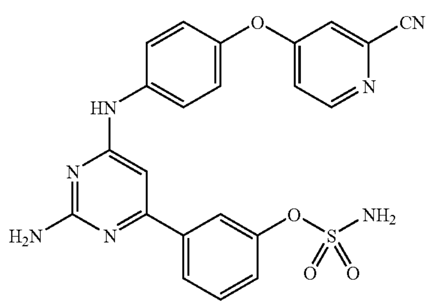 | 3-[2-amino-6-({4-[(2-cyanopyridin-4-yl)oxy]phenyl}amino)pyrimidin-4-yl] phenyl sulfamate | |
| 329 | 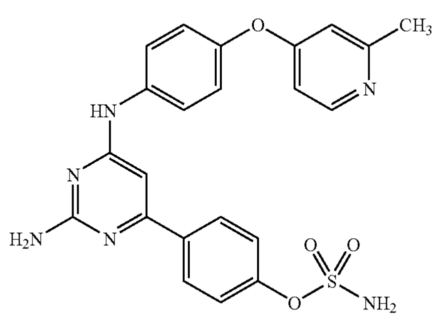 | 4-[2-amino-6-({4-[(2-methylpyridin-4-yl)oxy]phenyl}amino)pyrimidin-4-yl]phenyl sulfamate | |
| 330 | 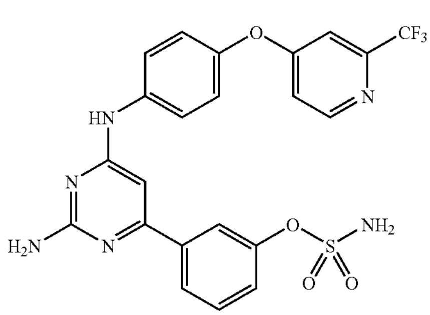 | 3-{2-amino-6-[(4-{(2-(trifluoromethyl)pyridin-4-yl]oxy}phenyl)amino]pyrimidin-4-yl}phenyl sulfamate | |

TABLE 1-continued

| Example No. | Structure | IUPAC Name* | LCMS: [M + H]+ (RT, min) |
|---|---|---|---|
| 331 | 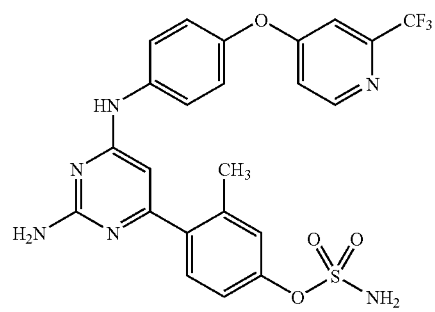 | 4-{2-amino-6-[(4-{[2-(trifluoromethyl)pyridin-4-yl]oxy}phenyl)amino]pyrimidin-4-yl}-3-methylphenyl sulfamate | |
| 332 | 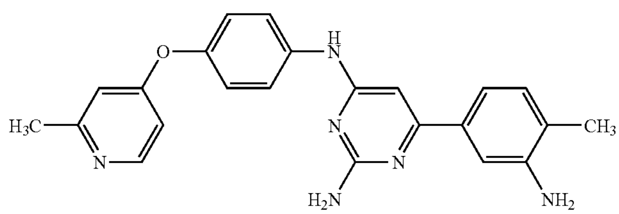 | 4-[2-amino-6-({4-[(2-chloropyridin-4-yl)oxy]phenyl}amino)pyrimidin-4-yl]phenyl sulfamate | 485.3 (2.42) |
| 333 | 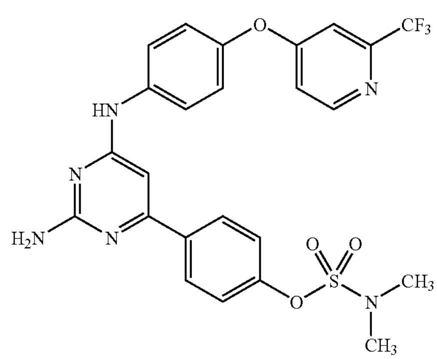 | 4-{2-amino-6-[(4-{[2-(trifluoromethyl)pyridin-4-yl]oxy}phenyl)amino]pyrimidin-4-yl}phenyl dimethylsulfamate | |
| 334 | 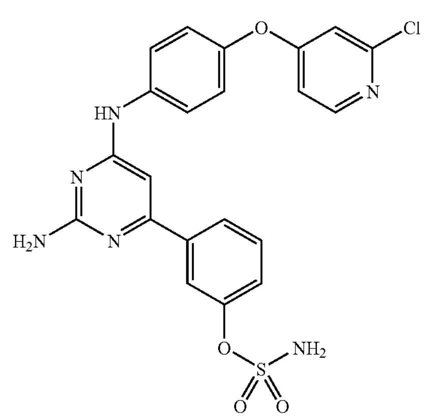 | 3-[2-amino-6-({4-[(2-chloropyridin-4-yl)oxy]phenyl}amino)pyrimidin-4-yl]phenyl sulfamate | |

Cytotoxic Activity of the Invention Compounds

The following section describes an assay that can be used to characterize compounds of the invention, e.g., to test for the cytotoxic activity of compounds on cells.

Human tumor cells, e.g., HCT116 cells, are seeded in a 96-well plate at $3.0 \times 10^3$ cells/well and grown in 100 μl of RPMI complete media (Invitrogen Corporation, Grand Island, N.Y.) containing 10% fetal bovine serum (Hyclone, Logan, Utah) and 10 mM HEPES and at 37° C. for 16 h in an incubator with 5% $CO_2$. To each well, 50 μl of additional growth media containing 20 μM to 60 nM concentrations of compound with 0.2% DMSO is added. Cells are grown for another 72 h at 37° C. 20 μl of Alamar Blue (Trek Diagnostic Systems, Inc., Cleveland, Ohio) reagent is added to each well and incubated for 4 h at 37° C. Plates are read in a SpectraMax Gemini (Molecular Devices, CA) with 544 nm excitation and 590 nm emission wavelength. $IC_{50}$ values are determined by linear regression analysis of log drug concentration versus percent inhibition.

Representative compounds of this invention were tested for cytotoxicity using the above-described assay procedure with the following results:

Examples 1, 2, 3, 4, 6, 7, 8, 9, 11, 13, 19, 21, 33, 34, 35, 37, 38, 39, 40, 45, 46, 48, 49, 50, 51, 52, 53, 58, 62, 63, 64, 66, 67, 69, 76, 80, 84, 88, 92, 94, 95, 96, 97, 98, 99, 113, 114, 116, 117, 118, 119, 120, 121, 123, 124, 125, 127, 129, 133, 134, 137, 139, 140, 142, 143, 145, 146, 149, 150, 151, 153, 154, 155, 156, 157, 158, 159, 160, 161, 162, 163, 164, 165, 166, 167, 168, 169, 170, 171, 173, 174, 175, 177, 179, 180, 181, 183, 185, 187, 188, 190, 191, 192, 193, 195, 196, 199, 200, 202, 204, 205, 206, 208, 209, 210, 211, 212, 213, 214, 215, 218, 219, 223, 227, 228, 229, 233, 234, 238, 240, 241, 246, 249, 250, 251, 252, 254, 259, 261, 262, 263, 264, 266, 267, 268, 269, 271, 273, 275, 278, 282, 288, 290, 292, 296, 298, 302, 305, 310, 311, 312, 313, 315, 316, 317, 318, 320, 321, 323 and 332 show an $IC_{50}$ of less than or equal to 500 nM in the HCT116 cytotoxic activity assay:

Examples 5, 10, 12, 23, 26, 30, 32, 41, 42, 47, 60, 61, 65, 68, 70, 73, 75, 79, 82, 85, 86, 89, 90, 91, 100, 101, 105, 107, 109, 112, 115, 128, 130, 131, 132, 135, 136, 138, 141, 144, 148, 152, 172, 176, 189, 194, 197, 198, 201, 203, 207, 220, 222, 226, 230, 231, 232, 235, 239, 242, 243, 245, 247, 248, 256, 257, 258, 276, 279, 281, 283, 284, 286, 291, 294, 297, 300, 304, 306, 308, 309, 319, 322, 324, and 325 show an $IC_{50}$ greater than 500 nM but less than or equal to 2 μM in the HCT116 cytotoxic activity assay.

Examples, 43, 44, 71, 72, 74, 77, 81, 83, 87, 93, 106, 108, 110, 111, 122, 126, 147, 178, 216, 217, 221, 224, 225, 236, 237, 244, 253, 255, 260, 265, 270, 272, 274, 277, 280, 285, 287, 289, 293, 295, 299, 301, 303, 307, and 314 show an $IC_{50}$ greater than 2 μM in the HCT116 cytotoxic activity assay.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. A compound having the structure

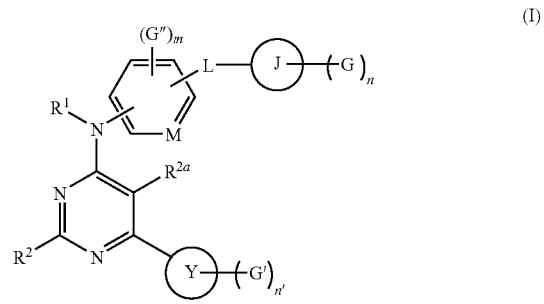

wherein
$R^1$ represents H, $(C_1-C_3)$alkyl, or cyclopropyl;
$R^2$ represents $(C_1-C_3)$alkyl, cyclopropyl, $O(C_1-C_3)$alkyl, or $NR^3R^4$ wherein $R^3$ and $R^4$ are H, $(C_1-C_3)$alkyl, or cyclopropyl;
$R^{2a}$ represents H or halogen;
M represents CH or N;
L represents a carbonyl group, O, $NR^5$, $CR^6R^7$, or $(C_2-C_3)$alkylenyl which is optionally substituted up to twice by groups independently selected from halogen and OH;
wherein
$R^5$ is H or $(C_1-C_3)$alkyl; and
$R^6$ and $R^7$ are independently H, $CH_3$, halogen, or OH;
J represents an aromatic or heteroaromatic ring selected from the group consisting of

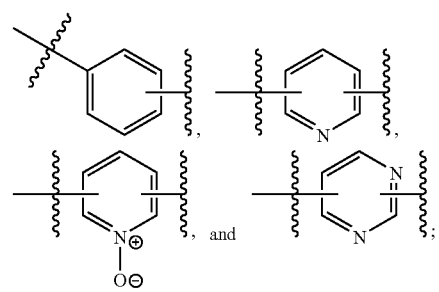

Y represents an aromatic or heteroaromatic ring selected from the group consisting of

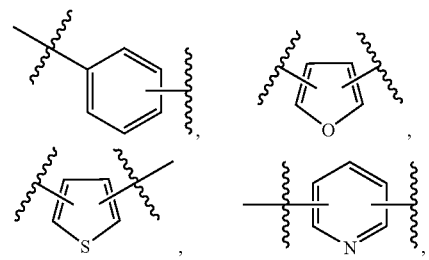

-continued

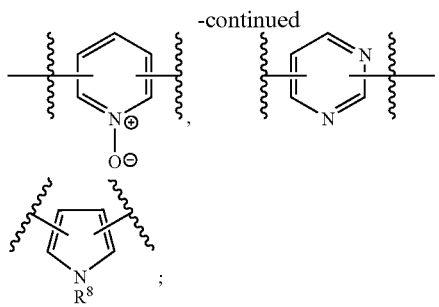

wherein R[8] represents H or $(C_1-C_3)$alkyl;
G" represents a substituent selected from the group consisting of $(C_1-C_3)$alkyl, cyclopropyl, $O(C_1-C_3)$alkyl, halogen, $CF_3$, CN and $CO_2R^9$;
wherein
R[9] H or $(C_1-C_3)$alkyl; and
m represents the number of substituents G", and is 0, 1, or 2;
G represents a substituent located on ring J;
G' represents a substituent located on ring Y;
n represents the number of substituents G; and
n' represents the number of substituents G';
n and n' are independently 0, 1, 2, or 3, subject to the provisos that
  1) ring J and ring Y each may be substituted independently up to 3 times by substituents listed below as numbers G1-G2, to a maximum total of 4 substituents on rings J and Y,
  2) ring J and ring Y each may be substituted independently up to 2 times by substituents listed below as numbers G3-G11, to a maximum total of 3 substituents on rings J and Y, and
  3) ring J and ring Y each may be substituted independently once by a substituent selected from those listed below as numbers G12-G37;
and subject to the further provisos
  4) when J is phenyl, G is other than OH or alkylthio; and when J is phenyl or pyridyl, n is 1, 2, or 3;
  5) when J is phenyl, and G is G4 shown below, then $R^2$ is $NR^3R^4$;
G and G' moieties are independently selected from the group consisting of:
G1) halogen;
G2) $O(C_1-C_4$alkyl which optionally is substituted up to two times by $O(C_1-C_2)$alkyl;
G3) OH;
G4) $(C_1-C_5)$alkyl, which is optionally substituted independently up to two times by groups selected from hydroxyl and cyano, or up to three times by halogen;
G5) $OCF_3$;
G6) $NHC(O)(C_1-C_3)$alkyl;
G7) $NHSO_2(C_1-C_3)$alkyl;
G8) $NR^{10}R^{11}$, wherein
  $R^{10}$ $R^{11}$ are independently selected from H, $CH_3$, cyclopropyl, benzyl, $NR^{12}R^{13}$ wherein
    $R^{12}$ and $R^{13}$ are independently H or $(C_1-C_3)$alkyl, provided that both $R^{10}$ and $R^{11}$ are not $NR^{12}R^{13}$ simultaneously, and
  $(C_2-C_4)$alkyl which is optionally substituted up to three times by halogen, and up to two times by substituent groups independently selected from hydroxyl, $O(C_1-C_3)$alkyl, and $NR^{14}R^{15}$, wherein $R^{14}$ and $R^{15}$ are independently H or $(C_1-C_3)$alkyl, or
$R^{14}$ and $R^{15}$ can join to form a heterocycle of formula

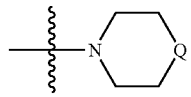

wherein
  Q represents $CH_2$, O, or $NR^{16}$, and
  $R^{16}$ H or $(C_1-C_3)$alkyl, or
$R^{10}$ and $R^{11}$ may be joined to form a saturated 5-6-membered N-containing ring which is optionally substituted up to two times by OH, $NR^{17}R^{18}$, wherein $R^{17}$ and $R^{18}$ are H or $(C_1-C_3)$ alkyl, or by $(C_1-C_3)$alkyl which is optionally substituted up to two times by halogen, OH, or $O(C_1-C_3)$alkyl;
G9) $(CH_2)_a$-$NR^{19}R^{20}$ wherein
  $R^{19}$ and $R^{20}$ are independently H, $(C_1-C_5)$alkyl, or $(C_3-C_6)$cycloalkyl, or may be joined to form a saturated 5-6-membered N-containing ring; and
  the subscript "a" is an integer of 1-4;

G10)

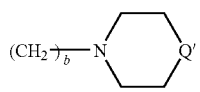

wherein
  Q' is O or $NR^{21}$;
  $R^{21}$ is H, $(C_1-C_3)$alkyl, or cyclopropyl; and
  the subscript "b" is an integer of 1-3;
G11) $CH_2NR^{22}(CH_2)_cOCH_3$ wherein
  $R^{22}$ is H, $(C_1-C_3)$alkyl, or cyclopropyl; and
  the subscript "c" is an integer of 2-4;
G12) $OSO_2NR^{23}R^{24}$ wherein
  $R^{23}$ and $R^{24}$ independently represent H, $CH_3$, or $(C_2-C_4)$alkyl which may optionally be substituted once by OH or $NR^{25}R^{26}$, wherein
  $R^{25}$ and $R^{26}$ independently represent H or $(C_1-C_3)$alkyl;
G13) CN;
G14) $NO_2$;
G15) cyclopropyl;
G16) $OR^{27}$, wherein
  $R^{27}$ represents phenyl or benzyl;
G17) $S(C_1-C_3)$alkyl;
G18) CH=CH—$(CH_2)_{1-3}$—$OR^5$; wherein
  $R^5$ represents H or $(C_1-C_3)$alkyl;

G19)

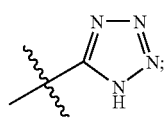

-continued

G20)

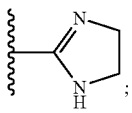

G21) $C(O)NR^{28}R^{29}$, wherein $R^{28}$ and $R^{29}$ are independently selected from H, cyclopropyl, provided that both $R^{28}$ and $R^{29}$ are not simultaneously cyclopropyl,

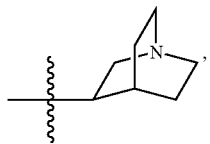

provided that this group does not constitute both $R^{28}$ and $R^{29}$ simultaneously, and $(C_1-C_3)$alkyl which is optionally substituted up to two times by OH; or $R^{28}$ and $R^{29}$ may be joined to form a saturated 5-6-membered N-containing ring which is optionally substituted up to two times by OH, or by $(C_1-C_3)$alkyl which in turn is optionally substituted up to two times by OH or $O(C_1-C_3)$alkyl;

G22)

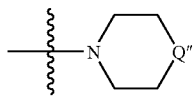

wherein $Q''$ is O or $NR^{30}$, and $R^{30}$ is H, cyclopropyl, or $(C_1-C_3)$alkyl which is optionally substituted once by halogen, OH, or $O(C_1-C_3)$alkyl;

G23) $O-(CH_2)_d-NR^{31}R^{32}$ wherein $R^{31}$ and $R^{32}$ are independently H, $(C_1-C_3)$alkyl, or cyclopropyl, or may be joined to form a saturated 5-6-membered N-containing ring; and the subscript "d" is an integer of 2-4;

G24)

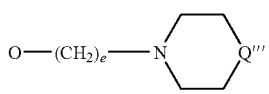

wherein the subscript "e" is an integer of 2-3; and $Q'''$ is O or $NR^{33}$; and $R^{33}$ is H, $(C_1-C_3)$alkyl, or cyclopropyl;

G25)

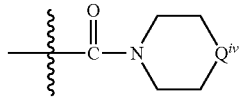

wherein $Q^{iv}$ is O or $NR^{34}$; and $R^{34}$ H, $(C_1-C_3)$alkyl, or cyclopropyl;

G26) $C(O)NR^{35}(CH_2)_fOR^{36}$ wherein $R^{35}$ is H, $(C_1-C_3)$alkyl, or cyclopropyl;

$R^{36}$ is $(C_1-C_6)$alkyl optionally substituted up to two times by halogen, OH, or $O(C_1-C_3)$alkyl, and the subscript "f" is an integer of 2-4;

G27) $CO_2R^{37}$ wherein $R^{37}$ is H or $(C_1-C_3)$alkyl;

G28) phenyl, which is optionally substituted by up to 2 groups selected from halogen, $(C_1-C_3)$alkyl, $OR^{38}$, CN, $CF_3$, and $NR^{39}R^{40}$ wherein $R^{38}$ represents H or $(C_1-C_3)$alkyl; and $R^{39}$ and $R^{40}$ represent H or $(C_1-C_3)$alkyl;

G29) $NR^{41}SO_2NR^{42}R^{43}$ wherein $R^{41}$ represents H, or $(C_1-C_4)$alkyl, and $R^{42}$ and $R^{43}$ independently represent H, $CH_3$, or $(C_2-C_3)$alkyl which may optionally be substituted once by —OH or $NR^{44}R^{45}$, wherein $R^{44}$ and $R^{45}$ independently represent H or $(C_1-C_3)$alkyl;

G30) $OC(O)-CH_2-NR^{46}R^{47}$ wherein $R^{46}$ and $R^{47}$ independently represent H, $(C_1-C_3)$alkyl, or $CO_2$(t-butyl), provided that $R^{46}$ and $R^{47}$ are not both simultaneously $CO_2$(t-butyl);

G31) $N(R^{48})C(O)R^{49}$ wherein $R^{48}$ represents H or $(C_1-C_3)$alkyl; and $R^{49}$ represents $(CH_2)_{1-3}-CO_2H$, $O(C_2-C_4alkyl)$, $(CH_2)_{1-4}-NR^{50}R^{51}$ wherein $R^{50}$ and $R^{51}$ independently represent H or $(C_1-C_3)$alkyl, or $CH(R^{52})-NR^{53}R^{54}$ wherein $R^{52}$ represents $(CH_2)_{1-4}-NH_2$, $CH_2OH$, $CH(CH_3)OH$, or $(C_1-C_3)$alkyl; and $R^{53}$ and $R^{54}$ independently represent H or $(C_1-C_3)$alkyl;

G32) $C(O)-(C_1-C_3)$alkyl;

G33) $(CH_2)_g-N(R^{55})-C(O)R^{56}$ wherein g represents 1, 2, or 3;

$R^{55}$ represents H or $(C_1-C_3)$alkyl;

$R^{56}$ represents $(C_1-C_3)$alkyl optionally substituted up to two times by $OR^{57}$ or $NR^{58}R^{59}$, wherein $R^{57}$ represents H or $(C_1-C_3)$alkyl, and $R^{58}$ and $R^{59}$ each represents H or $(C_1-C_3)$alkyl, or represents wherein

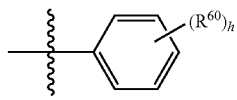

wherein $R^{60}$ represents halogen, $(C_1-C_3)$alkyl, $O(C_1-C_3)$alkyl, CN, OH, $CF_3$, or $NR^{61}R^{62}$, wherein $R^{61}$ and $R^{62}$ represent H or $(C_1-C_3)$alkyl; and h represents 0, 1, or 2;

G34) $(CH_2)_i$—$N(R^{63})$—$C(O)$—$NR^{64}R^{65}$ wherein
i represents 1, 2, or 3;
$R^{63}$ represents H or $(C_1-C_3)$alkyl;
$R^{64}$ and $R^{65}$ each represents H or $(C_1-C_3)$alkyl; or
$R^{64}$ and $R^{65}$ may be joined to form

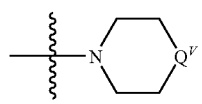

wherein $Q^V$ represents $CH_2$, O or $NR^{66}$ wherein $R^{66}$ represents H or $(C_1-C_3)$alkyl;

G35)

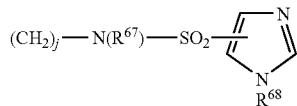

wherein
j represents 1, 2, or 3;
$R^{67}$ represents H or $(C_1-C_3)$alkyl; and
$R^{68}$ represents H or $(C_1-C_3)$alkyl;
G36) $(CH_2)_k$—$N(R^{69})$—$SO_2$—$R^{70}$ wherein
k represents 1, 2, or 3;
$R^{69}$ represents H or $(C_1-C_3)$alkyl; and
$R^{70}$ represents $(C_1-C_4$alkyl, or phenyl which is optionally substituted up to perhalo by halogen or up to three times by $OR^{71}$, CN, $CF_3$, or $NR^{72}R^{73}$, wherein
$R^{71}$ represents H or $(C_1-C_3)$alkyl; and
$R^{72}$ and $R^{73}$ each represents H or $(C_1-C_3)$alkyl;
G37) $CH=CH$—$(CH_2)_{1-3}$—$NR^{74}R^{75}$ wherein $R^{74}$ and $R^{75}$ represent H or $(C_1-C_3)$alkyl;
or a pharmaceutically acceptable salt or stereoisomer thereof.

2. The compound of claim 1 wherein $R^1$ H;
M represents CH;
J represents a heteroaromatic ring selected from the group consisting of

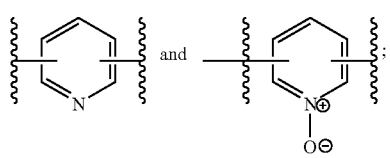

Y represents an aromatic or heteroaromatic ring selected from the group consisting of

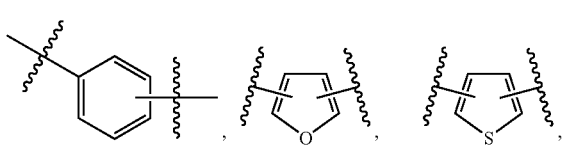

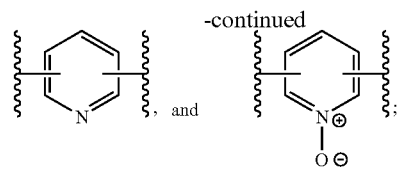

n and n' are independently 0, 1, 2, or 3, subject to the provisos that
1) ring J and ring Y each may be substituted independently up to 3 times by substituents listed below as numbers G1-G2, to a maximum total of 4 substituents on rings J and Y,
2) ring J and ring Y each may be substituted independently up to 2 times by substituents listed below as numbers G3-G5 and G8, to a maximum total of 3 substituents on rings J and Y, and
3) ring J and ring Y each may be substituted independently once by a substituent selected from those listed below as numbers G12, G13, G22, G29, and G31;
and subject to the further proviso
4) when J is pyridyl, n is 1, 2, or 3;
and proviso 5 does not apply;
G and G' moieties are independently selected from the group consisting of:
G1) halogen;
G2) $O(C_1-C_4)$alkyl which optionally is substituted up to two times by $O(C_1-C_2)$alkyl;
G3) OH;
G4) $(C_1-C_5)$alkyl, which is optionally substituted independently up to two times by groups selected from hydroxyl and cyano, or up to three times by halogen;
G5) $OCF_3$;
G8) $NR^{10}R^{11}$, wherein
$R^{10}$ $R^{11}$ are independently selected from H, $CH_3$, cyclopropyl, benzyl, $NR^{12}R^{13}$ wherein
$R^{12}$ and $R^{13}$ are independently H or $(C_1-C_3)$alkyl, provided that both $R^{10}$ and $R^{11}$ are not $NR^{12}R^{13}$ simultaneously, and $(C_2-C_4$alkyl which is optionally substituted up to three times by halogen, and up to two times by substituent groups independently selected from hydroxyl, $O(C_1-C_3)$alkyl, and $NR^{14}R^{15}$, wherein
$R^{14}$ and $R^{15}$ are independently H or $(C_1-C_3)$alkyl, or
$R^{14}$ and $R^{15}$ can join to form a heterocycle of formula

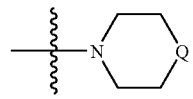

wherein
Q represents $CH_2$, O, or $NR^{16}$, and
$R^{16}$ H or $(C_1-C_3)$alkyl, or
$R^{10}$ and $R^{11}$ may be joined to form a saturated 5-6-membered N-containing ring which is optionally substituted up to two times by OH, $NR^{17}R^{18}$, wherein $R^{17}$ and $R^{18}$ are H or $(C_1-C_3)$alkyl, or by $(C_1-C_3)$alkyl which is optionally substituted up to two times by halogen, OH, or $O(C_1-C_3)$alkyl;

G12) $OSO_2NR^{23}R^{24}$ wherein
  $R^{23}$ and $R^{24}$ independently represent H, $CH_3$, or ($C_2$-$C_4$alkyl which may optionally be substituted once by OH or $NR^{26}R^{27}$, wherein
    $R^{25}$ and $R^{26}$ independently represent H or ($C_1$-$C_3$) alkyl;
G13) CN;

G22)
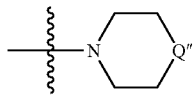

wherein
  Q" is O or $NR^{30}$, and
  $R^{30}$ is
    H, cyclopropyl, or ($C_1$-$C_3$)alkyl which is optionally substituted once by halogen, OH, or $O(C_1$-$C_3)$ alkyl;
G29) $NR^{41}SO_2NR^{42}R^{43}$ wherein
  $R^{41}$ represents H, or ($C_1$-$C_4$)alkyl, and
  $R^{42}$ and $R^{43}$ independently represent H, $CH_3$, or ($C_2$-$C_3$)alkyl which may optionally be substituted once by —OH or $NR^{44}R^{45}$, wherein
    $R^{44}R^{45}$ independently represent H or ($C_1$-$C_3$)alkyl; and
G31) $N(R^{48})C(O)R^{49}$ wherein
  $R^{48}$ represents H or ($C_1$-$C_3$)alkyl; and
  $R^{49}$ represents $(CH_2)_{1-3}$—$CO_2H$, $O(C_2$-$C_4$alkyl, $(CH_2)_{1-4}$—$NR^{50}R^{51}$ wherein
    $R^{50}$ and $R^{51}$ independently represent H or ($C_1$-$C_3$) alkyl, or
    $CH(R^{52})$—$NR^{53}R^{54}$ wherein
      $R^{52}$ represents $(CH_2)_{1-4}$—$NH_2$, $CH_2OH$, $CH(CH_3)OH$, or ($C_1$-$C_3$)alkyl; and
      $R^{53}R^{54}$ independently represent H or ($C_1$-$C_3$)alkyl.

3. The compound of claim 2 wherein
$R^1$ H;
$R^2$ represents $O(C_1$-$C_3)$alkyl or $NR^3R^4$ wherein $R^3$ and $R^4$ are H or ($C_1$-$C_3$)alkyl;
$R^{2a}$ represents H;
L represents O or $CR^6R^7$ wherein
  $R^6 R^7$ independently H, $CH_3$, or OH;
G" represents a substituent selected from the group consisting of $O(C_1$-$C_3)$alkyl, halogen, and $CF_3$;
n and n' are independently 0 or 1, and provisos 1-3 do not apply;
G and G' moieties are independently selected from the group consisting of:
  G1) Cl or F;
  G2) $O(C_1$-$C_3$)alkyl;
  G3) OH;
  G4) ($C_1$-$C_3$)alkyl, which is optionally substituted up to three times by halogen;
  G5) $OCF_3$;
  G8) $NR^{10}R^{11}$, wherein
    $R^{10} R^{11}$ are independently selected from
      H, $CH_3$, cyclopropyl, benzyl,
      $NR^{12}R^{13}$ wherein
        $R^{12}$ and $R^{13}$ are independently H or ($C_1$-$C_3$)alkyl, provided that both $R^{10}$ and $R^{11}$ are not $NR^{12}R^{13}$ simultaneously, and
      ($C_2$-$C_4$alkyl which is optionally substituted up to three times by halogen, and up to two times by substituent groups independently selected from hydroxyl, $O(C_1$-$C_3$)alkyl, and $NR^{14}R^{15}$, wherein
        $R^{14}$ and $R^{15}$ are independently H or ($C_1$-$C_3$)alkyl, or
        $R^{14}$ and $R^{15}$ can join to form a heterocycle of formula

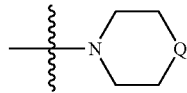

wherein
  Q represents $CH_2$, O, or $NR^{16}$, and
    $R^{16}$ represents H or ($C_1$-$C_3$)alkyl,
G12) $OSO_2NR^{23}R^{24}$ wherein
  $R^{23}$ and $R^{24}$ independently represent H, $CH_3$, or ($C_2$-$C_4$) alkyl which may optionally be substituted once by OH or $NR^{25}R^{26}$, wherein
    $R^{25}$ and $R^{26}$ independently represent H or ($C_1$-$C_3$)alkyl;
G13) CN;

G22)
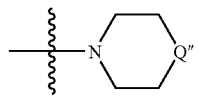

wherein
  Q" is O or $NR^{30}$, and
  $R^{30}$ is H or ($C_1$-$C_3$)alkyl; and
G31) $N(R^{48})C(O)R^{49}$ wherein
  $R^{48}$ represents H or ($C_1$-$C_3$)alkyl; and
  $R^9$ represents $(CH_2)_{1-3}$—$CO_2H$, $O(C_2$-$C_4$alkyl, $(CH_2)_{1-4}$—$NR^{50}R^{51}$ wherein
    $R^{50}$ and $R^{51}$ independently represent H or ($C_1$-$C_3$) alkyl, or $CH(R^{52})$—$NR^{53}R^{54}$ wherein
      $R^{52}$ represents $(CH_2)_{1-4}$—$NH_2$, $CH_2OH$, $CH(CH_3)OH$, or ($C_1$-$C_3$)alkyl; and
      $R^{53}$ and $R^{54}$ independently represent H or ($C_1$-$C_3$) alkyl.

4. The compound of claim 1 wherein
$R^1$ represents H;
M represents CH;
J represents a heteroaromatic ring selected from the group consisting of

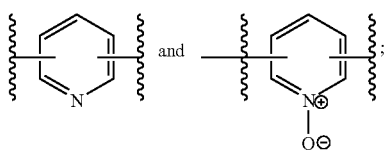

Y represents an aromatic or heteroaromatic ring selected from the group consisting of

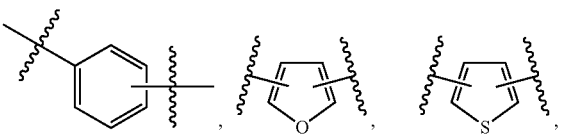

-continued

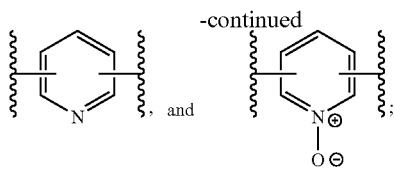

n and n' are independently 0, 1, 2, or 3, subject to the provisos that
1) ring J and ring Y each may be substituted independently up to 3 times by substituents listed below as numbers G1-G2, to a maximum total of 4 substituents on rings J and Y,
2) ring J and ring Y each may be substituted independently up to 2 times by substituents listed below as numbers G3-G5 and G8, to a maximum total of 3 substituents on rings J and Y, and
3) ring J and ring Y each may be substituted independently once by a substituent selected from those listed below as numbers G12, G21, G25, G26, and G31;

and subject to the further proviso
4) when J is pyridyl, n is 1, 2, or 3;
and proviso 5 does not apply;
G and G' moieties are independently selected from the group consisting of:
G1) halogen;
G2) $O(C_1-C_4)$alkyl which optionally is substituted up to two times by $O(C_1-C_2)$alkyl;
G3) OH;
G4) $(C_1-C_5)$alkyl, which is optionally substituted independently up to two times by groups selected from hydroxyl and cyano, or up to three times by halogen;
G5) $OCF_3$;
G8) $NR^{10}R^{11}$, wherein
  $R^{10}$ and $R^{11}$ are independently selected from H, $CH_3$, cyclopropyl, benzyl,
  $NR^{12}R^{13}$ wherein
    $R^{12}$ and $R^{13}$ are independently H or $(C_1-C_3)$alkyl, provided that both $R^{10}$ and $R^{11}$ are not $NR^{12}R^{13}$ simultaneously, and
  $(C_2-C_4)$alkyl which is optionally substituted up to three times by halogen, and up to two times by substituent groups independently selected from hydroxyl, $O(C_1-C_3)$alkyl, and $NR^{14}R^{15}$, wherein
    $R^{14}$ and $R^{15}$ are independently H or $(C_1-C_3)$alkyl, or
    $R^{14}$ and $R^{15}$ can join to form a heterocycle of formula

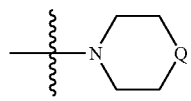

wherein
Q represents $CH_2$, O, or $NR^{16}$, and
$R^{16}$ H or $(C_1-C_3)$alkyl, or
$R^{10}$ and $R^{11}$ may be joined to form a saturated 5-6-membered N-containing ring which is optionally substituted up to two times by OH, $NR^{17}R^{18}$, wherein $R^{17}$ and $R^{18}$ are H or $(C_1-C_3)$alkyl, or by $(C_1-C_3)$alkyl which is optionally substituted up to two times by halogen, OH, or $O(C_1-C_3)$alkyl;

G12) $OSO_2NR^{23}R^{24}$ wherein
  $R^{23}$ and $R^{24}$ independently represent H, $CH_3$, or $(C_2-C_4)$alkyl which may optionally be substituted once by OH or $NR^{25}R^{26}$, wherein
  $R^{25}$ and $R^{26}$ independently represent H or $(C_1-C_3)$alkyl;
G21) $C(O)NR^{28}R^{29}$, wherein
  $R^{28}$ and $R^{29}$ are independently selected from H, cyclopropyl, provided that both $R^{28}$ and $R^{29}$ are not simultaneously cyclopropyl,

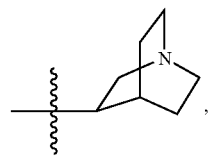

provided that this group does not constitute both $R^{28}$ and $R^{29}$ simultaneously, and $(C_1-C_3)$alkyl which is optionally substituted up to two times by OH; or
$R^{28}$ and $R^{29}$ may be joined to form a saturated 5-6-membered N-containing ring which is optionally substituted up to two times by OH, or by $(C_1-C_3)$alkyl which in turn is optionally substituted up to two times by OH or $O(C_1-C_3)$alkyl;

G25)

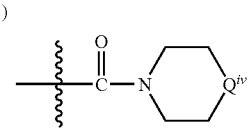

wherein
$Q^{iv}$ is O or $NR^{34}$; and
$R^{34}$ is H, $(C_1-C_3)$alkyl, or cyclopropyl;
G26) $C(O)NR^{35}(CH_2)_fOR^{36}$ wherein
  $R^{35}$ is H, $(C_1-C_3)$alkyl, or cyclopropyl;
  $R^{36}$ is $(C_1-C_6)$alkyl optionally substituted up to two times by halogen, OH, or $O(C_1-C_3)$alkyl, and the subscript "f" is an integer of 2-4; and
G31) $N(R^{48})C(O)R^{49}$ wherein
  $R^{48}$ represents H or $(C_1-C_3)$alkyl; and
  $R^{49}$ represents $(CH_2)_{1-3}$—$CO_2H$, $O(C_2-C_4)$alkyl, $(CH_2)_{1-4}$—$NR^{50}R^{51}$ wherein
    $R^{50}$ and $R^{51}$ independently represent H or $(C_1-C_3)$alkyl, or $CH(R^{52})$—$NR^{53}R^{54}$ wherein
      $R^{52}$ represents $(CH_2)_{1-4}$—$NH_2$, $CH_2OH$, $CH(CH_3)$OH, or $(C_1-C_3)$alkyl; and
      $R^{53}$ and $R^{54}$ independently represent H or $(C_1-C_3)$alkyl.

5. The compound of claim 4 wherein
$R^1$ represents H;
$R^2$ represents $O(C_1-C_3)$alkyl or $NR^3R^4$ wherein $R^3$ and $R^4$ are H or $(C_1-C_3)$alkyl;
$R^{2a}$ represents H;
L represents O or $CR^6R^7$, wherein
$R^6$ $R^7$ are independently H, $CH_3$, or OH;
$G^{41}$ represents a substituent selected from the group consisting of $O(C_1-C_3)$alkyl, halogen, and $CF_3$;
n and n' are independently 0 or 1, and provisos 1-3 do not apply;

G and G' moieties are independently selected from the group consisting of:
G1) Cl or F;
G2) O($C_1$-$C_3$)alkyl;
G3) OH;
G4) ($C_1$-$C_3$)alkyl, which is optionally substituted up to three times by halogen;
G5) $OCF_3$;
G8) $NR^{10}R^{11}$, wherein
  $R^{10}$ and $R^{11}$ are independently selected from H, $CH_3$, cyclopropyl, benzyl, $NR^{12}R^{13}$ wherein
    $R^{12}$ and $R^{13}$ are independently H or ($C_1$-$C_3$)alkyl, provided that both $R^{10}$ and $R^{11}$ are not $NR^{12}R^{13}$ simultaneously, and
  ($C_2$-$C_4$alkyl which is optionally substituted up to three times by halogen, and up to two times by substituent groups independently selected from hydroxyl, O($C_1$-$C_3$)alkyl, and $NR^{14}R^{15}$, wherein
    $R^{14}$ and $R^{15}$ are independently H or ($C_1$-$C_3$)alkyl, or
    $R^{14}$ and $R^{15}$ can join to form a heterocycle of formula

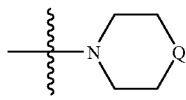

wherein
  Q represents $CH_2$, O, or $NR^{16}$, and
  $R^{16}$ represents H or ($C_1$-$C_3$)alkyl,
G12) $OSO_2NR^{23}R^{24}$ wherein
  $R^{23}$ and $R^{24}$ independently represent H, $CH_3$, or ($C_2$-$C_4$alkyl which may optionally be substituted once by OH or $NR^{25}R^{26}$, wherein
    $R^{25}$ and $R^{26}$ independently represent H or ($C_1$-$C_3$)alkyl;
G21) C(O)$NR^{28}R^{29}$, wherein
  $R^{28}$ and $R^{29}$ are independently selected from H and ($C_1$-$C_3$)alkyl which is optionally substituted up to two times by OH;

G25)

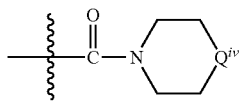

wherein
  $Q^{iv}$ is O or $NR^{34}$; and
  $R^{34}$ H or ($C_1$-$C_3$)alkyl;
G26) C(O)$NR^{35}(CH_2)_fOR^{36}$ wherein
  $R^{35}$ is H or ($C_1$-$C_3$)alkyl;
  $R^{36}$ is ($C_1$-$C_6$)alkyl optionally substituted up to two times by halogen, OH, or O($C_1$-$C_3$)alkyl, and the subscript "f" is an integer of 2-4; and
G31) $N(R^{48})C(O)R^{49}$ wherein
  $R^{48}$ represents H or ($C_1$-$C_3$)alkyl; and
  $R^{49}$ represents $(CH_2)_{1-3}$—$CO_2H$, O($C_2$-$C_4$alkyl, $(CH_2)_{1-4}$—$NR^{50}R^{51}$ wherein
    $R^{50}$ and $R^{51}$ independently represent H or ($C_1$-$C_3$) alkyl, or
  $CH(R^{52})$—$NR^{53}R^{54}$ wherein
    $R^{52}$ represents $(CH_2)_{1-4}$—$NH_2$, $CH_2OH$, $CH(CH_3)$ OH, or ($C_1$-$C_3$)alkyl; and $R^{53}$ and $R^{54}$ independently represent H or ($C_1$-$C_3$) alkyl.

6. The compound of claim 1 wherein
$R^1$ represents H;
M represents CH;
J represents an aromatic or heteroaromatic ring selected from the group consisting of

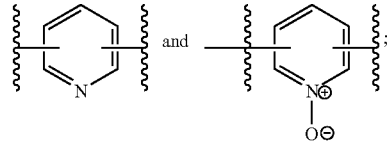

Y represents an aromatic or heteroaromatic ring selected from the group consisting of

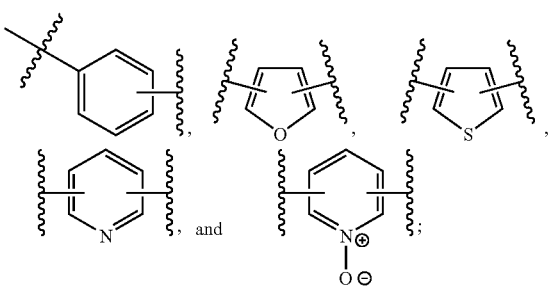

n and n' are independently 0, 1, 2, or 3, subject to the provisos that
  1) ring J and ring Y each may be substituted independently up to 3 times by substituents listed below as numbers G1-G2, to a maximum total of 4 substituents on rings J and Y,
  2) ring J and ring Y each may be substituted independently up to 2 times by substituents listed below as numbers G3-G5 and G8, to a maximum total of 3 substituents on rings J and Y, and
  3) ring J and ring Y each may be substituted independently once by a substituent selected from those listed below as numbers G12, G22, and G31;
and subject to the further proviso
  4) when J is pyridyl, n is 1, 2, or 3;
and proviso 5 does not apply;
G and G' moieties are independently selected from the group consisting of:
G1) halogen;
G2) O($C_1$-$C_4$alkyl which optionally is substituted up to two times by O($C_1$-$C_2$)alkyl;
G3) OH;
G4) ($C_1$-$C_5$)alkyl, which is optionally substituted independently up to two times by groups selected from hydroxyl and cyano, or up to three times by halogen;
G5) $OCF_3$;
G8) $NR^{10}R^{11}$, wherein
  $R^{10}$ $R^{11}$ are independently selected from H, $CH_3$, cyclopropyl, benzyl, $NR^{12}R^{13}$ wherein
    $R^{12}$ and $R^{13}$ are independently H or ($C_1$-$C_3$)alkyl, provided that both $R^{10}$ and $R^{11}$ are not $NR^{12}R^{13}$ simultaneously, and
  ($C_2$-$C_4$alkyl which is optionally substituted up to three times by halogen, and up to two times by substituent groups independently selected from hydroxyl, $O(C_1-C_3)$alkyl, and $NR^{14}R^{15}$, wherein
$R^{14}$ and $R^{15}$ are independently H or $(C_1-C_3)$alkyl, or
$R^{14}$ and $R^{15}$ can join to form a heterocycle of formula

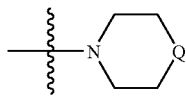

wherein
Q represents $CH_2$, O, or $NR^{16}$, and
$R^{16}$ represents H or $(C_1-C_3)$alkyl, or
$R^{10}$ and $R^{11}$ may be joined to form a saturated 5-6-membered N-containing ring which is optionally substituted up to two times by OH, $NR^{17}R^{18}$, wherein
$R^{17}$ and $R^{18}$ are H or $(C_1-C_3)$alkyl, or by
$(C_1-C_3)$alkyl which is optionally substituted up to two times by halogen, OH, or $O(C_1-C_3)$alkyl;
G12) $OSO_2NR^{23}R^{24}$ wherein
$R^{23}$ and $R^{24}$ independently represent H, $CH_3$, or $(C_2-C_4$alkyl which may optionally be substituted once by OH or $NR^{25}R^{26}$, wherein
$R^{25}$ and $R^{26}$ independently represent H or $(C_1-C_3)$alkyl;

G22)

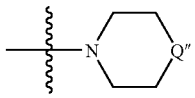

wherein
Q" is O or $NR^{30}$, and
$R^{30}$ is H, cyclopropyl, or $(C_1-C_3)$alkyl which is optionally substituted once by halogen, OH, or $O(C_1-C_3)$alkyl; and
G31) $N(R^{48})C(O)R^{49}$ wherein
$R^{48}$ represents H or $(C_1-C_3)$alkyl; and
$R^{49}$ represents $(CH_2)_{1-3}$—$CO_2H$, $O(C_2-C_4)$alkyl, $(CH_2)_{1-4}$—$NR^{50}R^{51}$ wherein
$R^{50}$ and $R^{51}$ independently represent H or $(C_1-C_3)$alkyl, or
$CH(R^{52})$—$NR^{53}R^{54}$ wherein
$R^{52}$ represents $(CH_2)_{1-4}$—$NH_2$, $CH_2OH$, $CH(CH_3)OH$, or $(C_1-C_3)$alkyl; and
$R^{53}$ and $R^{54}$ independently represent H or $(C_1-C_3)$alkyl.

7. The compound of claim 6 wherein
$R^1$ represents H;
$R^1$ represents $O(C_1-C_3)$alkyl, or $NR^3R^4$ wherein $R^3$ and $R^4$ are H or $(C_1-C_3)$alkyl;
$R^{2a}$ represents H;
L represents O or $CR^6R^7$, wherein
$R^6$ and $R^7$ are independently H, $CH_3$, or OH;
G" represents a substituent selected from the group consisting of $O(C_1-C_3)$alkyl, halogen, and $CF_3$;
n and n' are independently 0 or 1, and provisos 1-3 do not apply;

G and G' moieties are independently selected from the group consisting of:
G1) Cl or F;
G2) $O(C_1-C_3)$alkyl;
G3) OH;
G4) $(C_1-C_3)$alkyl, which is optionally substituted up to three times by halogen;
G5) $OCF_3$;
G8) $NR^{10}R^{11}$, wherein
$R^{10}$ and $R^{11}$ are independently selected from H, $CH_3$, cyclopropyl, benzyl, $NR^{12}R^{13}$ wherein
$R^{12}$ and $R^{13}$ are independently H or $(C_1-C_3)$alkyl, provided that both $R^{10}$ and $R^{11}$ are not $NR^{12}R^{13}$ simultaneously, and
$(C_2-C_4)$alkyl which is optionally substituted up to three times by halogen, and up to two times by substituent groups independently selected from hydroxyl, $O(C_1-C_3)$alkyl, and $NR^{14}R^{15}$, wherein
$R^{14}$ and $R^{15}$ are independently H or $(C_1-C_3)$alkyl, or
$R^{14}$ and $R^{15}$ can join to form a heterocycle of formula

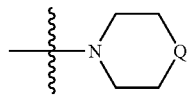

wherein
Q represents $CH_2$, O, or $NR^{16}$, and
$R^{16}$ represents H or $(C_1-C_3)$alkyl;
G12) $OSO_2R^{23}R^{24}$ wherein
$R^{23}$ and $R^{24}$ independently represent H, $CH_3$, or $(C_2-C_4)$alkyl which may optionally be substituted once by OH or $NR^{25}R^{26}$ wherein
$R^{25}$ and $R^{26}$ independently represent H or $(C_1-C_3)$alkyl;

G22)

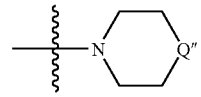

wherein
Q" is O or $NR^{30}$, and
$R^{30}$ is H or $(C_1-C_3)$alkyl; and
G31) $N(R^{48})C(O)R^{49}$ wherein
$R^{48}$ represents H or $(C_1-C_3)$alkyl; and
$R^{49}$ represents $(CH_2)_{1-3}$—$CO_2H$, $O(C_2-C_4)$alkyl, $(CH_2)_{1-4}$—$NR^{50}R^{51}$ wherein
$R^{50}$ and $R^{51}$ independently represent H or $(C_1-C_3)$alkyl, or
$(CH(R^{52})$—$NR^{53}R^{54}$ wherein
$R^{52}$ represents $(CH_2)_{1-4}$—$NH_2$, $CH_2OH$, $CH(CH_3)OH$, or $(C_1-C_3)$alkyl; and
$R^{53}$ and $R^{54}$ independently represent H or $(C_1-C_3)$alkyl.

8. A compound selected from the group consisting of
4-{3-[(2-amino-6-phenylpyrimidin-4-yl)amino]phenoxy}-N-methylpyridine-2-carboxamide;
4-{3-[(2-amino-6-phenylpyrimidin-4-yl)amino]phenoxy}pyridine-2-carboxamide;
4-{4-[(2-amino-6-phenylpyrimidin-4-yl)amino]phenoxy}pyridine-2-carbonitrile;
6-phenyl-$N^4$-(4-{[2-(trifluoromethyl)pyridin-4-yl]oxy}phenyl)pyrimidine-2,4-diamine;

$N^4$-{4-[(2-chloropyridin-4-yl)oxy]phenyl}-6-phenylpyrimidine-2,4-diamine;

4-{2-amino-6-[(4-{[2-(trifluoromethyl)pyridin-4-yl]oxy}phenyl)amino]pyrimidin-4-yl}phenyl sulfamate;

N-(4-{2-amino-6-[(4-{[2-(trifluoromethyl)pyridin-4-yl]oxy}phenyl)amino]pyrimidin-4-yl}phenyl)glycinamide trifluoroacetate;

6-(4-aminophenyl)-$N^4$-(4-{[2-(trifluoromethyl)pyridin-4-yl]oxy}phenyl)pyrimidine-2,4-diamine;

6-(6-aminopyridin-3-yl)-$N^4$-(4-{[2-(trifluoromethyl)pyridin-4-yl]oxy}phenyl)pyrimidine-2,4-diamine;

6-pyridin-3-yl-$N^4$-(4-{[2-(trifluoromethyl)pyridin-4-yl]oxy}phenyl)pyrimidine-2,4-diamine;

N-[(4-{4-[(2-amino-6-phenylpyrimidin-4-yl)amino]phenoxy}pyridin-2-yl)methyl]-4-methoxybenzenesulfonamide trifluoroacetate;

N-[(4-{4-[(2-amino-6-phenylpyrimidin-4-yl)amino]phenoxy}pyridin-2-yl)methyl]methanesulfonamide trifluoroacetate; and (4-{4-[(2-amino-6-phenylpyrimidin-4-yl)amino]phenoxy}pyridin-2-yl)methanol trifluoroacetate (salt).

9. A pharmaceutical composition comprising a compound of claim 1 and a pharmaceutically acceptable carrier.

10. A method of treatment of breast cancer comprising administering an effective amount of a compound of claim 1 to a subject in need thereof.

* * * * *